(12) United States Patent
Brown et al.

(10) Patent No.: US 11,945,796 B2
(45) Date of Patent: Apr. 2, 2024

(54) SUBSTITUTED PYRIDINE DERIVATIVES AS SARM1 INHIBITORS

(71) Applicant: Nura Bio, Inc., South San Francisco, CA (US)

(72) Inventors: Sean Pomeroy Brown, Half Moon Bay, CA (US); Keira Garland, San Francisco, CA (US); Shilpa Sambashivan, Los Altos, CA (US); Christopher Michael Tegley, Daly City, CA (US); Liusheng Zhu, Foster City, CA (US)

(73) Assignee: NURA BIO, INC., South San Francisco, CA (US)

( * ) Notice: Subject to any disclaimer, the term of this patent is extended or adjusted under 35 U.S.C. 154(b) by 0 days.

(21) Appl. No.: 17/475,896

(22) Filed: Sep. 15, 2021

(65) Prior Publication Data
US 2022/0081417 A1 Mar. 17, 2022

Related U.S. Application Data

(60) Provisional application No. 63/079,279, filed on Sep. 16, 2020.

(51) Int. Cl.
| | | |
|---|---|---|
| *C07D 401/14* | (2006.01) | |
| *A61K 45/06* | (2006.01) | |
| *C07D 401/06* | (2006.01) | |
| *C07D 405/14* | (2006.01) | |
| *C07D 409/14* | (2006.01) | |
| *C07D 417/14* | (2006.01) | |

(52) U.S. Cl.
CPC ............ *C07D 401/14* (2013.01); *A61K 45/06* (2013.01); *C07D 401/06* (2013.01); *C07D 405/14* (2013.01); *C07D 409/14* (2013.01); *C07D 417/14* (2013.01); *C07B 2200/05* (2013.01)

(58) Field of Classification Search
CPC ................ C07D 401/14; C07D 401/06; C07D 417/14; C07D 409/14; C07D 405/14
See application file for complete search history.

(56) References Cited

U.S. PATENT DOCUMENTS

| | | |
|---|---|---|
| 2004/0186129 A1 | 9/2004 | Koya et al. |
| 2006/0252778 A1 | 11/2006 | Guo et al. |
| 2017/0197981 A1 | 7/2017 | Shaw et al. |
| 2017/0355708 A1 | 12/2017 | Jefson et al. |
| 2023/0105696 A1 | 4/2023 | Kolluri et al. |
| 2023/0286941 A1 | 9/2023 | Kolluri et al. |
| 2023/0339913 A1 | 10/2023 | Kozak et al. |

FOREIGN PATENT DOCUMENTS

| | | |
|---|---|---|
| WO | WO-9918096 A1 | 4/1999 |
| WO | WO-2005085220 A1 | 9/2005 |
| WO | WO-2005105780 A2 | 11/2005 |
| WO | WO-2009046802 A1 | 4/2009 |
| WO | WO-2009114552 A1 | 9/2009 |
| WO | WO-2010093849 A2 | 8/2010 |
| WO | WO 2012/050141 * | 4/2012 |
| WO | WO-2012049161 A1 | 4/2012 |
| WO | WO-2014158998 A1 | 10/2014 |
| WO | WO-2014187928 A1 | 11/2014 |
| WO | WO-2015140130 A1 | 9/2015 |
| WO | WO-2016012474 A1 | 1/2016 |
| WO | WO-2016187324 A1 | 11/2016 |
| WO | WO-2018094362 A1 | 5/2018 |
| WO | WO-2019236890 A1 | 12/2019 |
| WO | WO-2020176863 A1 | 9/2020 |
| WO | WO-2020247701 A2 | 12/2020 |
| WO | WO-2020252229 A2 | 12/2020 |
| WO | WO-2021142006 A1 | 7/2021 |
| WO | WO-2022031736 A1 | 2/2022 |
| WO | WO-2022046606 A1 | 3/2022 |
| WO | WO-2022060812 A1 | 3/2022 |
| WO | WO-2023009663 A1 | 2/2023 |

OTHER PUBLICATIONS

Registry No. 1372613-10-9, File Registry on STN, entered STN May 3, 2012.*
Registry No. 1372613-27-8, File Registry on STN, entered STN May 3, 2012.*
Cecil Textbook of Medicine, 20th edition (1996), vol. 2, pp. 2050-2057.*
Cecil Textbook of Medicine, 20th edition (1996), vol. 2, pp. 1992-1996.*
FDA mulls drug to slow late-stage Alzheimer's [online], [retrieved on Sep. 23, 2003]. Retrieved from the internet, URL;http;//www.cnn/com/2003/HEALTH/conditions/09/24/alzheimers.drug.ap/index.html>.*
Ishita et al. Synthesis and biological evaluation of aminothiazoles against Histoplasma capsula-tum and Cryptococcus neoformans. Bioorg Med Chem 26:2251-2261 (2018).
Lipinski. Bioisosteric Design of Conformationally Restricted Pyridyltriazole Histamine H2 Receptor Antagonists. J Med Chem 26(1):1-6 (1983).
PCT/US2021/050426 International Search Report and Written Opinion dated Dec. 20, 2021.
Segapelo et al. Pyrazolylmethyl)amino-pyridine platinum (II) and gold (II) complexes. Syn-thesis, structures and evaluation as anti-cancer agents. Inorganic Chimica Acta 362(9):3314-3324 (2009).
Bosanac et al., Pharmacological SARM1 inhibition protects axon structure and function in paclitaxel-induced peripheral neuropathy. Brain 144(10):3226-3238 (2021).
Hughes et al., Small molecule SARM1 inhibitors recapitulate the SARM1−/− phenotype and allow recovery of a metastable pool of axons fated to degenerate. Cell Rep. 34(1):108588 (2021).
Loring et al. Identification of the First Noncompetitive SARM1 Inhibitors. Bioorg Med Chem 28(18):115644 (2020).

(Continued)

*Primary Examiner* — Rebecca L Anderson
(74) *Attorney, Agent, or Firm* — WILSON SONSINI GOODRICH & ROSATI

(57) ABSTRACT

This disclosure is drawn to substituted pyridine compounds and compositions, and associated methods, useful for inhibition of SARM1 activity and/or for treating or preventing neurological diseases.

66 Claims, No Drawings

(56) References Cited

OTHER PUBLICATIONS

PCT/US2021/044389 International Invitation to Pay Additional Fees dated Nov. 12, 2021.
PCT/US2021/044389 International Search Report and Written Opinion dated Jan. 10, 2022.
Shi et al. Structural basis of SARM1 activation, substrate recognition, and inhibition by small molecules. Mol Cell 82(9):1643-1659 (2022).
Berge et al. Pharmaceutical Salts. Journal of Pharmaceutical Sciences 66(1):1-19 (Jan. 1977).
Coleman et al. An 85-kb tandem triplication in the slow Wallerian degeneration (Wlds) mouse. PNAS USA 95(17):9985-90 (1998).
Essuman et al. The SARM1 Toll/Interleukin-1 Receptor Domain Possesses Intrinsic NAD + Cleavage Activity that Promotes Pathological Axonal Degeneration. Neuron 93(6):1334-43 (2017).
Flierl et al. Mouse closed head injury model induced by a weight-drop device. Na Protoc 4(9):1328-1337 (2009).
Geisler et al. Prevention of vincristine-induced peripheral neuropathy by genetic deletion of SARM1 in mice. Brain 139(Pt 12):3092-3108 (2016).
Gerdts et al. Axon Self-Destruction: New Links among SARM1, MAPKs, and NAD+ Metabolism. Neuron 89:449-60 (2016).
Gerdts et al. SARM1 activation triggers axon degeneration locally via $NAD^+$ destruction. Science 348(6233):453-57 (2015).
Henninger et al. Attenuated traumatic axonal injury and improved functional outcome after traumatic brain injury in mice lacking Sarm1. Brain 139(Pt 4):1094 (2016).
Kanamori et al. Retrograde and Wallerian axonal degeneration occur synchronously after retinal ganglion cell axotomy. Am. J. Pathol. 181(1):62-73 (2012).
Kurowska et al. Is Axonal Degeneration a Key Early Event in Parkinson's Disease? J. Parkinson's Dis. 6:703-07 (2016).
Lyons et al. B cells are critical to induction of experimental allergic encephalomyelitis by protein but not by a short encephalitogenic peptide. Eur J of Immunology 29(11):3432-9 (1999).
Ravin. Chapter 76: Preformulation. Remington's Pharmaceutical Sciences, 17th ed., Mack Publishing Company, Easton, Pa. (pp. 1409-1423) (1985).
Salvadores et al. Axonal Degeneration during Aging and Its Functional Role in Neurodegenerative Disorders. Front. Neurosci. 11:451 (2017).
Sprowl et al. Oxaliplatin-induced neurotoxicity is dependent on the organic cation transporter OCT2. PNAS USA 110(27):11199-11204 (2013).
Summers et al. Mitochondrial dysfunction induces Sarm1-dependent cell death in sensory neurons. J Neurosci. 34(28):9338-50 (2014).
Summers et al. SARM1-specific motifs in the TIR domain enable NAD+ loss and regulate injury-induced SARM1 activation. PNAS USA 113(41):E6271-E6280 (2016).
Wang et al. $Wld^s$ mice are resistant to paclitaxel (taxol) neuropathy. Ann. Neurol. 52(4):442-7 (2002).
Yang et al. Pathological axonal death through a MAPK cascade that triggers a local energy deficit. Cell 160(1-2):161-76 (2015).
Bratkowski et al., Structural and mechanistic regulation of the pro-degenerative NAD hydrolase SARM1. Cell Rep. 32(5):107999 (2020).
Cavaletti et al., Chemotherapy-induced peripheral neurotoxicity: a multifaceted, still unsolved issue. J Peripher Nerv Syst. 24(Suppl 2):S6-S12 (2019).
Essuman et al., TIR domain proteins are an ancient family of NAD+-consuming enzymes. Curr Biol. 28(3):421-430.e4 (2018).
Figley et al., SARM1 is a metabolic sensor activated by an increased NMN/NAD+ ratio to trigger axon degeneration. Neuron 109(7):1118-1136.e11 (2021).
Fischer et al. Amyotrophic lateral sclerosis is a distal axonopathy: evidence in mice and man. Exp Neurol 185:232-240 (2004).
Fukuda et al., A mechanistic understanding of axon degeneration in chemotherapy-induced peripheral neuropathy. Front Neurosci. 11:481 (2017).
Gaetani et al., Neurofilament light chain as a biomarker in neurological disorders. J Neurol Neurosurg Psychiatry 90(8):870-881 (2019).
Gagliardi et al., Diagnostic and prognostic value of CSF neurofilaments in a cohort of patients with motor neuron disease: A cross-sectional study. J Cell Mol Med. 25(8):3765-3771 (2021).
Gerdts et al., Image-based screening identifies novel roles for IkappaB kinase and glycogen synthase kinase 3 in axonal degeneration. J Biol Chem. 286(32):28011-28018 (2011).
Gerdts et al., Sarm1-mediated axon degeneration requires both SAM and TIR interactions. J Neurosci. 33(33):13569-13580 (2013).
Gordon. Neurofilaments in disease: what do we know? Curr Opin Neurobiol. 61:105-115 (2020).
Graham et al., Diffuse axonal injury predicts neurodegeneration after moderate-severe traumatic brain injury. Brain 143(12):3685-3698 (2020).
Haffner et al., Discovery, synthesis, and biological evaluation of thiazoloquin(az)olin(on)es as potent CD38 inhibitors. J Med Chem. 58(8):3548-3571 (2015).
Horsefield et al., NAD+ cleavage activity by animal and plant TIR domains in cell death pathways. Science 365(6455):793-799 (2019).
Huang et al., Longitudinal biomarkers in amyotrophic lateral sclerosis. Ann Clin Transl Neurol. 7(7):1103-1116 (2020).
Jiang et al., The NAD+-mediated self-inhibition mechanism of pro-neurodegenerative SARM1. Nature 588(7839):658-663 (2020).
Kaneko et al., Protecting axonal degeneration by increasing nicotinamide adenine dinucleotide levels in experimental autoimmune encephalomyelitis models. J Neurosci. 26(38):9794-9804 (2006).
Kim et al., MyD88-5 links mitochondria, microtubules, and JNK3 in neurons and regulates neuronal survival. J Exp Med. 204(9):2063-2074 (2007).
Koliatsos et al., Wallerian degeneration as a therapeutic target in traumatic brain injury. Curr Opin Neurol. 32(6):786-795 (2019).
Ma et al., Direct pathogen-induced assembly of an NLR immune receptor complex to form a holoenzyme. Science 370(6521):eabe3069 (2020).
Maglemose et al., Potassium channel abnormalities are consistent with early axon degeneration of motor axons in the G127X SOD1 mouse model of amyotrophic lateral sclerosis. Exp Neurol. 292:154-167 (2017).
Martin et al., Structure of the activated ROQ1 resistosome directly recognizing the pathogen effector XopQ. Science 370(6521):eabd9993 (2020).
Osterloh et al., dSarm/Sarm1 is required for activation of an injury-induced axon death pathway. Science 337(6093):481-484 (2012).
Perry et al., Evidence that very slow wallerian degeneration in C57BL/Ola mice is an intrinsic property of the peripheral nerve. Eur J Neurosci. 2(9):802-808 (1990).
RCSB Protein Data Bank, 7NAI Crystal structure of the TIR domain from human SARM1 in complex with 3AD. https://www.rcsb.org/structure/7NAI (2021).
Sasaki et al., Nicotinamide mononucleotide adenylyl transferase-mediated axonal protection requires enzymatic activity but not increased levels of neuronal nicotinamide adenine dinucleotide. J Neurosci. 29(17):5525-5535 (2009).
Schlaepfer. Calcium-induced degeneration of axoplasm in isolated segments of rat peripheral nerve. Brain Res. 69(2):203-215 (1974).
Scully et al., Synthesis and evaluation of thiazoloquinolinones with linkers to enable targeting of CD38. Acs Med Chem Lett. 8(2):196-200 (2017).
Shen et al., Multiple domain interfaces mediate SARM1 autoinhibition. Proc Natl Acad Sci USA. 118(4):e2023151118 (2021).
Sporny et al., Structural basis for SARM1 inhibition and activation under energetic stress. Elife 9:e62021 (2020).
Tarrago et al., A Potent and Specific CD38 Inhibitor Ameliorates Age-Related Metabolic Dysfunction by Reversing Tissue NAD+ Decline. Cell Metab. 27(5):1081-1095.e10 (2018).

(56) References Cited

OTHER PUBLICATIONS

Uccellini et al., Passenger mutations confound phenotypes of SARM1-deficient mice. BioRxiv. Oct. 18, 2019; Cell Reports 31(1):107498 (2020).
Viar et al., Sarm1 knockout protects against early but not late axonal degeneration in experimental allergic encephalomyelitis. PLoS One 15(6):e0235110 (2020).
Waller. Experiments on the section of the glossopharyngeal and hypoglossal nerves of the frog, and observations of the alterations produced thereby in the structure of their primitive fibres. Philosophical Transactions of the Royal Society of London 140(0):423-429 (1850).
Weber et al., Clarity reveals a more protracted temporal course of axon swelling and disconnection than previously described following traumatic brain injury. Brain Pathol. 29(3):437-450 (2019).
Williams et al., Neurofilaments in progressive multiple sclerosis: a systematic review. J Neurol. 268(9):3212-3222 (2021).
Zhao et al., A cell-permeant mimetic of NMN activates SARM1 to produce cyclic ADP-ribose and induce non-apoptotic cell death. iScience 15:452-466 (2019).
PCT/US2022/038577 International Search Report and Written Opinion dated Nov. 17, 2022.
U.S. Appl. No. 17/875,301 Office Action dated Nov. 8, 2022.
PCT/US2023/071058 International Search Report and Written Opinion dated Oct. 10, 2023.

* cited by examiner

SUBSTITUTED PYRIDINE DERIVATIVES AS SARM1 INHIBITORS

FIELD OF THE INVENTION

This disclosure is drawn to compounds and compositions, and associated methods, useful for inhibition of SARM1 activity and/or for treating tier preventing a neurological disorder.

BACKGROUND OF THE INVENTION

Aging constitutes the main risk factor for the development of neurodegenerative diseases. Axonal degeneration is an important pathological event in many neurodegenerative and neurological disorders, including peripheral neuropathy and traumatic brain injury (Gerdts, J. et al., Neuron, 2016, 89, 449-60). Axonal degeneration has also been implicated in, for example, Alzheimer's disease, Parkinson's disease and Amyotrophic Lateral Sclerosis, where degeneration precedes symptom onset and widespread neuronal loss (Kurowska, Z. et al., J. Parkinson's Dis., 2016, 6, 703-07). While these neurological conditions have unique underlying etiologies, inhibition of axonal degeneration in the conditions' early stages may slow or prevent their progression by preventing the loss of functional synapses and maintaining neuronal connectivity (Essuman, K. et al., Neuron, 2017 Mar. 22, 93(6), 1334-43).

Axonal degeneration after injury occurs both toward the proximal cell body (termed retrograde degeneration) and toward the distal axon terminal (termed Wallerian or orthograde degeneration) (Kanamori A. et al., Am. J. Pathol. 2012 July; 181(1):62-73). Wallerian degeneration, which occurs in that section of the axon that is distal to the site of injury, occurs after axonal injury in both the peripheral nervous system (PNS) and the central nervous system (CNS). Wallerian degeneration usually begins within 24-36 hours of a lesion. Prior to degeneration, the distal section of the axon tends to remain electrically excitable, while after injury, the axonal skeleton disintegrates, and the axonal membrane breaks apart.

The processes of death of the cell body and degeneration of the axon are independent events. As alluded to above, evidence exists indicating that the degeneration of axons precedes clinical symptoms in neurodegenerative diseases and occurs before cell body loss. Thus, axonal degeneration constitutes an early event in pathological processes and provides a potential therapeutic target to treat neurodegeneration prior to neuronal cell death (Salvadores, N. et al., Front. Neurosci., 2017, 11, 451).

In view of the above, new modalities are needed for the treatment of neurological disorders such as neurodegenerative disease by the prevention of axonal degeneration.

SUMMARY OF THE INVENTION

The present invention is directed to inhibitors of SARM1 such as a compound of Formula I, Ia, or Ib:

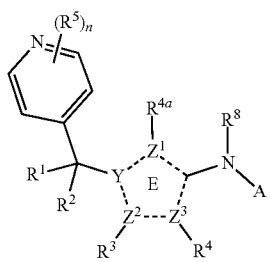

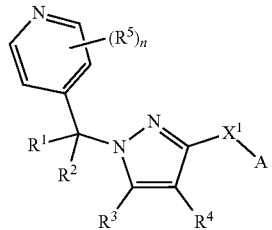

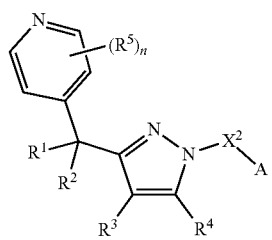

or a pharmaceutically acceptable salt thereof, wherein constituent members are defined herein.

The present invention is further directed to a pharmaceutical composition comprising a compound of the invention, or a pharmaceutically acceptable salt thereof, and at least one pharmaceutically acceptable carrier.

The present invention is further directed to a method of inhibiting SARM1 comprising contacting the SARM1 with a compound of the invention, or a pharmaceutically acceptable salt thereof.

The present invention is further directed to a method of inhibiting axonal degeneration in a patient in need thereof comprising administering to the patient an inhibiting amount of a compound of the invention, or a pharmaceutically acceptable salt thereof.

The present invention is further directed to a method of treating or preventing a neurological disorder in a patient in need thereof comprising administering to the patient a therapeutically effective amount of a compound of the invention, or a pharmaceutically acceptable salt thereof.

The present invention is further directed to a method of treating or preventing a neurological disorder in a patient in need thereof comprising administering to the patient a therapeutically effective amount of a compound of the invention, or a pharmaceutically acceptable salt thereof, in combination with a further pharmaceutically active agent.

DETAILED DESCRIPTION

Similar to programmed cell death pathways (e.g., apoptosis), axonal degeneration in response to injury or disease stimulates a local signaling cascade that causes destruction of the injured axon segment (Summers D. W., et al., PNAS USA, 2016 Oct. 11, 113(41):E6271-E6280). Following injury, the axonal skeleton disintegrates, and the axonal membrane breaks apart. Subsequent to axonal degeneration, the myelin sheath degrades and infiltration by macrophages follows; the macrophages, along with Schwann cells, clear the cellular debris resulting from the degeneration (Coleman M. P., et al., PNAS USA, 1998 August, 95(17):9985-90).

SARM1 (sterile alpha and TIR motif-containing 1) protein (NP_055892) is a 724 amino acid protein involved in axon degeneration. It has also been implicated in infectious and inflammatory disorders. The SARM1 protein, also known as FLJ36296, KIAA0524, MyD88-5, SAM domain-containing protein 2, and SAMD2, comprises four domains, i) a mitochondrial localization signal, ii) an auto-inhibitory N-terminus region consisting of armadillo/HEAT motifs, iii) two sterile alpha motifs responsible for multimerization, and iv) a C-terminus Toll/Interleukin-1 receptor that possesses enzymatic activity (Essuman K., et al., Neuron 2017 March, 93(6):1334-43.e5).

SARM1 protein plays a critical role in the Wallerian degeneration pathway. Activation of SARM1 triggers a rapid collapse of $NAD^+$ levels in the distal section of the injured axon, which then undergoes degeneration (Gerdts J. et al., Science 2015 April 348(6233):453-57). Promoting dimerization of the Toll/interleukin receptor (TIR) domain of SARM1 has been shown to be sufficient to promote $NAD^+$ loss and axon degeneration.

SARM1's activity is responsible for, at least in part, the protective nature of the survival factor NMNAT2, as NMKNAT enzymes have been found to prevent SARM1-mediated depletion of $NAD^+$. Other pro-degeneration signaling pathways, including the MAP kinase pathway, have been linked to SARM1 activation. MAPK signaling has been shown to promote the loss of NMNAT2, which promotes SARM1 activation (See, e.g., Yang J. et al., Cell 2015 January 160(1-2):161-76).

SARM1 is involved in the innate immune response. It promotes neuronal cell death in response to stress and other stimuli. SARM1 acts as a negative regulator of TICAM1/TRIF-dependent Toll-like receptor signaling by inhibiting induction of TLR3- and TLR4-dependent genes, which play a pivotal role in activating axonal degeneration following injury. In addition, SARM1 specifically blocks TICAM1/TRIF-dependent transcription factor activation and gene induction, without affecting the MYD88-dependent pathway or non-TLR signaling. It is also a negative regulator of NF-kappa-B and IRF activation. (See, e.g., Summers, D. W. et al., J Neurosci., 2014 Jul. 9, 34(28):9338-50).

In some embodiments, the present invention provides inhibitors (e.g., small molecules) of SARM1. SARM1 activation is known to cause a rapid reduction in $NAD^+$ levels in injured axons, which then undergo degeneration. In particular embodiments, the compounds inhibit axonal degeneration, including axonal degeneration that results from reduction or depletion of $NAD^+$ (e.g., inhibition of SARM1 NADase).

The present invention is directed to inhibitors of SARM1 such as a compound of Formula I:

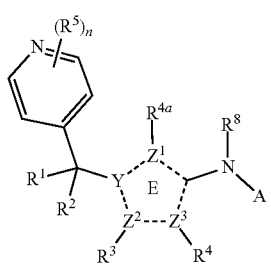

I or a pharmaceutically acceptable salt thereof, wherein:
Y is N or C;
$Z^1$, $Z^2$, and $Z^3$ are each independently selected from O, S, N, or C, wherein Ring E is a 5-membered aromatic ring;
A is H, —$C_{1-4}$ alkyl-CN, Cy, —$C_{1-4}$ alkyl-Cy, $C_{1-4}$ alkyl, or $C_{1-4}$ haloalkyl;

$R^1$, $R^2$, $R^3$, $R^4$, $R^{4a}$, and $R^5$ are each independently selected from H, D, halo, $CH_3$, $CH_2CH_3$, $CD_3$, $CH_2CD_3$, and $CD_2CD_3$;
wherein $R^3$ is absent when $Z^2$ is O, S, or N;
wherein $R^4$ is absent when $Z^3$ is O, S, or N;
wherein $R^{4a}$ is absent when $Z^1$ is O, S, or N;
$R^8$ is H or $C_{1-4}$ alkyl;
Cy is selected from $C_{6-10}$ aryl, $C_{3-7}$ cycloalkyl, 5-6 membered heteroaryl, and 4-7 membered heterocycloalkyl, each optionally substituted by 1, 2, 3, 4, or 5 $R^{Cy}$ substituents independently selected from halo, $C_{1-4}$ alkyl, $C_{1-4}$ haloalkyl, CN, $NO_2$, $OR^a$, $SR^a$, $C(O)R^b$, $C(O)NR^cR^d$, $C(O)OR^a$, $OC(O)R^b$, $OC(O)NR^cR^d$, $NR^cR^d$, $NR^cC(O)R^b$, $NR^cC(O)OR^a$, $NR^cC(O)NR^cR^d$, $C(=NR^e)R^b$, $C(=NR^e)NR^cR^d$, $NR^cC(=NR^e)NR^cR^d$, $NR^cS(O)R^b$, $NR^cS(O)_2R^b$, $NR^cS(O)_2NR^cR^d$, $S(O)R^b$, $S(O)NR^cR^d$, $S(O)_2R^b$, and $S(O)_2NR^cR^d$;

or two adjacent $R^{Cy}$ substituents together with the atoms to which they are attached form a fused phenyl, $C_{3-7}$ cycloalkyl, 5-6 membered heteroaryl, or 4-7 membered heterocycloalkyl ring, each optionally substituted by 1, 2, 3, 4, or 5 substituents independently selected from halo, $C_{1-4}$ alkyl, $C_{1-4}$ haloalkyl, CN, $NO_2$, $OR^a$, $SR^a$, $C(O)R^b$, $C(O)NR^cR^d$, $C(O)OR^a$, $OC(O)R^b$, $OC(O)NR^cR^d$, $NR^cR^d$, $NR^cC(O)R^b$, $NR^cC(O)OR^a$, $NR^cC(O)NR^cR^d$, $C(=NR^e)R^b$, $C(=NR^e)NR^cR^d$, $NR^cC(=NR^e)NR^cR^d$, $NR^cS(O)R^b$, $NR^cS(O)_2R^b$, $NR^cS(O)_2NR^cR^d$, $S(O)R^b$, $S(O)NR^cR^d$, $S(O)_2R^b$, and $S(O)_2NR^cR^d$;

each $R^a$, $R^b$, $R^c$, and $R^d$ is independently selected from H, $C_{1-4}$ alkyl, and $C_{1-4}$ haloalkyl, wherein said $C_{1-4}$ alkyl is optionally substituted with 1, 2, or 3 substituents independently selected from OH, CN, amino, halo, $C_{1-4}$ alkyl, $C_{1-4}$ alkoxy, $C_{1-4}$ haloalkyl, and $C_{1-4}$ haloalkoxy;

each $R^e$ is independently selected from H, $C_{1-4}$ alkyl, and CN; and
n is 0, 1, or 2.

In some embodiments, the compound is other than

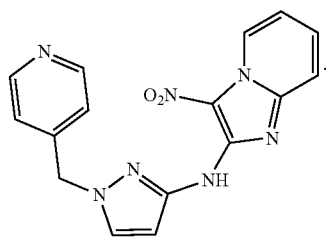 [SMILES: O=[N+]([O-])c1c(Nc2ccn(Cc3ccncc3)n2)nc2ccccn12]

In some embodiments, Y is N.
In some embodiments, Y is C.
In some embodiments, Ring E is an imidazole, thiazole, isothiazole, oxazole, isoxazole, or pyrazole ring.
In some embodiments, Ring E is a pyrazole ring.
In some embodiments, at least one of $Z^1$, $Z^2$, and $Z^3$ is N.
In some embodiments, $Z^1$ is N, $Z^2$ is C, and $Z^3$ is C.
In some embodiments, A is Cy, $C_{1-4}$ alkyl-Cy, $C_{1-4}$ alkyl, or $C_{1-4}$ haloalkyl.
In some embodiments, Cy is $C_{3-7}$ cycloalkyl or 5-6 membered heteroaryl.
In some embodiments, n is 0. In some embodiments, n is 1.
In some embodiments, $R^1$ and $R^2$ are each independently selected from H, $CH_3$, and $CH_2CH_3$.
In some embodiments, one of $R^1$ and $R^2$ is H and the other of $R^1$ and $R^2$ is H, $CH_3$, and $CH_2CH_3$.
In some embodiments, $R^3$ is H.

In some embodiments, $R^4$ is H.
In some embodiments, $R^5$ is $CH_3$.
In some embodiments, $R^8$ is methyl.

The present invention is further directed to inhibitors of SARM1 such as a compound of Formula Ia or Ib:

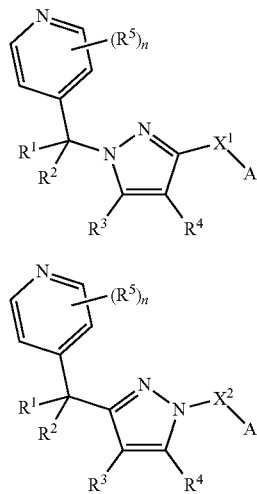

or a pharmaceutically acceptable salt thereof, wherein:

$X^1$ is $-(CR^6R^7)_m-$, $-(CR^6R^7)_p-NR^8-(CR^6R^7)_q-$, $-(CR^6R^7)_p-C(=O)-(CR^6R^7)_q-$, $-(CR^6R^7)_p-NR^8C(=O)-(CR^6R^7)_q-$, or $-(CR^6R^7)_p NR^8-S(=O)_2-(CR^6R^7)_q-$;

$X^2$ is $-(CR^6R^7)_m-$ or $-(CR^6R^7)_p-C(=O)-(CR^6R^7)_q-$;

A is H, D, halo, CN, Cy, $C_{1-3}$ alkyl, or $C_{1-3}$ haloalkyl;

$R^1$, $R^2$, $R^3$, $R^4$, and $R^5$ are each independently selected from H, D, halo, $CH_3$, $CH_2CH_3$, $CD_3$, $CH_2CD_3$, and $CD_2CD_3$;

$R^6$ and $R^7$ are each independently selected from H, D, halo, methyl, ethyl, and $C_{1-3}$ haloalkyl;

$R^8$ is H or $C_{1-4}$ alkyl;

Cy is selected from $C_{6-10}$ aryl, $C_{3-7}$ cycloalkyl, 5-6 membered heteroaryl, and 4-7 membered heterocycloalkyl, each optionally substituted by 1, 2, 3, 4, or 5 $R^{Cy}$ substituents independently selected from halo, $C_{1-4}$ alkyl, $C_{1-4}$ haloalkyl, CN, $NO_2$, $OR^a$, $SR^a$, $C(O)R^b$, $C(O)NR^cR^d$, $C(O)OR^a$, $OC(O)R^b$, $OC(O)NR^cR^d$, $NR^cR^d$, $NR^cC(O)R^b$, $NR^cC(O)OR^a$, $NR^cC(O)NR^cR^d$, $C(=NR^e)R^b$, $C(=NR^e)NR^cR^d$, $NR^cC(=NR^e)NR^cR^d$, $NR^cS(O)R^b$, $NR^cS(O)_2R^b$, $NR^cS(O)_2NR^cR^d$, $S(O)R^b$, $S(O)NR^cR^d$, $S(O)_2R^b$, and $S(O)_2NR^cR^d$;

or two adjacent $R^{Cy}$ substituents together with the atoms to which they are attached form a fused phenyl, $C_{3-7}$ cycloalkyl, 5-6 membered heteroaryl, or 4-7 membered heterocycloalkyl ring, each optionally substituted by 1, 2, 3, 4, or 5 substituents independently selected from halo, $C_{1-4}$ alkyl, $C_{1-4}$ haloalkyl, CN, $NO_2$, $OR^a$, $SR^a$, $C(O)R^b$, $C(O)NR^cR^d$, $C(O)OR^a$, $OC(O)R^b$, $OC(O)NR^cR^d$, $NR^cR^d$, $NR^cC(O)R^b$, $NR^cC(O)OR^a$, $NR^cC(O)NR^cR^d$, $C(=NR^e)R^b$, $C(=NR^e)NR^cR^d$, $NR^cC(=NR^e)NR^cR^d$, $NR^cS(O)R^b$, $NR^cS(O)_2R^b$, $NR^cS(O)_2NR^cR^d$, $S(O)R^b$, $S(O)NR^cR^d$, $S(O)_2R^b$, and $S(O)_2NR^cR^d$;

each $R^a$, $R^b$, $R^c$, and $R^d$ is independently selected from H, $C_{1-4}$ alkyl, and $C_{1-4}$ haloalkyl, wherein said $C_{1-4}$ alkyl is optionally substituted with 1, 2, or 3 substituents independently selected from OH, CN, amino, halo, $C_{1-4}$ alkyl, $C_{1-4}$ alkoxy, $C_{1-4}$ haloalkyl, and $C_{1-4}$ haloalkoxy;

each $R^e$ is independently selected from H, $C_{1-4}$ alkyl, and CN;

m is 1, 2, or 3;
n is 0, 1, or 2;
p is 0, 1, or 2; and
q is 0, 1, or 2.

In some embodiments: $-X^1$-A is other than $CF_3$.

In some embodiments, the compound is other than

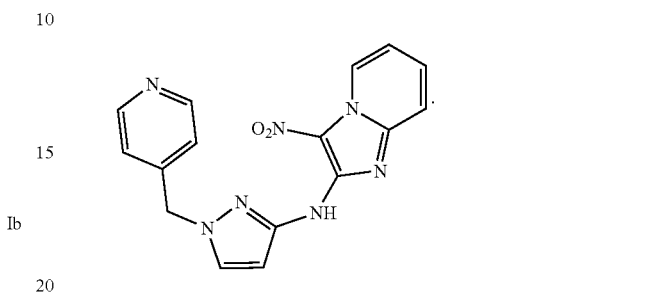

In some embodiments, the compound is other than one or more of the following:

N-(1-(Pyridin-4-ylmethyl)-1H-pyrazol-3-yl)-2,3-dihydrobenzofuran-5-carboxamide;

N-(1-(Pyridin-4-ylmethyl)-1H-pyrazol-3-yl)-2,3-dihydro-1H-indene-5-carboxamide;

N-(1-(Pyridin-4-ylmethyl)-1H-pyrazol-3-yl)benzenesulfonamide;

4-Methoxy-N-(1-(pyridin-4-ylmethyl)-1H-pyrazol-3-yl)benzenesulfonamide; and

3-Fluoro-N-(1-(pyridin-4-ylmethyl)-1H-pyrazol-3-yl)benzenesulfonamide.

In some embodiments, the compound has Formula Ia.
In some embodiments, the compound has Formula Ib.
In some embodiments, $X^1$ is $-(CR^6R^7)_m-$, $-(CR^6R^7)_p-NR^8-(CR^6R^7)_q-$, $-(CR^6R^7)_p-NR^8C(=O)-(CR^6R^7)_q-$, $-(CR^6R^7)_p-C(=O)-(CR^6R^7)_q-$, or $-(CR^6R^7)_p-NR^8-S(=O)_2-(CR^6R^7)_q-$.

In some embodiments, $X^1$ is $-(CR^6R^7)_m-$, $-(CR^6R^7)_p-NR^8-(CR^6R^7)_q-$, or $-(CR^6R^7)_p-NR^8C(=O)-(CR^6R^7)_q-$.

In some embodiments, $X^1$ is $-(CR^6R^7)_m-$.
In some embodiments, $X^1$ is $-CR^6R^7-$.
In some embodiments, $X^1$ is $-(CR^6R^7)_p-NR^8-(CR^6R^7)_q-$.
In some embodiments, $X^1$ is $-NR^8-$.
In some embodiments, $X^1$ is $-(CR^6R^7)_p-NR^8C(=O)-(CR^6R^7)_q-$.
In some embodiments, $X^1$ is $-NR^8C(=O)-$.
In some embodiments, $X^1$ is $-(CR^6R^7)_p-C(=O)-(CR^6R^7)_q-$.
In some embodiments, $X^1$ is $C(=O)$.
In some embodiments, $X^1$ is $-(CR^6R^7)_p-NR^8-S(=O)_2-(CR^6R^7)_q-$.
In some embodiments, $X^1$ is $-NR^8-S(=O)_2-$.
In some embodiments, $X^1$ is $CH_2$, $CF_2$, $CH_2CH_2$, NH, $NHCH_2$, $-NH-C(CH_3)H-$, $-N(CH_3)-$, $-N(CH_3)-CH_2-$, $-NH-C(=O)-$, $-NH-C(=O)-CH_2-$, $-NH-C(=O)-(CH_2)_2-$, $-C(=O)-$, $-N(CH_3)-S(O)_2-$, $-NH-S(O)_2-$, or $-NH-S(O)_2-CH_2-$.
In some embodiments, $X^1$ is $CH_2$, $CH_2CH_2$, NH, $NHCH_2$, or $-NH-C(=O)-$.
In some embodiments, $X^1$ is $CH_2$, NH, or $NHCH_2$.
In some embodiments, $X^1$ is $CH_2$.
In some embodiments, $X^1$ is $CH_2CH_2$.
In some embodiments, $X^1$ is NH.

In some embodiments, X¹ is NHCH₂.
In some embodiments, X¹ is —NH—C(=O)—.
In some embodiments, X² is —(CR⁶R⁷)ₘ—.
In some embodiments, X² is —CR⁶R⁷—.
In some embodiments, X² is CH₂.
In some embodiments, A is H, halo, CN, Cy, C₁₋₃ alkyl, C₁₋₃ haloalkyl.
In some embodiments, A is halo, CN, Cy, C₁₋₃ alkyl, or C₁₋₃ haloalkyl.
In some embodiments, A is C₁₋₃ haloalkyl.
In some embodiments, A is F, CN, CHF₂, or CF₃.
In some embodiments, A is Cy.
In some embodiments, R¹ and R² are each independently selected from H, D, halo, CH₃, CH₂CH₃, and CD₃.
In some embodiments, R¹ and R² are each independently selected from H, CH₃, CH₂CH₃, and CD₃.
In some embodiments, one of R¹ and R² is H and the other of R¹ and R² is H, D, halo, CH₃, CH₂CH₃, or CD₃.
In some embodiments, one of R¹ and R² is H and the other of R¹ and R² is H, CH₃, CH₂CH₃, or CD₃.
In some embodiments, R³ and R⁴ are each independently selected from H, halo, and CH₃.
In some embodiments, R³ and R⁴ are each independently selected from H and halo.
In some embodiments, R³ and R⁴ are each independently selected from H and F.
In some embodiments, R³ and R⁴ are both H.
In some embodiments, each R⁵ is independently selected from H, halo, and CH₃.
In some embodiments, each R⁵ is independently selected from H and CH₃.
In some embodiments, R⁶ and R⁷ are each independently selected from H, halo, and methyl.
In some embodiments, R⁶ and R⁷ are each independently selected from H and methyl.
In some embodiments, R⁶ and R⁷ are both H.
In some embodiments, R⁸ is H or methyl.
In some embodiments, Cy is C₃₋₇ cycloalkyl.
In some embodiments, Cy is cyclopropyl.
In some embodiments, Cy is cyclobutyl.
In some embodiments, Cy is 4-7 membered heterocycloalkyl substituted by 2 R$^{Cy}$ substituents that together with the atoms to which they are attached form a fused phenyl.
In some embodiments, Cy is selected from C₆₋₁₀ aryl and 5-6 membered heteroaryl, each optionally substituted by 1, 2, 3, 4, or 5 R$^{Cy}$ substituents independently selected from halo, C₁₋₄ alkyl, C₁₋₄ haloalkyl, CN, NO₂, OR$^a$, SR$^a$, C(O)R$^b$, C(O)NR$^c$R$^d$, C(O)OR$^a$, OC(O)R$^b$, OC(O)NR$^c$R$^d$, NR$^c$R$^d$, NR$^c$C(O)R$^b$, NR$^c$C(O)OR$^a$, NR$^c$C(O)NR$^c$R$^d$, C(=NR$^e$)R$^b$, C(=NR$^e$)NR$^c$R$^d$, NR$^c$C(=NR$^e$)NR$^c$R$^d$, NR$^c$S(O)R$^b$, NR$^c$S(O)₂R$^b$, NR$^c$S(O)₂NR$^c$R$^d$, S(O)R$^b$, S(O)NR$^c$R$^d$, S(O)₂R$^b$, and S(O)₂NR$^c$R$^d$;

or two adjacent R$^{Cy}$ substituents together with the atoms to which they are attached form a fused phenyl, C₃₋₇ cycloalkyl, 5-6 membered heteroaryl, or 4-7 membered heterocycloalkyl ring, each optionally substituted by 1, 2, 3, 4, or 5 substituents independently selected from halo, C₁₋₄ alkyl, C₁₋₄ haloalkyl, CN, NO₂, OR$^a$, SR$^a$, C(O)R$^b$, C(O)NR$^c$R$^d$, C(O)OR$^a$, OC(O)R$^b$, OC(O)NR$^c$R$^d$, NR$^c$R$^d$, NR$^c$C(O)R$^b$, NR$^c$C(O)OR$^a$, NR$^c$C(O)NR$^c$R$^d$, C(=NR$^e$)R$^b$, C(=NR$^e$)NR$^c$R$^d$, NR$^c$C(=NR$^e$)NR$^c$R$^d$, NR$^c$S(O)R$^b$, NR$^c$S(O)₂R$^b$, NR$^c$S(O)₂NR$^c$R$^d$, S(O)R$^b$, S(O)NR$^c$R$^d$, S(O)₂R$^b$, and S(O)₂NR$^c$R$^d$.

In some embodiments, Cy is selected from phenyl and 5-membered heteroaryl, each optionally substituted by 1, 2, 3, 4, or 5 R substituents independently selected from halo, C₁₋₄ alkyl, C₁₋₄ haloalkyl, CN, NO₂, OR$^a$, SR$^a$, C(O)R$^b$, C(O)NR$^c$R$^d$, C(O)OR$^a$, OC(O)R$^b$, OC(O)NR$^c$R$^d$, NR$^c$R$^d$, NR$^c$C(O)R$^b$, NR$^c$C(O)OR$^a$, NR$^c$C(O)NR$^c$R$^d$, C(=NR$^e$)R$^b$, C(=NR$^e$)NR$^c$R$^d$, NR$^c$C(=NR$^e$)NR$^c$R$^d$, NR$^c$S(O)R$^b$, NR$^c$S(O)₂R$^b$, NR$^c$S(O)₂NR$^c$R$^d$, S(O)R$^b$, S(O)NR$^c$R$^d$, S(O)₂R$^b$, and S(O)₂NR$^c$R$^d$;

or two adjacent R$^{Cy}$ substituents together with the atoms to which they are attached form a fused phenyl, C₃₋₇ cycloalkyl, 5-6 membered heteroaryl, or 4-7 membered heterocycloalkyl ring, each optionally substituted by 1, 2, 3, 4, or 5 substituents independently selected from halo, C₁₋₄ alkyl, C₁₋₄ haloalkyl, CN, NO₂, OR$^a$, SR$^a$, C(O)R$^b$, C(O)NR$^c$R$^d$, C(O)OR$^a$, OC(O)R$^b$, OC(O)NR$^c$R$^d$, NR$^c$R$^d$, NR$^c$C(O)R$^b$, NR$^c$C(O)OR$^a$, NR$^c$C(O)NR$^c$R$^d$, C(=NR$^e$)R$^b$, C(=NR$^e$)NR$^c$R$^d$, NR$^c$C(=NR$^e$)NR$^c$R$^d$, NR$^c$S(O)R$^b$, NR$^c$S(O)₂R$^b$, NR$^c$S(O)₂NR$^c$R$^d$, S(O)R$^b$, S(O)NR$^c$R$^d$, S(O)₂R$^b$, and S(O)₂NR$^c$R$^d$.

In some embodiments, each R$^{Cy}$ is independently selected from halo, C₁₋₄ alkyl, C₁₋₄ haloalkyl, CN, and OR$^a$.

In some embodiments, two adjacent R$^{Cy}$ substituents together with the atoms to which they are attached form a fused phenyl, C₃₋₇ cycloalkyl, 5-6 membered heteroaryl, or 4-7 membered heterocycloalkyl ring, wherein the fused 4-7 membered heterocycloalkyl ring is optionally substituted by 1 or 2 C₁₋₄ alkyl.

In some embodiments, Cy is selected from:

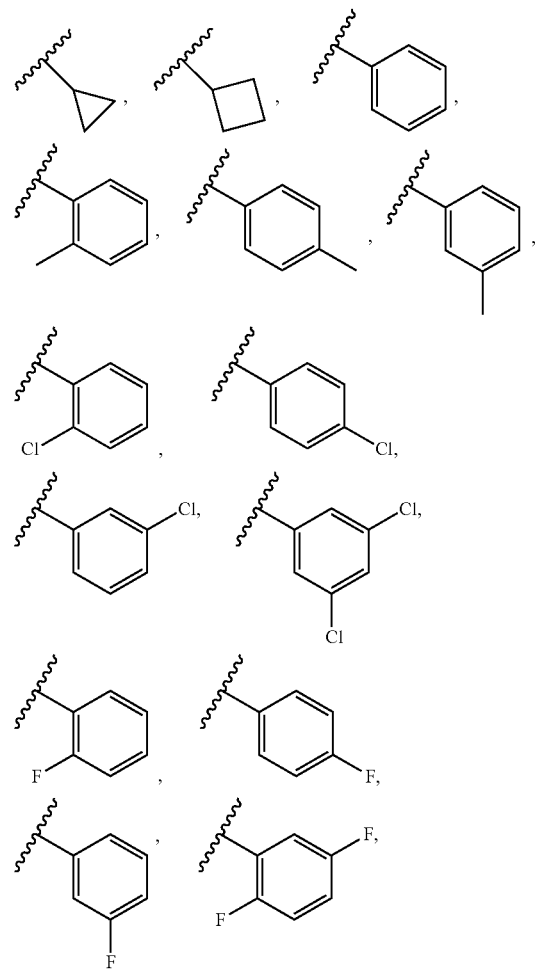

-continued

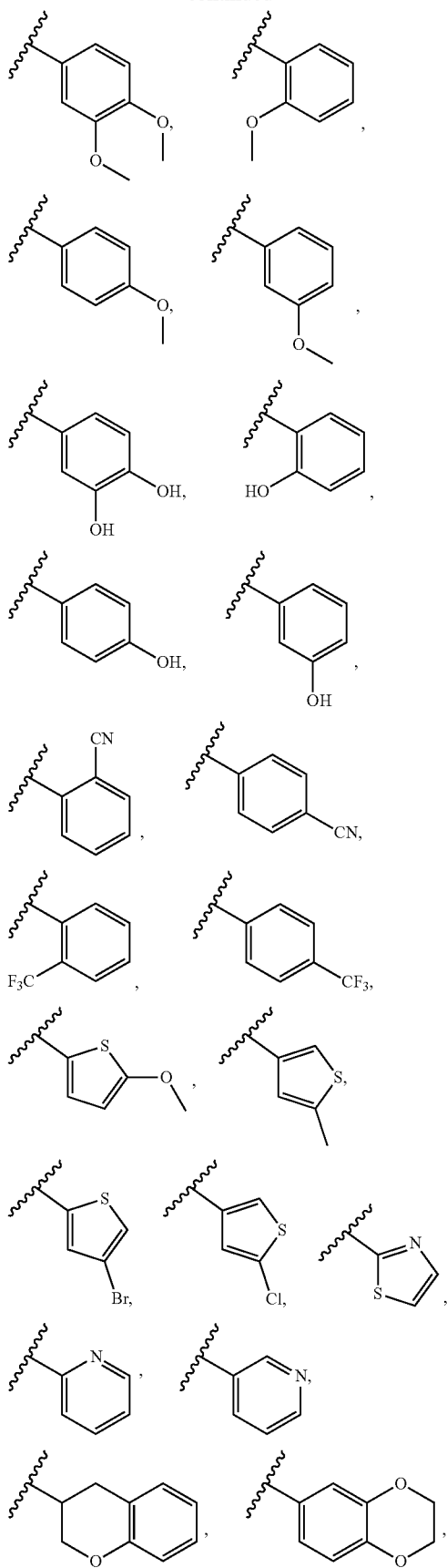

-continued

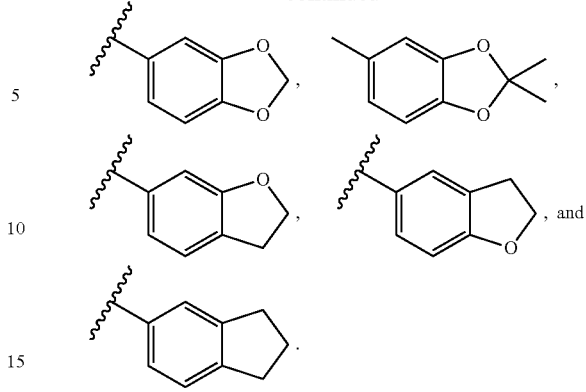

In some embodiments, n is 0 or 1.
In some embodiments, n is 0.
In some embodiments, m is 1 or 2.
In some embodiments, m is 1.
In some embodiments, p is 0 or 1 and q is 0 or 1.
In some embodiments, one of p and q is 1 and the other is 0.

It is further appreciated that certain features of the invention, which are, for clarity, described in the context of separate embodiments, can also be provided in combination in a single embodiment. Conversely, various features of the invention which are, for brevity, described in the context of a single embodiment, can also be provided separately or in any suitable subcombination.

At various places in the present specification, substituents of compounds of the invention are disclosed in groups or in ranges. It is specifically intended that the invention include each and every individual subcombination of the members of such groups and ranges. For example, the term "$C_{1-6}$ alkyl" is specifically intended to individually disclose methyl, ethyl, $C_3$ alkyl, $C_4$ alkyl, $C_5$ alkyl, and $C_6$ alkyl.

At various places in the present specification various aryl, heteroaryl, cycloalkyl, and heterocycloalkyl rings are described. Unless otherwise specified, these rings can be attached to the rest of the molecule at any ring member as permitted by valency. For example, the term "pyridinyl," "pyridyl," or "a pyridine ring" may refer to a pyridin-2-yl, pyridin-3-yl, or pyridin-4-yl ring.

At various places in the present specification a di-valent or linking group may be present. Each linking group is understood as linking in either direction. That is, if a linking group is described as -A-B—, then it is understood, unless otherwise specified, that the linking group is not directionally limited and can also be —B-A-. For example, when a linking group is written as —C(=O)—O—, it also means —O—C(=O)—.

The term "n-membered," where "n" is an integer, typically describes the number of ring-forming atoms in a moiety where the number of ring-forming atoms is "n". For example, piperidinyl is an example of a 6-membered heterocycloalkyl ring, pyrazolyl is an example of a 5-membered heteroaryl ring, pyridyl is an example of a 6-membered heteroaryl ring, and 1,2,3,4-tetrahydro-naphthalene is an example of a 10-membered cycloalkyl group.

For compounds of the invention in which a variable appears more than once, each variable can be a different moiety independently selected from the group defining the variable. For example, where a structure is described having two R groups that are simultaneously present on the same compound, the two R groups can represent different moieties independently selected from the group defined for R.

As used herein, the phrase "optionally substituted" means unsubstituted or substituted.

As used herein, the term "substituted" means that a hydrogen atom is replaced by a non-hydrogen group. It is to be understood that substitution at a given atom is limited by valency. In some embodiments, an atom substituted by oxo (=O) has two hydrogen atoms replaced by the oxo substituent.

As used herein, the term "$C_{i-j}$," where i and j are integers, employed in combination with a chemical group, designates a range of the number of carbon atoms in the chemical group with i-j defining the range. For example, $C_{1-6}$ alkyl refers to an alkyl group having 1, 2, 3, 4, 5, or 6 carbon atoms.

As used herein, the term "alkyl," employed alone or in combination with other terms, refers to a saturated hydrocarbon group that may be straight-chain or branched. In some embodiments, the alkyl group contains 1 to 7, 1 to 6, 1 to 4, or 1 to 3 carbon atoms. Examples of alkyl moieties include, but are not limited to, chemical groups such as methyl, ethyl, n-propyl, isopropyl, n-butyl, isobutyl, sec-butyl, tert-butyl, n-pentyl, 2-methyl-1-butyl, 3-pentyl, n-hexyl, 1,2,2-trimethylpropyl, n-heptyl, and the like. In some embodiments, the alkyl group is methyl, ethyl, or propyl.

As used herein, "halo" or "halogen", employed alone or in combination with other terms, includes fluoro, chloro, bromo, and iodo. In some embodiments, halo is F or Cl.

As used herein, the term "haloalkyl," employed alone or in combination with other terms, refers to an alkyl group having up to the full valency of halogen atom substituents, which may either be the same or different. In some embodiments, the halogen atoms are fluoro atoms. In some embodiments, the alkyl group has 1 to 6 or 1 to 4 carbon atoms. Example haloalkyl groups include $CF_3$, $C_2F_5$, $CHF_2$, $CCl_3$, $CHCl_2$, $C_2Cl_5$, and the like.

As used herein, the term "alkoxy," employed alone or in combination with other terms, refers to a group of formula —O-alkyl. Example alkoxy groups include methoxy, ethoxy, propoxy (e.g., n-propoxy and isopropoxy), t-butoxy, and the like. In some embodiments, the alkyl group has 1 to 6 or 1 to 4 carbon atoms.

As used herein, "haloalkoxy," employed alone or in combination with other terms, refers to a group of formula —O-(haloalkyl). In some embodiments, the alkyl group has 1 to 6 or 1 to 4 carbon atoms. An example haloalkoxy group is —$OCF_3$.

As used herein, "amino," employed alone or in combination with other terms, refers to $NH_2$.

As used herein, the term "cycloalkyl," employed alone or in combination with other terms, refers to a non-aromatic cyclic hydrocarbon including cyclized alkyl and alkenyl groups. Cycloalkyl groups can include mono- or polycyclic (e.g., having 2, 3, or 4 fused, bridged, or spiro rings) ring systems. Also included in the definition of cycloalkyl are moieties that have one or more aromatic rings (e.g., aryl or heteroaryl rings) fused (i.e., having a bond in common with) to the cycloalkyl ring, for example, benzo derivatives of cyclopentane, cyclohexene, cyclohexane, and the like, or pyrido derivatives of cyclopentane or cyclohexane. Ring-forming carbon atoms of a cycloalkyl group can be optionally substituted by oxo. Cycloalkyl groups also include cycloalkylidenes. The term "cycloalkyl" also includes bridgehead cycloalkyl groups (e.g., non-aromatic cyclic hydrocarbon moieties containing at least one bridgehead carbon, such as admantan-1-yl) and spirocycloalkyl groups (e.g., non-aromatic hydrocarbon moieties containing at least two rings fused at a single carbon atom, such as spiro[2.5] octane and the like). In some embodiments, the cycloalkyl group has 3 to 10 ring members, or 3 to 7 ring members. In some embodiments, the cycloalkyl group is monocyclic or bicyclic. In some embodiments, the cycloalkyl group is monocyclic. In some embodiments, the cycloalkyl group is a $C_{3-7}$ monocyclic cycloalkyl group. Example cycloalkyl groups include cyclopropyl, cyclobutyl, cyclopentyl, cyclohexyl, cycloheptyl, cyclopentenyl, cyclohexenyl, cyclohexadienyl, cycloheptatrienyl, norbornyl, norpinyl, norcarnyl, tetrahydronaphthalenyl, octahydronaphthalenyl, indanyl, and the like. In some embodiments, the cycloalkyl group is cyclopropyl, cyclobutyl, cyclopentyl, or cyclohexyl.

As used herein, the term "heterocycloalkyl," employed alone or in combination with other terms, refers to a non-aromatic ring or ring system, which may optionally contain one or more alkenylene or alkynylene groups as part of the ring structure, which has at least one heteroatom ring member independently selected from nitrogen, sulfur, oxygen, and phosphorus. Heterocycloalkyl groups can include mono- or polycyclic (e.g., having 2, 3 or 4 fused, bridged, or spiro rings) ring systems. In some embodiments, the heterocycloalkyl group is a monocyclic or bicyclic group having 1, 2, 3, or 4 heteroatoms independently selected from nitrogen, sulfur and oxygen. Also included in the definition of heterocycloalkyl are moieties that have one or more aromatic rings (e.g., aryl or heteroaryl rings) fused (i.e., having a bond in common with) to the non-aromatic heterocycloalkyl ring, for example, 1,2,3,4-tetrahydro-quinoline and the like. Heterocycloalkyl groups can also include bridgehead heterocycloalkyl groups (e.g., a heterocycloalkyl moiety containing at least one bridgehead atom, such as azaadmantan-1-yl and the like) and spiroheterocycloalkyl groups (e.g., a heterocycloalkyl moiety containing at least two rings fused at a single atom, such as [1,4-dioxa-8-aza-spiro[4.5]decan-N-yl] and the like). In some embodiments, the heterocycloalkyl group has 3 to 10 ring-forming atoms, 4 to 10 ring-forming atoms, or about 3 to 8 ring forming atoms. In some embodiments, the heterocycloalkyl group has 2 to 20 carbon atoms, 2 to 15 carbon atoms, 2 to 10 carbon atoms, or about 2 to 8 carbon atoms. In some embodiments, the heterocycloalkyl group has 1 to 5 heteroatoms, 1 to 4 heteroatoms, 1 to 3 heteroatoms, or 1 to 2 heteroatoms. The carbon atoms or heteroatoms in the ring(s) of the heterocycloalkyl group can be oxidized to form a carbonyl, an N-oxide, or a sulfonyl group (or other oxidized linkage) or a nitrogen atom can be quaternized. In some embodiments, the heterocycloalkyl portion is a $C_{2-7}$ monocyclic heterocycloalkyl group. In some embodiments, the heterocycloalkyl group is a morpholine ring, pyrrolidine ring, piperazine ring, piperidine ring, tetrahydropyran ring, tetrahydropyridine, azetidine ring, or tetrahydrofuran ring.

As used herein, the term "aryl," employed alone or in combination with other terms, refers to a monocyclic or polycyclic (e.g., a fused ring system) aromatic hydrocarbon moiety, such as, but not limited to, phenyl, 1-naphthyl, 2-naphthyl, and the like. In some embodiments, aryl groups have from 6 to 10 carbon atoms or 6 carbon atoms. In some embodiments, the aryl group is a monocyclic or bicyclic group. In some embodiments, the aryl group is phenyl or naphthyl. In some embodiments, the aryl group is phenyl.

As used herein, the term "heteroaryl," employed alone or in combination with other terms, refers to a monocyclic or polycyclic (e.g., a fused ring system) aromatic hydrocarbon moiety, having one or more heteroatom ring members independently selected from nitrogen, sulfur and oxygen. In some embodiments, the heteroaryl group is a monocyclic or a bicyclic group having 1, 2, 3, or 4 heteroatoms independently selected from nitrogen, sulfur and oxygen. In some embodiments, the heteroaryl group is a 5-14 membered heteroaryl group. In some embodiments, the heteroaryl group is a 5-10 membered heteroaryl group. In some embodiments, the heteroaryl group is a 5-6 membered heteroaryl group. Example heteroaryl groups include, but are not limited to, pyridyl, pyrimidinyl, pyrazinyl, pyridazinyl, triazinyl, furyl, thienyl, imidazolyl, thiazolyl, indolyl, pyrryl, oxazolyl, benzofuryl, benzothienyl, benzthiazolyl, isoxazolyl, pyrazolyl, triazolyl, tetrazolyl, indazolyl, 1,2,4-thiadiazolyl, isothiazolyl, purinyl, carbazolyl, benzimidazolyl, indolinyl, pyrrolyl, azolyl, quinolinyl, isoquinolinyl, benzisoxazolyl, imidazo[1,2-b]thiazolyl or the like. The carbon atoms or heteroatoms in the ring(s) of the heteroaryl group can be oxidized to form a carbonyl, an N-oxide, or a sulfonyl group (or other oxidized linkage) or a nitrogen atom can be quaternized, provided the aromatic nature of the ring is preserved. In some embodiments, the heteroaryl group has from 3 to 10 carbon atoms, from 3 to 8 carbon atoms, from 3 to 5 carbon atoms, from 1 to 5 carbon atoms, or from 5 to 10 carbon atoms. In some embodiments, the heteroaryl group contains 3 to 14, 4 to 12, 4 to 8, 9 to 10, or 5 to 6 ring-forming atoms. In some embodiments, the heteroaryl group has 1 to 4, 1 to 3, or 1 to 2 heteroatoms.

The compounds described herein can be asymmetric (e.g., having one or more stereocenters). All stereoisomers, such as enantiomers and diastereomers, are intended unless otherwise indicated. Compounds of the present invention that contain asymmetrically substituted carbon atoms can be isolated in optically active or racemic forms. Methods on how to prepare optically active forms from optically inactive starting materials are known in the art, such as by resolution of racemic mixtures or by stereoselective synthesis. Geometric isomers of olefins, C=N double bonds, and the like can also be present in the compounds described herein, and all such stable isomers are contemplated in the present invention. Cis and trans geometric isomers of the compounds of the present invention may be isolated as a mixture of isomers or as separated isomeric forms.

Compounds of the invention also include tautomeric forms. Tautomeric forms result from the swapping of a single bond with an adjacent double bond together with the concomitant migration of a proton. Tautomeric forms include prototropic tautomers which are isomeric protonation states having the same empirical formula and total charge. Example prototropic tautomers include ketone-enol pairs, amide-imidic acid pairs, lactam-lactim pairs, enamine-imine pairs, and annular forms where a proton can occupy two or more positions of a heterocyclic system, for example, 1H- and 3H-imidazole, 1H-, 2H- and 4H-1,2,4-triazole, 1H- and 2H-isoindole, and 1H- and 2H-pyrazole.

Compounds of the invention also include all isotopes of atoms occurring in the intermediates or final compounds. Isotopes include those atoms having the same atomic number but different mass numbers. For example, isotopes of hydrogen include tritium and deuterium. In some embodiments, the compounds of the invention include at least one deuterium atom.

The term, "compound," as used herein is meant to include all stereoisomers, geometric isomers, tautomers, and isotopes of the structures depicted, unless otherwise specified. The term "compound" is also not limited by the way in which it was made. Thus, a compound of the invention includes molecules that were made by a synthetic process or by a biological process (such as through enzyme conversion or metabolism), or combinations thereof.

All compounds, and pharmaceutically acceptable salts thereof, can be found together with other substances such as water and solvents (e.g., in the form of hydrates and solvates) or can be isolated.

In some embodiments, the compounds of the invention, or salts thereof, are substantially isolated. By "substantially isolated" is meant that the compound is at least partially or substantially separated from the environment in which it was formed or detected. Partial separation can include, for example, a composition enriched in the compounds of the invention. Substantial separation can include compositions containing at least about 50%, at least about 60%, at least about 70%, at least about 80%, at least about 90%, at least about 95%, at least about 97%, or at least about 99% by weight of a compound of the invention, or salt thereof. Methods for isolating compounds and their salts are routine in the art.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The present invention also includes pharmaceutically acceptable salts of the compounds described herein. As used herein, "pharmaceutically acceptable salts" refers to derivatives of the disclosed compounds wherein the parent compound is modified by converting an existing acid or base moiety to its salt form. Examples of pharmaceutically acceptable salts include, but are not limited to, mineral or organic acid salts of basic residues such as amines; alkali or organic salts of acidic residues such as carboxylic acids; and the like. The pharmaceutically acceptable salts of the present invention include the non-toxic salts of the parent compound formed, for example, from non-toxic inorganic or organic acids. The pharmaceutically acceptable salts of the present invention can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two. Lists of suitable salts are found in *Remington's Pharmaceutical Sciences*, 17th ed., Mack Publishing Company, Easton, Pa., 1985, p. 1418 and *Journal of Pharmaceutical Science*, 66, 2 (1977), each of which is incorporated herein by reference in its entirety.

Methods of Preparation

Compounds of the invention can be prepared by any number of appropriate synthetic processes. In some embodiments, a compound of Formula Ia, or a pharmaceutically acceptable salt thereof can be prepared by reacting an intermediate of Formula A:

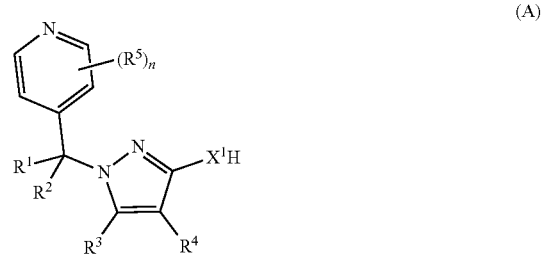

(A)

or a salt thereof, with reagent L-A, wherein L is a leaving group (e.g., Cl, Br, I, tosylate, etc.).

In some embodiments, a compound of Formula Ib, or a pharmaceutically acceptable salt thereof can be prepared by reacting an intermediate of Formula B:

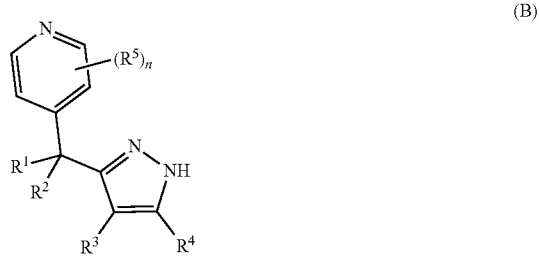

(B)

or salt thereof, with reagent L-X²-A, wherein L is a leaving group (e.g., Cl, Br, I, tosylate, etc.).

Methods of Use

Compounds of the invention can inhibit the activity of SARM1. For example, the compounds of the invention can be used to inhibit activity or a function of SARM1 in a cell or in an individual or patient in need of inhibition of the enzyme by administering an inhibiting amount of a compound of the invention to the cell, individual, or patient. As used herein, the term "in a cell" includes both inside the cell membrane and on the surface of the cell membrane.

Compounds of the invention, as SARM1 inhibitors, can increase levels of NAD+ in a cell. Accordingly, the present invention is further directed to a method of increasing the level of NAD+ in a sample or in a patient, comprising contacting the sample or administering to the patient a compound of of the invention, or a pharmaceutically acceptable salt thereof, wherein the increased level of NAD+ is relative to the level of NAD+ prior to the contacting or administering.

Compounds of the invention, as SARM1 inhibitors, can inhibit axonal degeneration. Accordingly, the present invention is further directed to a method of inhibiting axonal degeneration in a sample or in a patient, comprising contacting the sample or administering to the patient an inhibiting amount of a compound of the invention, or a pharmaceutically acceptable salt thereof.

The compounds of the invention are useful in the treatment and prevention of various diseases associated with abnormal expression or activity of SARM1. For example, the compounds of the invention are useful in the treatment and prevention of neurological disorders. The term "neurological disorder" generally refers to a disorder affecting the nervous system, including the central nervous system or the peripheral nervous system. The term "neurological disorder" also includes ocular indications having a nexus to the nervous system.

In some embodiments, the neurological disorder treatable or preventable by administration of a compound of the invention includes neurodegenerative diseases. Neurodegenerative diseases are characterized by damage to the central nervous system and can be identified by progressive dysfunction, degeneration and death of specific populations of neurons which are often synaptically interconnected. Examples of neurodegenerative diseases include Parkinson's disease (PD), Alzheimer's disease (AD), Huntington's disease (HD), prion disease, motor neuron diseases (MND), spinocerebellar ataxia (SCA), spinal muscular atrophy (SMA), amyotrophic lateral sclerosis (ALS), and epilepsy.

Examples of neurological disorders treatable or preventable according to the methods of the invention include spinal muscular atrophy (SMA), Chemotherapy Induced Peripheral Neuropathy (representative chemotherapeutic agents include vinca-alkaloids, taxols and platins), multiple sclerosis (MS), traumatic brain injury (TBI), spinal cord injury, stroke, Parkinson' disease, glaucoma, Huntington's disease, Alzheimer's disease, Charcot-Marie-Tooth disease (CMT), retinitis pigmentosa (RP), age-related macular degeneration (AMD), small fiber neuropathies, peripheral neuropathy (e.g., viral neuropathy), spinocerebellar ataxias, cystic fibrosis, familial amyloidotic polyneuropathy, spongiform encephalopathies, spinal and bulbar muscular atrophy, hereditary dentatorubral-pallidoluysian atrophy, adrenoleukodystrophy, adrenomyeloneuropathy, Alexander's disease, amyotrophic lateral sclerosis (ALS), Bassen-Kornzweig syndrome, Bell's palsy, progressive supra nuclear palsy (PSP), central pontine myelolysis, cluster headache, congenital hypomyelination, corticobasal degeneration, Creutzfeldt-Jakob disease, epilepsy, dementia (e.g., frontotemporal dementia and Lewy body dementia), demyelination disorders (e.g., ischemic demyelination), encephalomyelitis, Friedrich's ataxia, Gaucher's disease, hereditary sensory and autonomic neuropathy (HSAN), Hurler syndrome, Krabbe's disease, metachromatic leukodystrophy, migraine and tension headaches, mild cognitive impairment, motor spinoneuron disease, neuromyelitis optica, Niemann-Pick disease, optic neuritis, Pelizaeus Merzbacher disease, peripheral neuropathy, periventricular leukomalacia, postherpetic neuralgia, prion disease, progressive supranuclear palsy, progressive multifocal leukoencephalopathy, Tay-Sacks disease, thoracic disc herniation, traverse myelitis, trigeminal neuralgia, Wallerian degeneration, cerebellar degeneration, chiari malformation, dystonia, encephalitis (e.g., pediatric viral encephalitis and La Crosse virus encephalitis), hyperekplexia, multifocal motor neuropathy, muscular dystrophy, myasthenia gravis, myopathy, neurofibromatosis, neuronal ceroid lipofuscinosis, neuropathies (e.g., peripheral neuropathy), pseudobulbar affect, restless legs syndrome, spina bifida, syringomyelia, thoracic outlet syndrome, and transverse myelitis.

In other embodiments, the neurological disorder treatable or preventable by administration of a compound of the invention is a neuropathy. As used herein, the term "neuropathy" refers broadly to diseased conditions of the nervous system, including polyneuropathy; neuropathy, ataxia, and retinosa pigmentosa (NARP); familial amyloid neuropathies; diabetic neuropathy (peripheral neuropathy due to diabetes mellitus); peripheral neuropathy (e.g., chemotherapy-induced peripheral neuropathy (CIPN), including CIPN caused by vinca alkaloids, bortezomib, Ixabepilone, thalidomide and its analogs, taxanes, and platinum-based agents); and cranial neuropathy (e.g., auditory neuropathy and optic neuropathy). The term also includes other neuropathies associated with genetic disorders (e.g., NMNAT2 genetic mutation disorders).

In still other embodiments, the neurological disorder treatable or preventable by administration of a compound of the invention is an ocular neuropathy (e.g., optic neuropathy). The term "optic neuropathy" refers to damage to the optic nerve from a number of causes. Types of optic neuropathy include ischemic optic neuropathy (e.g., anterior and posterior ischemic optic neuropathy); optic neuritis (e.g., chronic relapsing inflammatory optic neuropathy (CRION), single isolated optic neuritis (SION), and relapsing isolated optic neuritis); compressive optic neuropathy; infiltrative optic neuropathy; traumatic optic neuropathy; mitochondrial optic neuropathies; and hereditary optic neuropathies (e.g., Leber's hereditary optic neuropathy (LHON), hereditary neuropathy with liability to pressure palsy (HNPP), and dominant optic atrophy).

In still other embodiments, the neurological disorder treatable or preventable by administration of a compound of the invention is multiple sclerosis (MS), chemotherapy-induced peripheral neuropathy (CIPN), amyotrophic lateral sclerosis (ALS), glaucoma, traumatic brain injury (TBI), or stroke.

As used herein, the term "cell" is meant to refer to a cell that is in vitro, ex vivo or in vivo. In some embodiments, an ex vivo cell can be part of a tissue sample excised from an organism such as a mammal. In some embodiments, an in vitro cell can be a cell in a cell culture. In some embodiments, an in vivo cell is a cell living in an organism such as a mammal.

As used herein, the term "contacting" refers to the bringing together of indicated moieties in an in vitro system or an in vivo system. For example, "contacting" SARM1 or "contacting" a cell with a compound of the invention includes the administration of a compound of the present invention to an individual or patient, such as a human, having SARM1, as well as, for example, introducing a compound of the invention into a sample containing a cellular or purified preparation containing SARM1.

As used herein, the term "individual" or "patient," used interchangeably, refers to mammals, and particularly humans. The individual or patient can be in need of treatment.

As used herein, the phrase "therapeutically effective amount" refers to the amount of active compound or pharmaceutical agent that elicits the biological or medicinal response in a tissue, system, animal, individual or human that is being sought by a researcher, veterinarian, medical doctor or other clinician.

As used herein, the phrase "inhibiting amount" refers to the amount of active compound or pharmaceutical agent that elicits a measurable SARM1 inhibition or axonal degeneration in a tissue, system, animal, individual or human.

As used herein the term "treating" or "treatment" refers to 1) inhibiting the disease in an individual who is experiencing or displaying the pathology or symptomatology of the disease (i.e., arresting further development of the pathology and/or symptomatology), or 2) ameliorating the disease in an individual who is experiencing or displaying the pathology or symptomatology of the disease (i.e., reversing the pathology and/or symptomatology).

As used herein the term "preventing" or "prevention" refers to preventing the disease in an individual who may be predisposed to the disease but does not yet experience or display the pathology or symptomatology of the disease. In some embodiments, the invention is directed to a method of preventing a disease in a patient, by administering to the patient a therapeutically effective amount of a compound of the invention, or a pharmaceutically acceptable salt thereof.

Combination Therapy

One or more additional pharmaceutically active agents or treatment methods can be used in combination with the compounds of the present invention. The agents can be combined with the present compounds in a single dosage form, or the agents can be administered simultaneously or sequentially as separate dosage forms. Examples of additional agents include acamprosate, agomelatine, almotriptan, amantadine, amisulpride, amitriptyline, apomorphine, aripiprazole, asenapine, atomoxetine, baclofen, botulinum toxin type A, bromocriptine, buccal midazolam, buprenorphine, buspirone, cabergoline, carbamazepine, chlordiazepoxide, chlorpromazine, citalopram, clobazam, clomethiazole, clomipramine, clonazepam, clozapine, denzapine, co-beneldopa, co-careldopa, dantrolene, dexamfetamine, diazepam, divalproex sodium, donepezil, doxepin, duloxetine, eletriptan, entacapone, epinephrine, escitalopram, eslicarbazepine, ethosuximide, fingolimod, fluoxetine, flupentixol, flupentixol, fluphenazine long-acting injection (modecate), fluvoxamine (Faverin), frovatriptan, gabapentin, galantamine, haloperidol, imipramine, lacosamide, lamotrigine, levetiracetam, levomepromazine, lisdexamfetamine, lithium, lofepramine, loprazolam, lorazepam, lormetazepam, lurasidone, melatonin, memantine, methylphenidate, mianserin, mirtazapine, moclobemide, modafinil, naratriptan, neostigmine, nitrazepam, nortriptyline, olanzapine, orlistat, orphenadrine, oxazepam, oxcarbazepine, paliperidone, paliperidone, paroxetine, perampanel, pergolide, pericyazine, phenobarbital, phenytoin, piracetam, pizotifen, pramipexole, pregabalin, primidone, prochlorperazine, procyclidine, pyridostigmine, quetiapine, rasagiline, reboxetine, risperidone, rivastigmine, rizatriptan, ropinirole, rotigotine, rufinamide, selegiline, sertraline, sodium oxybate, sodium valproate, sulpiride, sumatriptan, temazepam, tetrabenazine, tiagabine, tizanidine, tolcapone, topiramate, trazodone, trihexyphenidyl, trimipramine, valproate semisodium, venlafaxine, vigabatrin, vortioxetine, zolmitriptan, zolpidem, zonisamide, zopiclone, and zuclopenthixol.

In some embodiments, the one or more additional pharmaceutically active agent can include a neuroprotective agent. In some embodiments, the neuroprotective agent is a dual leucine-zipper kinase (DLK) inhibitor. In some embodiments, the neuroprotective agent is a nicotinamide phosphoribosyltransferase (NAMPT) inhibitor.

In some embodiments, the one or more additional pharmaceutically active agent can be NAD+ or an NAD+ precursor. NAD+ precursors include, for example, nicotinamide riboside (NR), nicotinic acid (NA), nicotinic acid riboside (NaR), nicotinamide (NAM), nicotinamide mononucleotide (NMN), nicotinic acid mononucleotide (NaMN), tryptophan, vitamin B3, and nicotinic acid adenine dinucleotide (NAAD).

Pharmaceutical Formulations and Dosage Forms

When employed as pharmaceuticals, the compounds of the invention can be administered in the form of pharmaceutical compositions. A pharmaceutical composition refers to a combination of a compound of the invention, or its pharmaceutically acceptable salt, and at least one pharmaceutically acceptable carrier. These compositions can be prepared in a manner well known in the pharmaceutical art, and can be administered by a variety of routes, depending upon whether local or systemic treatment is desired and upon the area to be treated. Administration may be oral, topical (including ophthalmic and to mucous membranes including intranasal, vaginal and rectal delivery), pulmonary (e.g., by inhalation or insufflation of powders or aerosols, including by nebulizer; intratracheal, intranasal, epidermal and transdermal), ocular (e.g., eye drops or intravitreal, subconjunctival, subtenon, or retrobulbar injection), or parenteral.

This invention also includes pharmaceutical compositions which contain, as the active ingredient, one or more of the compounds of the invention above in combination with one or more pharmaceutically acceptable carriers. In making the compositions of the invention, the active ingredient is typically mixed with an excipient, diluted by an excipient or enclosed within such a carrier in the form of, for example, a capsule, sachet, paper, or other container. When the excipient serves as a diluent, it can be a solid, semi-solid, or liquid material, which acts as a vehicle, carrier or medium for the active ingredient. Thus, the compositions can be in the form of tablets, pills, powders, lozenges, sachets, cachets, elixirs, suspensions, emulsions, solutions, syrups, aerosols (as a solid or in a liquid medium), ointments containing, for example, up to 10% by weight of the active compound, soft and hard gelatin capsules, suppositories, sterile injectable solutions, and sterile packaged powders.

The compositions can be formulated in a unit dosage form. The term "unit dosage form" refers to a physically discrete unit suitable as unitary dosages for human subjects and other mammals, each unit containing a predetermined quantity of active material calculated to produce the desired therapeutic effect, in association with a suitable pharmaceutical excipient.

The active compound can be effective over a wide dosage range and is generally administered in a pharmaceutically effective amount. It will be understood, however, that the amount of the compound actually administered will usually be determined by a physician, according to the relevant circumstances, including the condition to be treated, the chosen route of administration, the actual compound administered, the age, weight, and response of the individual patient, the severity of the patient's symptoms, and the like.

For preparing solid compositions such as tablets, the principal active ingredient is mixed with a pharmaceutical excipient to form a solid pre-formulation composition containing a homogeneous mixture of a compound of the present invention. When referring to these pre-formulation compositions as homogeneous, the active ingredient is typically dispersed evenly throughout the composition so that the composition can be readily subdivided into equally effective unit dosage forms such as tablets, pills and capsules. This solid pre-formulation is then subdivided into unit dosage forms of the type described above containing from, for example, 0.1 to about 500 mg of the active ingredient of the present invention.

The tablets or pills of the present invention can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permit the inner component to pass intact into the duodenum or to be delayed in release. A variety of materials can be used for such enteric layers or coatings, such materials including a number of polymeric acids and mixtures of polymeric acids with such materials as shellac, cetyl alcohol, and cellulose acetate.

The liquid forms in which the compounds and compositions of the present invention can be incorporated for administration orally or by injection include aqueous solutions, suitably flavored syrups, aqueous or oil suspensions, and flavored emulsions with edible oils such as cottonseed oil, sesame oil, coconut oil, or peanut oil, as well as elixirs and similar pharmaceutical vehicles.

Compositions for inhalation or insufflation include solutions and suspensions in pharmaceutically acceptable, aqueous or organic solvents, or mixtures thereof, and powders. The liquid or solid compositions may contain suitable pharmaceutically acceptable excipients as described supra. In some embodiments, the compositions are administered by the oral or nasal respiratory route for local or systemic effect. Compositions can be nebulized by use of inert gases. Nebulized solutions may be breathed directly from the nebulizing device or the nebulizing device can be attached to a face masks tent, or intermittent positive pressure breathing machine. Solution, suspension, or powder compositions can be administered orally or nasally from devices which deliver the formulation in an appropriate manner.

The amount of compound or composition administered to a patient will vary depending upon what is being administered, the purpose of the administration, such as prophylaxis or therapy, the state of the patient, the manner of administration, and the like. In therapeutic applications, compositions can be administered to a patient already suffering from a disease in an amount sufficient to cure or at least partially arrest the symptoms of the disease and its complications. Effective doses will depend on the disease condition being treated as well as by the judgment of the attending clinician depending upon factors such as the severity of the disease, the age, weight and general condition of the patient, and the like.

The compositions administered to a patient can be in the form of pharmaceutical compositions described above. These compositions can be sterilized by conventional sterilization techniques, or may be sterile filtered. Aqueous solutions can be packaged for use as is, or lyophilized, the lyophilized preparation being combined with a sterile aqueous carrier prior to administration.

The therapeutic dosage of the compounds of the present invention can vary according to, for example, the particular use for which the treatment is made, the manner of administration of the compound, the health and condition of the patient, and the judgment of the prescribing physician. The proportion or concentration of a compound of the invention in a pharmaceutical composition can vary depending upon a number of factors including dosage, chemical characteristics (e.g., hydrophobicity), and the route of administration. For example, the compounds of the invention can be provided in an aqueous physiological buffer solution containing about 0.1 to about 10% w/v of the compound for parenteral administration. Some typical dose ranges are from about 1 µg/kg to about 1 g/kg of body weight per day. In some embodiments, the dose range is from about 0.01 mg/kg to about 100 mg/kg of body weight per day. The dosage is likely to depend on such variables as the type and extent of progression of the disease or disorder, the overall health status of the particular patient, the relative biological efficacy of the compound selected, formulation of the excipient, and its route of administration. Effective doses can be extrapolated from dose-response curves derived from in vitro or animal model test systems.

The invention will be described in greater detail by way of specific examples. The following examples are offered for illustrative purposes, and are not intended to limit the invention in any manner. Those of skill in the art will readily recognize a variety of non-critical parameters which can be changed or modified to yield essentially the same results. The compounds of the Examples were found to be inhibitors of SARM1 according to one or more of the assays provided herein.

EXAMPLES

General Experimental

All reactions sensitive to air or moisture were carried out in flame-dried glassware under an atmosphere of nitrogen. All commercially available reagents were purchased from suppliers such as Sigma-Aldrich (MilliporeSigma), Combi-Blocks, Enamine, Sinopharm Chemical Reagent Co. (SCRC), and Alfa Aesar and were used without purification unless otherwise noted. Proton nuclear magnetic resonance ($^1$H NMR) spectra were recorded on Bruker AVIII 400 or Bruker AVIII 500 spectrometers. Samples were dissolved in deuterated chloroform (CDCl$_3$), dimethyl sulfoxide (DMSO-d$_6$), acetonitrile (CD$_3$CN) or methanol (CD$_3$OD). Chemical shifts are recorded in parts per million (ppm) and are referenced to the centerline of deuterochloroform ($\delta$ 7.26 ppm), of DMSO-d$_6$ ($\delta$ 2.50 ppm), of CD$_3$CN ($\delta$ 1.94 ppm) or of CD$_3$OD ($\delta$ 3.31 ppm). Data were recorded as follows: chemical shift, multiplicity (s=singlet, d=doublet, t=triplet, q=quartet, qt=quintet, m=multiplet, br=broad). Coupling constants (J values) are given in Hertz (Hz). Low resolution ESI mass spectra were recorded on a either an Agilent 1200 HPLC/6100 SQ system or an Agilent 1260 Infinity II HPLC/6125 SQ system.

List of Abbreviations

Boc tert-butyloxycarbonyl
Boc$_2$O Boc-anhydride or di-tert-butyl dicarbonate
CDI 1,1'-carbonyl-diimidazole
d day(s)
D $^2$H (deuterium)
DABCO 1,4-diazabicyclo[2.2.2]octane
dba dibenzylideneacetone
DCM dichloromethane
DEA diethylamine
DHP 3,4-dihydropyran
DIAD diisopropyl azodicarboxylate
DIPEA N,N-diisopropylethylamine
DMAP 4-(dimethylamino)pyridine
DMF dimethylformamide
DMSO dimethylsulfoxide
DPPA diphenyl phosphoryl azide
EDC.HCl N-Ethyl-N'-(3-dimethylaminopropyl)carbodiimide hydrochloride
ESI-MS electrospray ionization-mass spectrometry
Et ethyl
EtOAc ethyl acetate
EtOH ethanol
equiv equivalent(s)
FA formic acid
h hour(s)
HATU 1-[bis(dimethylamino)methylene]-1H-1,2,3-triazolo[4,5-b]pyridinium 3-oxide hexafluorophosphate
HOBt 1-hydroxybenzotriazole
LAH lithium aluminum hydride
LCMS liquid chromatography mass spectrometry
LiHMDS lithium bis(trimethylsilyl)amide
MS mass spectrometry
MeOH methanol
MHz megahertz
min minute(s)
mg milligram(s)
mL milliliter(s)
mmol millimolar
M molar
MeCN acetonitrile
mol mole(s)
Ms methanesulfonyl
MW microwave
N normal
NBS N-bromosuccinimide
NCS N-chlorosuccinimide
OTf trifluoromethanesulfonate
Pd/C palladium on carbon
PE petroleum ether
Ph phenyl
PTSA p-toluenesulfonic acid
$^1$H NMR proton nuclear magnetic resonance
RP-HPLC reverse-phase high performance liquid chromatography
rt room temperature
SEM 2-(trimethylsilyl)ethoxymethyl
SFC supercritical fluid chromatography
T3P propylphosphonic anhydride
TBAF tetrabutylammonium fluoride
TBPH tert-butyl hydroperoxide solution (Luperox®, TBH70X)
THF tetrahydrofuran
THP tetrahydropyran
TFA trifluoroacetic acid
TLC thin layer chromatography
Tol toluene
wt % weight percent
v/v % volume by volume percent
w/v % weight by volume percent
XPhos 2-dicyclohexylphosphino-2',4',6'-triisopropylbiphenyl Reverse-Phase HPLC Purification:

Compounds purified by RP-HPLC were run on one of the following four types of columns:

Method A: RediSep® C18 prep column, 20×150 mm (100 Å/5 micron)

Method B: Phenomenex® C18 prep column, 21.2×250 mm (100 Å/Luna 10 micron)

Method C: Xtimate® C18 prep column, 21.2×250 mm (10 micron)

Method D: Boston Prep® C18 prep column 21.2×250 mm (10 micron).

Chiral SFC Purification and Analysis:

Chiral Separation Conditions:

Instrument: Gilson-281

Column: IG 20*250, 10 μm

Column temperature: 35° C.

Mobile phase: n-Hexane (0.1% DEA): EtOH (0.1% DEA)=95:5

Flow rate: 40-50 mL/min

Back pressure: 100 bar

Detection wavelength: 214 nm

Cycle time: 2 min

Sample solution: 2-3 mg/mL in MeOH

Injection volume: 1-2.0 mL

Chiral Analysis Conditions:

Column: IG (4.6*250 mm 5 μm)

Column temperature: 40° C.

Co-solvent: n-Hexane (0.1% DEA): EtOH (0.1% DEA)=95:5

Detection wavelength: 260-270 nm

Injection volume: 1 μL

Intermediates:

Intermediate #1

(rac)-1-(1-(Pyridin-4-yl)ethyl)-1H-pyrazol-3-amine

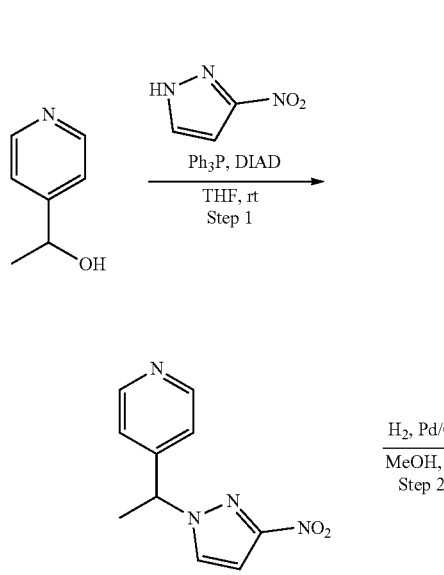

Step 1: rac-4-(1-(3-Nitro-1H-pyrazol-1-yl)ethyl)pyridine. A solution of (rac)-1-(pyridin-4-yl)ethan-1-ol (300 mg, 2.4 mmol, 1.0 equiv.) in THF (5.0 mL, 0.49 M) was treated with 3-nitro-1H-pyrazole (300 mg, 2.7 mmol, 1.1 equiv.) and triphenylphosphine (830 mg, 3.2 mmol, 1.3 equiv.) and stirred at 90° C. for 30 min, then cooled to 0° C. DIAD (640 mg, 3.2 mmol, 1.3 equiv.) was added and the mixture stirred at rt for 1.5 h. The mixture was diluted with EtOAc (30 mL) and sequentially washed with water (2×20 mL) and brine (20 mL). The organic phase was dried over anhydrous sodium sulfate, filtered, and concentrated in vacuo. The resulting residue was purified by silica gel column chromatography (33% EtOAc in PE) to give (rac)-4-(1-(3-nitro-1H-pyrazol-1-yl)ethyl)pyridine (150 mg, 28% yield) as a white solid. LCMS: ESI-MS m/z: 219.0 [M+H]$^+$.

Step 2: (rac)-1-(1-(Pyridin-4-yl)ethyl)-1H-pyrazol-3-amine. A mixture of (rac)-4-(1-(3-nitro-1H-pyrazol-1-yl)ethyl)pyridine (150 mg, 0.69 mmol, 1.0 equiv.) and Pd/C (10% Pd basis, 30 mg) in MeOH (10 mL, 0.069 M) stirred at rt under an atmosphere of hydrogen gas (balloon) for 2 h. The mixture was filtered; the filtrate was concentrated in vacuo and the resulting residue was purified by silica gel column chromatography (50% EtOAc in PE) to afford (rac)-1-(1-(pyridin-4-yl)ethyl)-1H-pyrazol-3-amine (50 mg, 39% yield) as a white solid. LCMS: ESI-MS m/z: 189.0 [M+H]$^+$.

Intermediate #2

1-(Pyridin-4-ylmethyl)-1H-pyrazol-3-amine

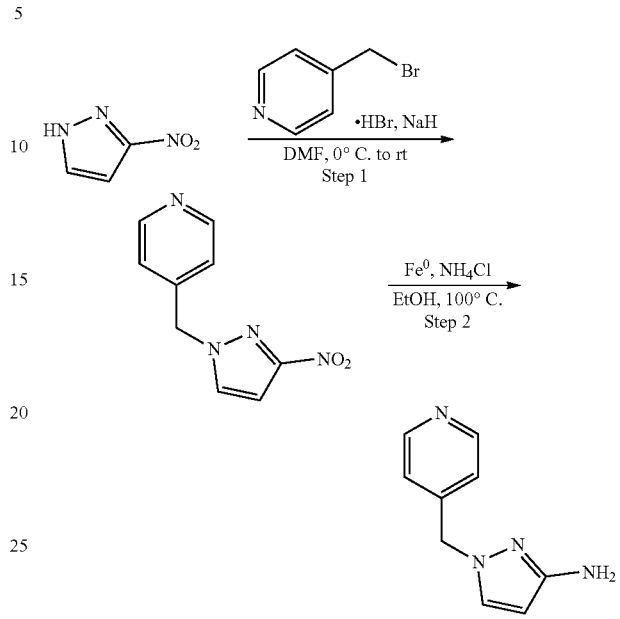

Step 1: 4-((3-Nitro-1H-pyrazol-1-yl)methyl)pyridine. A solution of 3-nitro-1H-pyrazole (1.0 g, 8.9 mmol, 1.0 equiv.) in anhydrous DMF (20 mL, 0.44 M) was cooled at 0° C., and then NaH (60 wt % dispersion in mineral oil, 530 mg, 13 mmol, 1.5 equiv.) was carefully added portion-wise. After the addition, the mixture was stirred at 0° C. for 1 h. 4-(Bromomethyl)pyridine, hydrobromide salt (3.3 g, 13 mmol, 1.5 equiv.) was added and the mixture stirred at rt for an additional 1 h. The reaction was quenched with water (30 mL) and extracted with EtOAc (3×30 mL). The combined organic extracts were washed with a saturated aqueous solution of NH$_4$Cl (2×50 mL), dried over anhydrous sodium sulfate, filtered, and concentrated in vacuo. The residue was purified by silica gel column chromatography (0-5% MeOH/DCM) to give 4-((3-nitro-1H-pyrazol-1-yl)methyl)pyridine (700 mg, 39% yield) as a yellow solid. LCMS: ESI-MS m/z: 205.1 [M+H]$^+$.

Step 2: 1-(Pyridin-4-ylmethyl)-1H-pyrazol-3-amine. A mixture of 4-((3-nitro-1H-pyrazol-1-yl)methyl)pyridine (700 mg, 3.4 mmol, 1.0 equiv.), iron powder (960 mg, 17 mmol, 5.0 equiv.), and ammonium chloride (930 mg, 17 mmol, 5.0 equiv.) in EtOH (10 mL, 0.34 M) was stirred at 100° C. for 2 h. The mixture was filtered and the filtrate was concentrated in vacuo to afford 1-(pyridin-4-ylmethyl)-1H-pyrazol-3-amine (500 mg, 84% yield) as a yellow solid. LCMS: ESI-MS m/z: 175.0 [M+H]$^+$.

Intermediate #3

(rac)-Pyridin-4-yl(1-(tetrahydro-2H-pyran-2-yl)-1H-pyrazol-3-yl)methanol

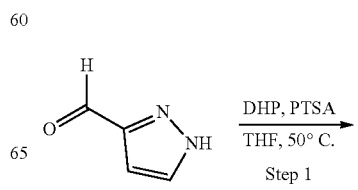

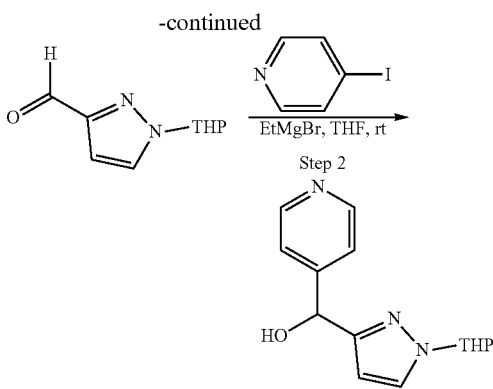

Step 1: 1-(Tetrahydro-2H-pyran-2-yl)-1H-pyrazole-3-carbaldehyde. To a solution of 1H-pyrazole-3-carbaldehyde (5.0 g, 52 mmol, 1.0 equiv.) in anhydrous THF (50 mL, 1.0 M), 3,4-dihydropyran (4.5 g, 54 mmol, 1.0 equiv.) and p-toluenesulfonic acid (0.90 g, 5.2 mmol, 0.10 equiv.) were added under an atmosphere of nitrogen gas. The mixture was stirred for 3 h at 50° C. The organic material was concentrated in vacuo and the crude product was directly purified by silica gel column chromatography (5-10% EtOAc in PE) to afford 1-(tetrahydro-2H-pyran-2-yl)-1H-pyrazole-3-carbaldehyde (7.1 g, 75% yield) as a white solid. LCMS: ESI-MS m/z: 203.1 [M+Na]⁺.

Step 2: (rac)-Pyridin-4-yl(1-(tetrahydro-2H-pyran-2-yl)-1H-pyrazol-3-yl)methanol. To a solution of 4-iodopyridine (8.2 g, 40 mmol, 1.0 equiv.) in anhydrous THF (100 mL, 0.39 M), ethylmagnesium bromide (1.0 M in THF, 40 mL, 40 mmol, 1.0 equiv.) was added under an atmosphere of nitrogen gas. The mixture was stirred for 30 min at rt. Subsequently, 1-(tetrahydro-2H-pyran-2-yl)-1H-pyrazole-3-carbaldehyde (7.1 g, 39 mmol, 1.0 equiv.) was added as a solution in anhydrous THF (10 mL). After stirring for 1 h at rt, a saturated aqueous solution of NH₄Cl was added to quench the reaction. The mixture was diluted with water (50 mL) and extracted with EtOAc (4×100 mL). The combined organic layers were washed with brine (50 mL), dried over anhydrous sodium sulfate, filtered, and concentrated in vacuo. The crude product was purified by silica gel column chromatography (40-50% EtOAc in PE) to afford pyridin-4-yl(1-(tetrahydro-2H-pyran-2-yl)-1H-pyrazol-3-yl)methanol (6.2 g, 61% yield) as a dark brown oil. LCMS: ESI-MS m/z: 260.1 [M+H]⁺.

Intermediate #4

4-((1H-Pyrazol-3-yl)methyl)pyridine

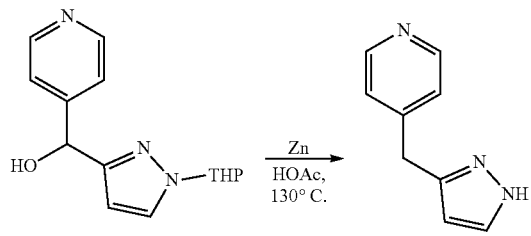

A solution of pyridin-4-yl(1-(tetrahydro-2H-pyran-2-yl)-1H-pyrazol-3-yl)methanol (Intermediate 3, 2.6 g, 10 mmol, 1.0 equiv.) in acetic acid (30 mL, 0.33 M) was treated with zinc powder (13 g, 200 mmol, 20 equiv.). The mixture was stirred for 16 h at 130° C. After filtration, the solution was treated with sodium carbonate until the pH was adjusted to 9-10. The mixture was diluted with water (200 mL) and extracted with EtOAc (4×100 mL). The combined organic layers were dried over anhydrous sodium sulfate, filtered, and concentrated in vacuo. The crude product was purified by silica gel column chromatography (0-10% MeOH/DCM) to afford 4-((1H-pyrazol-3-yl)methyl)pyridine (0.31 g, 19% yield) as a yellow solid. LCMS: ESI-MS m/z: 160.1 [M+H]⁺.

Intermediate #5

(rac)-4-(1-(1H-Pyrazol-3-yl)ethyl)pyridine

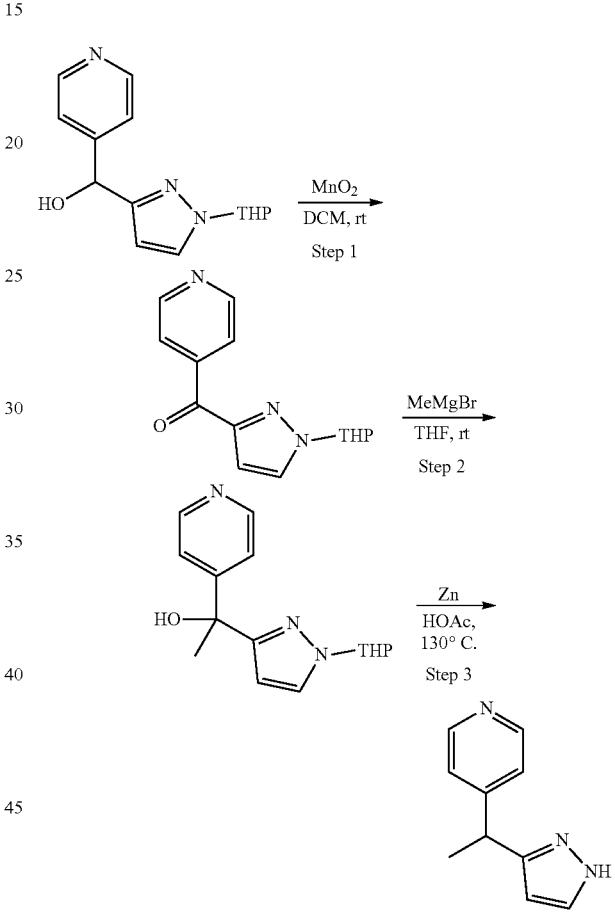

Step 1: Pyridin-4-yl(1-(tetrahydro-2H-pyran-2-yl)-1H-pyrazol-3-yl)methanone. To a solution of pyridin-4-yl(1-(tetrahydro-2H-pyran-2-yl)-1H-pyrazol-3-yl)methanol (Intermediate 3, 6.2 g, 24 mmol, 1.0 equiv.) in anhydrous DCM (100 mL, 0.24 M) was added manganese dioxide (19 g, 220 mmol, 8.9 equiv.) under an atmosphere of nitrogen gas. The mixture was stirred for 20 h at rt. The reaction was filtered, and the filtrate was concentrated in vacuo. The crude product was purified by silica gel column chromatography (10-100% EtOAc in PE) to afford pyridin-4-yl(1-(tetrahydro-2H-pyran-2-yl)-1H-pyrazol-3-yl)methanone (5.1 g, 82% yield) as a yellow solid. LCMS: ESI-MS m/z: 258.1 [M+H]⁺.

Step 2: 1-(Pyridin-4-yl)-1-(1-(tetrahydro-2H-pyran-2-yl)-1H-pyrazol-3-yl)ethan-1-ol. To a solution of pyridin-4-yl(1-(tetrahydro-2H-pyran-2-yl)-1H-pyrazol-3-yl)methanone (5.1 g, 20 mmol, 1.0 equiv.) in anhydrous THF (50 mL, 0.40 M) was added methylmagnesium bromide (3.0 M in diethyl ether, 6.6 mL, 20 mmol, 1.0 equiv.) under an atmosphere of nitrogen. After stirring for 2 h at rt, an aqueous saturated solution NH₄Cl was added to quench the reaction. The mixture was diluted with water (200 mL) and extracted with EtOAc (4×100 mL). The combined organic layers were washed with brine (100 mL), dried over anhydrous sodium sulfate, filtered, and concentrated in vacuo to afford 1-(pyridin-4-yl)-1-(1-(tetrahydro-2H-pyran-2-yl)-1H-pyrazol-3-yl)ethan-1-ol (5.2 g) as a light yellow oil. The material was carried forward to the next step without further purification. LCMS: ESI-MS m/z: 274.1 [M+H]⁺.

Step 3: (rac)-4-(1-(1H-Pyrazol-3-yl)ethyl)pyridine. A solution of 1-(pyridin-4-yl)-1-(1-(tetrahydro-2H-pyran-2-yl)-1H-pyrazol-3-yl)ethan-1-ol (5.2 g, 17 mmol, 1.0 equiv.) in acetic acid (30 mL, 0.57 M) was treated with zinc powder (12 g, 190 mmol, 11 equiv.). The mixture was heated to 130° C. and stirred for 16 h. After filtration, the solution was treated with sodium carbonate until the pH reached 9-10. The mixture was diluted with water (200 mL) and extracted with EtOAc (4×100 mL). The combined organic layers were washed with brine (100 mL), dried over anhydrous sodium sulfate, filtered and concentrated in vacuo. The crude product was purified by silica gel column chromatography (0-3% MeOH/DCM) to afford (rac)-4-(1-(1H-pyrazol-3-yl)ethyl)pyridine (2.5 g, 84% yield) as a yellow oil. LCMS: ESI-MS m/z: 174.1 [M+H]⁺.

Intermediate #6

1-(2,2,2-Trifluoroethyl)-1H-pyrazole-3-carbaldehyde

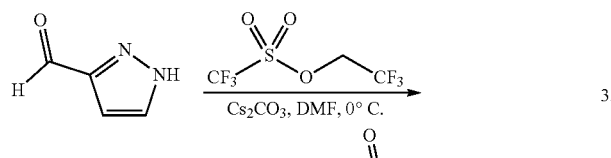

To a solution of 1H-pyrazole-3-carbaldehyde (1.0 g, 10 mmol, 1.0 equiv.) and 2,2,2-trifluoroethyl trifluoromethanesulfonate (2.7 g, 11 mmol, 1.1 equiv.) in anhydrous DMF (12 mL, 0.83 M) at 0° C. was added cesium carbonate (4.2 g, 13 mmol, 1.3 equiv.). The resulting mixture was stirred at rt for 15 h. The reaction mixture was diluted with EtOAc (160 mL), washed with water (60 mL) and brine (60 mL), dried over anhydrous sodium sulfate, filtered, and concentrated in vacuo. The crude product was then purified by silica gel column chromatography (10-40% EtOAc/hexanes) to afford 1-(2,2,2-trifluoroethyl)-1H-pyrazole-3-carbaldehyde (1.5 g, 82% yield) a colorless oil. ESI-MS m/z: 179.0 [M+H]⁺.

Intermediate #7

(rac)-1-(Pyridin-4-yl)-1-(1-(2,2,2-trifluoroethyl)-1H-pyrazol-3-yl)ethan-1-ol

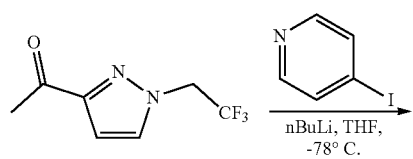

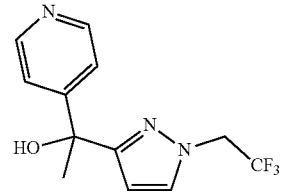

(rac)-1-(Pyridin-4-yl)-1-(1-(2,2,2-trifluoroethyl)-1H-pyrazol-3-yl)ethan-1-ol. To a solution of 4-iodopyridine (1.3 g, 6.7 mmol, 2.9 equiv.) in anhydrous THF (20 mL, 0.34 M) at −78° C. was added n-butyllithium (1.6 M in hexanes, 4.5 mL, 7.2 mmol, 3.1 equiv.) dropwise via syringe. The resulting solution was stirred at −78° C. for 10 min. The resulting solution of lithium reagent was then added dropwise to a solution of 1-(1-(2,2,2-trifluoroethyl)-1H-pyrazol-3-yl)ethan-1-one (Intermediate 6, 0.43 g, 2.3 mmol, 1.0 equiv.) in anhydrous THF (5 mL, 0.46 M) at −78° C. The mixture was stirred at −78° C. for 30 min. The reaction mixture was then quenched with water and concentrated in vacuo. The resulting crude residue was purified by silica gel column chromatography (1-7% MeOH/DCM) to afford (rac)-1-(pyridin-4-yl)-1-(1-(2,2,2-trifluoroethyl)-1H-pyrazol-3-yl)ethan-1-ol (0.16 g, 26% yield) as a white solid. LCMS: ESI-MS m/z: 272.1 [M+H]⁺.

Intermediate #8

(S)-1-(Pyridin-4-yl)ethyl methanesulfonate and (R)-1-(pyridin-4-yl)ethyl methanesulfonate

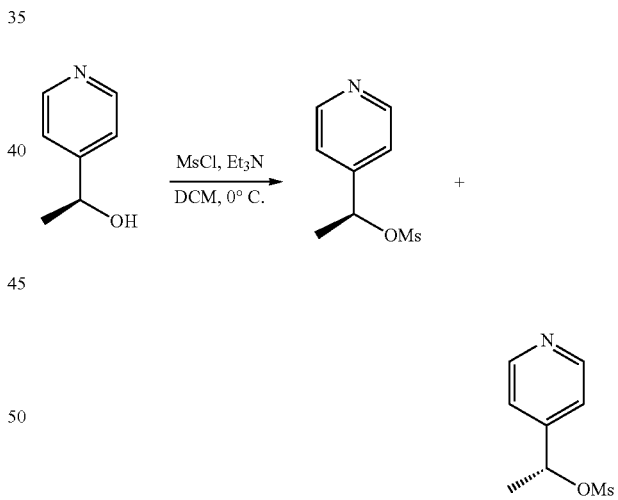

To a solution of (S)-1-(pyridin-4-yl)ethan-1-ol (160 mg, 1.3 mmol, 1.3 equiv.) in DCM (2 mL, 0.65 M) was added triethylamine (0.18 mL, 1.3 mmol, 1.3 equiv.). The reaction was cooled to 0° C. and methanesulfonyl chloride (0.077 mL, 1.0 mmol, 1.0 equiv.) was added. The reaction mixture was stirred at 0° C. for 2 min, then was warmed to rt and stirred for 1 h. After 1 h, the reaction mixture was concentrated in vacuo to afford the crude products (S)-1-(pyridin-4-yl)ethyl methanesulfonate and (R)-1-(pyridin-4-yl)ethyl methanesulfonate. This crude mixture was used in subsequent reactions without further characterization or purification.

Intermediate #9

(R)-1-(Pyridin-4-yl)ethyl methanesulfonate and (S)-1-(pyridin-4-yl)ethyl methanesulfonate

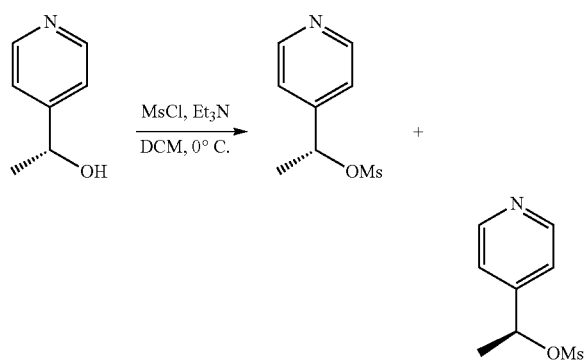

To a solution of (R)-1-(pyridin-4-yl)ethan-1-ol (160 mg, 1.3 mmol, 1.3 equiv.) in DCM (2 mL, 0.65 M) was added triethylamine (0.18 mL, 1.3 mmol, 1.3 equiv.). The reaction was cooled to 0° C. and methanesulfonyl chloride (0.077 mL, 1.0 mmol, 1.0 equiv.) was added. The reaction mixture was stirred at 0° C. for 2 min, then was warmed to rt and stirred for 1 h. After 1 h, the reaction mixture was concentrated in vacuo to afford the crude products (R)-1-(pyridin-4-yl)ethyl methanesulfonate and (S)-1-(pyridin-4-yl)ethyl methanesulfonate. This crude mixture was used in subsequent reactions without further characterization or purification.

Intermediate #10

Pyridin-4-yl(1-(2,2,2-trifluoroethyl)-1H-pyrazol-3-yl)methanone

Step 1: (rac)-Pyridin-4-yl(1-(2,2,2-trifluoroethyl)-1H-pyrazol-3-yl)methanol. To a solution of 4-iodopyridine (13 g, 62 mmol, 1.0 equiv.) in anhydrous THF (250 mL, 0.25 M) under an atmosphere of argon gas was added a solution of ethylmagnesium bromide (2 M in THF, 31 mL, 62 mmol, 1.0 equiv.). The resulting mixture was stirred at rt for 30 min. Next, a solution of 1-(2,2,2-trifluoroethyl)-1H-pyrazole-3-carbaldehyde (Intermediate 6, 11 g, 62 mmol, 1.0 equiv.) in anhydrous THF (30 mL, 2.1 M) was added to the reaction mixture. The resulting solution was stirred at rt for 2.5 h. An aqueous saturated solution of NH$_4$Cl was added to quench the reaction, and then the resulting mixture was extracted with EtOAc (2×300 mL). The combined organic fractions were washed with water (100 mL) and brine (100 mL), then dried over anhydrous sodium sulfate, filtered, and concentrated in vacuo to afford crude (rac)-pyridin-4-yl(1-(2,2,2-trifluoroethyl)-1H-pyrazol-3-yl)methanol (14 g crude). This material was moved onto the next reaction with no further purification. LCMS: ESI-MS m/z: 258.1 [M+H]$^+$.

Step 2: Pyridin-4-yl(1-(2,2,2-trifluoroethyl)-1H-pyrazol-3-yl)methanone. To a solution of (rac)-pyridin-4-yl(1-(2,2,2-trifluoroethyl)-1H-pyrazol-3-yl)methanol (14 g, 53 mmol, 1.0 equiv.) in DCM (150 mL, 0.35 M) was added manganese dioxide (46 g, 530 mmol, 10 equiv.). The resulting suspension was stirred at rt for 5 h. After 5 h, the reaction mixture was filtered over Celite® and the filtrate was concentrated in vacuo to afford a crude oil. The crude product was purified by silica gel column chromatography (60-75% EtOAc in PE) to afford pyridin-4-yl(1-(2,2,2-trifluoroethyl)-1H-pyrazol-3-yl)methanone (7.1 g, 45% yield over two steps) as a white solid. LCMS: ESI-MS m/z: 256.1 [M+H]$^+$.

EXAMPLES

Example 1

(rac)-N-(1-(1-(Pyridin-4-yl)ethyl)-1H-pyrazol-3-yl)thiazol-2-amine

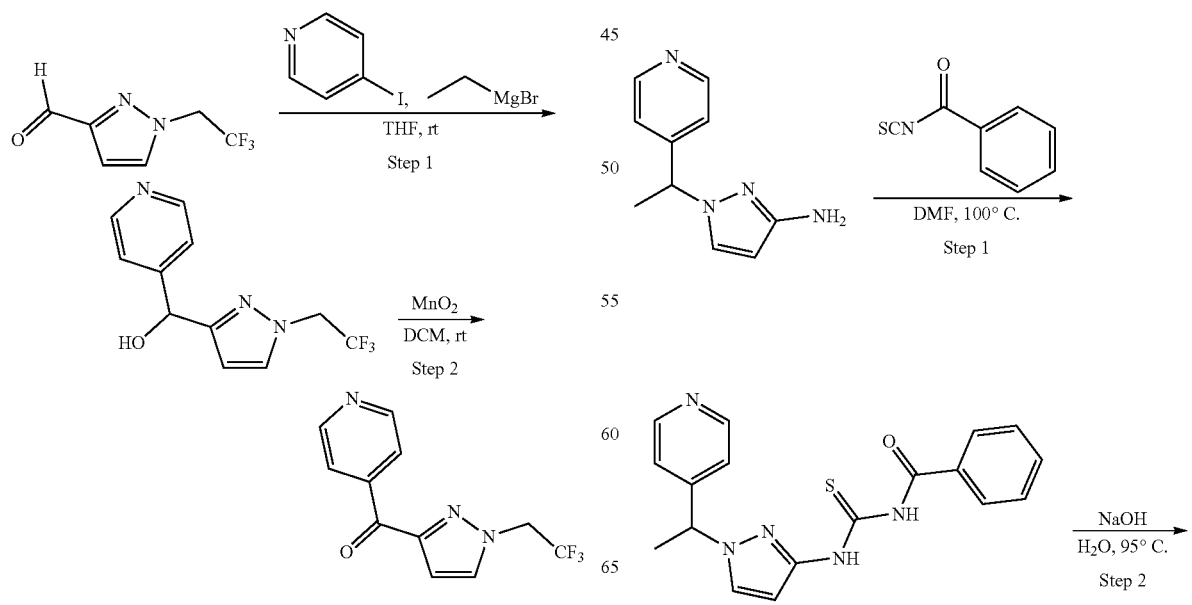

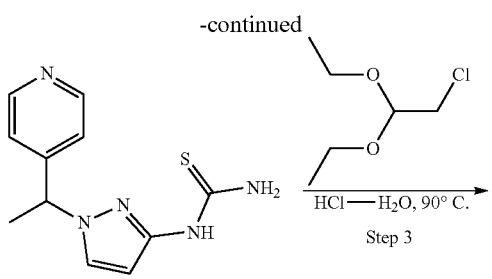

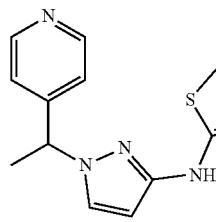

Step 1: (rac)-N-((1-(1-(Pyridin-4-yl)ethyl)-1H-pyrazol-3-yl)carbamothioyl)benzamide. (rac)-1-(1-(Pyridin-4-yl)ethyl)-1H-pyrazol-3-amine (Intermediate 1, 180 mg, 0.96 mmol, 1.0 equiv.) was added to a solution of benzoyl isothiocyanate (160 mg, 0.95 mmol, 1.0 equiv.) in anhydrous DMF (3.0 mL, 0.32 M). The mixture stirred at 100° C. for 30 min, then was cooled to rt and concentrated in vacuo to afford crude (rac)-N-((1-(1-(pyridin-4-yl)ethyl)-1H-pyrazol-3-yl)carbamothioyl)benzamide (200 mg) as a brown solid, which was carried forward in the next step without purification. LCMS: ESI-MS m/z: 352.0 [M+H]$^+$.

Step 2: (rac)-1-(1-(1-(Pyridin-4-yl)ethyl)-1H-pyrazol-3-yl)thiourea. A mixture of (rac)-N-((1-(1-(pyridin-4-yl)ethyl)-1H-pyrazol-3-yl)carbamothioyl)benzamide (200 mg, 0.57 mmol, 1.0 equiv.) in aqueous sodium hydroxide (2.0 N, 5.0 mL, 0.11 M) was stirred at 95° C. for 30 min. The mixture was cooled to rt and was treated with an aqueous solution of HCl (3.0 N) to adjust the pH to 6. The solution was extracted with EtOAc (3×15 mL). The combined organic extracts were dried over anhydrous sodium sulfate, filtered, and concentrated in vacuo. The crude filtrate was triturated with 10% EtOAc in PE (10 mL) to get (rac)-1-(1-(1-(pyridin-4-yl)ethyl)-1H-pyrazol-3-yl)thiourea (90 mg, 64% yield) as a white solid. LCMS: ESI-MS m/z: 248.0 [M+H]$^+$.

Step 3: (rac)-N-(1-(1-(Pyridin-4-yl)ethyl)-1H-pyrazol-3-yl)thiazol-2-amine. A mixture of (rac)-1-(1-(1-(pyridin-4-yl)ethyl)-1H-pyrazol-3-yl)thiourea (90 mg, 0.36 mmol, 1.0 equiv.) and 2-chloro-1,1-diethoxyethane (55 mg, 0.36 mmol, 1.0 equiv.) was heated in aqueous HCl (3.0 N, 5.0 mL, 0.072 M) at 90° C. for 1.5 h. The mixture was cooled to rt, treated with a saturated aqueous solution of sodium bicarbonate to adjust the solution to pH 8, and extracted with EtOAc (3×15 mL). The combined organic extracts were concentrated in vacuo and purified by RP-HPLC (Method C, 15-40% MeCN/10 mM NH$_4$HCO$_3$+0.025% NH$_3$·H$_2$O in H$_2$O) to give (rac)-N-(1-(1-(pyridin-4-yl)ethyl)-1H-pyrazol-3-yl)thiazol-2-amine (15 mg, 15% yield) as a white solid. $^1$H NMR (400 MHz, CD$_3$OD) δ 8.49 (dd, J=6.0 Hz, 2H), 7.67 (d, J=2.8 Hz, 1H), 7.32 (dd, J=6.0 Hz, 2H), 7.21 (d, J=4.0 Hz, 1H), 6.79 (d, J=3.6 Hz, 1H), 6.07 (d, J=2.4 Hz, 1H), 5.58-5.52 (m, 1H), 1.92 (d, J=7.2 Hz, 3H); LCMS: ESI-MS m/z: 272.0 [M+H]$^+$.

Example 2

(S)-1-(1-(Pyridin-4-yl)ethyl)-N-(2,2,2-trifluoroethyl)-1H-pyrazol-3-amine

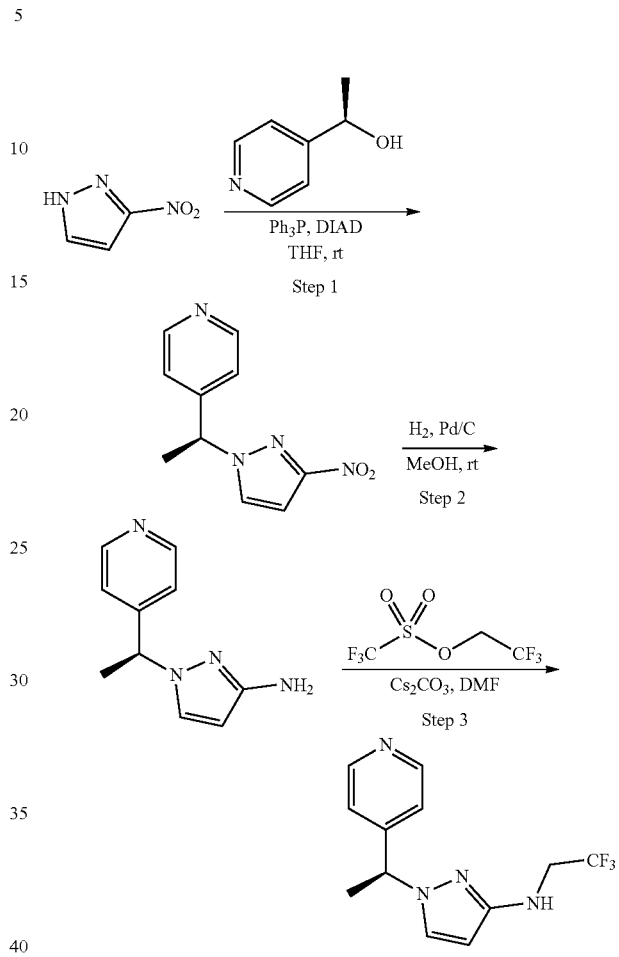

Step 1: (S)-4-(1-(3-Nitro-1H-pyrazol-1-yl)ethyl)pyridine. To a solution of (R)-1-(pyridin-4-yl) ethan-1-ol (200 mg, 1.6 mmol, 1.0 equiv.), 3-nitro-1H-pyrazole (240 mg, 2.1 mmol, 1.3 equiv.), and triphenylphosphine (550 mg, 2.1 mmol, 1.3 equiv.) in anhydrous THF (7.0 mL, 0.23 M) at 0° C. and under an atmosphere of nitrogen gas was added DIAD (430 mg, 2.1 mmol, 1.3 equiv.) dropwise via syringe. After the addition, the mixture was warmed to rt and stirred for 72 h. The reaction mixture was then concentrated in vacuo and the residue was purified directly by silica gel column chromatography (90-100% MeOH/DCM) to afford (S)-4-(1-(3-nitro-1H-pyrazol-1-yl)ethyl)pyridine (190 mg, 54% yield) as a light yellow liquid. LCMS: ESI-MS m/z: 219.1 [M+H]$^+$.

Step 2: (S)-1-(1-(Pyridin-4-yl)ethyl)-1H-pyrazol-3-amine. A suspension of (S)-4-(1-(3-nitro-1H-pyrazol-1-yl)ethyl)pyridine (190 mg, 0.87 mmol, 1.0 equiv.) and Pd/C (10% Pd basis, 5.0 mg) in MeOH (5.0 mL, 0.17 M) was stirred under an atmosphere of hydrogen gas (balloon) at rt for 2 h. After 2 h, the mixture was filtered over Celite and the filtrate was concentrated in vacuo to give the crude product. The crude residue was purified by silica gel column chromatography (95-100% MeOH/DCM) to afford (S)-1-(1-(pyridin-4-yl)ethyl)-1H-pyrazol-3-amine (130 mg, 80% yield) as a light yellow solid. LCMS: ESI-MS m/z: 189.1 [M+H]$^+$.

Step 3: (S)-1-(1-(Pyridin-4-yl)ethyl)-N-(2,2,2-trifluoroethyl)-1H-pyrazol-3-amine. To a solution of (S)-1-(1-(pyridin-4-yl)ethyl)-1H-pyrazol-3-amine (60 mg, 0.32 mmol, 1.0 equiv.) and cesium carbonate (200 mg, 0.64 mmol, 2.0 equiv.) in anhydrous DMF (2.0 mL, 0.15 M) under an atmosphere of nitrogen gas was added 2,2,2-trifluoroethyl trifluoromethanesulfonate (80 mg, 0.35 mmol, 1.1 equiv.) dropwise via syringe. The resulting mixture was stirred at rt for 16 h. The solution was then concentrated in vacuo and purified directly by RP-HPLC (Method C, 10-90% MeCN/10 mM $NH_4HCO_3$+0.025% $NH_3 \cdot H_2O$ in $H_2O$) to afford (S)-1-(1-(pyridin-4-yl)ethyl)-N-(2,2,2-trifluoroethyl)-1H-pyrazol-3-amine (20 mg, 0.070 mmol, 23% yield) as a colorless liquid. $^1$H NMR (400 MHz, $CD_3OD$) δ 8.53 (dd, J=1.6 Hz, 4.8 Hz, 2H), 7.29 (d, J=2.4 Hz, 1H), 7.00 (dd, J=1.2 Hz, 4.4 Hz, 2H), 5.67 (d, J=2.4 Hz, 1H), 5.28 (dd, J=7.2 Hz, 14.4 Hz, 1H), 4.04 (t, J=6.8 Hz, 1H), 3.83-3.73 (m, 2H), 1.81 (d, J=7.6 Hz, 3H). LCMS: ESI-MS m/z: 271.1 [M+H]$^+$.

Chiral analysis conditions (ee %: 99%):
Injection Volume: 5 μL
Co-Solvent: MeOH (0.2% Methanol Ammonia)
Column: Amylose-2 4.6*150 mm 5 μm
Column Temperature: 40.1° C.
$CO_2$ Flow Rate: 3.6 mL/min
Co-Solvent Flow Rate: 0.4 mL/min
Co-Solvent %: 10
Total Flow: 4 mL/min
Front Pressure: 146 kPa
Back Pressure: 121 kPa
Pressure Drop: 25 kPa
PDA Start Wavelength: 214 nm
PDA Start Wavelength: 359 nm
Retention time: 1.49 min.

Example 3

N-(2,2-Difluoroethyl)-1-(pyridin-4-ylmethyl)-1H-pyrazol-3-amine

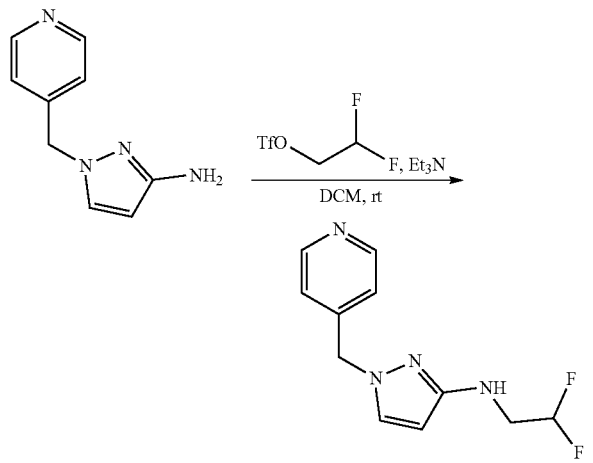

A mixture of 1-(pyridin-4-ylmethyl)-1H-pyrazol-3-amine (Intermediate 2, 130 mg, 0.74 mmol, 1.0 equiv.), 2,2-difluoroethyl trifluoromethanesulfonate (200 mg, 0.93 mmol, 1.3 equiv.), and triethylamine (150 mg, 1.5 mmol, 2.0 equiv.) in DCM (5 mL, 0.15 M) was stirred at rt for 16 h. The mixture was concentrated in vacuo and the residue was purified by RP-HPLC (Method C, 15-40% MeCN/10 mM $NH_4HCO_3$+0.025% $NH_3 \cdot H_2O$ in $H_2O$) to obtain N-(2,2-difluoroethyl)-1-(pyridin-4-ylmethyl)-1H-pyrazol-3-amine (6.5 mg, 3.7%) as a white solid. $^1$H NMR (400 MHz, DMSO-$d_6$) δ 8.50 (dd, J=4.4, 1.6 Hz, 2H), 7.56 (d, J=2.4 Hz, 1H), 7.08 (d, J=6.0 Hz, 2H), 6.18-5.88 (m, 1H), 5.73 (t, J=6.4 Hz, 1H), 5.57 (d, J=2.0 Hz, 1H), 5.15 (s, 2H), 3.44-3.38 (m, 2H); LCMS: ESI-MS m/z: 239.0 [M+H]$^+$.

Example 4

N-(1-(Pyridin-4-ylmethyl)-1H-pyrazol-3-yl)thiazol-2-amine

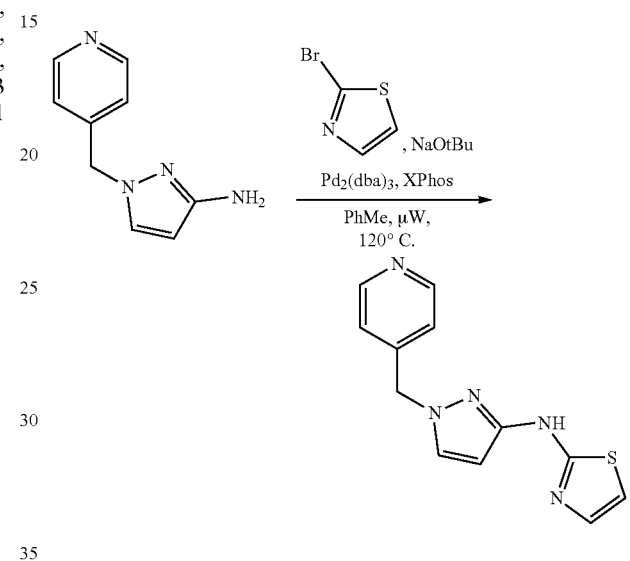

A mixture of 1-(pyridin-4-ylmethyl)-1H-pyrazol-3-amine (Intermediate 2, 50 mg, 0.29 mmol, 1.0 equiv.), 2-bromothiazole (49 mg, 0.30 mmol, 1.0 equiv.), $Pd_2(dba)_3$ (28 mg, 0.030 mmol, 10 mol %), XPhos (14 mg, 0.030 mmol, 10 mol %), and sodium tert-butoxide (55 mg, 0.57 mmol, 2.0 equiv.) in anhydrous toluene (1.5 mL, 0.19 M) was stirred at 120° C. with microwave heating for 1 h. The mixture was diluted with EtOAc (5.0 mL) and filtered. The filtrate was concentrated in vacuo and purified by RP-HPLC (Method C, 15-40% MeCN/10 mM $NH_4HCO_3$+0.025% $NH_3 \cdot H_2O$ in $H_2O$) to obtain N-(1-(pyridin-4-ylmethyl)-1H-pyrazol-3-yl)thiazol-2-amine (5.0 mg, 6.8% yield) as a while solid. $^1$H NMR (400 MHz, DMSO-$d_6$) δ 10.56 (s, 1H), 8.54-8.52 (m, 2H), 7.78 (d, J=2.4 Hz, 1H), 7.21 (d, J=3.6 Hz, 1H), 7.18-7.16 (m, 2H), 6.83 (d, J=3.6 Hz, 1H), 6.08 (d, J=2.0 Hz, 1H), 5.30 (s, 2H); LCMS: ESI-MS m/z: 258.0 [M+H]$^+$.

Example 5

(rac)-2-((1-(1-(Pyridin-4-yl)ethyl)-1H-pyrazol-3-yl)amino)acetonitrile

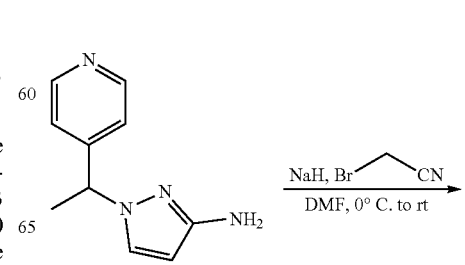

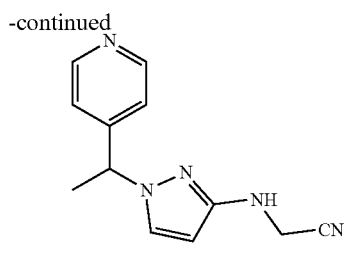

To solution of (rac)-1-(1-(pyridin-4-yl)ethyl)-1H-pyrazol-3-amine (Intermediate 1, 50 mg, 0.27 mmol, 1.0 equiv.) in anhydrous DMF (3.0 mL, 0.089 M) was carefully added sodium hydride (60 wt % dispersion in mineral oil, 13 mg, 0.32 mmol, 1.2 equiv.) at 0° C. After the addition, the mixture was stirred at rt for 30 min, then 2-bromoacetonitrile (35 mg, 0.29 mmol, 1.1 equiv.) was added. The mixture was stirred at rt for another 1.5 h. The mixture was diluted with EtOAc (20 mL) and sequentially washed with water (2×10 mL) and brine (10 mL). The organic phase was separated and concentrated in vacuo and the residue was purified by silica gel column chromatography (33% EtOAc in PE) to obtain (rac)-2-((1-(1-(pyridin-4-yl)ethyl)-1H-pyrazol-3-yl)amino)acetonitrile (31 mg, 51%) as a white solid. $^1$H NMR (400 MHz, CD$_3$OD) δ 8.45 (dd, J=6.4 Hz, 2H), 7.60 (d, J=2.4 Hz, 1H), 7.20 (t, J=6.4 Hz, 2H), 5.77 (d, J=2.4 Hz, 1H), 5.49-5.43 (m, 1H), 4.12 (d, J=1.2 Hz, 2H), 1.84 (d, J=7.2 Hz, 3H); LCMS: ESI-MS m/z: 228.0 [M+H]$^+$.

Example 6

(R)-2-((1-(1-(Pyridin-4-yl)ethyl)-1H-pyrazol-3-yl)amino)acetonitrile and (S)-2-((1-(1-(pyridin-4-yl)ethyl)-1H-pyrazol-3-yl)amino)acetonitrile

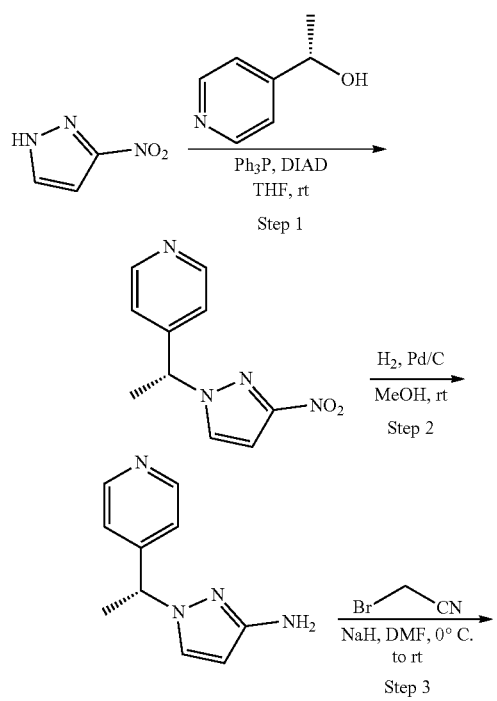

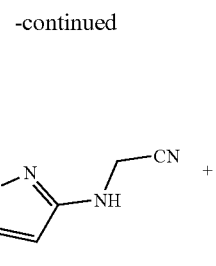

Step 1: (R)-4-(1-(3-Nitro-1H-pyrazol-1-yl)ethyl)pyridine. To a solution of (S)-1-(pyridin-4-yl) ethan-1-ol (200 mg, 1.6 mmol, 1.0 equiv.), 3-nitro-1H-pyrazole (240 mg, 2.1 mmol, 1.3 equiv.), and triphenylphosphine (550 mg, 2.1 mmol, 1.3 equiv.) in anhydrous THF (7.0 mL, 0.23 M) at 0° C. and under an atmosphere of nitrogen gas was added DIAD (430 mg, 2.1 mmol, 1.3 equiv.) dropwise via syringe. After the addition, the mixture was warmed to rt and stirred for 72 h. The reaction mixture was then concentrated in vacuo and the residue was purified directly by silica gel column chromatography (90-100% MeOH/DCM) to afford (R)-4-(1-(3-nitro-1H-pyrazol-1-yl)ethyl)pyridine (190 mg, 54% yield) as a light yellow liquid. LCMS: ESI-MS m/z: 219.1 [M+H]$^+$.

Step 2: (R)-1-(1-(Pyridin-4-yl)ethyl)-1H-pyrazol-3-amine. A suspension of (R)-4-(1-(3-nitro-1H-pyrazol-1-yl)ethyl)pyridine (190 mg, 0.87 mmol, 1.0 equiv.) and Pd/C (10% Pd basis, 5.0 mg) in MeOH (5.0 mL, 0.17 M) was stirred under an atmosphere of hydrogen gas (balloon) at rt for 2 h. After 2 h, the mixture was filtered over Celite® and the filtrate was concentrated in vacuo to give the crude product. The crude residue was purified by silica gel column chromatography (95-100% MeOH/DCM) to afford (R)-1-(1-(pyridin-4-yl)ethyl)-1H-pyrazol-3-amine (130 mg, 0.69 mmol, 80% yield) as a light yellow solid. LCMS: ESI-MS m/z: 189.1 [M+H]$^+$.

Step 3: (R)-2-((1-(1-(Pyridin-4-yl)ethyl)-1H-pyrazol-3-yl)amino)acetonitrile and (S)-2-((1-(1-(Pyridin-4-yl)ethyl)-1H-pyrazol-3-yl)amino)acetonitrile. This reaction was carried out under similar conditions to EXAMPLE 5, to afford a mixture of (R)-2-((1-(1-(pyridin-4-yl)ethyl)-1H-pyrazol-3-yl)amino)acetonitrile and (S)-2-((1-(1-(pyridin-4-yl)ethyl)-1H-pyrazol-3-yl)amino)acetonitrile (41 mg, 0.18 mmol, 31%) as a light brown liquid. $^1$H NMR (400 MHz, CDCl$_3$) δ 8.56 (d, J=4.8 Hz, 2H), 7.33 (d, J=2.0 Hz, 1H), 7.00 (d, J=6.0 Hz, 2H), 5.74 (d, J=2.4 Hz, 1H), 5.33 (dd, J=14.4, 7.2 Hz, 1H), 4.15-4.12 (m, 2H), 3.99 (t, J=6.8 Hz, 1H), 1.85 (d, J=7.2 Hz, 3H); LCMS: ESI-MS m/z: 228.0 [M+H]$^+$.

Example 7

(S)-2-((1-(1-(Pyridin-4-yl)ethyl)-1H-pyrazol-3-yl)amino)acetonitrile and (R)-2-((1-(1-(Pyridin-4-yl)ethyl)-1H-pyrazol-3-yl)amino)acetonitrile

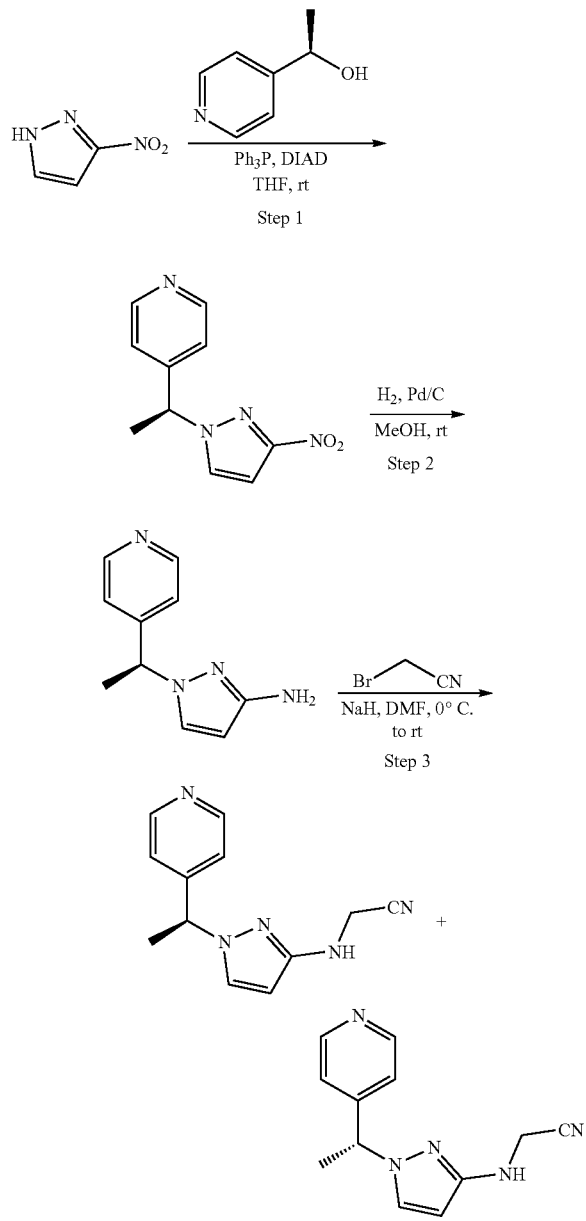

This material was made in the same was as EXAMPLE 6, starting instead with (S)-1-(pyridin-4-yl) ethan-1-ol. The final mixture of (S)-2((1-(1-(pyridin-4-yl)ethyl)-1H-pyrazol-3-yl)amino)acetonitrile and (R)-2-((1-(1-(pyridin-4-yl)ethyl)-1H-pyrazol-3-yl)amino)acetonitrile was obtained in 31% yield as a white solid. $^1$H NMR (400 MHz, CD$_3$OD) δ 8.46 (dd, J=6.0 Hz, 2H), 7.61 (d, J=2.4 Hz, 1H), 7.22 (dd, J=6.0 Hz, 2H), 5.78 (d, J=2.4 Hz, 1H), 5.50-5.45 (m, 1H), 4.13 (d, J=1.6 Hz, 2H), 1.86 (d, J=7.2 Hz, 3H); LCMS: ESI-MS m/z: 228.0 [M+H]$^+$.

Example 8

(S)—N-(2,2-Difluoroethyl)-1-(1-(pyridin-4-yl)ethyl)-1H-pyrazol-3-amine and (R)—N-(2,2-Difluoroethyl)-1-(1-(pyridin-4-yl)ethyl)-1H-pyrazol-3-amine

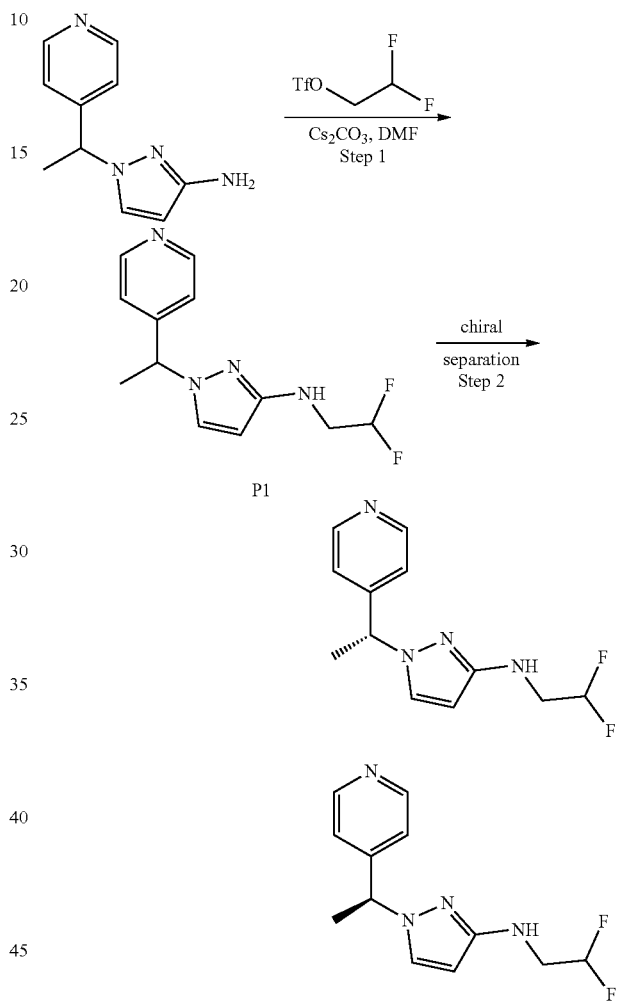

Step 1: (rac)-N-(2,2-Difluoroethyl)-1-(1-(pyridin-4-yl)ethyl)-1H-pyrazol-3-amine. A mixture of (rac)-1-(1-(pyridin-4-yl)ethyl)-1H-pyrazol-3-amine (Intermediate 1, 130 mg, 0.69 mmol, 1.0 equiv.), cesium carbonate (450 mg, 1.4 mmol, 2.0 equiv.), and 2,2-difluoroethyl trifluoromethanesulfonate (150 mg, 0.70 mmol, 1.0 equiv.) in anhydrous DMF (3.0 mL, 0.23 M) was stirred at rt overnight. The mixture was diluted with EtOAc (10 mL) and filtered. The filtrate was concentrated in vacuo, then purified by RP-HPLC (Method C, 15-40% MeCN/10 mM NH$_4$HCO$_3$+ 0.025% NH$_3$·H$_2$O in H$_2$O) to get (rac)-N-(2,2-difluoroethyl)-1-(1-(pyridin-4-yl)ethyl)-1H-pyrazol-3-amine (P1 (Ex. 8), 30 mg, 17% yield) as a white solid. $^1$H NMR (400 MHz, CD$_3$OD) δ 8.45 (d, J=6.4 Hz, 2H), 7.55 (d, J=2.8 Hz, 1H), 7.15 (d, J=6.4 Hz, 2H), 6.06-5.89 (m, 1H), 5.68 (d, J=2.4 Hz, 1H), 5.39 (dd, J=7.2, 6.8 Hz, 1H), 3.41-3.49 (m, 2H), 1.80 (d, J=6.4 Hz, 3H); LCMS: ESI-MS m/z: 253.1 [M+H]$^+$.

Step 2: (S)—N-(2,2-Difluoroethyl)-1-(1-(pyridin-4-yl)ethyl)-1H-pyrazol-3-amine and (R)—N-(2,2-Difluoroethyl)-1-(1-(pyridin-4-yl)ethyl)-1H-pyrazol-3-amine. (rac)-N-(2,2-Difluoroethyl)-1-(1-(pyridin-4-yl)ethyl)-1H-pyrazol-3-amine was separated by chiral HPLC into its pure enantiomers. Absolute stereochemistry was not determined.

P2 (Ex. 8a): $^1$H NMR (400 MHz, CD$_3$OD) δ 8.45 (d, J=6.4 Hz, 2H), 7.55 (d, J=2.8 Hz, 1H), 7.15 (d, J=6.4 Hz, 2H), 5.89-6.06 (m, 1H), 5.68 (d, J=2.4 Hz, 2H), 5.39 (dd, J=7.2, 6.8 Hz, 1H), 3.41-3.49 (m, 2H), 1.80 (d, J=6.4 Hz, 3H); LCMS: ESI-MS m/z: 253.1 [M+H]$^+$. 100% ee

P3 (Ex. 8b): $^1$H NMR (400 MHz, CD$_3$OD) δ 8.45 (d, J=6.4 Hz, 2H), 7.55 (d, J=2.8 Hz, 1H), 7.15 (d, J=6.4 Hz, 2H), 5.89-6.06 (m, 1H), 5.68 (d, J=2.4 Hz, 2H, 5.39 (dd, J=7.2, 6.8 Hz, 1H), 3.41-3.49 (m, 2H), 1.80 (d, J=6.4 Hz, 3H); LCMS: ESI-MS m/z: 253.1 [M+H]$^+$. 97.4% ee

Chiral Separation Conditions:
Instrument: SFC-80 (Thar, Waters)
Column: AD 20×250 mm, 10 micron (Daicel)
Column temperature: 35° C.
Mobile phase: CO$_2$/EtOH (1.0% MeOH·NH$_4$)=75/25
Flow rate: 70 g/min
Back pressure: 100 bar
Detection wavelength: 214 nm
Cycle time: 6 min
Sample solution: 30 mg dissolved in 10 ml MeOH
Injection volume: 2.0 mL
Chiral Analysis Conditions:
Column: AD-H 100×4.6 mm, 5 micron
Column temperature: 40° C.
Mobile phase: MeOH (0.2% MeOH·NH$_4$)
Detection wavelength: 254 nm
Injection volume: 5 μL
Retention times: P2=1.98 min; P3=2.98 min Example 9

2-(3-(Pyridin-4-ylmethyl)-1H-pyrazol-1-yl)acetonitrile (P2)

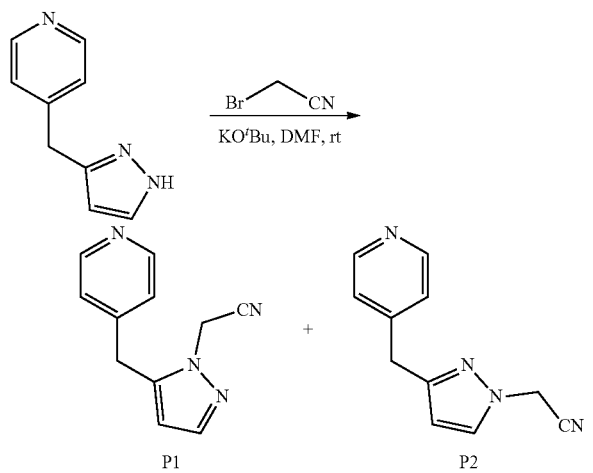

To a solution of 4-((1H-pyrazol-3-yl)methyl)pyridine (Intermediate 4, 200 mg, 1.3 mmol, 1.0 equiv.) in dry DMF (5.0 mL, 0.26 M) was added potassium tert-butoxide (280 mg, 2.5 mmol, 2.0 equiv.). After 10 min, 2-bromoacetonitrile (300 mg, 2.5 mmol, 2.0 equiv.) was added and the reaction was stirred for 16 h at rt. The mixture was then diluted with water (25 mL) and extracted with EtOAc (3×20 mL). The combined extracts were washed with brine (30 mL). The organic material was filtered over anhydrous sodium sulfate and concentrated in vacuo. The crude material was purified by RP-HPLC (Method C, 10-90% MeCN/10 mM NH$_4$HCO$_3$+0.025% NH$_3$·H$_2$O in H$_2$O). Fractions containing the desired mass were combined and concentrated by lyophilization to afford a mixture of regioisomers (P1) and (P2). The mixture was separated into its regioisomers by chiral SFC separation to afford 2-(5-(pyridin-4-ylmethyl)-1H-pyrazol-1-yl)acetonitrile (P1) (4.0 mg, 1.6% yield) and 2-(3-(pyridin-4-ylmethyl)-1H-pyrazol-1-yl)acetonitrile (P2) (20 mg, 8.0% yield) as colorless oils.

P1: $^1$H NMR (400 MHz, CDCl$_3$) δ 8.60 (d, J=6.0 Hz, 2H), 7.54 (d, J=1.6 Hz, 1H), 7.13 (d, J=6.0 Hz, 2H), 6.15 (d, J=1.6 Hz, 1H), 4.89 (s, 2H), 4.11 (s, 2H); LCMS: ESI-MS m/z: 199.1 [M+H]$^+$.

P2 (Ex. 9): $^1$H NMR (400 MHz, CDCl$_3$) δ 8.52 (d, J=6.0 Hz, 2H), 7.48 (d, J=2.4 Hz, 1H), 7.18 (d, J=5.6 Hz, 2H), 6.13 (d, J=2.4 Hz, 1H), 5.05 (s, 2H), 3.98 (s, 2H); LCMS: ESI-MS m/z: 199.1 [M+H]$^+$.

Chiral Separation Conditions:
Instrument: SFC-80 (Thar, Waters)
Column: AD 20×250 mm, 10 micron (Daicel)
Column temperature: 35° C.
Mobile phase: CO$_2$/MeOH (0.2% MeOH·NH$_4$)=80/20
Flow rate: 80 g/min
Back pressure: 100 bar
Detection wavelength: 214 nm
Cycle time: 5 min
Sample solution: 100 mg dissolved in 15 ml MeOH
Injection volume: 2.0 mL
Chiral Analysis Conditions:
Column: AD-H 100×4.6 mm, 5 micron
Column temperature: 40° C.
Mobile phase: MeOH (0.2% MeOH·NH$_4$)
Detection wavelength: 254 nm
Injection volume: 5 μL
Retention times: P1=2.21 min P2=2.52 min Example 10

4-((1-(2,2-Difluoroethyl)-1H-pyrazol-3-yl)methyl)pyridine

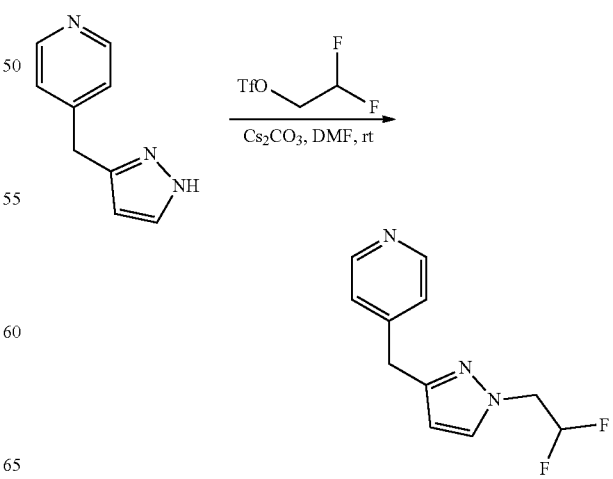

To a solution of 4-((1H-pyrazol-3-yl)methyl)pyridine (Intermediate 4, 50 mg, 0.30 mmol, 1.0 equiv.) in dry DMF (3.0 mL, 0.10 M) was added cesium carbonate (150 mg, 0.45 mmol, 1.5 equiv.) and 2,2-difluoroethyl trifluoromethanesulfonate (77 mg, 0.36 mmol, 1.2 equiv.) at 0° C. The reaction was then warmed to rt and stirred for 2 h. The mixture was then diluted with EtOAc (160 mL) and washed with water (30 mL) and brine (30 mL). The organic layer was dried over anhydrous sodium sulfate, filtered, and concentrated in vacuo. The crude material was purified by RP-HPLC (Method C, 10-90% MeCN/10 mM NH$_4$HCO$_3$+ 0.025% NH$_3$·H$_2$O in H$_2$O). Fractions containing the desired mass were combined and concentrated by lyophilization to afford 4-((1-(2,2-difluoroethyl)-1H-pyrazol-3-yl)methyl)pyridine (6.0 mg, 9.0% yield) as a yellow oil. $^1$H NMR (400 MHz, CDCl$_3$) δ 8.51 (d, J=6.0 Hz, 2H), 7.40 (d, J=2.0 Hz, 1H), 7.26 (m, 2H), 6.08 (m, 2H), 4.46 (m, 2H), 3.98 (s, 2H); LCMS: ESI-MS m/z: 224.7 [M+H]$^+$.

Example 11

(rac)-4-(1-(1-Isobutyl-1H-pyrazol-3-yl)ethyl)pyridine

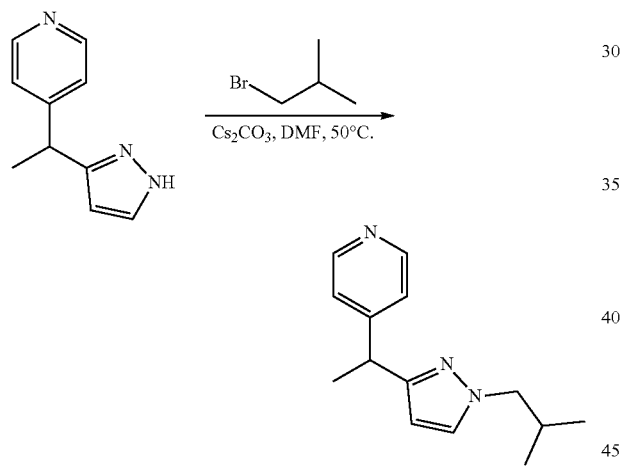

To a solution of (rac)-4-(1-(1H-pyrazol-3-yl)ethyl)pyridine (Intermediate 5, 200 mg, 1.2 mmol, 1.0 equiv.) in dry DMF (20 mL, 0.057 M) was added cesium carbonate (750 mg, 2.3 mmol, 2.0 equiv.) and 1-bromo-2-methylpropane (310 mg, 2.3 mmol, 2.0 equiv.) at 0° C. The mixture was warmed to rt, and then heated to 50° C. for 16 h. The mixture was then diluted with water (50 mL) and extracted with EtOAc (4×50 mL). The combined organic layers were washed with brine (30 mL), dried over anhydrous sodium sulfate, filtered, and concentrated in vacuo. The crude material was purified by RP-HPLC (Method C, 10-90% MeCN/ 10 mM NH$_4$HCO$_3$+0.025% NH$_3$·H$_2$O in H$_2$O). Fractions containing the desired mass were combined and concentrated by lyophilization to afford (rac)-4-(1-(1-isobutyl-1H-pyrazol-3-yl)ethyl)pyridine (26 mg, 10% yield) as a yellow oil. $^1$H NMR (400 MHz, CDCl$_3$) δ 8.49 (d, J=5.6 Hz, 2H), 7.28 (d, J=2.0 Hz, 1H), 7.18 (d, J=5.6 Hz, 2H), 6.00 (d, J=2.0 Hz, 1H), 4.18 (m, 1H), 3.69-3.51 (m, 2H), 2.20-2.14 (m, 1H), 1.63 (d, J=7.2 Hz, 3H), 0.84 (d, J=6.8 Hz, 3H), 0.75 (d, J=6.8 Hz, 3H); LCMS: ESI-MS m/z: 230.1 [M+H]$^+$.

Example 12

(rac)-2-(3-(1-(Pyridin-4-yl)ethyl)-1H-pyrazol-1-yl) acetonitrile, (R)-2-(3-(1-(Pyridin-4-yl)ethyl)-1H-pyrazol-1-yl)acetonitrile, and (S)-2-(3-(1-(Pyridin-4-yl)ethyl)-1H-pyrazol-1-yl)acetonitrile

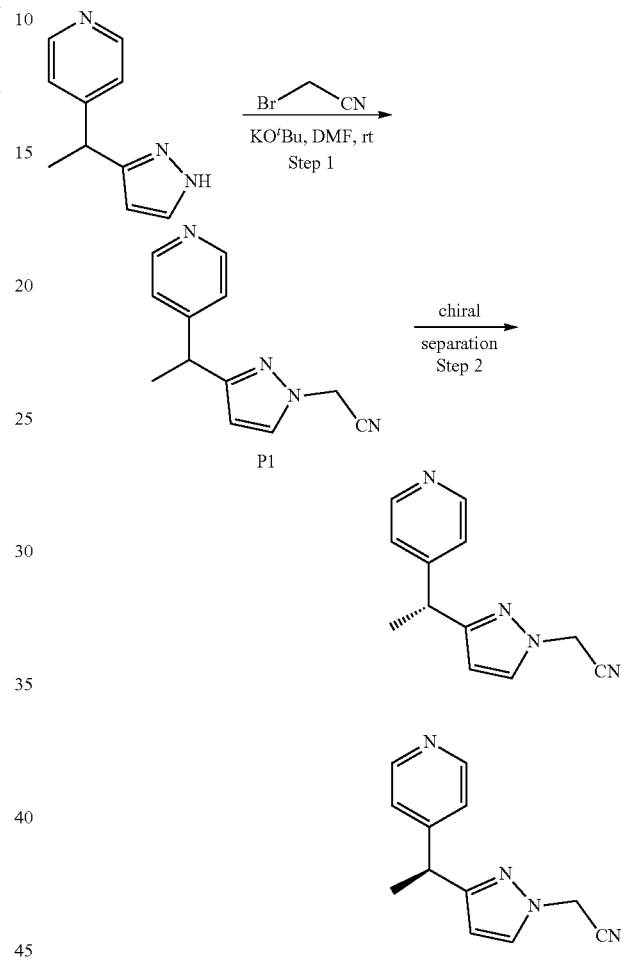

Step 1: (rac)-2-(3-(1-(Pyridin-4-yl)ethyl)-1H-pyrazol-1-yl)acetonitrile (Ex. 12). To a solution of (rac)-4-(1-(1H-pyrazol-3-yl)ethyl)pyridine (Intermediate 5, 200 mg, 1.2 mmol, 1.0 equiv.) in dry DMF (5.0 mL, 0.24 M) was added potassium tert-butoxide (260 mg, 2.3 mmol, 2.0 equiv.). After 10 min, 2-bromoacetonitrile (420 mg, 3.5 mmol, 3.0 equiv.) was added and the reaction was stirred for 5 h at rt. The mixture was then diluted with water (25 mL) and extracted with EtOAc (4×20 mL). The combined organic layers were washed with brine (30 mL). The organic solution was dried over anhydrous sodium sulfate, filtered, and concentrated in vacuo. The crude material was purified by RP-HPLC (Method C, 10-90% MeCN/10 mM NH$_4$HCO$_3$+ 0.025% NH$_3$·H$_2$O in H$_2$O). Fractions containing the desired mass were combined and concentrated by lyophilization to afford (rac)-2-(3-(1-(pyridin-4-yl)ethyl)-1H-pyrazol-1-yl) acetonitrile (40 mg, 0.19 mmol, 16% yield) as a yellow oil. P1 (Ex. 12): $^1$H NMR (400 MHz, CDCl$_3$) δ 8.54 (d, J=5.6 Hz, 2H), 7.48 (d, J=2.4 Hz, 1H), 7.25 (d, J=5.6 Hz, 2H), 6.15 (d, J=2.4 Hz, 1H), 5.03 (s, 2H), 4.22 (q, J=7.2 Hz, 1H), 1.66 (d, J=7.2 Hz, 3H); LCMS: ESI-MS m/z: 213.1 [M+H]$^+$.

Step 2: (R)-2-(3-(1-(Pyridin-4-yl)ethyl)-1H-pyrazol-1-yl)acetonitrile and (S)-2-(3-(1-(Pyridin-4-yl)ethyl)-1H-pyrazol-1-yl)acetonitrile. (rac)-2-(3-(1-(Pyridin-4-yl)ethyl)-1H-pyrazol-1-yl)acetonitrile (P1) was separated into its enantiomers by chiral SFC separation. Absolute stereochemistry was not determined. (P2=1.90 min) or (P3=2.17 min).

P2 (Ex. 12a): $^1$H NMR (400 MHz, CDCl$_3$) δ 8.52 (d, J=6.0 Hz, 2H), 7.47 (d, J=2.0 Hz, 1H), 7.18 (d, J=6.0 Hz, 2H), 6.14 (d, J=2.4 Hz, 1H), 5.04 (s, 2H), 4.19 (q, J=7.2 Hz, 1H), 1.64 (d, J=7.6 Hz, 3H); LCMS: ESI-MS m/z: 213.1 [M+H]$^+$.

P3 (Ex. 12b): $^1$H NMR (400 MHz, CDCl$_3$) δ 8.52 (d, J=6.0 Hz, 2H), 7.47 (d, J=2.8 Hz, 1H), 7.18 (d, J=6.0 Hz, 2H), 6.14 (d, J=2.4 Hz, 1H), 5.04 (s, 2H), 4.19 (q, J=7.2 Hz, 1H), 1.64 (d, J=7.2 Hz, 3H); LCMS: ESI-MS m/z: 213.1 [M+H]$^+$.

Chiral Separation Conditions:
Instrument: SFC-80 (Thar, Waters)
Column: OJ-H 20×250 mm, 10 micron (Daicel)
Column temperature: 35° C.
Mobile phase: CO$_2$/EtOH (1.0% MeOH·NH$_4$)=85/15
Flow rate: 60 g/min
Back pressure: 100 bar
Detection wavelength: 214 nm
Cycle time: 4.5 min
Sample solution: 30 mg dissolved in 8 ml MeOH
Injection volume: 2.0 mL
Chiral Analysis Conditions:
Column: OD-H 100×4.6 mm, 5 micron
Column temperature: 40° C.
Mobile phase: EtOH (1.0% MeOH·NH$_4$)
Detection wavelength: 254 nm
Injection volume: 5
Retention times: P2=1.90 min; P3=2.17 min Example 13

(S)-4-(1-(1-(2,2,2-Trifluoroethyl)-1H-pyrazol-3-yl)ethyl)pyridine and (R)-4-(1-(1-(2,2,2-Trifluoroethyl)-1H-pyrazol-3-yl)ethyl)pyridine

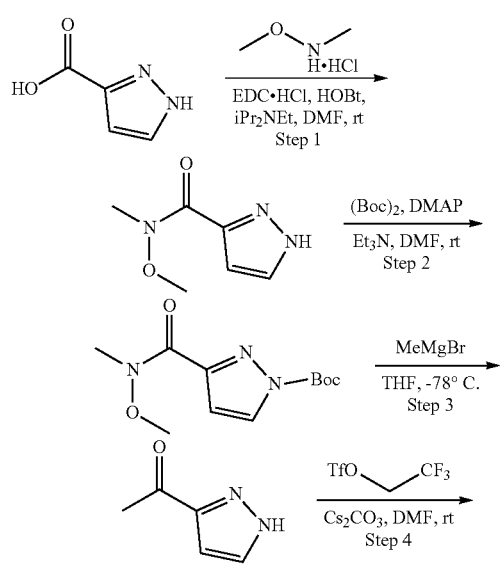

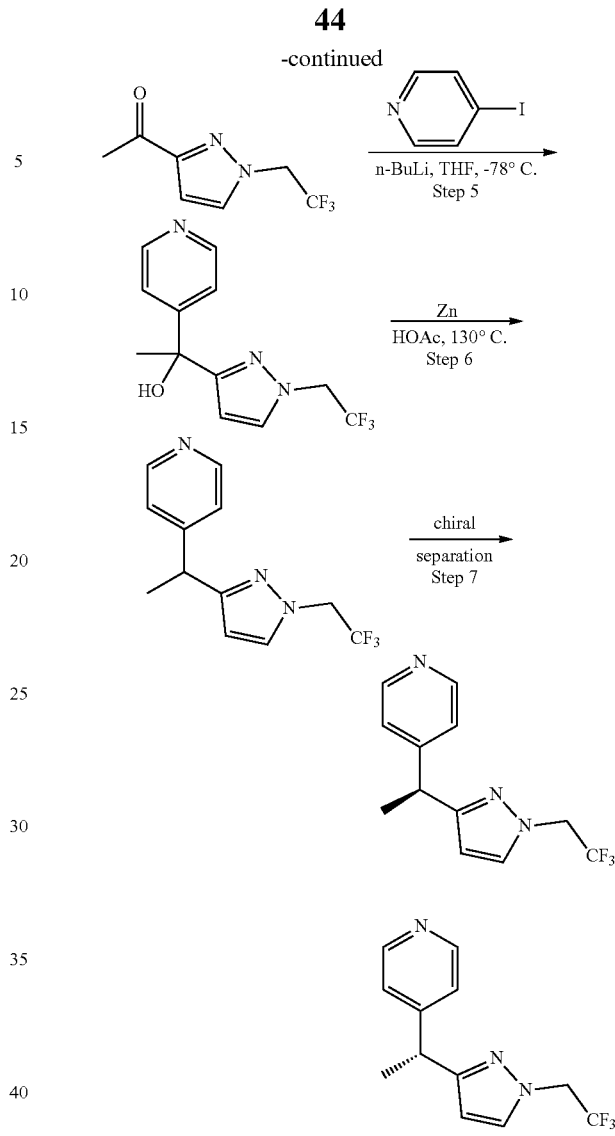

Step 1: N-Methoxy-N-methyl-1H-pyrazole-3-carboxamide. To a solution of 1H-pyrazole-3-carboxylic acid (25 g, 0.22 mol, 1.0 equiv.) and N,O-dimethylhydroxylamine hydrochloride (21 g, 0.22 mol, 1.0 equiv.) in DCM (250 mL, 0.89 M) was added EDC.HCl (89 g, 0.47 mol, 2.0 equiv.), HOBt (78 g, 0.58 mol, 2.6 equiv.) and DIPEA (150 g, 1.1 mol, 5.0 equiv). The resulting mixture was stirred at rt for 16 h. The mixture was concentrated in vacuo, and the crude product was purified directly by silica gel column chromatography (10-80% EtOAc in hexanes) to afford N-methoxy-N-methyl-1H-pyrazole-3-carboxamide (15 g, 44% yield) as a white solid. LCMS: ESI-MS m/z: 156.1 [M+H]$^+$.

Step 2: tert-Butyl 3-(methoxy(methyl)carbamoyl)-1H-pyrazole-1-carboxylate. A solution of N-methoxy-N-methyl-1H-pyrazole-3-carboxamide (15 g, 97 mmol, 1.0 equiv.) and DMAP (1.2 g, 9.7 mmol, 0.10 equiv.) in DCM (200 mL, 0.49 M) was treated with triethylamine (41 mL, 290 mmol, 3.0 equiv.), followed by Boc anhydride (32 g, 145 mmol, 1.5 equiv.) at 0° C. The resulting solution was then warmed to rt and stirred for 2 h. The reaction mixture was diluted with DCM (200 mL) and washed with water (2×100 mL). The organic fractions were filtered over anhydrous sodium sulfate and concentrated in vacuo to afford tert-butyl 3-(methoxy(methyl)carbamoyl)-1H-pyrazole-1- carboxylate (22 g) as a light yellow oil. The material was carried forward to the next step without further purification. LCMS: ESI-MS m/z: 256.1 [M+H]+.

Step 3: 1-(1H-Pyrazol-3-yl)ethan-1-one. A solution of tert-butyl 3-(methoxy(methyl)carbamoyl)-1H-pyrazole-1-carboxylate (22 g, 86 mmol, 1.0 equiv.) in anhydrous THF (150 mL, 0.57 M) under an atmosphere of nitrogen gas was cooled to −78° C. To the cold solution was then added methylmagnesium bromide (3.0 M in diethyl ether, 86 mL, 260 mmol, 3.0 equiv.), and the resulting mixture was stirred for 2 h. The solution was then warmed to rt and stirred for 16 h, after which an aqueous, saturated solution of $NH_4Cl$ (100 mL) was added to quench the reaction. The mixture was diluted with water (200 mL) and extracted with EtOAc (4×100 mL). The combined organic layers were washed with brine (100 mL), dried over anhydrous sodium sulfate, filtered, and concentrated in vacuo to afford 1-(1H-pyrazol-3-yl)ethan-1-one (9.0 g) as a light yellow solid. The material was carried forward to the next step without further purification. LCMS: ESI-MS m/z: 111.2 [M+H]+.

Step 4: 1-(1-(2,2,2-Trifluoroethyl)-1H-pyrazol-3-yl)ethan-1-one. To a solution of 1-(1H-pyrazol-3-yl)ethan-1-one (1.0 g, 9.1 mmol, 1.0 equiv.) in anhydrous DMF (13 mL, 0.70 M) was added cesium carbonate (3.8 g, 12 mmol, 1.3 equiv.) and 2,2,2-trifluoroethyl trifluoromethanesulfonate (2.5 g, 11 mmol, 1.2 equiv.) at 0° C. The reaction was then warmed to rt and stirred for 2 h. The mixture was diluted with EtOAc (160 mL) and washed with water (100 mL) and brine (100 mL). The organic material was filtered over anhydrous sodium sulfate and concentrated in vacuo. The crude material was purified by silica gel column chromatography (5-50% EtOAc in hexanes) to afford 1-(1-(2,2,2-trifluoroethyl)-1H-pyrazol-3-yl)ethan-1-one (1.0 g, 58% yield) as a brown oil. LCMS: ESI-MS m/z: 193.1 [M+H]+.

Step 5: 1-(Pyridin-4-yl)-1-(1-(2,2,2-trifluoroethyl)-1H-pyrazol-3-yl)ethan-1-ol. A solution of 4-iodopyridine (12 g, 61 mmol, 2.6 equiv.) in anhydrous THF (20 mL, 1.2 M) under an atmosphere of nitrogen gas was cooled to −78° C. To the cold solution was added n-butyllithium (1.6 M in hexanes, 40 mL, 64 mmol, 2.7 equiv.). The resulting mixture was stirred at −78° C. for 10 min, then 1-(1-(2,2,2-trifluoroethyl)-1H-pyrazol-3-yl)ethan-1-one (4.5 g, 23 mmol, 1.0 equiv.) was added as a solution in anhydrous THF (15 mL). After stirring at −78° C. for 1 h, water was added to quench the reaction and the mixture was concentrated in vacuo. The crude product was purified by silica gel column chromatography (10-60% EtOAc in PE) to afford 1-(pyridin-4-yl)-1-(1-(2,2,2-trifluoroethyl)-1H-pyrazol-3-yl)ethan-1-ol (2.0 g, 31% yield) as a solid. LCMS: ESI-MS m/z: 272.0 [M+H]+.

Step 6: (rac)-4-(1-(1-(2,2,2-Trifluoroethyl)-1H-pyrazol-3-yl)ethyl)pyridine (Ex. 13). A solution of 1-(pyridin-4-yl)-1-(1-(2,2,2-trifluoroethyl)-1H-pyrazol-3-yl)ethan-1-ol (2.0 g, 7.3 mmol, 1.0 equiv.) in acetic acid (100 mL, 0.073 M) was treated with zinc powder (10 g, 150 mmol, 20 equiv.). The mixture was stirred at 130° C. for 16 h. The mixture was filtered, and then the solution was treated with sodium carbonate until the pH was adjusted to 9-10. The mixture was diluted with water (200 mL) and extracted with EtOAc (4×100 mL). The combined organic layers were dried over sodium sulfate, filtered, and concentrated in vacuo. The crude product was purified by silica gel column chromatography (0-5% MeOH/DCM) to afford (rac)-4-(1-(1-(2,2,2-trifluoroethyl)-1H-pyrazol-3-yl)ethyl)pyridine (0.750 mg, 40% yield) as a white solid. LCMS: ESI-MS m/z: 256.0 [M+H]+.

Step 7: (S)-4-(1-(1-(2,2,2-Trifluoroethyl)-1H-pyrazol-3-yl)ethyl)pyridine and (R)-4-(1-(1-(2,2,2-trifluoroethyl)-1H-pyrazol-3-yl)ethyl)pyridine. The racemic mixture was separated into its enantiomers by chiral SFC separation to afford (S)-4-(1-(1-(2,2,2-trifluoroethyl)-1H-pyrazol-3-yl)ethyl)pyridine and (R)-4-(1-(1-(2,2,2-trifluoroethyl)-1H-pyrazol-3-yl)ethyl)pyridine. Absolute stereochemistry was not determined.

P1 (Ex. 13a): $^1$H NMR (400 MHz, CDCl$_3$) δ 8.50 (d, J=6.0 Hz, 2H), 7.43 (d, J=2.0 Hz, 1H), 7.20 (d, J=6.0 Hz, 2H), 6.13 (d, J=2.4 Hz, 1H), 4.67 (q, J=8.4 Hz, 2H), 4.20 (q, J=7.2 Hz, 1H), 1.65 (d, J=7.2 Hz, 3H).

P2 (Ex. 13b): $^1$H NMR (400 MHz, CDCl$_3$) δ 8.52 (d, J=6.0 Hz, 2H), 7.44 (d, J=2.8 Hz, 1H), 7.25 (d, J=6.0 Hz, 2H), 6.14 (d, J=2.4 Hz, 1H), 4.70 (q, J=8.4 Hz, 2H), 4.23 (q, J=7.2 Hz, 1H), 1.66 (d, J=7.2 Hz, 3H).

Chiral Separation Conditions:
Instrument: SFC-150 (Thar, Waters)
Column: OD 20×250 mm, 10 micron (Daicel)
Column temperature: 35° C.
Mobile phase: CO$_2$/IPA (0.5% MeOH·NH$_4$)=90/10
Flow rate: 100 g/min
Back pressure: 100 bar
Detection wavelength: 214 nm
Cycle time: 2 min
Sample solution: 1000 mg dissolved in 80 ml MeOH
Injection volume: 1.0 mL
Chiral Analysis Conditions:
Column: OD-H 100×4.6 mm, 5 micron
Column temperature: 40° C.
Co-solvent: Hexanes/MeOH/EtOH (100/15/15)
Detection wavelength: 254 nm
Injection volume: 5 μL
Retention times: P1=1.31 min; P2=1.46 min Example 14

(rac)-1-(1-(3-Methylpyridin-4-yl)ethyl)-N-(2,2,2-trifluoroethyl)-1H-pyrazol-3-amine

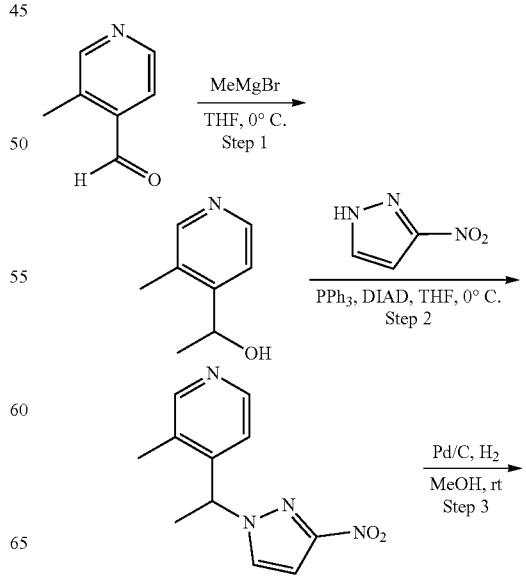

-continued

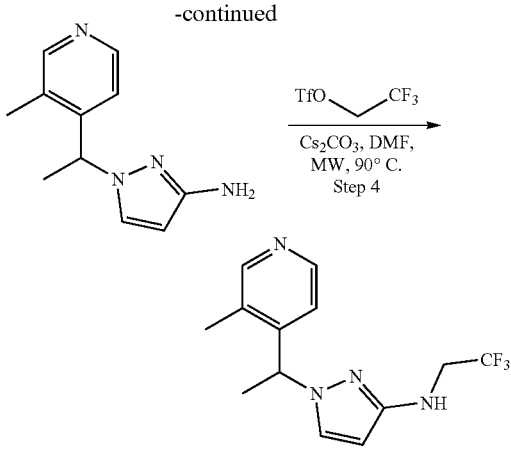

Step 1: (rac)-1-(3-Methylpyridin-4-yl)ethan-1-ol. To a solution of 3-methylisonicotinaldehyde (300 mg, 2.5 mmol, 1.0 equiv.) in anhydrous THF (5.0 mL, 0.5 M) at 0° C., under an atmosphere of nitrogen gas, was added methyl magnesium bromide (3.0 M in diethyl ether, 1.7 mL, 5.0 mmol, 2.0 equiv.). The solution was stirred at 0° C. for 30 min, then warmed to rt. After 2 h, a saturated aqueous solution of NH$_4$Cl (10 mL) was added to quench the reaction. The mixture was diluted with water (20 mL) and extracted with EtOAc (2×30 mL). The combined organic layers were washed with brine (10 mL), filtered over anhydrous sodium sulfate, and concentrated in vacuo to afford (rac)-1-(3-methylpyridin-4-yl)ethan-1-ol (280 mg) as a light yellow solid. The material was carried forward to the next step without further purification. LCMS: ESI-MS m/z: 138.2 [M+H]$^+$.

Step 2: (rac)-3-Methyl-4-(1-(3-nitro-1H-pyrazol-1-yl)ethyl)pyridine. A solution of (rac)-1-(3-methylpyridin-4-yl)ethan-1-ol (280 mg, 2.0 mmol, 1.0 equiv.), 3-nitro-1H-pyrazole (280 mg, 2.5 mmol, 1.2 equiv.) and triphenylphosphine (690 mg, 2.7 mmol, 1.3 equiv.) in THF (8.0 mL, 0.25 M) under an atmosphere of nitrogen gas was cooled to 0° C. Subsequently, diisopropyl azodicarboxylate (540 mg, 2.7 mmol, 1.3 equiv.) was added, and the resulting reaction mixture was warmed to rt. The mixture was stirred at rt for 4 h. The organic material was concentrated in vacuo. The crude product was purified by silica gel column chromatography (0-2% MeOH/DCM) to afford (rac)-3-methyl-4-(1-(3-nitro-1H-pyrazol-1-yl)ethyl)pyridine (330 mg, 70% yield) as a light yellow liquid. LCMS: ESI-MS m/z: 233.1 [M+H]$^+$.

Step 3: (rac)-1-(1-(3-Methylpyridin-4-yl)ethyl)-1H-pyrazol-3-amine. A vial was charged with (rac)-3-methyl-4-(1-(3-nitro-1H-pyrazol-1-yl)ethyl)pyridine (330 mg, 1.4 mmol, 1.0 equiv.). The compound was dissolved in anhydrous MeOH (5.0 mL, 0.28 M) and treated with palladium on carbon (10 wt. %, matrix activated; 30 mg, 10 mol %). The resulting mixture was stirred under an atmosphere of hydrogen (balloon) at rt for 12 h. The mixture was then filtered over Celite®, concentrated in vacuo, and purified by silica gel column chromatography (0-4% MeOH/DCM) to afford (rac)-1-(1-(3-methylpyridin-4-yl)ethyl)-1H-pyrazol-3-amine (250 mg, 87% yield) as a light yellow liquid. LCMS: ESI-MS m/z: 203.2 [M+H]$^+$.

Step 4: (rac)-1-(1-(3-Methylpyridin-4-yl)ethyl)-N-(2,2,2-trifluoroethyl)-1H-pyrazol-3-amine. To a solution of (rac)-1-(1-(3-methylpyridin-4-yl)ethyl)-1H-pyrazol-3-amine (100 mg, 0.50 mmol, 1.0 equiv.) in anhydrous DMF (3.0 mL, 0.17 M) was added cesium carbonate (320 mg, 0.99 mmol, 2.0 equiv.) and 2,2,2-trifluoroethyl trifluoromethanesulfonate (170 mg, 0.74 mmol, 1.5 equiv.). The reaction was stirred for 3 h at 90° C. under microwave irradiation. The organic material was filtered and concentrated in vacuo. The crude material was purified by RP-HPLC (Method C, 10-90% MeCN/10 mM NH$_4$HCO$_3$+0.025% NH$_3$·H$_2$O in H$_2$O). Fractions containing the desired mass were combined and concentrated by lyophilization to afford (rac)-1-(1-(3-methylpyridin-4-yl)ethyl)-N-(2,2,2-trifluoroethyl)-1H-pyrazol-3-amine (12 mg, 8.0% yield) as a white solid. $^1$H NMR (400 MHz, DMSO-d$_6$) δ 8.34 (s, 1H), 8.31 (d, J=5.1 Hz, 1H), 7.59 (d, J=2.4 Hz, 1H), 6.92 (d, J=5.1 Hz, 1H), 5.98 (t, J=6.9 Hz, 1H), 5.60 (d, J=2.4 Hz, 1H), 5.51 (q, J=7.0 Hz, 1H), 3.82-3.72 (m, 2H), 2.31 (s, 3H), 1.66 (d, J=7.0 Hz, 3H); LCMS: ESI-MS m/z: 285.1 [M+H]$^+$.

Example 15

3,3,3-Trifluoro-N-(1-(pyridin-4-ylmethyl)-1H-pyrazol-3-yl)-2-(trifluoromethyl)propenamide

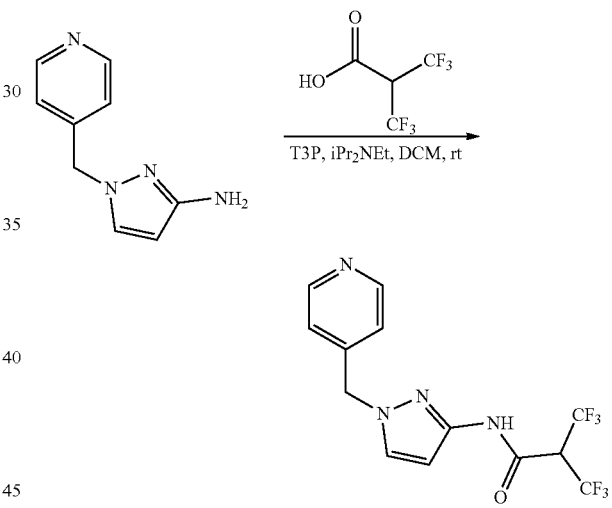

A solution of 3,3,3-trifluoro-2-(trifluoromethyl)propanoic acid (Intermediate 2, 70 mg, 0.86 mmol, 1.0 equiv.) and DIPEA (170 mg, 1.3 mmol, 1.5 equiv.) in DCM (10 mL, 0.086 M) was cooled to 0° C. Subsequently, T3P (50 w/v % in EtOAc, 640 mg, 1.0 mmol, 1.2 equiv.) and 1-(pyridin-4-ylmethyl)-1H-pyrazol-3-amine (150 mg, 0.86 mmol, 1.0 equiv.) were added. The reaction mixture was warmed to rt and stirred for 1 h. The reaction mixture was then concentrated in vacuo, and the crude material was purified directly by RP-HPLC (Method C, 10-90% MeCN/10 mM NH$_4$HCO$_3$+0.025% NH$_3$·H$_2$O in H$_2$O). Fractions containing the desired mass were combined and concentrated by lyophilization to afford 3,3,3-trifluoro-N-(1-(pyridin-4-ylmethyl)-1H-pyrazol-3-yl)-2-(trifluoromethyl)propanamide (85 mg, 28% yield) as a white solid. $^1$H NMR (400 MHz, DMSO-d$_6$) δ 11.5 (s, 1H), 8.54 (d, J=5.7 Hz, 2H), 7.91 (d, J=2.3 Hz, 1H), 7.15 (t, J=6.6 Hz, 2H), 6.55 (dd, J=7.3, 2.3 Hz, 1H), 5.32 (d, J=12.4 Hz, 2H), 4.80 (dt, J=16.0, 8.0 Hz, 1H); LCMS: ESI-MS m/z: 353.1 [M+H]$^+$.

Example 16

1-(Pyridin-4-ylmethyl)-N-(3,3,3-trifluoro-2-(trifluoromethyl)propyl)-1H-pyrazol-3-amine

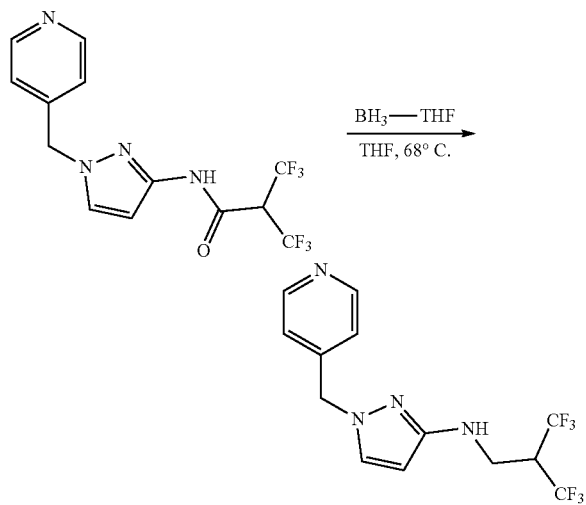

Under an atmosphere of nitrogen gas, borane-THF complex (1.0 M in THF, 1.5 mL, 1.5 mmol, 10 equiv.) was added to a solution of 3,3,3-trifluoro-N-(1-(pyridin-4-ylmethyl)-1H-pyrazol-3-yl)-2-(trifluoromethyl)propanamide (EXAMPLE 15, 50 mg, 0.14 mmol, 1.0 equiv.) in THF (1.0 mL, 0.14 M) at 0° C., over a period of 10 min. The resulting solution was stirred at 68° C. for 2 h. Upon completion, the mixture was cooled to rt and MeOH (1.0 mL) was carefully added. The mixture was diluted with water (20 mL) and extracted with DCM (3×30 mL). The combined organic layers were washed with brine (2×30 mL), dried over anhydrous sodium sulfate, filtered, and concentrated in vacuo. The crude material was purified by RP-HPLC (Method C, 5-45% MeCN/10 mM NH$_4$HCO$_3$+0.025% NH$_3$·H$_2$O in H$_2$O). Fractions containing the desired mass were combined and concentrated by lyophilization to afford 1-(pyridin-4-ylmethyl)-N-(3,3,3-trifluoro-2-(trifluoromethyl)propyl)-1H-pyrazol-3-amine (14 mg, 29% yield) as a white solid. $^1$H NMR (400 MHz, DMSO-d$_6$) δ 8.50 (d, J=5.8 Hz, 2H), 7.59 (d, J=2.2 Hz, 1H), 7.09 (d, J=5.6 Hz, 2H), 5.73 (t, J=6.4 Hz, 1H), 5.58 (d, J=2.2 Hz, 1H), 5.17 (s, 2H), 4.07-3.93 (m, 1H), 3.58 (t, J=6.1 Hz, 2H); LCMS: ESI-MS m/z: 339.1 [M+H]$^+$.

Example 17

2-((1-(Pyridin-4-ylmethyl)-1H-pyrazol-3-yl)amino)acetonitrile

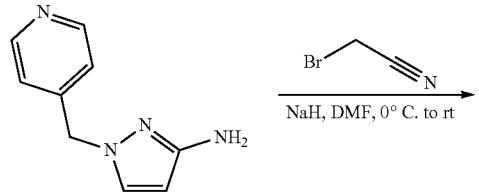

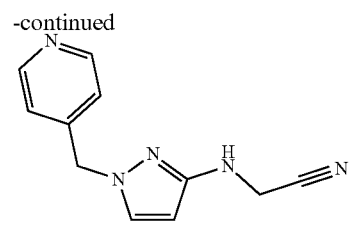

To an oven-dried vial was added 1-(pyridin-4-ylmethyl)-1H-pyrazol-3-amine (100 mg, 0.57 mmol, 1.0 equiv.) and DMF (1.3 mL, 0.4 M). The solution was cooled to 0° C., and sodium hydride (60 wt % dispersion in mineral oil, 26 mg, 0.63 mmol, 1.1 equiv.) was added. The reaction was slowly warmed to rt and stirred for 10 min. The reaction was again cooled to 0° C., and 2-bromoacetonitrile (0.044 mL, 0.63 mmol, 1.1 equiv.) was added. The reaction was stirred at rt overnight. The crude reaction mixture was concentrated in vacuo and directly purified by silica gel column chromatography (0-15% MeOH/DCM) to give 2-((1-(pyridin-4-ylmethyl)-1H-pyrazol-3-yl)amino)acetonitrile (15 mg, 12% yield) as a dark waxy solid. $^1$H NMR (400 MHz, DMSO-d$_6$) δ 8.55-8.47 (m, 2H), 7.64 (d, J=2.3 Hz, 1H), 7.15-7.08 (m, 2H), 6.05 (t, J=6.9 Hz, 1H), 5.67 (d, J=2.3 Hz, 1H), 5.21 (s, 2H), 4.07 (d, J=6.7 Hz, 2H); LCMS: ESI-MS m/z: 214.1 [M+H]$^+$.

Example 18

(rac)-4-(1-(1-(2,2-Difluoroethyl)-1H-pyrazol-3-yl)ethyl)pyridine

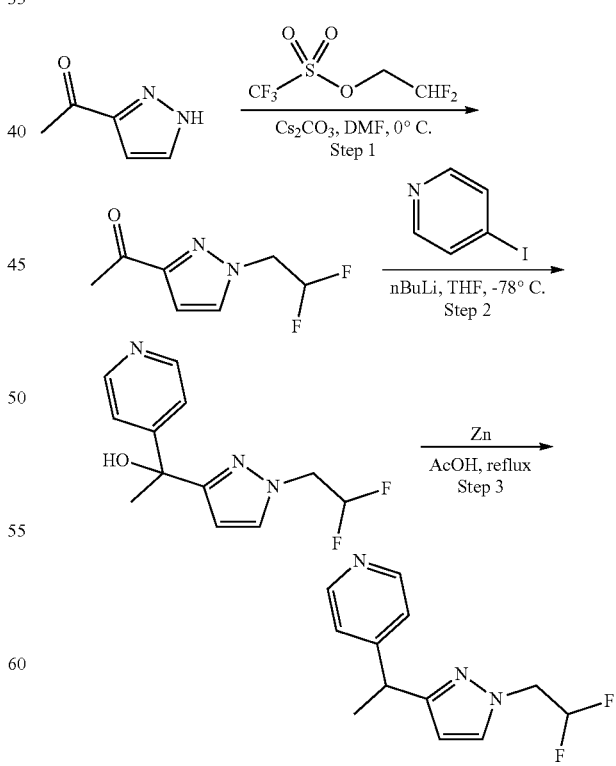

Step 1: 1-(1-(2,2-Difluoroethyl)-1H-pyrazol-3-yl)ethan-1-one. A solution of 1-(1H-pyrazol-3-yl)ethan-1-one (710 mg, 4.8 mmol, 1.0 equiv.) and cesium carbonate (1.4 g, 7.2 mmol, 1.5 equiv.) in anhydrous DMF (14 mL, 0.34 M) was cooled to 0° C., and then treated with 2,2-difluoroethyl trifluoromethanesulfonate (1.3 g, 6.3 mmol, 1.3 equiv.). The reaction was stirred at rt for 2.5 h, then quenched with water and extracted with EtOAc (3×20 mL). The combined organic layers were washed with water (20 mL), dried over anhydrous magnesium sulfate, filtered, and concentrated in vacuo. Purification of the crude product by silica gel column chromatography (5-100% EtOAc in hexanes) gave 1-(1-(2,2-difluoroethyl)-1H-pyrazol-3-yl)ethan-1-one (360 mg, 43% yield) as a white solid. $^1$H NMR (400 MHz, CDCl$_3$) δ 7.49 (d, J=2.4 Hz, 1H), 6.83 (d, J=2.5 Hz, 1H), 6.13 (tt, J=55.3, 4.3 Hz, 1H), 4.52 (td, J=13.4, 4.3 Hz, 2H), 2.57 (s, 3H); LCMS: ESI-MS m/z: 175.1 [M+H]$^+$.

Step 2: (rac)-1-(1-(2,2-Difluoroethyl)-1H-pyrazol-3-yl)-1-(pyridin-4-yl)ethan-1-ol. An oven-dried flask containing 4-iodopyridine (1.0 g, 5.0 mmol, 2.4 equiv.) and THF (16 mL, 0.13 M) was cooled to −78° C. Once cooled, n-butyllithium (1.6 M in THF, 3.8 mL, 6.0 mmol, 2.9 equiv.) was gradually added. After stirring for 5 min at −78° C., a solution of 1-(1-(2,2-difluoroethyl)-1H-pyrazol-3-yl)ethan-1-one (360 mg, 2.1 mmol, 1.0 equiv.) in THF (8.0 mL, 0.26 M) cooled to −78° C., was added gradually via syringe. After 20 min, the reaction was quenched with water and extracted with EtOAc (3×20 mL). The combined organic fractions were dried over anhydrous magnesium sulfate, filtered, and concentrated in vacuo. The crude residue was then purified by silica gel column chromatography (0-20% EtOAc in hexanes, then 0-10% MeOH/DCM) to give (rac)-1-(1-(2,2-difluoroethyl)-1H-pyrazol-3-yl)-1-(pyridin-4-yl)ethan-1-ol (120 mg, 23% yield) as a yellow oil. $^1$H NMR (400 MHz, CDCl$_3$) δ 8.5-8.50 (m, 2H), 7.47-7.39 (m, 3H), 6.23 (d, J=2.3 Hz, 1H), 6.05 (tt, J=55.5, 4.3 Hz, 1H), 4.42 (td, J=13.5, 4.3 Hz, 2H), 3.39 (s, 1H), 1.88 (s, 3H); LCMS: ESI-MS m/z: 254.1 [M+H]$^+$.

Step 3: (rac)-4-(1-(1-(2,2-Difluoroethyl)-1H-pyrazol-3-yl)ethyl)pyridine. A solution of (rac)-1-(1-(2,2-difluoroethyl)-1H-pyrazol-3-yl)-1-(pyridin-4-yl)ethan-1-ol (50 mg, 0.20 mmol, 1.0 equiv.) and zinc powder (180 mg, 2.8 mmol, 14 equiv.) in acetic acid (1.1 mL, 20 mmol, 100 equiv.) heated to reflux and stirred overnight. The reaction mixture was then concentrated in vacuo and purified directly by silica gel column chromatography (0-100% EtOAc in hexanes) to give (rac)-4-(1-(1-(2,2-difluoroethyl)-1H-pyrazol-3-yl)ethyl)pyridine (14 mg, 30% yield). $^1$H NMR (400 MHz, CDCl$_3$) δ 8.55 (d, J=5.8 Hz, 2H), 7.48 (s, 2H), 7.43 (d, J=2.4 Hz, 1H), 6.37-5.79 (m, 2H), 4.42 (td, J=13.6, 4.3 Hz, 2H), 4.29 (q, J=7.3 Hz, 1H), 1.68 (d, J=7.2 Hz, 3H); LCMS: ESI-MS m/z: 238.1 [M+H]$^+$.

Example 19

(rac)-N-(1-(1-(Pyridin-4-yl)ethyl)-1H-pyrazol-3-yl)benzo[d][1,3]dioxole-5-carboxamide

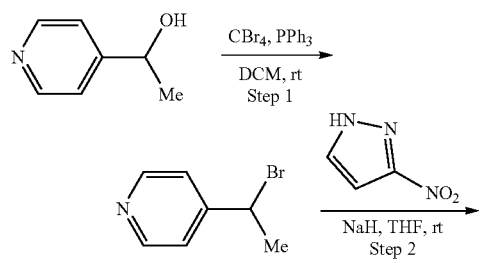

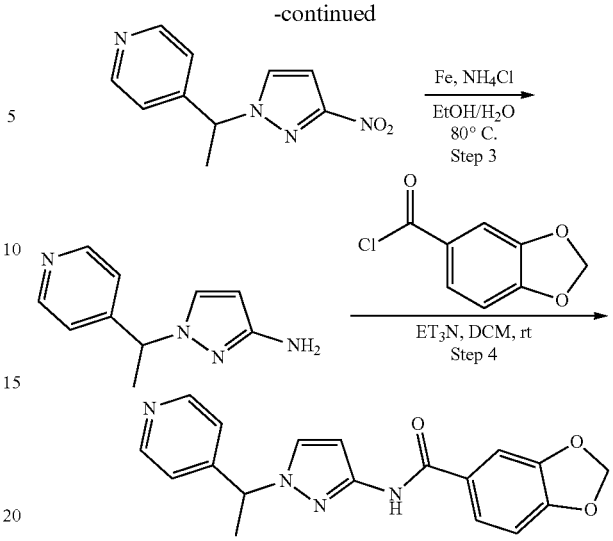

Step 1: (rac)-4-(1-Bromoethyl)pyridine. To a solution of (rac)-1-(pyridin-4-yl)ethan-1-ol (300 mg, 3.3 mmol, 1.0 equiv.) in DCM (5.0 mL, 0.66 M) was added triphenylphosphine (640 mg, 3.3 mmol, 1.0 equiv.) and carbon tetrabromide (1.20 g, 4.90 mmol) and the mixture was stirred at rt for 2 h. The mixture was concentrated in vacuo, the residue was purified by silica gel column chromatography (2:1 EtOAc in PE) to get (rac)-4-(1-bromoethyl)pyridine (300 mg, 50% yield) as a light yellow liquid. LCMS: ESI-MS m/z: 186.0 [M+H]$^+$.

Step 2: (rac)-4-(1-(3-Nitro-1H-pyrazol-1-yl)ethyl)pyridine. To a solution of (rac)-3-nitro-1H-pyrazole (300 mg, 2.7 mmol, 1.0 equiv.) in anhydrous THF (5.0 mL, 0.54 M) was added (rac)-4-(1-bromoethyl)pyridine (540 mg, 2.9 mmol, 1.1 equiv.) and sodium hydride (60 wt % dispersion in mineral oil, 63 mg, 2.7 mmol, 1.0 equiv.). The mixture was stirred at rt for 3 h. It was then cooled to 0° C., treated with water (10 mL), extracted with ethyl acetate (3×10 mL). The combined organic layers were washed with brine (10 mL), dried over anhydrous sodium sulfate, filtered, and concentrated in vacuo. The resulting residue was purified by RP-HPLC (Method C, 10-90% MeCN/10 mM NH$_4$HCO$_3$+ 0.025% NH$_3$·H$_2$O in H$_2$O) to afford (rac)-4-(1-(3-nitro-1H-pyrazol-1-yl)ethyl)pyridine (80 mg, 14% yield) as a white solid. LCMS: ESI-MS m/z: 219.0 [M+H]$^+$.

Step 3: (rac)-1-(1-(pyridin-4-yl)ethyl)-1H-pyrazol-3-amine. To a solution of (rac)-4-(1-(3-nitro-1H-pyrazol-1-yl)ethyl)pyridine (100 mg, 0.46 mmol, 1.0 equiv.) in a 3:1 mixture of ethanol:water (10 mL, 0.046 M) was added iron powder (130 mg, 2.3 mmol, 5.0 equiv.) and ammonium chloride (250 mg, 4.6 mmol, 10 equiv.). The mixture was heated at 80° C. for 2 h. The mixture was filtered and the solid was washed with ethyl acetate. The filtrate was concentrated in vacuo to get crude (rac)-1-(1-(pyridin-4-yl)ethyl)-1H-pyrazol-3-amine (50 mg, 59% yield) as a light yellow solid. LCMS: ESI-MS m/z: 189.0 [M+H]$^+$.

Step 4: (rac)-N-(1-(1-(pyridin-4-yl)ethyl)-1H-pyrazol-3-yl)benzo[d][1,3]dioxole-5-carboxamide. To a solution of (rac)-1-(1-(pyridin-4-yl)ethyl)-1H-pyrazol-3-amine (20 mg, 0.11 mmol, 1.0 equiv.) in DCM (3 mL, 0.037 M) was added benzo[d][1,3]dioxole-5-carbonyl chloride (22 mg, 0.12 mmol, 1.1 equiv.), followed by the addition of triethylamine (20 mg, 0.20 mmol, 1.8 equiv.) at rt. The resulting mixture was stirred at rt for 2 h, then subsequently concentrated in vacuo and purified by RP-HPLC (Method C, 10-90%

MeCN/10 mM NH₄HCO₃+0.025% NH₃·H₂O in H₂O) to afford (rac)-N-(1-(1-(pyridin-4-yl)ethyl)-1H-pyrazol-3-yl)benzo[d][1,3]dioxole-5-carboxamide (12 mg, 34% yield) as a white solid. $^1$H NMR (400 MHz, DMSO-d$_6$) δ 10.7 (s, 1H), 8.52 (dd, J=6.0 Hz, 2H), 7.89 (d, J=2.4 Hz, 1H), 7.61 (d, J=10.0 Hz, 1H), 7.56 (d, J=1.6 Hz, 1H), 7.15 (dd, J=6.0 Hz, 2H), 6.98 (d, J=8.4 Hz, 1H), 6.69 (d, J=2.4 Hz, 1H), 6.10 (s, 2H), 5.62-5.56 (m, 1H), 1.80 (d, J=7.2 Hz, 3H); LCMS: ESI-MS m/z: 337.0 [M+H]⁺.

Example 20

4-((1-(2,2,2-Trifluoroethyl)-1H-pyrazol-3-yl)methyl)pyridine

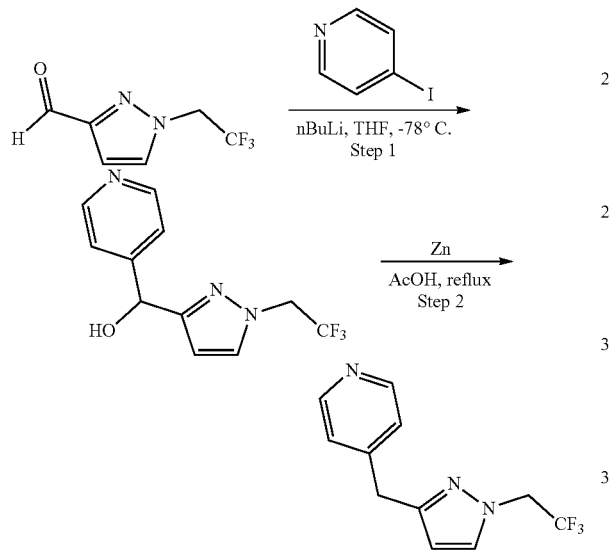

Step 1: (rac)-Pyridin-4-yl(1-(2,2,2-trifluoroethyl)-1H-pyrazol-3-yl)methanol. To a solution of 4-iodopyridine (1.4 g, 6.7 mmol, 2.9 equiv.) in anhydrous THF (10 mL, 0.67 M) at −78° C. was added n-butyllithium (1.6 M in hexanes, 4.2 mL, 6.7 mmol, 1.0 equiv.) dropwise via syringe. The reaction mixture was then warmed to rt and stirred for 10 min. The resulting solution of lithium reagent was then added slowly to a solution of 1-(2,2,2-trifluoroethyl)-1H-pyrazole-3-carbaldehyde (Intermediate, 400 mg, 2.3 mmol, 1.0 equiv.) in THF (5.0 mL, 0.46 M) at −78° C. The reaction mixture was stirred for 30 min, then was quenched with a saturated, aqueous solution of NH₄Cl. The mixture was extracted with EtOAc (3×10 mL), dried over anhydrous sodium sulfate, filtered, and concentrated in vacuo. The crude product was purified by silica gel column chromatography (10-40% EtOAc in hexanes) to afford (rac)-pyridin-4-yl(1-(2,2,2-trifluoroethyl)-1H-pyrazol-3-yl)methanol (65 mg, 21% yield) as a colorless oil. ESI-MS m/z: 258.1 [M+H]⁺.

Step 2: 4-((1-(2,2,2-Trifluoroethyl)-1H-pyrazol-3-yl)methyl)pyridine. To a solution of (rac)-pyridin-4-yl(1-(2,2,2-trifluoroethyl)-1H-pyrazol-3-yl)methanol (37 mg, 0.14 mmol, 1.0 equiv.) in acetic acid (10 mL, 0.014 M) was added zinc powder (190 mg, 2.9 mmol, 21 equiv.). The reaction mixture was refluxed for 24 h. After 24 h, the reaction mixture was cooled to rt and filtered through a short plug of Celite®, eluting with 10% MeOH/DCM to remove the solid. The filtrate was concentrated in vacuo to afford a residue, which was neutralized by the addition of an aqueous, saturated solution of Na₂CO₃. The mixture was concentrated in vacuo and purified by RP-HPLC (Method A, 10-90% MeCN/0.1% TFA in H₂O) to afford 4-((1-(2,2,2-trifluoroethyl)-1H-pyrazol-3-yl)methyl)pyridine (19 mg, 55% yield) as a white solid. $^1$H NMR (400 MHz, DMSO-d$_6$) δ 8.77-8.65 (m, 2H), 7.81 (d, J=2.3 Hz, 1H), 7.72-7.62 (m, 2H), 6.27 (d, J=2.3 Hz, 1H), 5.08 (q, J=9.2 Hz, 2H), 4.15 (s, 2H); LCMS: ESI-MS m/z: 242.1 [M+H]⁺.

Example 21

(rac)-4-(1-(1-(2,2,2-Trifluoroethyl)-1H-pyrazol-3-yl)ethyl-2,2,2-d₃)pyridine

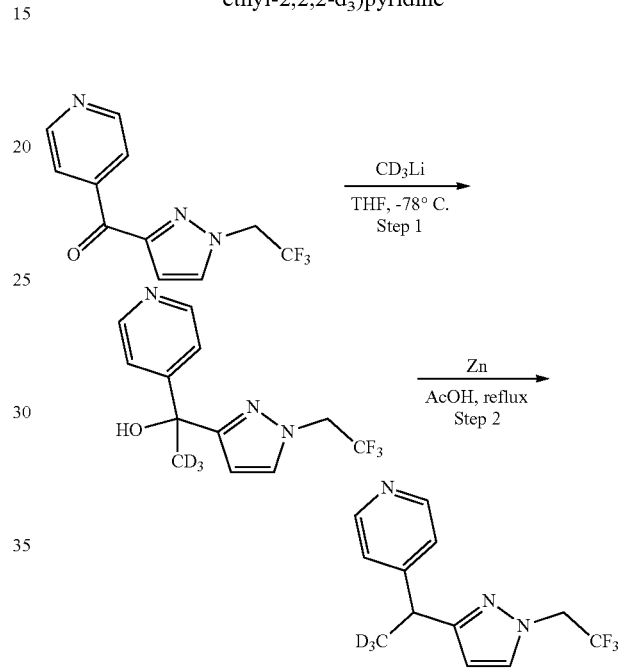

Step 1: (rac)-1-(Pyridin-4-yl)-1-(1-(2,2,2-trifluoroethyl)-1H-pyrazol-3-yl)ethan-2,2,2-d₃-1-ol. To a solution of iodomethane-d₃ (230 mg, 1.6 mmol, 4.1 equiv.) in THF (7.0 mL, 0.23 M) at −78° C. was added n-butyllithium (1.6 M in hexanes, 1.5 mL, 2.4 mmol, 6.2 equiv.) dropwise via syringe. This solution was stirred at −78° C. for 10 min. The resulting solution of lithium reagent was then added slowly to a solution of pyridin-4-yl(1-(2,2,2-trifluoroethyl)-1H-pyrazol-3-yl)methanone (Intermediate 10, 100 mg, 0.39 mmol, 1.0 equiv.) in THF (3.5 mL, 0.11 M) at −78° C. Stirring at −78° C. was continued for a subsequent 15 min. The reaction mixture was then quenched with water (1.0 mL) and concentrated in vacuo and directly purified by silica gel column chromatography (1-10% MeOH/DCM) to afford (rac)-1-(pyridin-4-yl)-1-(1-(2,2,2-trifluoroethyl)-1H-pyrazol-3-yl)ethan-2,2,2-d₃-1-ol (120 mg, 37% yield) as a gel. ESI-MS m/z: 275.1 [M+H]⁺.

Step 2: (rac)-4-(1-(1-(2,2,2-Trifluoroethyl)-1H-pyrazol-3-yl)ethyl-2,2,2-d₃)pyridine. To a solution of (rac)-1-(pyridin-4-yl)-1-(1-(2,2,2-trifluoroethyl)-1H-pyrazol-3-yl)ethan-2,2,2-d₃-1-ol (130 mg, 0.47 mmol, 1.0 equiv.) in acetic acid (25 mL, 0.019 M) was added zinc powder (620 mg, 9.5 mmol, 20 equiv.). The reaction mixture was refluxed for 10 h. After 10 h, the reaction mixture was cooled to rt and filtered through a short plug of Celite®, eluting with 10% MeOH/DCM. The filtrate was concentrated in vacuo and purified directly by RP-HPLC (Method A, 10-90% MeCN/0.1% TFA in H$_2$O) to afford (rac)-4-(1-(1-(2,2,2-trifluoroethyl)-1H-pyrazol-3-yl)ethyl-2,2,2-d$_3$)pyridine (55 mg, 45% yield) as a gel. $^1$H NMR (400 MHz, acetonitrile-d$_3$) δ 8.48-8.42 (m, 2H), 7.64-7.55 (m, 1H), 7.26-7.19 (m, 2H), 6.21 (d, J=2.4 Hz, 1H), 4.78 (q, J=8.9 Hz, 2H), 4.16 (s, 1H); LCMS: ESI-MS m/z: 259.1 [M+H]$^+$.

Example 22

(rac)-4-(1-(4-Fluoro-1-(2,2,2-trifluoroethyl)-1H-pyrazol-3-yl)ethyl)pyridine

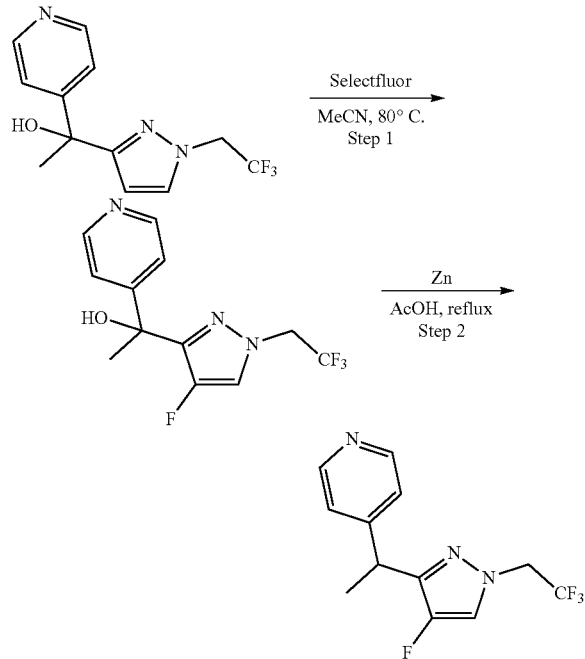

Step 1: (rac)-1-(4-Fluoro-1-(2,2,2-trifluoroethyl)-1H-pyrazol-3-yl)-1-(pyridin-4-yl)ethan-1-ol. To a solution of (rac)-1-(pyridin-4-yl)-1-(1-(2,2,2-trifluoroethyl)-1H-pyrazol-3-yl)ethan-1-ol (Intermediate 7, 100 mg, 0.37 mmol, 1.0 equiv.) in anhydrous acetonitrile (2.0 mL, 0.19 M) was added Selectfluor (260 mg, 0.74 mmol, 2.0 equiv.). The resulting solution was degassed with argon gas and then heated to 80° C. for 7 h. The mixture was cooled to rt and concentrated in vacuo. The crude material was purified by RP-HPLC (Method A, 10-90% MeCN/0.1% TFA in H$_2$O) to afford (rac)-1-(4-fluoro-1-(2,2,2-trifluoroethyl)-1H-pyrazol-3-yl)-1-(pyridin-4-yl)ethan-1-ol (4.7 mg, 4.0% yield) as an oil. LCMS: ESI-MS m/z: 290.1 [M+H]$^+$.

Step 2: (rac)-4-(1-(4-Fluoro-1-(2,2,2-trifluoroethyl)-1H-pyrazol-3-yl)ethyl)pyridine. To a solution of (rac)-1-(4-fluoro-1-(2,2,2-trifluoroethyl)-1H-pyrazol-3-yl)-1-(pyridin-4-yl)ethan-1-ol (4.7 mg, 0.016 mmol, 1.0 equiv.) in acetic acid (10 mL, 0.0016 M) was added zinc powder (11 mg, 0.16 mmol, 10 equiv.). The suspension was refluxed for 10 h. The reaction mixture was cooled to rt and filtered through a short plug of Celite®, eluting with 10% MeOH/DCM. The filtrate was concentrated in vacuo and purified by RP-HPLC (Method A, 10-90% MeCN/0.1% TFA in H$_2$O) to afford (rac)-4-(1-(4-fluoro-1-(2,2,2-trifluoroethyl)-1H-pyrazol-3-yl)ethyl) (3.2 mg, 72% yield) as an oil. $^1$H NMR (400 MHz, acetonitrile-d$_3$) δ 8.49 (s, 2H), 7.60 (d, J=4.7 Hz, 1H), 7.27 (d, J=5.9 Hz, 2H), 4.72 (q, J=8.7 Hz, 2H), 4.25 (q, J=7.2 Hz, 1H), 1.60 (d, J=7.3 Hz, 3H); LCMS: ESI-MS m/z: 274.1 [M+H]$^+$.

Example 23

3-Methyl-4-((1-(2,2,2-trifluoroethyl)-1H-pyrazol-3-yl)methyl)pyridine

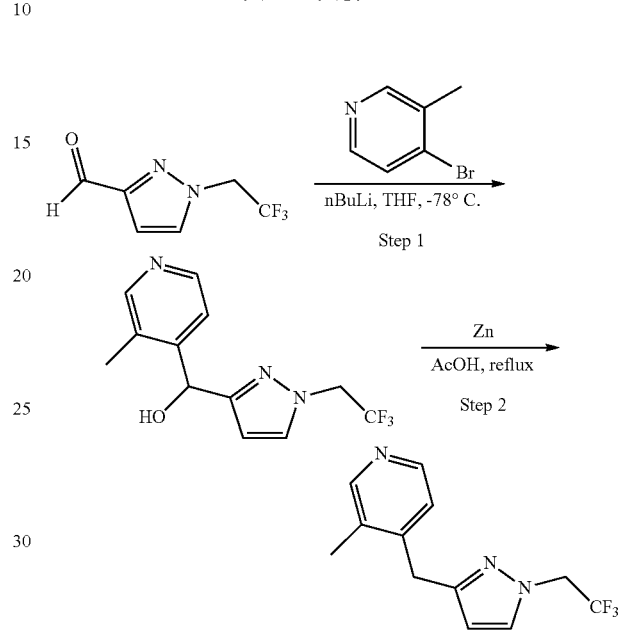

Step 1: (3-Methylpyridin-4-yl)(1-(2,2,2-trifluoroethyl)-1H-pyrazol-3-yl)methanol. To a solution of 4-bromo-3-methylpyridine (700 mg, 3.4 mmol, 3.0 equiv.) in THF (15 mL, 0.27 M) at −78° C. was added n-butyllithium (1.6 M in hexanes, 3.2 mL, 5.1 mmol, 4.5 equiv.) dropwise via syringe. The resulting solution was stirred at −78° C. for 5 min. The resulting solution of lithium reagent was then added dropwise to a solution of 1-(2,2,2-trifluoroethyl)-1H-pyrazole-3-carbaldehyde (Intermediate 6, 200 mg, 1.1 mmol, 1.0 equiv.) in THF (5 mL, 0.22 M) at −78° C., and was then stirred for 30 min. The cold reaction mixture was then quenched with water (1.0 mL) and concentrated in vacuo. The crude residue was purified directly by silica gel column chromatography (1-7% MeOH/DCM) to afford (rac)-(3-methylpyridin-4-yl)(1-(2,2,2-trifluoroethyl)-1H-pyrazol-3-yl)methanol (15 mg, 4.9% yield) as a white solid. LCMS: ESI-MS m/z: 272.1 [M+H]$^+$.

Step 2: 3-Methyl-4-((1-(2,2,2-trifluoroethyl)-1H-pyrazol-3-yl)methyl)pyridine. To a solution of (rac)-(3-methylpyridin-4-yl)(1-(2,2,2-trifluoroethyl)-1H-pyrazol-3-yl)methanol (11 mg, 0.041 mmol, 1.0 equiv.) in acetic acid (6.0 mL, 0.0068 M) was added zinc powder (27 mg, 0.41 mmol, 10 equiv.). The suspension was refluxed for 10 h. The reaction mixture was cooled to rt and filtered through a short plug of Celite®, eluting with 10% MeOH/DCM. The filtrate was concentrated in vacuo and purified by RP-HPLC (Method A, 10-90% MeCN/0.1% TFA in H$_2$O) to afford 3-methyl-4-((1-(2,2,2-trifluoroethyl)-1H-pyrazol-3-yl)methyl)pyridine (6.8 mg, 66% yield) as a gel. $^1$H NMR (400 MHz, DMSO-d$_6$) δ 8.34-8.26 (m, 2H), 7.75 (d, J=2.3 Hz, 1H), 7.11 (d, J=5.0 Hz, 1H), 6.12 (d, J=2.3 Hz, 1H), 5.06 (q, J=9.2 Hz, 2H), 3.91 (s, 2H), 2.23 (s, 3H); LCMS: ESI-MS m/z: 256.1 [M+H]$^+$.

Example 24

(rac)-4-(1-(1-(2,2,2-Trifluoroethyl)-1H-pyrazol-3-yl)ethyl)pyridine

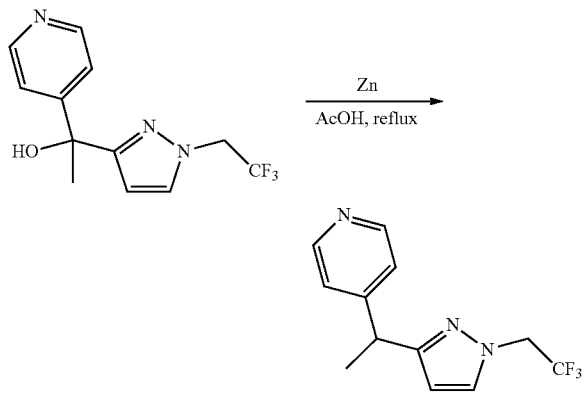

To a solution of (rac)-1-(pyridin-4-yl)-1-(1-(2,2,2-trifluoroethyl)-1H-pyrazol-3-yl)ethan-1-ol (Intermediate 7, 49 mg, 0.18 mmol, 1.0 equiv.) in acetic acid (4.0 mL, 0.045 M) was added zinc powder (120 mg, 1.8 mmol, 10 equiv.). The suspension was refluxed for 5 h. The reaction mixture was cooled to rt and filtered through a short plug of Celite®, eluting with 10% MeOH/DCM. The filtrate was concentrated in vacuo and neutralized by the addition of an aqueous saturated solution of $Na_2CO_3$ solution until the pH was 9-10. This mixture was again concentrated in vacuo and directly purified by silica gel column chromatography (1-7% MeOH/DCM) to afford (rac)-4-(1-(1-(2,2,2-trifluoroethyl)-1H-pyrazol-3-yl)ethyl)pyridine (8.7 mg, 0.034 mmol, 19% yield) as a gel. $^1$H NMR (400 MHz, DMSO-$d_6$) δ 8.48-8.41 (m, 2H), 7.75 (d, J=2.4 Hz, 1H), 7.28-7.22 (m, 2H), 6.24 (d, J=2.3 Hz, 1H), 5.06 (q, J=9.2 Hz, 2H), 4.16 (q, J=7.3 Hz, 1H), 1.53 (d, J=7.2 Hz, 3H); LCMS: ESI-MS m/z: 256.1 [M+H]$^+$.

Example 25

(rac)-4-(1-(1-(2,2-Difluoroethyl)-1H-pyrazol-3-yl)ethyl-2,2,2-$d_3$)pyridine

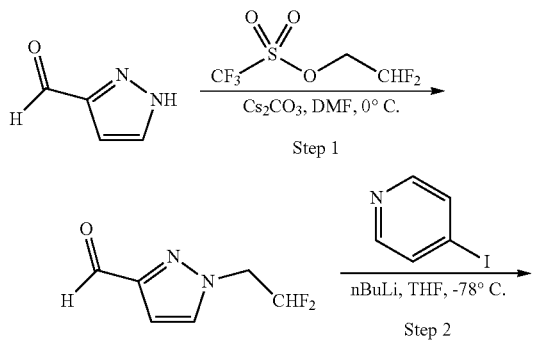

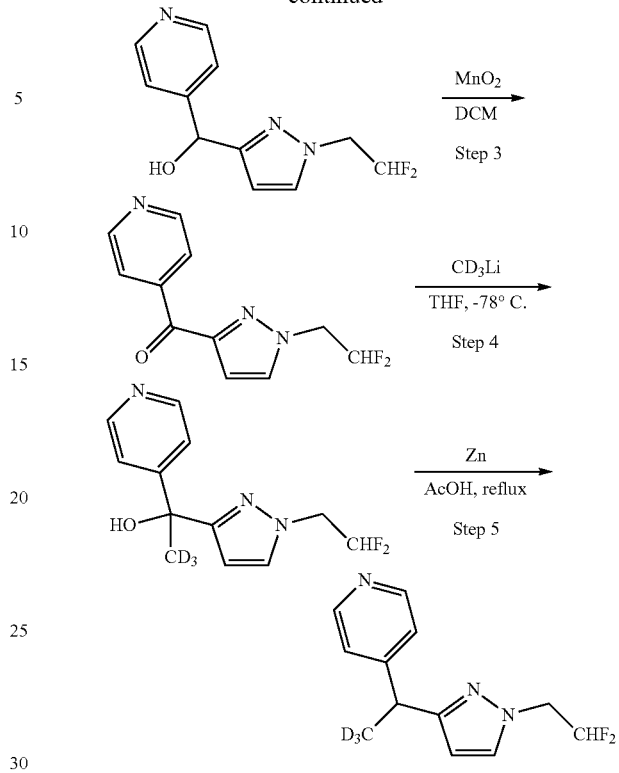

Step 1: 1-(2,2-Difluoroethyl)-1H-pyrazole-3-carbaldehyde. To a solution of 1H-pyrazole-3-carbaldehyde (1.0 g, 10 mmol, 1.0 equiv.) and 2,2-difluoroethyl trifluoromethanesulfonate (2.7 g, 13 mmol, 1.3 equiv.) in DMF (15 mL, 0.67 M) at 0° C. was added cesium carbonate (4.4 g, 14 mmol, 1.4 equiv.). The resulting mixture was warmed to rt and stirred for 1.5 h. The reaction mixture was then diluted with EtOAc (200 mL) and washed with water (100 mL) and brine (100 mL). The organic fraction was dried over anhydrous sodium sulfate, filtered, and concentrated in vacuo. The crude material was purified by silica gel column chromatography (5-60% DCM in hexanes) to afford 1-(2,2-difluoroethyl)-1H-pyrazole-3-carbaldehyde (1.0 g, 60% yield) as an oil. LCMS: ESI-MS m/z: 161.1 [M+H]$^+$.

Step 2: (rac)-(1-(2,2-Difluoroethyl)-1H-pyrazol-3-yl)(pyridin-4-yl)methanol. To a solution of 4-iodopyridine (2.3 g, 11 mmol, 1.8 equiv.) in THF (40 mL, 0.28 M) at −78° C. was added n-butyllithium (1.6 M in hexanes, 9.3 mL, 15 mmol, 2.4 equiv.) dropwise via syringe. The resulting mixture was stirred at −78° C. for 5 min. The resulting solution of lithium reagent was then added slowly to a solution of 1-(2,2-difluoroethyl)-1H-pyrazole-3-carbaldehyde (0.99 g, 6.2 mmol, 1.0 equiv.) in THF (10 mL, 0.62 M) at −78° C., and was stirred for 5 min. The reaction mixture was then quenched with water and extracted with EtOAc (3×10 mL). The combined organic layers were dried over anhydrous sodium sulfate, filtered, and concentrated in vacuo to afford the crude product. The crude material was purified by silica gel column chromatography (1-13% MeOH/DCM) to afford (rac)-(1-(2,2-difluoroethyl)-1H-pyrazol-3-yl)(pyridin-4-yl)methanol (1.4 g, 94% yield) as a white solid. LCMS: ESI-MS m/z: 240.1 [M+H]$^+$.

Step 3: (1-(2,2-Difluoroethyl)-1H-pyrazol-3-yl)(pyridin-4-yl)methanone. To a solution of (1-(2,2-difluoroethyl)-1H-pyrazol-3-yl)(pyridin-4-yl)methanol (1.2 g, 4.9 mmol, 1.0 equiv.) in DCM (44 mL, 0.11 M) was added manganese dioxide (44 g, 44 mmol, 9.0 equiv.) and the resulting mixture was stirred at rt for 3 h. The reaction mixture was filtered through Celite®, eluting with 10% MeOH/DCM. The filtrate was concentrated in vacuo and purified by RP-HPLC (Method A, 10-90% MeCN/0.1% TFA in H₂O) to afford (1-(2,2-difluoroethyl)-1H-pyrazol-3-yl)(pyridin-4-yl)methanone (0.45 g, 39% yield) as a white solid. LCMS: ESI-MS m/z: 238.1 [M+H]⁺.

Step 4: (rac)-1-(1-(2,2-Difluoroethyl)-1H-pyrazol-3-yl)-1-(pyridin-4-yl)ethan-2,2,2-d₃-1-ol. To a solution of iodomethane-d₃ (230 mg, 1.6 mmol, 4.0 equiv.) in THF (7.0 mL, 0.23 M) at −78° C. was added n-butyllithium (1.6 M in hexanes, 1.5 mL, 2.4 mmol, 6.0 equiv.) dropwise via syringe. The resulting mixture was stirred at −78° C. for 10 min. The resulting lithium reagent was added very slowly to a solution of 1-(2,2-difluoroethyl)-1H-pyrazol-3-yl)(pyridin-4-yl)methanone (94 mg, 0.40 mmol, 1.0 equiv.) in THF (3.5 mL, 0.11 M) at −78° C. Stirring was continued at −78° C. for 3 min and the reaction was then quenched with water (1.0 mL). The mixture was concentrated in vacuo and purified by silica gel column chromatography (1-10% MeOH/DCM) to afford (rac)-1-(1-(2,2-difluoroethyl)-1H-pyrazol-3-yl)-1-(pyridin-4-yl)ethan-2,2,2-d₃-1-ol (74 mg, 73% yield) as a gel. LCMS: ESI-MS m/z: 257.1 [M+H]⁺.

Step 5: (rac)-4-(1-(1-(2,2-Difluoroethyl)-1H-pyrazol-3-yl)ethyl-2,2,2-d₃)pyridine. To a solution of (rac)-1-(1-(2,2-difluoroethyl)-1H-pyrazol-3-yl)-1-(pyridin-4-yl)ethan-2,2,2-d₃-1-ol (150 mg, 0.59 mmol, 1.0 equiv.) in acetic acid (20 mL, 0.030 M) was added zinc powder (380 mg, 5.9 mmol, 10 equiv.). The resulting suspension was refluxed for 10 h. After 10 h, the mixture was cooled to rt and filtered through a short plug of Celite®. The filtrate was concentrated in vacuo and the crude product was purified by RP-HPLC (Method A, 10-90% MeCN/0.1% TFA in H₂O) to afford (rac)-4-(1-(1-(2,2-difluoroethyl)-1H-pyrazol-3-yl)ethyl-2,2,2-d₃)pyridine (85 mg, 0.35 mmol, 59% yield) as an oil. ¹H NMR (400 MHz, acetonitrile-d₃) δ 8.53-8.43 (m, 2H), 7.54 (d, J=2.4 Hz, 1H), 7.30-7.22 (m, 2H), 6.19 (d, J=2.3 Hz, 1H), 6.15 (d, J=3.8 Hz, 1H), 4.47 (td, J=14.7, 3.8 Hz, 2H), 4.17 (s, 1H); LCMS: ESI-MS m/z: 241.1 [M+H]⁺.

Example 26

1-(Pyridin-4-ylmethyl)-N-(2,2,2-trifluoroethyl)-1H-pyrazol-3-amine

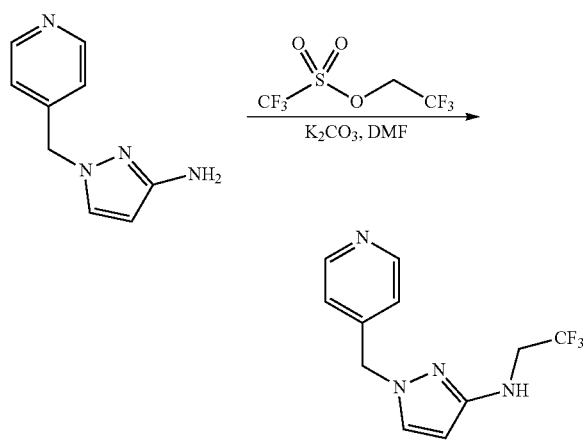

To a solution of 1-(pyridin-4-ylmethyl)-1H-pyrazol-3-amine (Intermediate 2, 36 mg, 0.21 mmol, 1.0 equiv.) and 2,2,2-trifluoroethyl trifluoromethanesulfonate (58 mg, 0.25 mmol, 1.2 equiv.) in anhydrous DMF (1.2 mL, 0.18 M) at 0° C. was added potassium carbonate (58 mg, 0.41 mmol, 2.0 equiv.). The resulting mixture was stirred at rt for 15 h. The mixture was concentrated in vacuo and purified directly by RP-HPLC (Method A, 10-90% MeCN/0.1% TFA in H₂O) to afford 1-(pyridin-4-ylmethyl)-N-(2,2,2-trifluoroethyl)-1H-pyrazol-3-amine (18 mg, 24% yield) as an oil. ¹H NMR (400 MHz, CDCl₃) δ 8.93-8.83 (m, 2H), 7.55 (d, J=6.0 Hz, 2H), 7.39 (d, J=2.6 Hz, 1H), 5.80 (d, J=2.6 Hz, 1H), 5.39 (s, 2H), 3.77 (t, J=8.9 Hz, 2H); LCMS: ESI-MS m/z: 257.1 [M+H]⁺.

Example 27

(S)-2-(1-(1-(Pyridin-4-yl)ethyl)-1H-pyrazol-3-yl)acetonitrile and (R)-2-(1-(1-(Pyridin-4-yl)ethyl)-1H-pyrazol-3-yl)acetonitrile

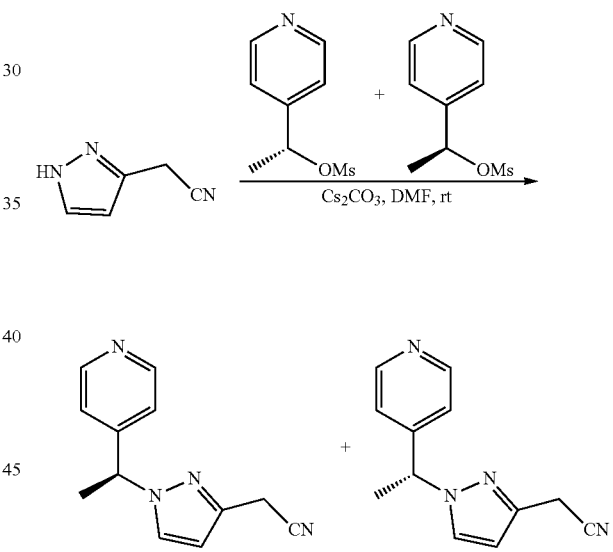

To a mixture of 2-(1H-pyrazol-3-yl)acetonitrile (25 mg, 0.23 mmol, 1.0 equiv.) in anhydrous DMF (1.0 mL, 0.23 M) was added cesium carbonate (91 mg, 0.28 mmol, 1.2 equiv.) followed by Intermediate 9 (56 mg, 0.280 mmol, 1.2 equiv.). The resulting mixture was stirred at rt for 4 h. The reaction was quenched with water and purified directly by RP-HPLC (Method D, 0-70% MeCN/0.1% TFA in H₂O) to afford (S)-2-(1-(1-(pyridin-4-yl)ethyl)-1H-pyrazol-3-yl)acetonitrile and (R)-2-(1-(1-(pyridin-4-yl)ethyl)-1H-pyrazol-3-yl)acetonitrile (5.8 mg, 11% yield) as a yellow oil. ¹H NMR (400 MHz, CDCl₃) δ 8.60 (d, J=8 Hz, 2H), 7.49 (d, J=4 Hz, 1H), 7.08 (d, J=8 Hz, 2H), 6.39 (d, J=4 Hz, 1H), 5.50 (q, J=4 Hz, 8 Hz, 1H), 3.80 (s, 2H), 1.90 (d, J=8 Hz, 3H); LCMS: ESI-MS m/z: 213.1 [M+H]⁺.

Example 28

(R)-2-(1-(1-(Pyridin-4-yl)ethyl)-1H-pyrazol-3-yl)acetonitrile and (S)-2-(1-(1-(Pyridin-4-yl)ethyl)-1H-pyrazol-3-yl)acetonitrile

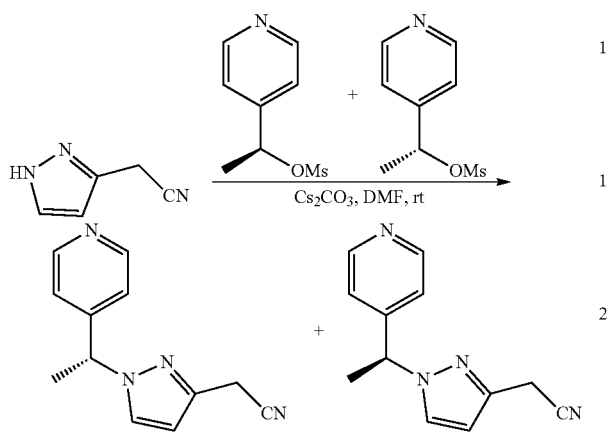

To a mixture of 2-(1H-pyrazol-3-yl)acetonitrile (25 mg, 0.23 mmol, 1.0 equiv.) in anhydrous DMF (1.0 mL, 0.23 M) was added cesium carbonate (91 mg, 0.28 mmol, 1.2 equiv.) followed by Intermediate 8 (47 mg, 0.23 mmol, 1.0 equiv.). The resulting mixture was stirred at rt for 4 h. The reaction was quenched with water and purified directly by RP-HPLC (Method D, 0-70% MeCN/0.1% TFA in H$_2$O) to afford (R)-2-(1-(1-(pyridin-4-yl)ethyl)-1H-pyrazol-3-yl)acetonitrile and (S)-2-(1-(1-(pyridin-4-yl)ethyl)-1H-pyrazol-3-yl)acetonitrile (9.9 mg, 19% yield) as a yellow oil. $^1$H NMR (400 MHz, CDCl$_3$) δ 8.59 (d, J=8 Hz, 2H), 7.49 (d, J=4 Hz, 1H), 7.06 (d, J=8 Hz, 2H), 6.38 (d, J=4 Hz, 1H), 5.49 (q, J=4 Hz, 8 Hz, 1H), 3.79 (s, 2H), 1.90 (d, J=4 Hz, 3H); LCMS: ESI-MS m/z: 213.1 [M+H]$^+$.

Example 29

4-((3-(2,2,2-Trifluoroethyl)-1H-pyrazol-1-yl)methyl)pyridine

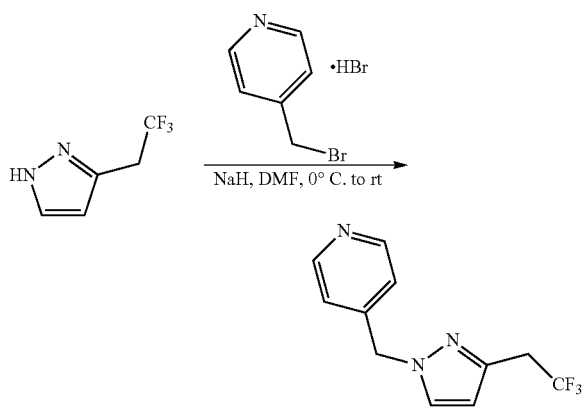

To a solution of 3-(2,2,2-trifluoroethyl)-1H-pyrazole (25 mg, 0.17 mmol, 1.0 equiv.) and DMF (1.0 mL, 0.17 M) at 0° C. was added 4-(bromomethyl)pyridine hydrobromide (76 mg, 0.30 mmol, 1.8 equiv.) then sodium hydride (60 wt % dispersion in mineral oil, 20 mg, 0.83 mmol, 4.9 equiv.) under an atmosphere of nitrogen gas. The reaction mixture was warmed to rt and stirred for 2 h. The crude product was purified directly by RP-HPLC (Method D, 0-70% MeCN/0.1% TFA in H$_2$O) to afford 4-((3-(2,2,2-trifluoroethyl)-1H-pyrazol-1-yl)methyl)pyridine (17 mg, 43% yield) as an amber oil. $^1$H NMR (400 MHz, CDCl$_3$) δ 8.60 (d, J=8 Hz, 2H), 7.39 (d, J=4 Hz, 1H), 7.04 (d, J=8 Hz, 2H), 6.37 (d, J=4 Hz, 1H), 5.32 (s, 2H), 3.50 (q, J=12 Hz, 2H); LCMS: ESI-MS m/z: 242.1 [M+H]$^+$.

Example 30

2-(1-(Pyridin-4-ylmethyl)-1H-pyrazol-3-yl)acetonitrile

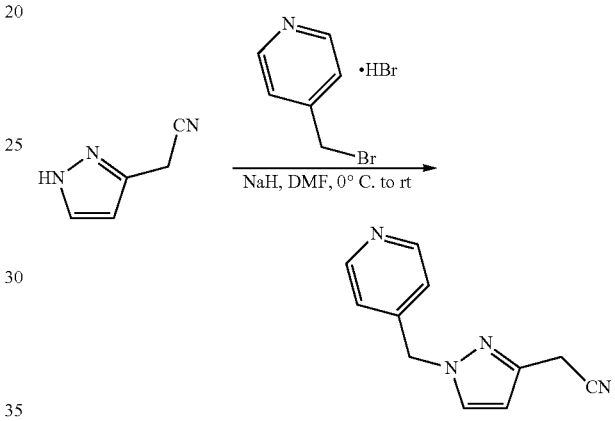

To solution of 2-(1H-pyrazol-3-yl)acetonitrile (30 mg, 0.28 mmol, 1.0 equiv.) and DMF (1.0 mL, 0.28 M) at 0° C. was added 4-(bromomethyl)pyridine hydrobromide (71 mg, 0.28 mmol, 1.0 equiv.), then sodium hydride (60 wt % dispersion in mineral oil, 10 mg, 0.42 mmol, 1.5 equiv.) under an atmosphere of nitrogen gas. The reaction mixture was then warmed to rt and stirred for 15 h. The crude product was purified by RP-HPLC (Method D, 0-10% MeCN/0.1% TFA in H$_2$O) to afford 2-(1-(pyridin-4-ylmethyl)-1H-pyrazol-3-yl)acetonitrile (5.0 mg, 9.4% yield) as a yellow oil. $^1$H NMR (400 MHz, CDCl$_3$) δ 8.61 (d, J=8 Hz, 2H), 7.46 (d, J=4 Hz, 1H), 7.05 (d, J=8 Hz, 2H), 6.40 (d, J=4 Hz, 1H), 5.32 (s, 2H), 3.80 (s, 2H); LCMS: ESI-MS m/z: 199.1 [M+H]$^+$.

Example 31

(rac)-4-(1-(1-(2,2,2-Trifluoroethyl)-1H-pyrazol-3-yl)propyl)pyridine

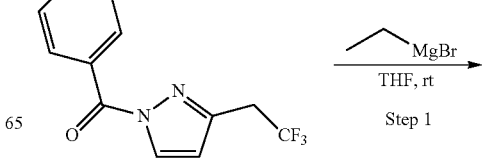

Step 1

-continued

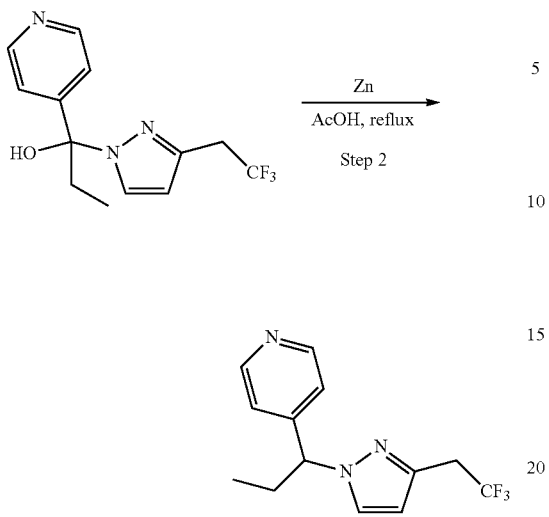

Step 1: (rac)-1-(Pyridin-4-yl)-1-(1-(2,2,2-trifluoroethyl)-1H-pyrazol-3-yl)propan-1-ol. To a solution of pyridin-4-yl (1-(2,2,2-trifluoroethyl)-1H-pyrazol-3-yl)methanone (150 mg, 5.9 mmol, 1.0 equiv.) in anhydrous THF (10 mL, 0.59 M) under an atmosphere of argon gas was added a solution of ethylmagnesium bromide (2 M in THF, 3.0 mL, 6.0 mmol, 1.0 equiv.). The resulting mixture was stirred at rt for 1 h. After 1 h, an aqueous saturated solution of sodium chloride (10 mL) was added to quench the reaction. The resulting solution was extracted with EtOAc (2×30 mL). The combined organic layers were dried over anhydrous sodium sulfate, filtered, and concentrated in vacuo to afford crude (rac)-1-(pyridin-4-yl)-1-(1-(2,2,2-trifluoroethyl)-1H-pyrazol-3-yl)propan-1-ol (200 mg). This material was used in the next reaction with no further purification. LCMS: ESI-MS m/z: 286.1 [M+H]$^+$.

Step 2: (rac)-4-(1-(1-(2,2,2-Trifluoroethyl)-1H-pyrazol-3-yl)propyl)pyridine. A solution of crude (rac)-1-(pyridin-4-yl)-1-(1-(2,2,2-trifluoroethyl)-1H-pyrazol-3-yl)propan-1-ol (200 mg, 0.74 mmol, 1.0 equiv.) and zinc powder (480 mg, 7.4 mmol, 10 equiv.) in acetic acid (20 mL, 0.037 M) was refluxed for 12 h. After 12 h, the reaction mixture was cooled to rt and filtered over a short plug of Celite®, eluting with a 10% mixture of MeOH/DCM. The filtrate was concentrated in vacuo, and then neutralized with an aqueous saturated solution of Na$_2$CO$_3$. The resulting solution was extracted with EtOAc (3×20 mL). The combined organic layers were dried over anhydrous sodium sulfate, filtered, and concentrated in vacuo to afford the crude product. The crude residue was purified by RP-HPLC (Method C, 5-85% MeCN/10 mM NH$_4$HCO$_3$+0.025% NH$_3$·H$_2$O in H$_2$O) to afford (rac)-4-(1-(1-(2,2,2-trifluoroethyl)-1H-pyrazol-3-yl)propyl)pyridine (20 mg, 13% yield over two steps) as a colorless oil. $^1$H NMR (400 MHz, CDCl$_3$) δ 8.49 (d, J=6.0 Hz, 2H), 7.42 (d, J=2.0 Hz, 1H), 7.19 (d, J=6.0 Hz, 2H), 6.14 (d, J=2.4 Hz, 1H), 4.69 (q, J=8.0 Hz, 2H), 3.89 (t, J=8.0 Hz, 1H), 2.14-2.08 (m, 1H), 2.02-1.96 (m, 1H), 0.91 (t, J=3.2 Hz, 3H). LCMS: ESI-MS m/z: 270.1 [M+H]$^+$.

Example 32

3-(3-Chlorophenyl)-N-(1-(pyridin-4-ylmethyl)-1H-pyrazol-3-yl)propenamide

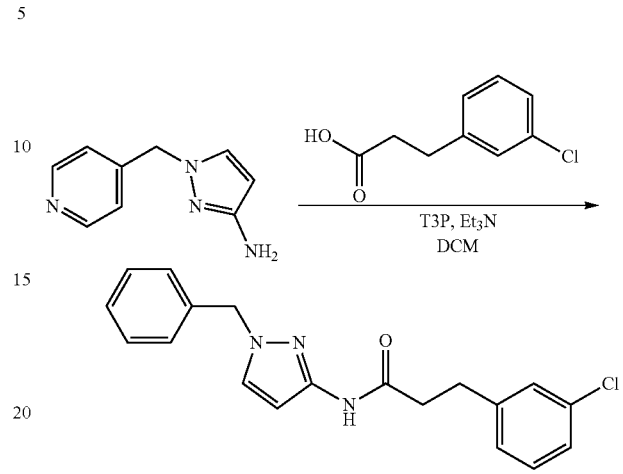

3-(3-Chlorophenyl)-N-(1-(pyridin-4-ylmethyl)-1H-pyrazol-3-yl)propanamide. A mixture of 1-(pyridin-4-ylmethyl)-1H-pyrazol-3-amine (Intermediate 2, 25 mg, 0.143 mmol, 1.0 equiv.), T3P (136.7 mg, 50% sol. in ethyl acetate, 0.215 mmol, 1.50 equiv.), triethylamine (22 mg, 0.215 mmol, 1.50 equiv.) and 3-(3-chlorophenyl)propanoic acid (39.56 mg, 0.215 mmol, 1.50 equiv.) in DCM (2 mL) was stirred at 25° C. for 2 h. The resulting mixture was concentrated in vacuo and the crude product was purified by RP-HPLC (Method C, 15-40% MeCN/10 mM NH$_4$HCO$_3$+0.025% NH$_3$ in H$_2$O) to afford 3-(3-chlorophenyl)-N-(1-(pyridin-4-ylmethyl)-1H-pyrazol-3-yl)propanamide (10 mg, 20% yield) as a white solid. $^1$H NMR (CDCl$_3$, 400 MHz) δ 8.50 (s, 2H), 8.03-7.98 (m, 1H), 7.31 (s, 1H), 7.17-7.07 (m, 3H), 7.04-7.02 (m, 1H), 6.99-6.88 (m, 2H), 6.73 (s, 1H), 5.11 (s, 2H), 2.94 (t, J=7.2 Hz, 2H), 2.56 (t, J=7.2 Hz, 2H); LCMS: ESI-MS m/z: 341.0 [M+H]$^+$.

EXAMPLES 33-67 were prepared and purified according to the method of EXAMPLE 32 except as noted.

Example 33

3-(2,5-Difluorophenyl)-N-(1-(pyridin-4-ylmethyl)-1H-pyrazol-3-yl)propanamide

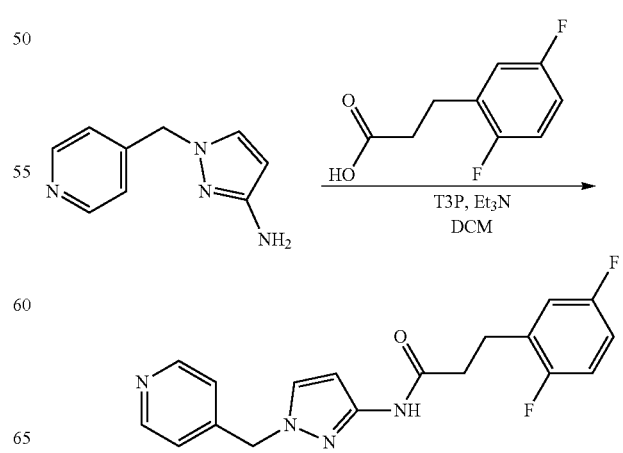

3-(2,5-Difluorophenyl)-N-(1-(pyridin-4-ylmethyl)-1H-pyrazol-3-yl)propanamide. $^1$H NMR (CDCl$_3$, 400 MHz) δ 8.59 (s, 2H), 7.78 (s, 1H), 7.40-7.39 (d, J=2.0 Hz, 1H), 7.03-6.95 (m, 4H), 6.90-6.85 (m, 1H), 6.81-6.80 (d, J=2.0 Hz, 1H), 5.20 (s, 2H), 3.08-3.04 (t, J=8.0 Hz, 2H), 2.62-2.63 (t, J=8.0 Hz, 2H); LCMS: ESI-MS m/z: 343.0 [M+H]$^+$.

Example 34

3-Phenyl-N-(1-(pyridin-4-ylmethyl)-1H-pyrazol-3-yl)propanamide

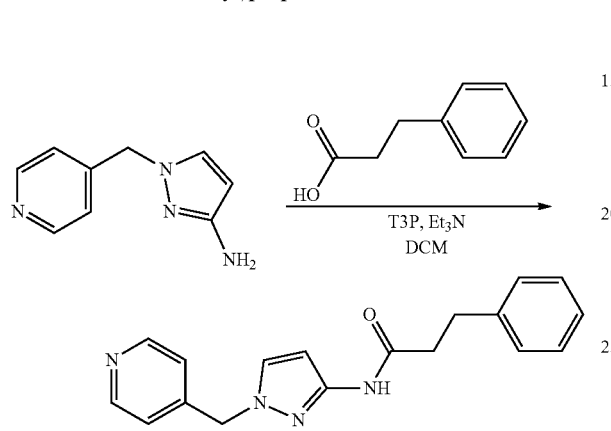

3-Phenyl-N-(1-(pyridin-4-ylmethyl)-1H-pyrazol-3-yl)propanamide. $^1$H NMR (DMSO-d$_6$, 400 MHz) δ 10.45 (s, 1H), 8.51 (dd, J=4.8, 1.6 Hz, 2H), 7.77 (d, J=2.0 Hz, 1H), 7.29-7.15 (m, 5H), 7.10 (d, J=5.6 Hz, 2H), 6.55 (d, J=2.0 Hz, 1H), 5.27 (s, 2H), 2.86 (t, J=7.8 Hz, 2H), 2.53 (t, J=7.8 Hz, 2H); LCMS: ESI-MS m/z: 307.0 [M+H]$^+$.

Example 35

3-(3,5-Dichlorophenyl)-N-(1-(pyridin-4-ylmethyl)-1H-pyrazol-3-yl)propanamide

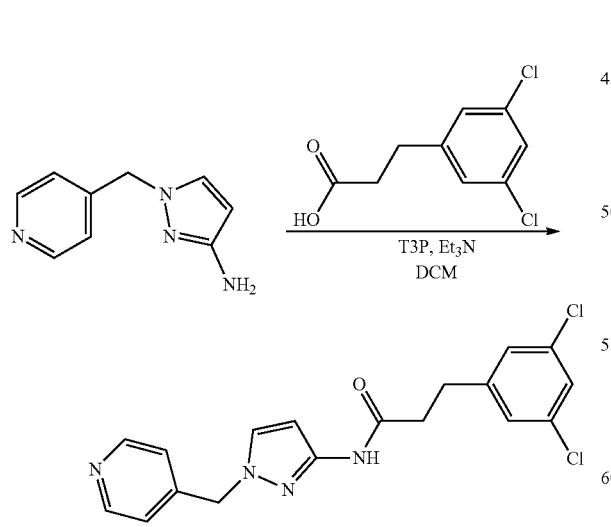

3-(3,5-Dichlorophenyl)-N-(1-(pyridin-4-ylmethyl)-1H-pyrazol-3-yl)propanamide. $^1$H NMR (DMSO-d$_6$, 400 MHz) δ 10.46 (s, 1H), 8.52 (dd, J=4.4, 2.8 Hz, 2H), 7.78 (d, J=2 Hz, 1H), 7.42 (t, J=1.8 Hz, 1H), 7.32 (d, J=1.6 Hz, 2H), 7.11 (d, J=5.6 Hz, 2H), 6.54 (d, J=2.4 Hz, 1H), 5.28 (s, 2H), 2.88 (t, J=7.6 Hz, 2H), 2.59 (t, J=7.6 Hz, 2H); LCMS: ESI-MS m/z: 375.0 [M+H]$^+$.

Example 36

2-Phenyl-N-(1-(pyridin-4-ylmethyl)-1H-pyrazol-3-yl)acetamide

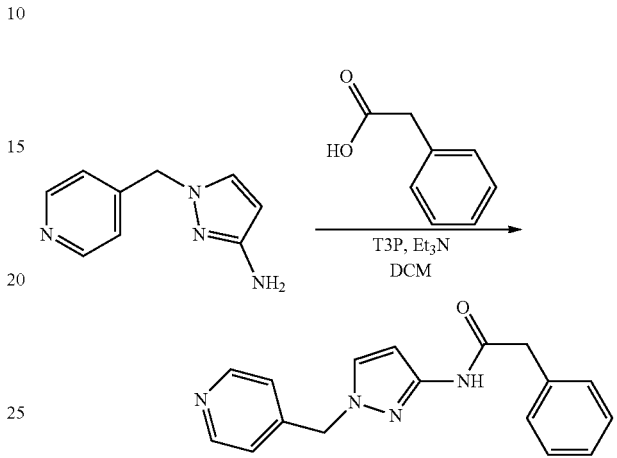

2-Phenyl-N-(1-(pyridin-4-ylmethyl)-1H-pyrazol-3-yl)acetamide. $^1$H NMR (CDCl$_3$, 400 MHz) δ 8.54 (dd, J=4.4, 1.6 Hz, 2H), 7.79 (s, 1H), 7.38-7.29 (m, 6H), 6.91 (d, J=6 Hz, 2H), 6.81 (d, J=2.4 Hz, 1H), 5.15 (s, 2H), 3.73 (s, 2H); LCMS: ESI-MS m/z: 293.0 [M+H]$^+$;

Example 37

N-(1-(Pyridin-4-ylmethyl)-1H-pyrazol-3-yl)-2,3-dihydrobenzo[b][1,4]dioxine-6-carboxamide

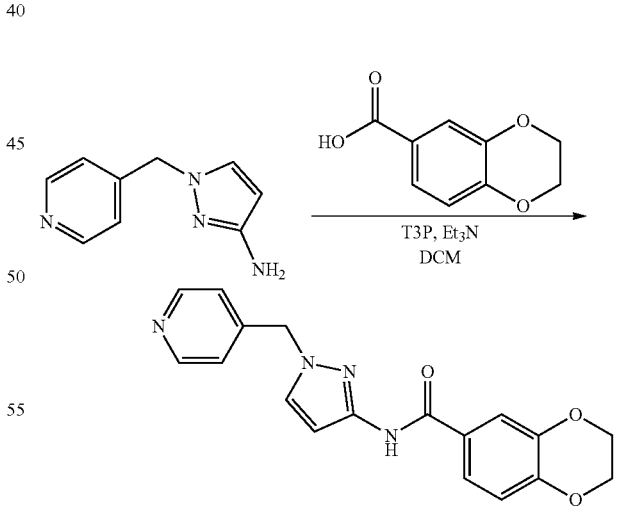

N-(1-(Pyridin-4-ylmethyl)-1H-pyrazol-3-yl)-2,3-dihydrobenzo[b][1,4]dioxine-6-carboxamide. Purified by RP-HPLC, 26% yield. $^1$H NMR (DMSO-d$_6$, 400 MHz) δ 10.71 (s, 1H), 8.53 (dd, J=4.4, 1.2 Hz, 2H), 7.85 (d, J=2 Hz, 1H), 7.56-7.55 (m, 2H), 7.14 (d, J=6.0 Hz, 2H), 6.91 (d, J=8.4 Hz, 1H), 6.69 (d, J=2.4 Hz, 1H), 5.34 (s, 2H), 4.32-4.28 (s, 4H); LCMS: ESI-MS m/z: 337.0 [M+H]$^+$.

Example 38

N-(1-(Pyridin-4-ylmethyl)-1H-pyrazol-3-yl)-2,3-dihydrobenzofuran-6-carboxamide

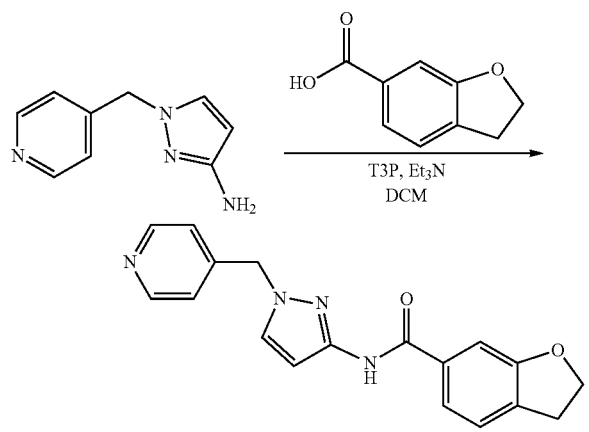

N-(1-(Pyridin-4-ylmethyl)-1H-pyrazol-3-yl)-2,3-dihydrobenzofuran-6-carboxamide. $^1$H NMR (DMSO-$d_6$, 400 MHz) δ 10.76 (s, 1H), 8.53 (dd, J=4.6, 1.2 Hz, 2H), 7.86 (d, J=2.4 Hz, 1H), 7.51-7.49 (m, 1H), 7.36 (d, J=0.8 Hz, 1H), 7.31-7.29 (m, 1H), 7.15 (d, J=6.0 Hz, 2H), 6.7 (d, J=2.4 Hz, 1H), 5.34 (s, 2H), 4.57 (t, J=8.8 Hz, 2H), 3.22 (t, J=8.6 Hz, 2H); LCMS: ESI-MS m/z: 321.0 [M+H]$^+$.

Example 39

N-(1-(Pyridin-4-ylmethyl)-1H-pyrazol-3-yl)-2,3-dihydrobenzofuran-5-carboxamide

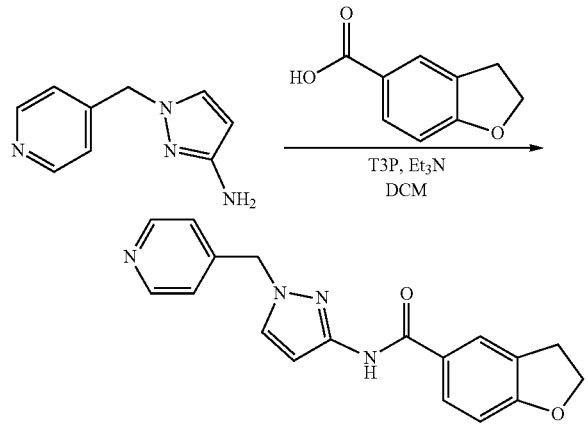

N-(1-(Pyridin-4-ylmethyl)-1H-pyrazol-3-yl)-2,3-dihydrobenzofuran-5-carboxamide. $^1$H NMR (DMSO-$d_6$, 400 MHz) δ 10.64 (s, 1H), 8.53 (dd, J=4.4, 1.4 Hz, 2H), 7.91 (s, 1H), 7.84-7.81 (m, 2H), 7.14 (d, J=6.0 Hz, 2H), 6.84 (d, J=8.8 Hz, 1H), 6.69 (d, J=2.0 Hz, 1H), 5.33 (s, 2H), 4.60 (t, J=8.8 Hz, 2H), 3.21 (t, J=8.6 Hz, 2H); LCMS: ESI-MS m/z: 319.1 [M–H]$^-$.

Example 40

N-(1-(Pyridin-4-ylmethyl)-1H-pyrazol-3-yl)-2,3-dihydro-1H-indene-5-carboxamide

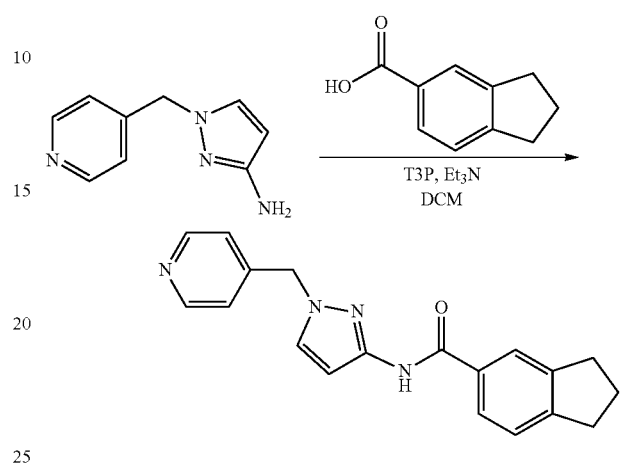

N-(1-(Pyridin-4-ylmethyl)-1H-pyrazol-3-yl)-2,3-dihydro-1H-indene-5-carboxamide. $^1$H NMR (DMSO-$d_6$, 400 MHz) δ 10.75 (s, 1H), 8.53 (dd, J=4.6, 1.2 Hz, 2H), 7.85 (d, J=2.0 Hz, 2H), 7.77-7.76 (m, 1H), 7.29 (d, J=8.0 Hz, 1H), 7.14 (d, J=6.0 Hz, 2H), 6.71 (d, J=2.4 Hz, 1H), 5.34 (s, 2H), 2.89 (t, J=7.4 Hz, 4H), 2.08-2.02 (m, 2H); LCMS: ESI-MS m/z: 319.0 [M+H]$^+$.

Example 41

3,4-Dimethoxy-N-(1-(pyridin-4-ylmethyl)-1H-pyrazol-3-yl)benzamide

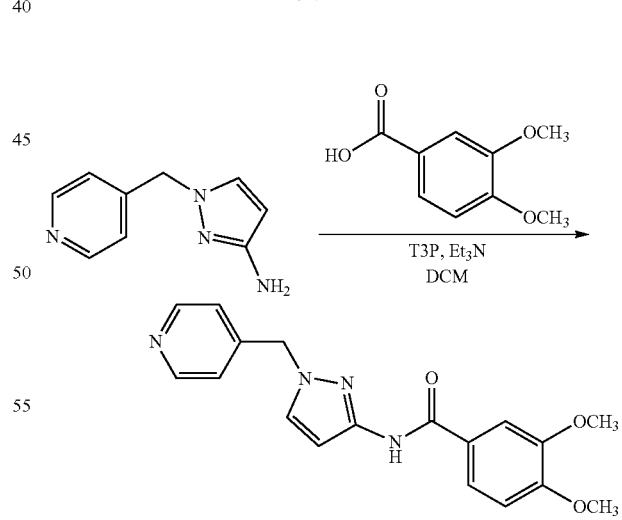

3,4-Dimethoxy-N-(1-(pyridin-4-ylmethyl)-1H-pyrazol-3-yl)benzamide. $^1$H NMR (DMSO-$d_6$, 400 MHz) δ 10.77 (s, 1H), 8.54 (dd, J=4.8, 1.6 Hz, 2H), 7.86 (d, J=2.4 Hz, 1H), 7.66-7.63 (m, 2H), 7.15 (d, J=6.0 Hz, 2H), 7.03 (d, J=8.4 Hz, 1H), 6.72 (d, J=2.0 Hz, 1H), 5.34 (s, 2H), 3.81 (d, J=2.4 Hz, 6H); LCMS: ESI-MS m/z: 339.0 [M+H]$^+$.

Example 42

4-Methoxy-N-(1-(pyridin-4-ylmethyl)-1H-pyrazol-3-yl)benzamide

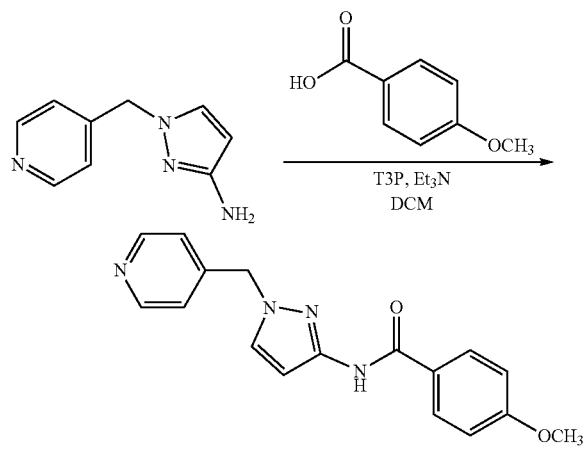

4-Methoxy-N-(1-(pyridin-4-ylmethyl)-1H-pyrazol-3-yl)benzamide. $^1$H NMR (CDCl$_3$, 400 MHz) δ 8.61 (d, J=5.2 Hz, 2H), 8.40 (s, 1H), 7.86 (d, J=11.6 Hz, 2H), 7.46 (d, J=2.4 Hz, 1H), 7.09 (d, J=5.2 Hz, 2H), 7.00-6.97 (m, 3H), 5.26 (s, 2H), 3.89 (m, 3H); LCMS: ESI-MS m/z: 309.0 [M+H]$^+$.

Example 43

3-Methoxy-N-(1-(pyridin-4-ylmethyl)-1H-pyrazol-3-yl)benzamide

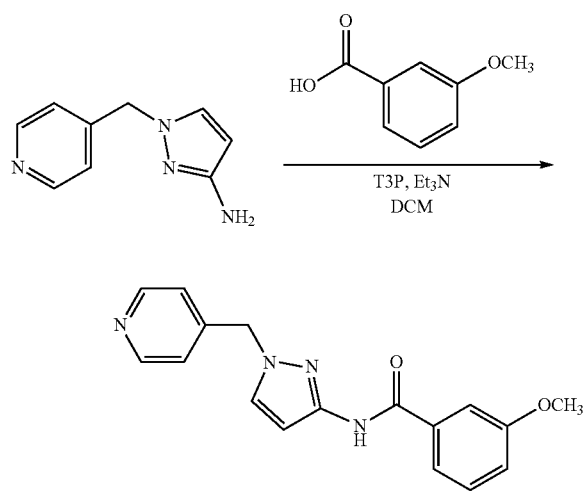

3-Methoxy-N-(1-(pyridin-4-ylmethyl)-1H-pyrazol-3-yl)benzamide. $^1$H NMR (DMSO-d$_6$, 400 MHz) δ 10.91 (s, 1H), 8.54 (dd, J=4.4, 1.6 Hz, 2H), 7.87 (d, J=2.4 Hz, 1H), 7.58-7.57 (m, 2H), 7.38 (t, J=8.0 Hz, 1H), 7.15 (d, J=5.6 Hz, 2H), 7.12-7.09 (m, 1H), 6.72 (d, J=2.0 Hz, 1H), 5.35 (s, 2H), 3.81 (s, 3H); LCMS: ESI-MS m/z: 309.0 [M+H]$^+$.

Example 44

2-Methoxy-N-(1-(pyridin-4-ylmethyl)-1H-pyrazol-3-yl)benzamide

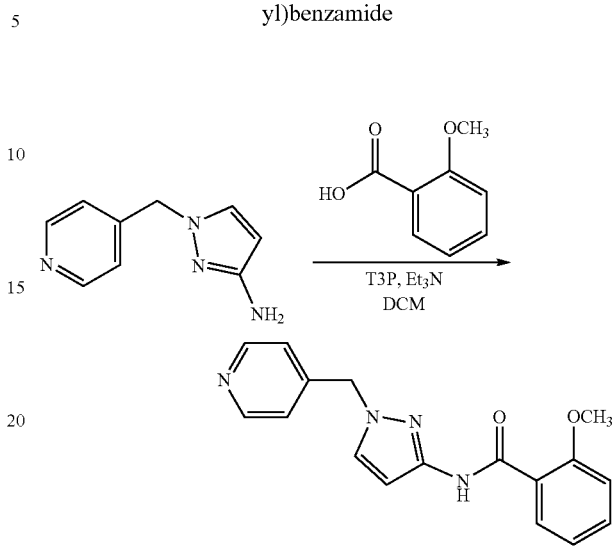

2-Methoxy-N-(1-(pyridin-4-ylmethyl)-1H-pyrazol-3-yl)benzamide. Purified by RP-HPLC, 25% yield. $^1$H NMR (CDCl$_3$, 400 MHz) δ 10.19 (s, 1H), 8.59 (d, J=6.0 Hz, 2H), 8.31 (d, J=10.0 Hz, 1H), 7.54-7.50 (m, 1H), 7.43 (d, J=2.4 Hz, 1H), 7.17-7.01 (m, 5H), 5.28 (s, 2H), 4.05 (s, 3H); LCMS: ESI-MS m/z: 309.0 [M+H]$^+$.

Example 45

4-Hydroxy-N-(1-(pyridin-4-ylmethyl)-1H-pyrazol-3-yl)benzamide

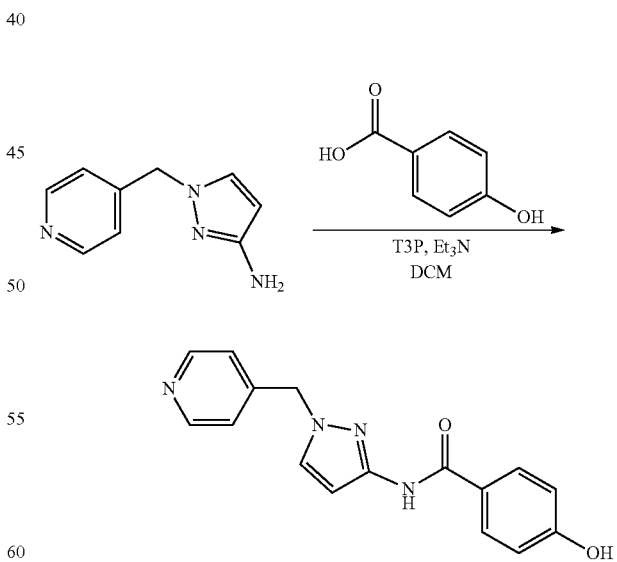

4-Hydroxy-N-(1-(pyridin-4-ylmethyl)-1H-pyrazol-3-yl)benzamide. $^1$H NMR (DMSO-d$_6$, 400 MHz) δ 10.60 (s, 1H), 10.06 (s, 1H), 8.53 (d, J=6.0 Hz, 2H), 7.89-7.84 (m, 3H), 7.14 (d, J=6.0 Hz, 2H), 6.79 (d, J=8.8 Hz, 2H), 6.69 (d, J=2.4 Hz, 1H), 5.33 (s, 2H); LCMS: ESI-MS m/z: 295.0 [M+H]$^+$.

Example 46

3-Hydroxy-N-(1-(pyridin-4-ylmethyl)-1H-pyrazol-3-yl)benzamide

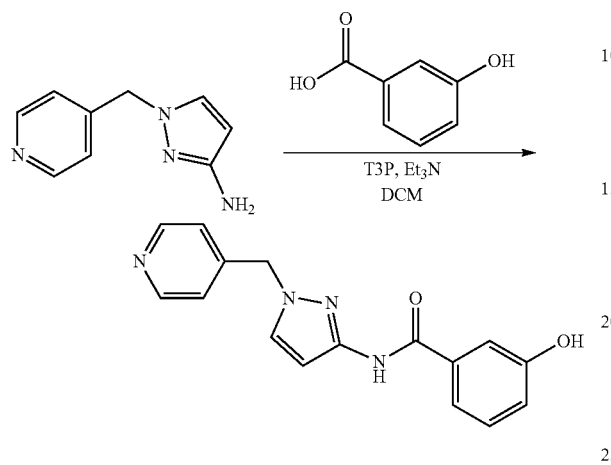

3-Hydroxy-N-(1-(pyridin-4-ylmethyl)-1H-pyrazol-3-yl)benzamide. $^1$H NMR (DMSO-d$_6$, 400 MHz) δ 10.77 (s, 1H), 9.67 (s, 1H), 8.54 (d, J=6.4 Hz, 2H), 7.86 (d, J=2.4 Hz, 1H), 7.43 (d, J=7.6 Hz, 1H), 7.35-7.23 (m, 2H), 7.14 (d, J=6.0 Hz, 2H), 6.93 (d, J=10.0 Hz, 1H), 6.70 (d, J=2.4 Hz, 1H), 5.34 (s, 2H); LCMS: ESI-MS m/z: 295.0 [M+H]$^+$.

Example 47

2-Hydroxy-N-(1-(pyridin-4-ylmethyl)-1H-pyrazol-3-yl)benzamide

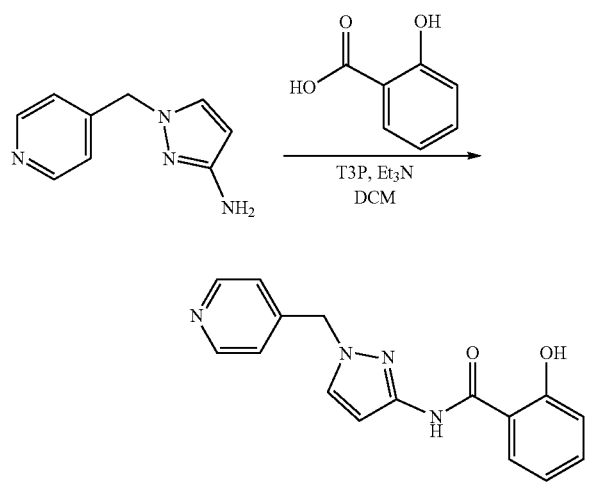

2-Hydroxy-N-(1-(pyridin-4-ylmethyl)-1H-pyrazol-3-yl)benzamide. $^1$H NMR (DMSO-d$_6$, 400 MHz) δ 8.53 (d, J=4.4 Hz, 2H), 8.01 (d, J=7.2 Hz, 1H), 7.87 (d, J=2.0 Hz, 1H), 7.41-7.37 (m, 1H), 7.14 (d, J=5.6 Hz, 2H), 6.95-6.87 (m, 2H), 6.70 (d, J=2.4 Hz, 1H), 5.35 (s, 2H); LCMS: ESI-MS m/z: 295.0 [M+H]$^+$.

Example 48

2-Methyl-N-(1-(pyridin-4-ylmethyl)-1H-pyrazol-3-yl)benzamide

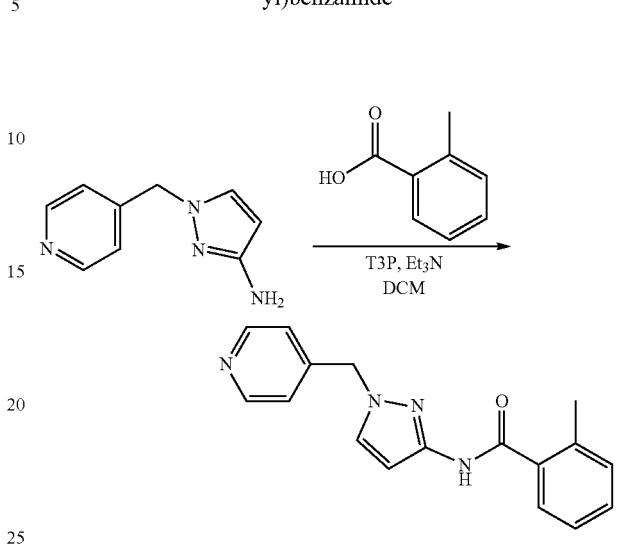

2-Methyl-N-(1-(pyridin-4-ylmethyl)-1H-pyrazol-3-yl)benzamide. $^1$H NMR (CDCl$_3$, 400 MHz) δ 8.60 (d, J=4.8 Hz, 2H), 8.15 (s, 1H), 7.54-7.36 (m, 3H), 7.30-7.24 (m, 2H), 7.08 (d, J=5.6 Hz, 2H), 6.98 (d, J=2.4 Hz, 1H), 5.22 (s, 2H), 2.55 (s, 3H); LCMS: ESI-MS m/z: 293.0 [M+H]$^+$.

Example 49

3-Methyl-N-(1-(pyridin-4-ylmethyl)-1H-pyrazol-3-yl)benzamide

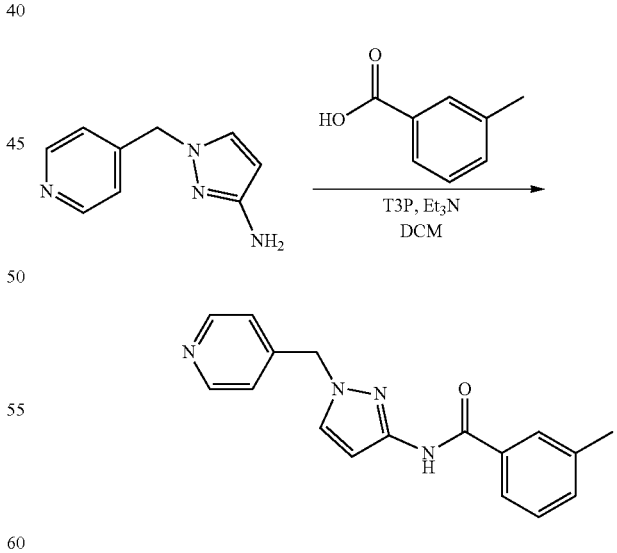

3-Methyl-N-(1-(pyridin-4-ylmethyl)-1H-pyrazol-3-yl)benzamide. $^1$H NMR (DMSO-d$_6$, 400 MHz) δ 10.82 (s, 1H), 8.54 (d, J=6.0 Hz, 2H), 7.87-7.78 (m, 3H), 7.36 (d, J=5.6 Hz, 2H), 7.15 (d, J=5.2 Hz, 2H), 6.72 (s, 1H), 5.35 (s, 2H), 2.36 (s, 3H); LCMS: ESI-MS m/z: 293.0 [M+H]$^+$.

Example 50

4-Methyl-N-(1-(pyridin-4-ylmethyl)-1H-pyrazol-3-yl)benzamide

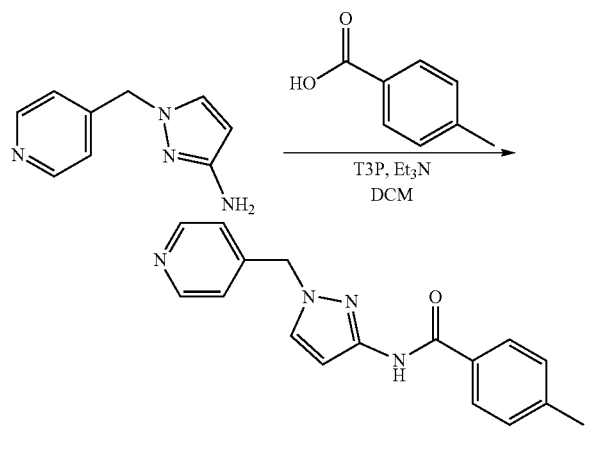

4-Methyl-N-(1-(pyridin-4-ylmethyl)-1H-pyrazol-3-yl)benzamide. $^1$H NMR (DMSO-d$_6$, 400 MHz) δ 10.80 (s, 1H), 8.53 (d, J=6.0 Hz, 2H), 7.90-7.85 (m, 3H), 7.27 (d, J=8.0 Hz, 2H), 7.14 (d, J=6.0 Hz, 2H), 6.70 (d, J=2.0 Hz, 1H), 5.34 (s, 2H), 2.35 (s, 3H); LCMS: ESI-MS m/z: 293.0 [M+H]$^+$.

Example 51

2-Cyano-N-(1-(pyridin-4-ylmethyl)-1H-pyrazol-3-yl)benzamide

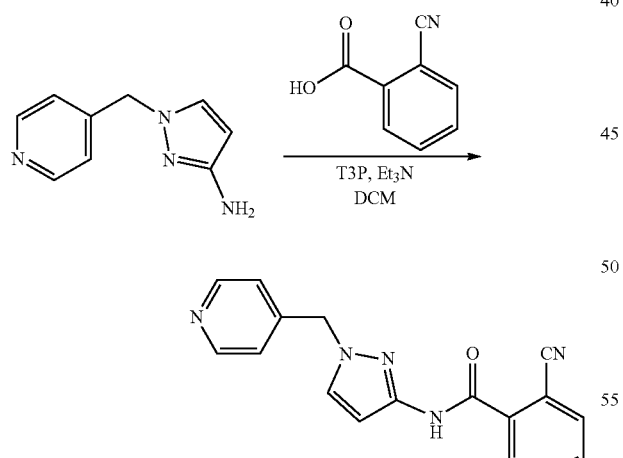

2-Cyano-N-(1-(pyridin-4-ylmethyl)-1H-pyrazol-3-yl)benzamide. $^1$H NMR (CDCl$_3$, 400 MHz) δ 8.61 (d, J=6.0 Hz, 2H), 8.17 (d, J=6.8 Hz, 1H), 7.93 (d, J=7.2 Hz, 1H), 7.72 (t, J=7.0 Hz, 1H), 7.71 (t, J=7.8 Hz, 1H), 7.54 (d, J=2.4 Hz, 1H), 7.12 (d, J=5.6 Hz, 2H), 6.92 (d, J=2.0 Hz, 1H), 5.38 (s, 2H); LCMS: ESI-MS m/z: 304.0 [M+H]$^+$.

Example 52

4-Cyano-N-(1-(pyridin-4-ylmethyl)-1H-pyrazol-3-yl)benzamide

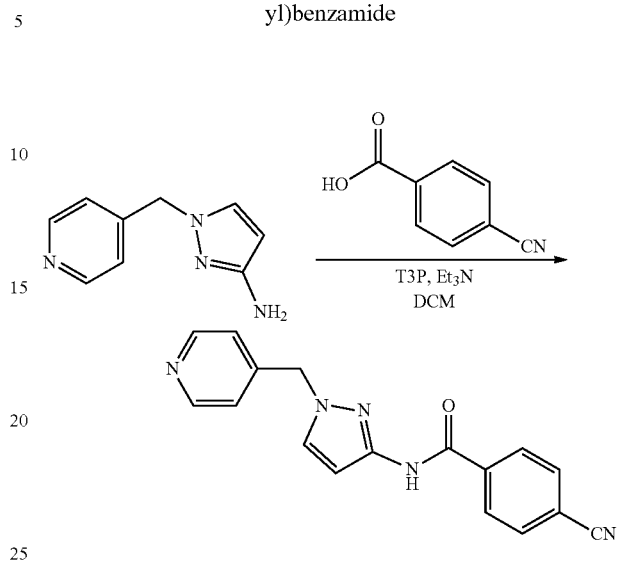

4-Cyano-N-(1-(pyridin-4-ylmethyl)-1H-pyrazol-3-yl)benzamide. $^1$H NMR (CDCl$_3$, 400 MHz) δ 8.56 (s, 2H), 7.98 (d, J=8.4 Hz, 2H), 7.79 (d, J=8.4 Hz, 2H), 7.47 (d, J=2.4 Hz, 1H), 7.07 (s, 2H), 6.94 (d, J=2.0 Hz, 1H), 5.23 (s, 2H); LCMS: ESI-MS m/z: 304.0 [M+H]$^+$.

Example 53

2-Chloro-N-(1-(pyridin-4-ylmethyl)-1H-pyrazol-3-yl)benzamide

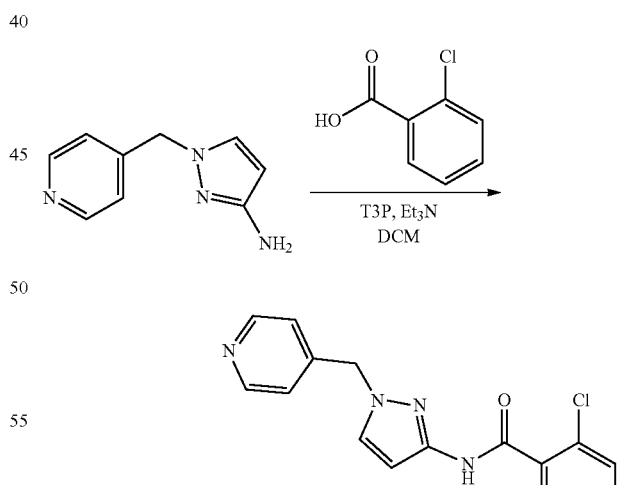

2-Chloro-N-(1-(pyridin-4-ylmethyl)-1H-pyrazol-3-yl)benzamide. $^1$H NMR (CDCl$_3$, 400 MHz) δ 8.59 (d, J=6.4 Hz, 2H), 8.51 (s, 1H), 7.80 (dd, J=2.0, 1.6 Hz, 1H), 7.26-7.47 (m, 4H), 7.09 (d, J=6.0 Hz, 2H), 6.97 (d, J=2.4 Hz, 1H), 5.26 (s, 2H); LCMS: ESI-MS m/z: 313.0 [M+H]$^+$.

Example 54

3-Chloro-N-(1-(pyridin-4-ylmethyl)-1H-pyrazol-3-yl)benzamide

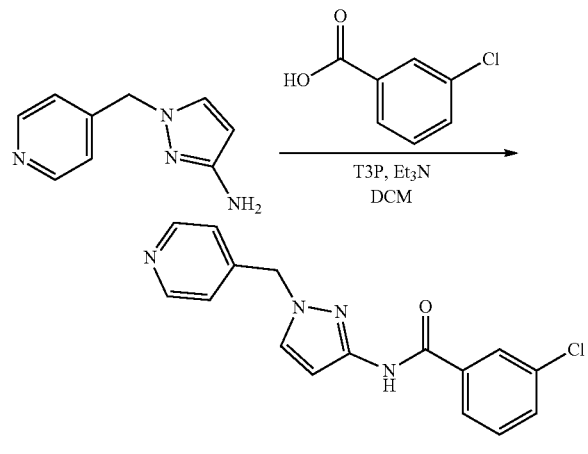

3-Chloro-N-(1-(pyridin-4-ylmethyl)-1H-pyrazol-3-yl)benzamide. $^1$H NMR (CDCl$_3$, 400 MHz) δ 8.59 (d, J=5.2 Hz, 2H), 8.48 (s, 1H), 7.88 (s, 1H), 7.73 (d, J=7.2 Hz, 1H), 7.52 (d, J=10 Hz, 1H), 7.45 (d, J=2.4 Hz, 1H), 7.42 (t, J=8.0 Hz, 1H), 7.08 (d, J=5.2 Hz, 2H), 6.95 (s, 1H), 5.25 (s, 2H); LCMS: ESI-MS m/z: 313.0 [M+H]$^+$.

Example 55

4-Chloro-N-(1-(pyridin-4-ylmethyl)-1H-pyrazol-3-yl)benzamide

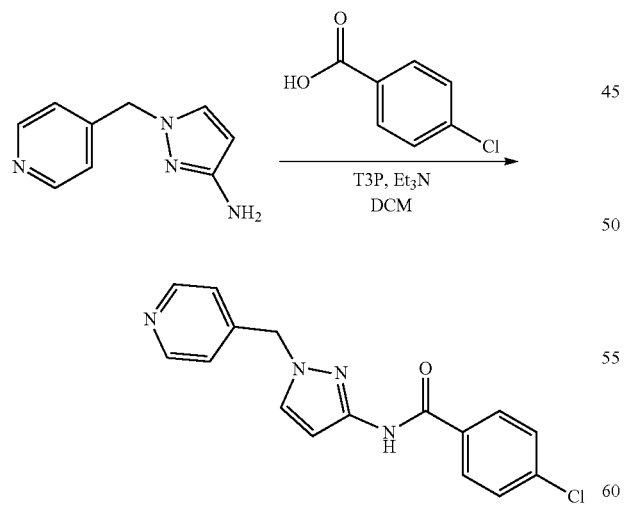

4-Chloro-N-(1-(pyridin-4-ylmethyl)-1H-pyrazol-3-yl)benzamide. $^1$H NMR (CDCl$_3$, 400 MHz) δ 8.59 (s, 2H), 8.47 (s, 1H), 7.82 (d, J=8.8 Hz, 2H), 7.45 (d, J=8.4 Hz, 3H), 7.05 (s, 2H), 6.94 (d, J=2.4 Hz, 1H), 5.23 (s, 2H); LCMS: ESI-MS m/z: 313.0 [M+H]$^+$.

Example 56

N-(1-(Pyridin-4-ylmethyl)-1H-pyrazol-3-yl)-2-(trifluoromethyl)benzamide

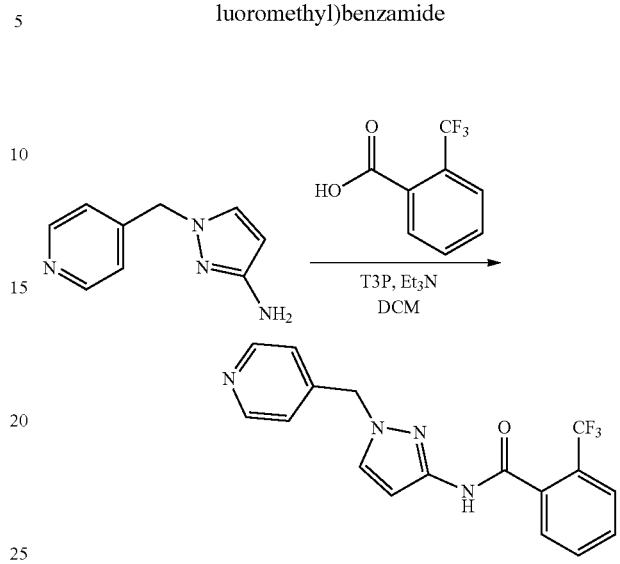

N-(1-(Pyridin-4-ylmethyl)-1H-pyrazol-3-yl)-2-(trifluoromethyl)benzamide. $^1$H NMR (CDCl$_3$, 400 MHz) δ 8.57 (d, J=6.0 Hz, 2H), 8.23 (s, 1H), 7.75 (d, J=7.2 Hz, 1H), 7.59-7.75 (m, 3H), 7.43 (d, J=2.0 Hz, 1H), 7.05 (d, J=5.2 Hz, 2H), 6.94 (d, J=2.4 Hz, 1H), 5.21 (s, 2H); LCMS: ESI-MS m/z: 347.0 [M+H]$^+$.

Example 57

N-(1-(Pyridin-4-ylmethyl)-1H-pyrazol-3-yl)-4-(trifluoromethyl)benzamide

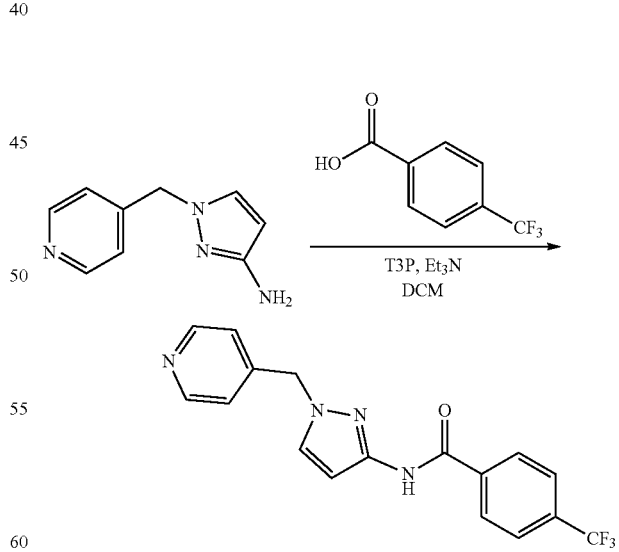

N-(1-(Pyridin-4-ylmethyl)-1H-pyrazol-3-yl)-4-(trifluoromethyl)benzamide. $^1$H NMR (CDCl$_3$, 400 MHz) δ 8.59 (d, J=5.2 Hz, 3H), 8.00 (d, J=8.0 Hz, 2H), 7.75 (d, J=8.4 Hz, 2H), 7.46 (d, J=2.4 Hz, 1H), 7.06 (d, J=5.2 Hz, 2H), 6.97 (s, 1H), 5.24 (s, 2H); LCMS: ESI-MS m/z: 347.0 [M+H]$^+$.

Example 58

2-Fluoro-N-(1-(pyridin-4-ylmethyl)-1H-pyrazol-3-yl)benzamide

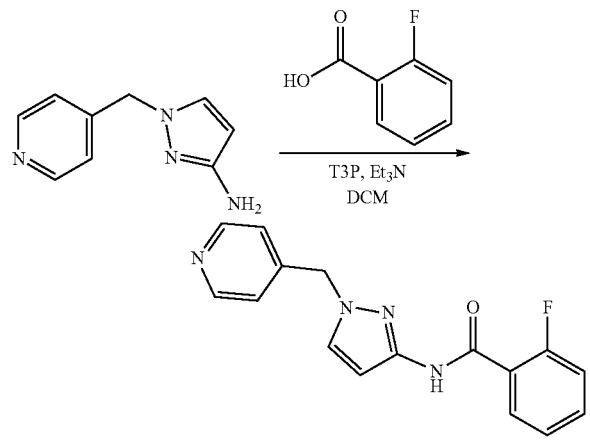

2-Fluoro-N-(1-(pyridin-4-ylmethyl)-1H-pyrazol-3-yl)benzamide. $^1$H NMR (DMSO-d$_6$, 400 MHz) δ 8.97 (d, J=14.0 Hz, 1H), 8.59 (s, 2H), 8.21-8.16 (m, 1H), 7.55-7.50 (m, 1H), 7.43 (d, J=2.4 Hz, 1H), 7.34-7.29 (m, 1H), 7.20-7.15 (m, 1H), 7.05 (d, J=4.0 Hz, 2H), 6.96 (d, J=2.4 Hz, 1H), 5.25 (s, 2H); LCMS: ESI-MS m/z: 297.0 [M+H]$^+$.

Example 59

3-Fluoro-N-(1-(pyridin-4-ylmethyl)-1H-pyrazol-3-yl)benzamide

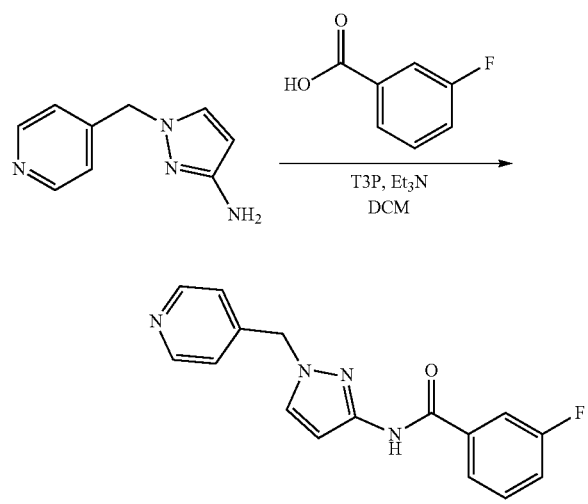 [SMILES: Nc1ccn(Cc2ccncc2)n1 ; O=C(O)c1cccc(F)c1 ; O=C(Nc1ccn(Cc2ccncc2)n1)c1cccc(F)c1]

3-Fluoro-N-(1-(pyridin-4-ylmethyl)-1H-pyrazol-3-yl)benzamide. $^1$H NMR (CDCl$_3$, 400 MHz) δ 5.58 (s, 3H), 7.64-7.60 (m, 2H), 7.48-7.42 (m, 2H), 7.26-7.22 (m, 1H), 7.04 (d, J=5.2 Hz, 2H), 6.94 (d, J=2.0 Hz, 1H), 5.23 (s, 2H); LCMS: ESI-MS m/z: 297.0 [M+H]$^+$.

Example 60

3-Fluoro-N-(1-(pyridin-4-ylmethyl)-1H-pyrazol-3-yl)benzamide

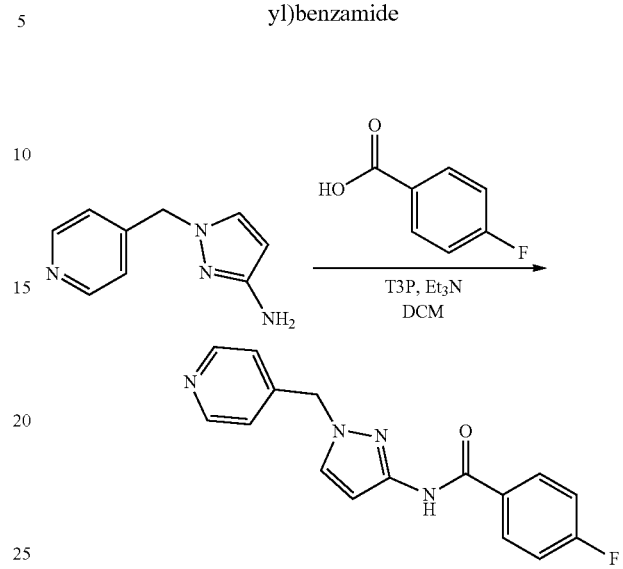

3-Fluoro-N-(1-(pyridin-4-ylmethyl)-1H-pyrazol-3-yl)benzamide. $^1$H NMR (CDCl$_3$, 400 MHz) δ 8.58 (dd, J=4.8, 1.6 Hz, 2H), 8.42 (s, 1H), 7.91-7.87 (m, 2H), 7.45 (d, J=2.4 Hz, 1H), 7.19-7.13 (m, 2H), 7.04 (d, J=6.0 Hz, 2H), 6.94 (d, J=2.4 Hz, 1H), 5.23 (s, 2H); LCMS: ESI-MS m/z: 297.0 [M+H]$^+$.

Example 61

N-(1-(Pyridin-4-ylmethyl)-1H-pyrazol-3-yl)picolinamide

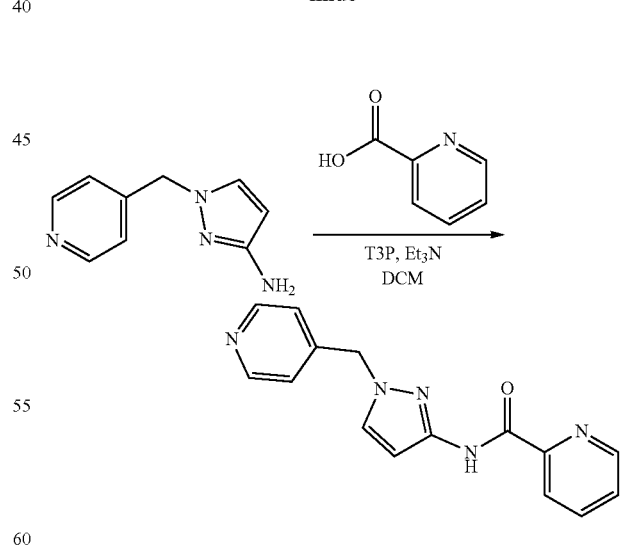

N-(1-(Pyridin-4-ylmethyl)-1H-pyrazol-3-yl)picolinamide. $^1$H NMR (DMSO-d$_6$, 400 MHz) δ 10.47 (s, 1H), 8.69 (d, J=4.8 Hz, 1H), 8.53 (dd, J=4.4, 1.6 Hz, 2H), 8.15-8.13 (m, 1H), 8.09-8.05 (m, 1H), 7.90 (d, J=2.4 Hz, 1H), 7.69-7.66 (m, 1H), 7.16 (d, J=5.6 Hz, 2H), 6.74 (d, J=2.4 Hz, 1H), 5.36 (s, 2H); LCMS: ESI-MS m/z: 280.1 [M+H]$^+$.

Example 62

N-(1-(Pyridin-4-ylmethyl)-1H-pyrazol-3-yl)nicotinamide

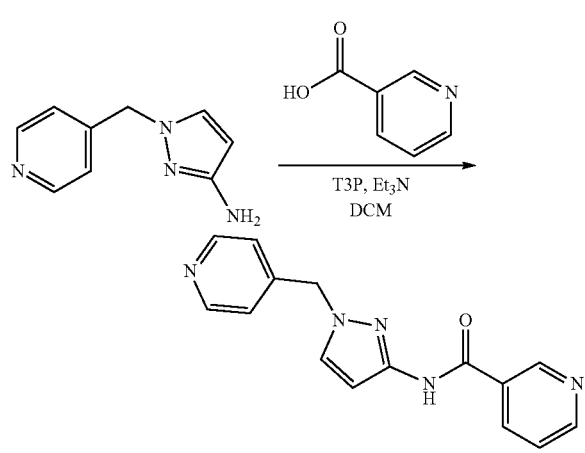

N-(1-(Pyridin-4-ylmethyl)-1H-pyrazol-3-yl)nicotinamide. ¹H NMR (DMSO-d₆, 400 MHz) δ 11.17 (s, 1H), 9.11 (d, J=1.6 Hz, 1H), 8.72 (d, J=6.4 Hz, 1H), 8.54 (d, J=6.0 Hz, 2H), 8.33-8.30 (m, 1H), 7.89 (d, J=2.4 Hz, 1H), 7.53-7.50 (m, 1H), 7.15 (d, J=6.0 Hz, 2H), 6.73 (d, J=2.4 Hz, 1H), 5.36 (s, 2H); LCMS: ESI-MS m/z: 280.1 [M+H]⁺.

Example 63

N-(1-(Pyridin-4-ylmethyl)-1H-pyrazol-3-yl)chromane-3-carboxamide

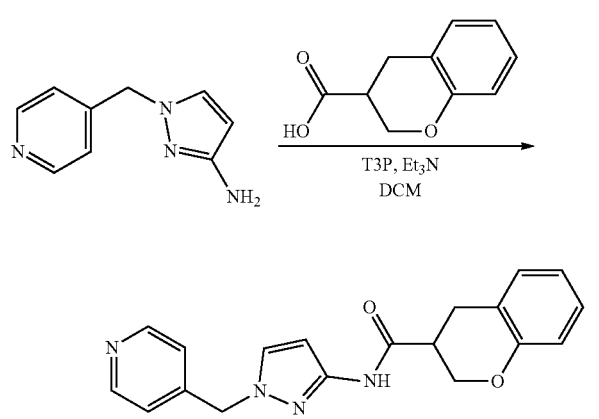

N-(1-(Pyridin-4-ylmethyl)-1H-pyrazol-3-yl)chromane-3-carboxamide. ¹H NMR (DMSO-d₆, 400 MHz) δ 10.78 (s, 1H), 8.53 (dd, J=4.4, 1.6 Hz, 2H), 7.82 (d, J=2.4 Hz, 1H), 7.13-7.07 (m, 4H), 6.86-6.82 (m, 1H), 6.76 (d, J=8.0 Hz, 1H), 6.56 (d, J=2.4 Hz, 1H), 5.30 (s, 2H), 4.38-4.35 (m, 1H), 3.96 (t, J=10.0 Hz, 1H), 3.00-2.86 (m, 3H); LCMS: ESI-MS m/z: 335.0 [M+H]⁺.

Example 64

5-Methoxy-N-(1-(pyridin-4-ylmethyl)-1H-pyrazol-3-yl)thiophene-2-carboxamide

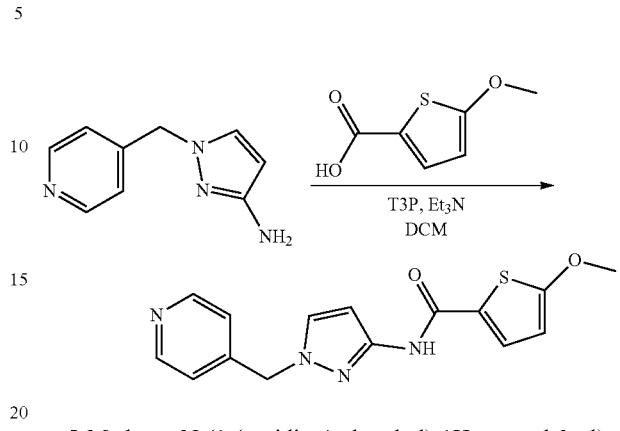

5-Methoxy-N-(1-(pyridin-4-ylmethyl)-1H-pyrazol-3-yl)thiophene-2-carboxamide. ¹H NMR (DMSO-d₆, 400 MHz) δ 10.80 (s, 1H), 8.53 (dd, J=4.8, 1.2 Hz, 2H), 7.84-7.82 (m, 2H), 7.14 (dd, J=4.6, 1.6 Hz, 2H), 6.60 (d, J=2.4 Hz, 1H), 6.37 (d, J=4.4 Hz, 1H), 5.33 (s, 2H), 3.91 (s, 3H); LCMS: ESI-MS m/z: 315.1 [M+H]⁺.

Example 65

4-Bromo-N-(1-(pyridin-4-ylmethyl)-1H-pyrazol-3-yl)thiophene-2-carboxamide

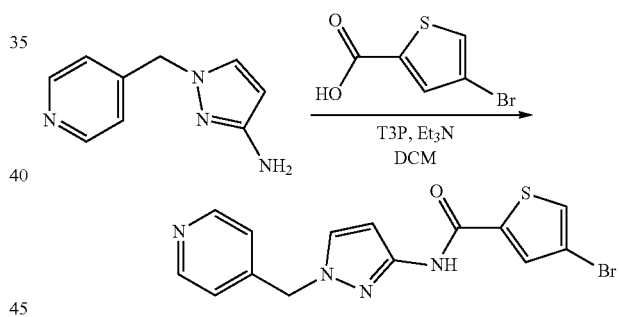

4-Bromo-N-(1-(pyridin-4-ylmethyl)-1H-pyrazol-3-yl)thiophene-2-carboxamide. ¹H NMR (DMSO-d₆, 400 MHz) δ 11.15 (s, 1H), 8.54 (dd, J=4.4, 1.6 Hz, 2H), 8.12 (d, J=0.8 Hz, 1H), 7.97 (d, J=1.2 Hz, 1H), 7.88 (d, J=2.4 Hz, 1H), 7.15 (d, J=6.0 Hz, 2H), 6.65 (d, J=2.4 Hz, 1H), 5.35 (s, 2H); LCMS: ESI-MS m/z: 362.0 [M+H]⁺.

Example 66

5-Methyl-N-(1-(pyridin-4-ylmethyl)-1H-pyrazol-3-yl)thiophene-3-carboxamide

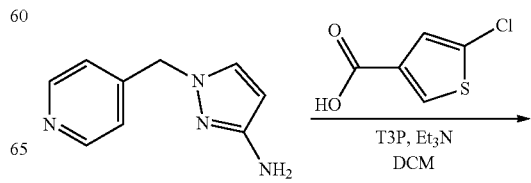

-continued

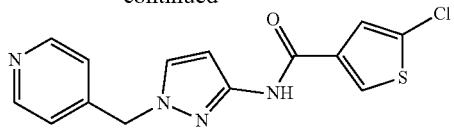

5-Chloro-N-(1-(pyridin-4-ylmethyl)-1H-pyrazol-3-yl)thiophene-3-carboxamide. ¹H NMR (DMSO-d₆, 400 MHz) δ 11.13 (s, 1H), 8.53 (d, J=6.0 Hz, 2H), 7.97 (d, J=4.0 Hz, 1H), 7.88 (d, J=2.4 Hz, 1H), 7.21 (d, J=4.0 Hz, 1H), 7.14 (d, J=5.6 Hz, 2H), 6.63 (d, J=2.0 Hz, 1H), 5.35 (s, 2H); LCMS: ESI-MS m/z: 319.0 [M+H]⁺.

Example 67

5-Methyl-N-(1-(pyridin-4-ylmethyl)-1H-pyrazol-3-yl)thiophene-3-carboxamide

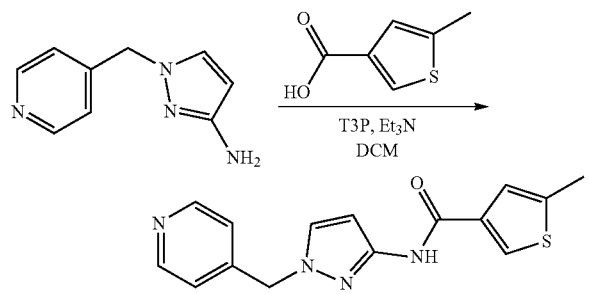

5-Methyl-N-(1-(pyridin-4-ylmethyl)-1H-pyrazol-3-yl)thiophene-3-carboxamide. ¹H NMR (DMSO-d₆, 400 MHz) δ 10.87 (s, 1H), 8.53 (d, J=6.0 Hz, 2H), 7.89-7.85 (m, 2H), 7.14 (d, J=6.0 Hz, 2H), 6.86 (d, J=4.8 Hz, 1H), 6.63 (d, J=2.4 Hz, 1H), 5.34 (s, 2H), 2.47 (s, 3H); LCMS: ESI-MS m/z: 299.0 [M+H]⁺.

Example 68

2,2,2-Trifluoro-N-(1-(pyridin-4-ylmethyl)-1H-pyrazol-3-yl)acetamide

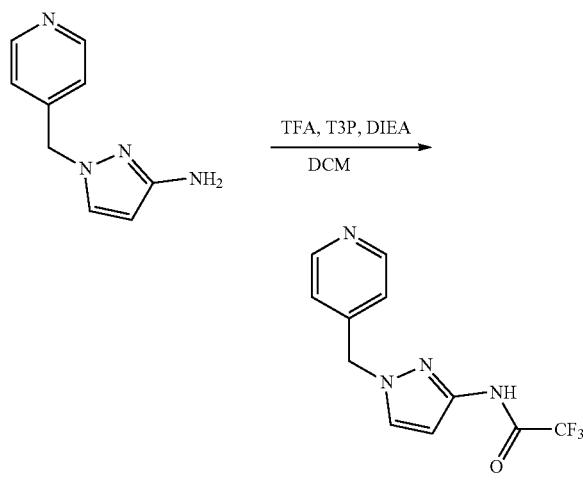

2,2,2-Trifluoro-N-(1-(pyridin-4-ylmethyl)-1H-pyrazol-3-yl)acetamide. A mixture of 1-(pyridin-4-ylmethyl)-1H-pyrazol-3-amine (Intermediate 2, 50 mg, 0.287 mmol, 1.0 equiv.), T3P (273 mg, 50% sol. in ethyl acetate, 0.431 mmol, 1.5 equiv.), DIPEA (74 mg, 0.574 mmol, 2.0 equiv.) and TFA (49 mg, 0.431 mmol, 1.5 equiv.) in dichloromethane (2 mL) was stirred at 25° C. for 2 h. The mixture was concentrated in vacuo, and the crude product was purified by silica gel column chromatography (0-5% methanol in DCM) to afford 2,2,2-trifluoro-N-(1-(pyridin-4-ylmethyl)-1H-pyrazol-3-yl)acetamide (20 mg, 26% yield) as a white solid. ¹H-NMR (DMSO-d₆, 400 MHz) δ 12.08 (s, 1H), 8.54 (d, J=6.0 Hz, 2H), 7.94 (s, 1H), 7.15 (d, J=6.0 Hz, 2H), 6.59 (d, J=2.4 Hz, 1H), 5.38 (s, 2H); LCMS: ESI-MS m/z: 271.0 [M+H]⁺.

Example 69

N-(1-(Pyridin-4-ylmethyl)-1H-pyrazol-3-yl)benzamide

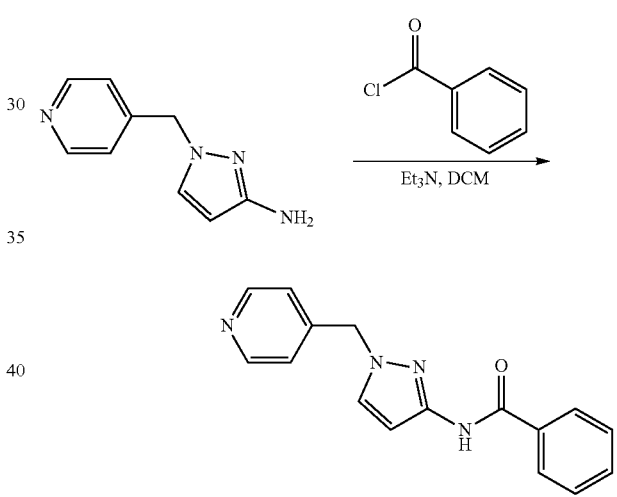

N-(1-(Pyridin-4-ylmethyl)-1H-pyrazol-3-yl)benzamide. To a stirred solution of 1-(pyridin-4-ylmethyl)-1H-pyrazol-3-amine (Intermediate 2, 80 mg, 0.457 mmol, 1.0 equiv.) and triethylamine (92.3 mg, 0.914 mmol, 2.0 equiv.) in anhydrous DCM (1.5 mL) at room temperature was added benzoyl chloride (96 mg, 0.685 mmol, 1.50 equiv.). The resulting mixture was stirred at room temperature for 2 h. The mixture was diluted with DCM (10 mL) and washed with water (3×8 mL). The organic layer was dried over sodium sulfate, filtered, and concentrated in vacuo. The crude product was purified by RP-HPLC (Method C, 15-40% MeCN/10 mM NH₄HCO₃+0.025% NH₃ in H₂O) to afford N-(1-(pyridin-4-ylmethyl)-1H-pyrazol-3-yl)benzamide (30 mg, 24% yield) as a white solid. ¹H NMR (DMSO-d₆, 400 MHz) δ 10.90 (s, 1H), 8.54 (d, J=6.0 Hz, 2H), 7.99 (d, J=8.8 Hz, 2H), 7.87 (d, J=2.0 Hz, 1H), 7.57-7.53 (m, 1H), 7.49-7.46 (m, 2H), 7.15 (d, J=6.0 Hz, 1H), 6.73 (d, J=2.4 Hz, 2H), 5.35 (s, 2H); LCMS: ESI-MS m/z: 279.0 [M+H]⁺.

Example 70

N-(1-(Pyridin-4-ylmethyl)-1H-pyrazol-3-yl)benzenesulfonamide

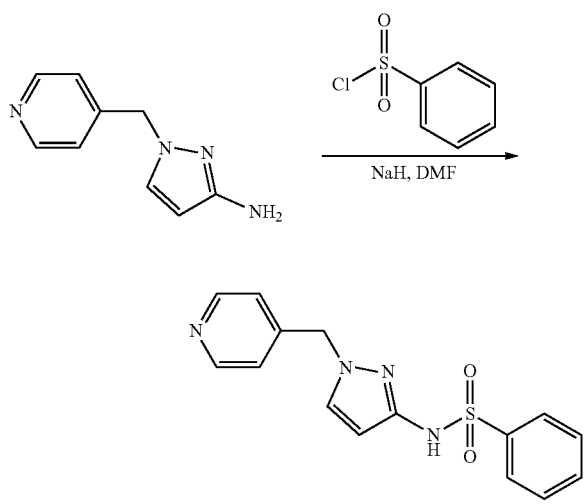 [SMILES: Nc1ccn(Cc2ccncc2)n1 ; O=S(=O)(Cl)c1ccccc1 ; O=S(=O)(Nc1ccn(Cc2ccncc2)n1)c1ccccc1]

N-(1-(Pyridin-4-ylmethyl)-1H-pyrazol-3-yl)benzenesulfonamide. To a stirred solution of 1-(pyridin-4-ylmethyl)-1H-pyrazol-3-amine (80 mg, 0.457 mmol, 1.0 equiv.) in anhydrous DMF (2 mL) was added sodium hydride (36.6 mg, 60% in mineral oil, 0.914 mmol, 2.0 equiv.). The resulting mixture was stirred at room temperature for 45 min and benzenesulfonyl chloride (120 mg, 0.685 mmol, 1.50 equiv.) was then added. The mixture was stirred at room temperature for 2 h. The mixture was diluted with ethyl acetate (10 mL) and washed with saturated aqueous NH$_4$Cl (3×5 mL). The organic layer was dried over sodium sulfate, filtered and concentrated in vacuo. The crude product was purified by RP-HPLC (Method C, 15-40% MeCN/10 mM NH$_4$HCO$_3$+0.025% NH$_3$ in H$_2$O) to afford N-(1-(pyridin-4-ylmethyl)-1H-pyrazol-3-yl)benzenesulfonamide (30 mg, 21% yield) as a white solid. $^1$H NMR (DMSO-d$_6$, 400 MHz) δ 8.44 (d, J=6.0 Hz, 2H), 7.73 (d, J=8.4 Hz, 2H), 7.68 (m, 1H), 7.59-7.56 (m, 1H), 7.51-7.47 (m, 2H), 6.87 (d, J=6.0 Hz, 2H), 5.99 (s, 1H), 5.17 (s, 2H); LCMS: ESI-MS m/z: 315.0 [M+H]$^+$.

Example 71

1-Phenyl-N-(1-(pyridin-4-ylmethyl)-1H-pyrazol-3-yl)methanesulfonamide

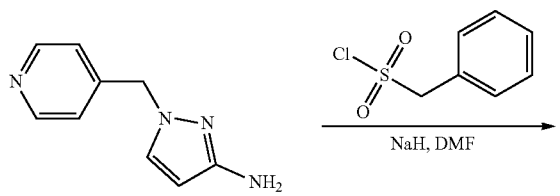

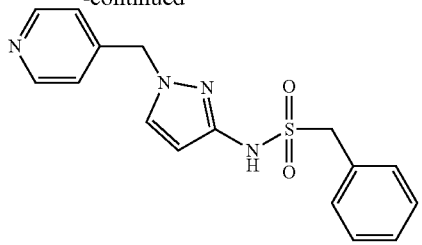

1-Phenyl-N-(1-(pyridin-4-ylmethyl)-1H-pyrazol-3-yl)methanesulfonamide. Prepared and purified according to EXAMPLE 68. $^1$H NMR (DMSO-d$_6$, 400 MHz) δ 8.58 (dd, J=4.8, 1.6 Hz, 2H), 8.43 (br, 1H), 7.27 (d, J=2.4 Hz, 1H), 7.20 (s, 5H), 7.04 (d, J=5.6 Hz, 2H), 6.26 (d, J=2.4 Hz, 1H), 5.11 (s, 2H), 4.26 (s, 2H); LCMS: ESI-MS m/z: 329.0 [M+H]$^+$.

Example 72

2,2-Dimethyl-N-(1-(pyridin-4-ylmethyl)-1H-pyrazol-3-yl)benzo[d][1,3]dioxole-5-carboxamide

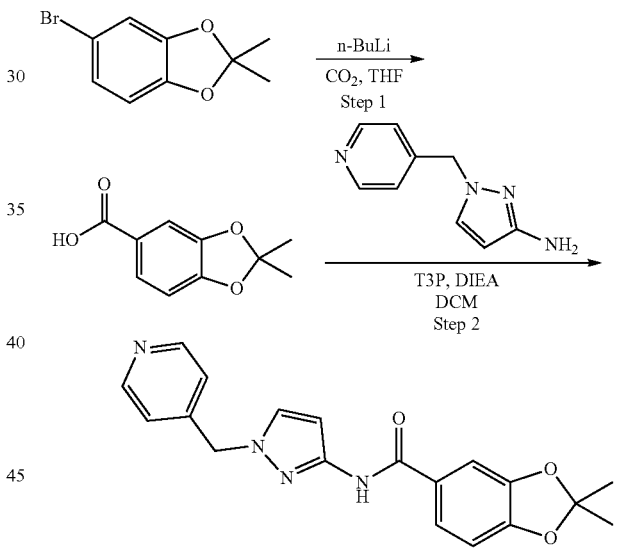

Step 1: 2,2-Dimethylbenzo[d][1,3]dioxole-5-carboxylic acid. To a stirred solution of 5-bromo-2,2-dimethylbenzo[d][1,3]dioxole (500 mg, 2.19 mmol, 1.0 equiv.) in anhydrous THF (10 mL) was added n-BuLi (1.31 mL, 2.5 M in hexane, 3.3 mmol, 1.50 equiv.) dropwise at −60° C. under nitrogen. After the addition, the mixture was stirred at −60° C. for 1 h, then dry ice (1 g solid, 22.7 mmol, 10.4 equiv.) was added. The resulting mixture was stirred at 0° C. for 1.5 h. The mixture was diluted with ethyl acetate (25 mL), treated with aqueous HCl (0.5 M) to adjust to pH 6. The organic layer was separated and dried over sodium sulfate, filtered, and concentrated in vacuo. The crude product was purified by silica gel column chromatography (0-5% methanol in DCM) to afford 2,2-dimethylbenzo[d][1,3]dioxole-5-carboxylic acid (300 mg, 70% yield) as a light yellow solid. $^1$H NMR (DMSO-d$_6$, 400 MHz) δ 12.71 (br, 1H), 7.51 (d, J=8.0 Hz, 1H), 7.29 (s, 1H), 6.92 (d, J=8.0 Hz, 1H), 1.67 (s, 6H); LCMS: ESI-MS m/z: 195 [M+H]$^+$.

Step 2: 2,2-Dimethyl-N-(1-(pyridin-4-ylmethyl)-1H-pyrazol-3-yl)benzo[d][1,3]dioxole-5-carboxamide. A mixture of 1-(pyridin-4-ylmethyl)-1H-pyrazol-3-amine (Intermediate 2, 150 mg, 0.862 mmol, 1.0 equiv.), T3P (822 mg, 50% sol. in ethyl acetate, 1.29 mmol, 1.50 equiv.), triethylamine (130.6 mg, 1.29 mmol, 1.50 equiv.) and 2,2-dimethylbenzo[d][1,3]dioxole-5-carboxylic acid (250 mg, 1.29 mmol, 1.50 equiv.) in DCM (10 mL) was stirred at 25° C. for 2 h. The mixture was concentrated in vacuo and the crude product was purified by RP-HPLC (Method C, 15-40% MeCN/10 mM NH$_4$HCO$_3$+0.025% NH$_3$ in H$_2$O) to afford 2,2-dimethyl-N-(1-(pyridin-4-ylmethyl)-1H-pyrazol-3-yl)benzo[d][1,3]dioxole-5-carboxamide (60 mg, 20% yield) as a white solid. $^1$H NMR (DMSO-d$_6$, 400 MHz) δ 10.68 (s, 1H), 8.53 (dd, J=4.4, 1.6 Hz, 2H), 7.85 (d, J=2.4 Hz, 1H), 7.58 (d, J=8.2, 2.0 Hz, 1H), 7.47 (d, J=1.6 Hz, 1H), 7.14 (dd, J=4.4, 1.6 Hz, 2H), 6.90 (d, J=8.0 Hz, 1H), 6.69 (d, J=2.4 Hz, 1H), 5.34 (s, 2H), 1.67 (s, 6H); LCMS: ESI-MS m/z: 351.1 [M+H]$^+$.

Example 73

3,4-Dihydroxy-N-(1-(pyridin-4-ylmethyl)-1H-pyrazol-3-yl)benzamide

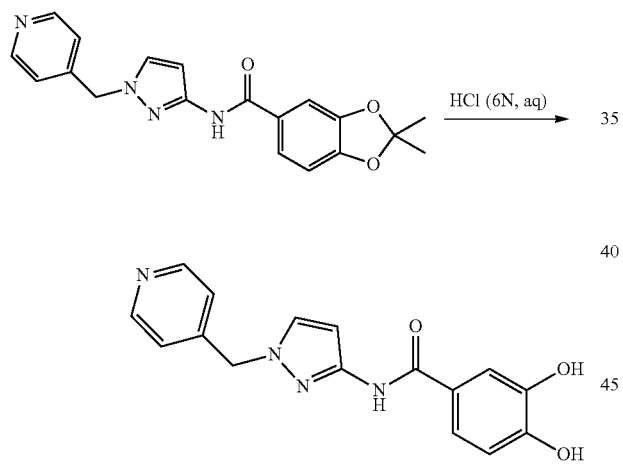

3,4-Dihydroxy-N-(1-(pyridin-4-ylmethyl)-1H-pyrazol-3-yl)benzamide. A mixture of 2,2-dimethyl-N-(1-(pyridin-4-ylmethyl)-1H-pyrazol-3-yl)benzo[d][1,3]dioxole-5-carboxamide (Example 71, 20 mg, 0.057 mmol, 1.0 equiv.) and aqueous HCl (6 N, 1 mL, 6 mmol, 105 equiv.) was stirred at room temperature for 2 h. The mixture was treated with saturated aqueous NaHCO$_3$ to adjust to pH 7-8 and concentrated in vacuo. The crude product was purified by RP-HPLC (Method C, 15-40% MeCN/10 mM NH$_4$HCO$_3$+ 0.025% NH$_3$ in H$_2$O) to afford 3,4-dihydroxy-N-(1-(pyridin-4-ylmethyl)-1H-pyrazol-3-yl)benzamide (10 mg, 0.032 mmol, 56% yield) as a white solid. $^1$H NMR (DMSO-d$_6$, 400 MHz) δ 10.50 (s, 1H), 9.51-9.11 (m, 2H), 8.53 (d, J=6.0 Hz, 2H), 7.82 (d, J=2.4 Hz, 1H), 7.39-7.37 (m, 2H), 7.14 (d, J=5.6 Hz, 2H), 6.74 (d, J=8.8 Hz, 1H), 6.67 (d, J=2.0 Hz, 1H), 5.33 (s, 2H); LCMS: ESI-MS m/z: 351.1 [M+H]$^+$.

Example 74

4-Methoxy-N-(1-(pyridin-4-ylmethyl)-1H-pyrazol-3-yl)benzenesulfonamide

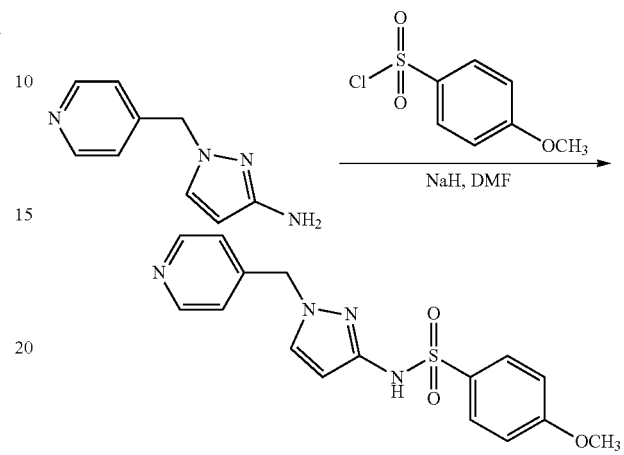

4-Methoxy-N-(1-(pyridin-4-ylmethyl)-1H-pyrazol-3-yl)benzenesulfonamide. To a stirred solution of 1-(pyridin-4-ylmethyl)-1H-pyrazol-3-amine (80 mg, 0.457 mmol, 1.0 equiv.) in anhydrous DMF (2 mL) was added sodium hydride (36.6 mg, 60% in mineral oil, 0.914 mmol, 2.0 equiv.). The resulting mixture was stirred at room temperature for 45 min and 4-methoxybenzenesulfonyl chloride (141.1 mg, 0.685 mmol, 1.50 equiv.) was then added. The mixture was stirred at room temperature for 2 h. The mixture was diluted with ethyl acetate (10 mL) and washed with saturated aqueous NH$_4$Cl (3×5 mL). The organic layer was dried over sodium sulfate, filtered and concentrated in vacuo. The crude product was purified by silica gel column chromatography (0-10% methanol in DCM) to afford 4-methoxy-N-(1-(pyridin-4-ylmethyl)-1H-pyrazol-3-yl)benzenesulfonamide (80 mg, 51% yield) as a light yellow solid. LCMS: ESI-MS m/z: 345.0 [M+H]$^+$.

Example 75

4-Methoxy-N-methyl-N-(1-(pyridin-4-ylmethyl)-1H-pyrazol-3-yl)benzenesulfonamide

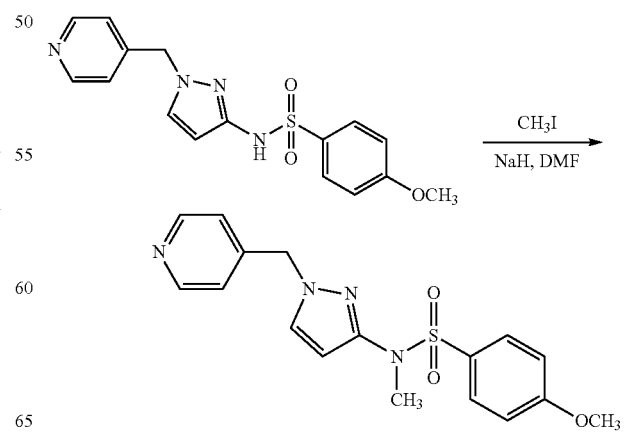

4-Methoxy-N-methyl-N-(1-(pyridin-4-ylmethyl)-1H-pyrazol-3-yl)benzenesulfonamide. To a stirred solution of 4-methoxy-N-(1-(pyridin-4-ylmethyl)-1H-pyrazol-3-yl)benzenesulfonamide (Example 73 80 mg, 0.232 mmol, 1.0 equiv.) in anhydrous DMF (1 mL) was added sodium hydride (14 mg, 60% in mineral oil, 0.348 mmol, 1.50 equiv.). The resulting mixture was stirred at room temperature for 45 min and methyl iodide (49.4 mg, 0.348 mmol, 1.50 equiv.) was then added. The mixture was stirred at room temperature for 2 h. The mixture was diluted with ethyl acetate (10 mL), washed with saturated aqueous NH$_4$Cl (2×4 mL). The organic layer was dried over sodium sulfate, filtered and concentrated in vacuo. The crude product was purified by RP-HPLC (Method C, 15-40% MeCN/10 mM NH$_4$HCO$_3$+0.025% NH$_3$·H$_2$O in H$_2$O) to afford 4-methoxy-N-methyl-N-(1-(pyridin-4-ylmethyl)-1H-pyrazol-3-yl)benzenesulfonamide (25 mg, 30% yield) as a white solid. $^1$H NMR (DMSO-d$_6$, 400 MHz) δ 8.47 (d, J=5.6 Hz, 2H), 7.83 (d, J=2.0 Hz, 1H), 7.53 (d, J=8.8 Hz, 2H), 7.04 (d, J=8.8 Hz, 2H), 6.89 (d, J=6.0 Hz, 2H), 6.34 (d, J=2.0 Hz, 1H), 5.27 (s, 2H), 3.82 (s, 3H), 3.06 (s, 3H); LCMS: ESI-MS m/z: 359.0 [M+H]$^+$.

Example 76

3-Fluoro-N-(1-(pyridin-4-ylmethyl)-1H-pyrazol-3-yl)benzenesulfonamide

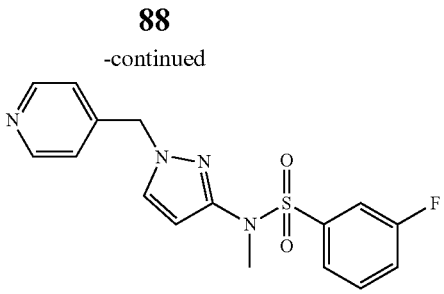

3-Fluoro-N-methyl-N-(1-(pyridin-4-ylmethyl)-1H-pyrazol-3-yl)benzenesulfonamide. Prepared and purified according to Example 74. $^1$H NMR (DMSO-d$_6$, 400 MHz) δ 8.47 (d, J=6 Hz, 2H), 7.86 (d, J=6.4 Hz, 1H), 7.57-7.63 (m, 2H), 7.41-7.48 (m, 2H), 6.89 (d, J=5.6 Hz, 2H), 6.36 (d, J=6 Hz, 1H), 5.29 (s, 2H), 3.34 (s, 3H); LCMS: ESI-MS m/z: 347.0 [M+H]$^+$.

Example 78 and Example 78a (R)-3-Fluoro-4-(1-(1-(2,2,2-trifluoroethyl)-1H-pyrazol-3-yl)ethyl)pyridine and (S)-3-Fluoro-4-(1-(1-(2,2,2-trifluoroethyl)-1H-pyrazol-3-yl)ethyl)pyridine

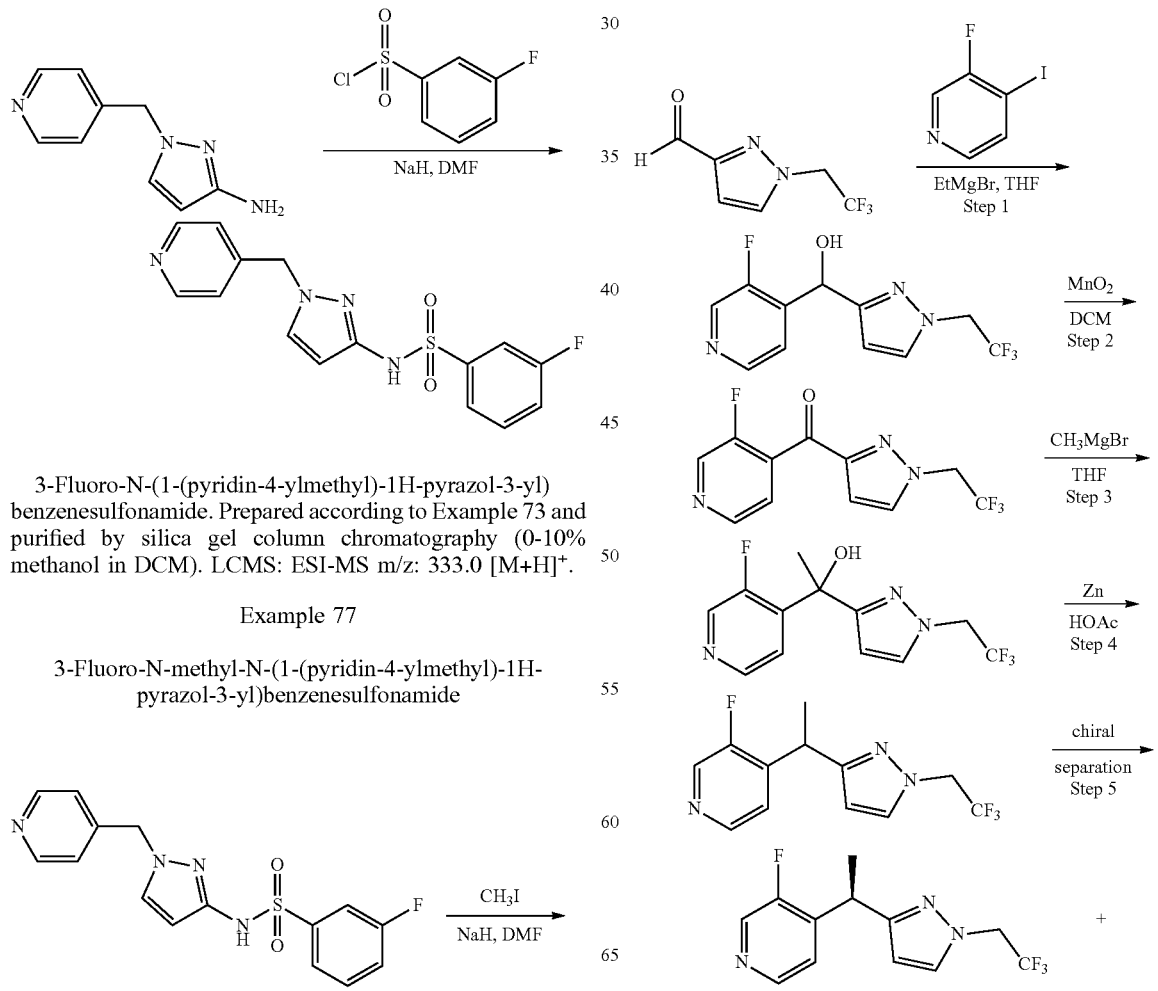

3-Fluoro-N-(1-(pyridin-4-ylmethyl)-1H-pyrazol-3-yl)benzenesulfonamide. Prepared according to Example 73 and purified by silica gel column chromatography (0-10% methanol in DCM). LCMS: ESI-MS m/z: 333.0 [M+H]$^+$.

Example 77

3-Fluoro-N-methyl-N-(1-(pyridin-4-ylmethyl)-1H-pyrazol-3-yl)benzenesulfonamide

-continued

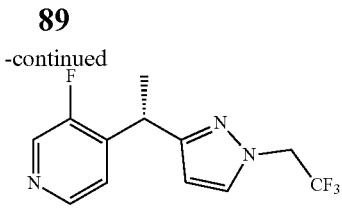

Step 1: (3-Fluoropyridin-4-yl)(1-(2,2,2-trifluoroethyl)-1H-pyrazol-3-yl)methanol. To a solution of 3-fluoro-4-iodopyridine (222 mg, 1.0 mmol, 1.0 equiv.) in anhydrous THF (10 mL, 0.1 M) under an atmosphere of nitrogen gas was added ethylmagnesium bromide (3.0 M in diethyl ether, 0.4 mL, 1.2 mmol, 1.2 equiv.). The resulting mixture was stirred at room temperature for 30 min and a solution of 1-(2,2,2-trifluoroethyl)-1H-pyrazole-3-carbaldehyde (Intermediate 6, 178 mg, 1.0 mmol, 1.0 equiv.) in anhydrous THF (1 mL) was added. The resulting mixture was stirred at room temperature for 1 h. The reaction mixture was quenched with and water (5 mL) and extracted with EtOAc (3×10 mL). The combined organic layers were dried over anhydrous sodium sulfate, filtered, and concentrated in vacuo to afford (3-fluoropyridin-4-yl)(1-(2,2,2-trifluoroethyl)-1H-pyrazol-3-yl)methanol (210 mg) as a brown oil. The material was carried forward to the next step without further purification. LCMS: ESI-MS m/z: 276.0 [M+H]$^+$.

Step 2: (3-Fluoropyridin-4-yl)(1-(2,2,2-trifluoroethyl)-1H-pyrazol-3-yl)methanone. A solution of (3-fluoropyridin-4-yl)(1-(2,2,2-trifluoroethyl)-1H-pyrazol-3-yl)methanol (210 mg, 0.76 mmol, 1.0 equiv.) in DCM (20 mL) was treated with MnO$_2$ powder (0.66 g, 7.6 mmol, 10 equiv.) and allowed to stir at room temperature for 5 h. The resulting mixture was filtered and concentrated in vacuo to afford (3-fluoropyridin-4-yl)(1-(2,2,2-trifluoroethyl)-1H-pyrazol-3-yl)methanone (190 mg) as a brown oil. The material was carried forward to the next step without further purification. LCMS: ESI-MS m/z: 274.0 [M+H]$^+$.

Step 3: 1-(3-Fluoropyridin-4-yl)-1-(1-(2,2,2-trifluoroethyl)-1H-pyrazol-3-yl)ethan-1-ol. To a solution of (3-fluoropyridin-4-yl)(1-(2,2,2-trifluoroethyl)-1H-pyrazol-3-yl) methanone (190 mg, 0.70 mmol, 1.0 equiv.) in anhydrous THF (10 mL, 0.07 M) under an atmosphere of nitrogen gas was added methylmagnesium bromide (3.0 M in diethyl ether, 0.6 mL, 1.75 mmol, 2.5 equiv.). The resulting mixture was allowed to stir at room temperature for 2 h. The reaction was quenched with water (5 mL) and extracted with EtOAc (3×10 mL). The combined organic layers were dried over anhydrous sodium sulfate, filtered, and concentrated in vacuo to afford 1-(3-fluoropyridin-4-yl)-1-(1-(2,2,2-trifluoroethyl)-1H-pyrazol-3-yl)ethan-1-ol (100 mg) as a brown oil. The material was carried forward to the next step without further purification. LCMS: ESI-MS m/z: 290.0 [M+H]$^+$.

Step 4: (rac)-3-Fluoro-4-(1-(1-(2,2,2-trifluoroethyl)-1H-pyrazol-3-yl)ethyl)pyridine. A solution of 1-(3-fluoropyridin-4-yl)-1-(1-(2,2,2-trifluoroethyl)-1H-pyrazol-3-yl)ethan-1-ol (100 mg, 0.35 mmol, 1.0 equiv.) in acetic acid (20 mL, 0.018 M) was treated with zinc powder (458 mg, 7.0 mmol, 20 equiv.). The resulting mixture was stirred at 130° C. for 16 h. The mixture was filtered, and the filtrate treated with sodium carbonate solution until the pH measured 9-10. The mixture was diluted with water (40 mL) and extracted with EtOAc (4×20 mL). The combined organic layers were dried over sodium sulfate, filtered, and concentrated in vacuo. The residue was purified by silica gel column chromatography (0-5% MeOH/DCM) to afford (rac)-3-fluoro-4-(1-(1-(2,2,2-trifluoroethyl)-1H-pyrazol-3-yl)ethyl)pyridine (20 mg, 21% yield) as a white solid. LCMS: ESI-MS m/z: 274.0 [M+H]$^+$.

Step 5: (R)-3-Fluoro-4-(1-(1-(2,2,2-trifluoroethyl)-1H-pyrazol-3-yl)ethyl)pyridine and (S)-3-fluoro-4-(1-(1-(2,2,2-trifluoroethyl)-1H-pyrazol-3-yl)ethyl)pyridine. The racemic mixture was separated into its enantiomers by chiral SFC separation to afford (R)-3-fluoro-4-(1-(1-(2,2,2-trifluoroethyl)-1H-pyrazol-3-yl)ethyl)pyridine and (S)-3-fluoro-4-(1-(1-(2,2,2-trifluoroethyl)-1H-pyrazol-3-yl)ethyl)pyridine. Absolute stereochemistry was not determined.

Example 78; first eluting peak, retention time: P1=9.587 min: $^1$H NMR (400 MHz, CDCl$_3$) δ 8.38 (d, J=2.0 Hz, 1H), 8.31 (d, J=5.2 Hz, 1H), 7.45 (d, J=2.4 Hz, 1H), 7.15 (dd, J=4.8 Hz, J=5.2 Hz, 1H), 6.20 (d, J=2.4 Hz, 1H), 4.70 (q, J=8.4 Hz, 2H), 4.56 (q, J=7.2 Hz, 1H), 1.65 (d, J=7.6 Hz, 3H); LCMS: ESI-MS m/z: 274.0 [M+H]$^+$. Example 78a; second eluting; retention time: P2=11.325 min: $^1$H NMR (400 MHz, CDCl$_3$) δ 8.38 (d, J=2.0 Hz, 1H), 8.31 (d, J=5.2 Hz, 1H), 7.45 (d, J=2.4 Hz, 1H), 7.15 (dd, J=4.8 Hz, J=5.2 Hz, 1H), 6.20 (d, J=2.4 Hz, 1H), 4.70 (q, J=8.4 Hz, 2H), 4.56 (q, J=7.2 Hz, 1H), 1.65 (d, J=7.6 Hz, 3H); LCMS: ESI-MS m/z: 274.0 [M+H]$^+$.

Example 79

(rac)-4-(Fluoro(1-(2,2,2-trifluoroethyl)-1H-pyrazol-3-yl)methyl)pyridine

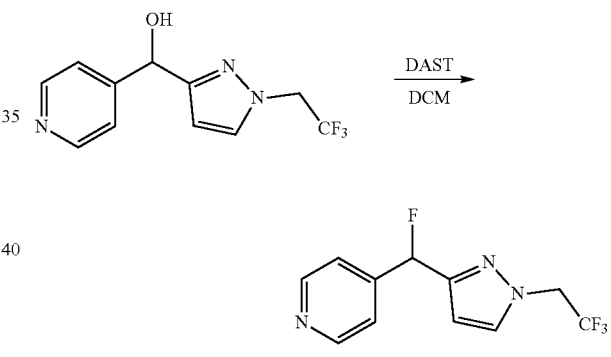

(rac)-4-(Fluoro(1-(2,2,2-trifluoroethyl)-1H-pyrazol-3-yl)methyl)pyridine. To a solution of pyridin-4-yl(1-(2,2,2-trifluoroethyl)-1H-pyrazol-3-yl)methanol (Step 1, Intermediate 10, 60 mg, 0.23 mmol, 1.0 equiv.) in anhydrous dichloromethane (3 mL, 0.08 M) was added DAST [(diethylamino)sulfur trifluoride] (45 mg, 0.28 mmol, 1.2 equiv.) at 0° C. The reaction was allowed to warmed to room temperature and stirred for 2 h. The solution was treated with sodium bicarbonate solution until the pH measured 7-8. The mixture was diluted with water (5 mL) and extracted with dichloromethane (3×20 mL). The combined organic layers were dried over sodium sulfate, filtered, and concentrated in vacuo. The residue was purified by silica gel column chromatography (5-50% EtOAc in hexanes) to afford 4-(fluoro (1-(2,2,2-trifluoroethyl)-1H-pyrazol-3-yl)methyl)pyridine (13 mg, 22% yield) as a yellow oil. $^1$H NMR (400 MHz, CDCl$_3$) δ 8.65 (d, J=4.8 Hz, 1H), 7.51 (d, J=1.6 Hz, 1H), 7.35 (d, J=5.6 Hz, 2H), 6.60 (d, J=44 Hz, 2H), 6.30 (d, J=1.6 Hz, 1H), 4.75 (q, J=8.4 Hz, 2H). LCMS: ESI-MS m/z: 260.0 [M+H]$^+$.

Example 80

(rac)-4-(1-(1-(2,2,2-Trifluoroethyl)-1H-pyrazol-3-yl)ethyl-1,2,2,2-$d_4$)pyridine

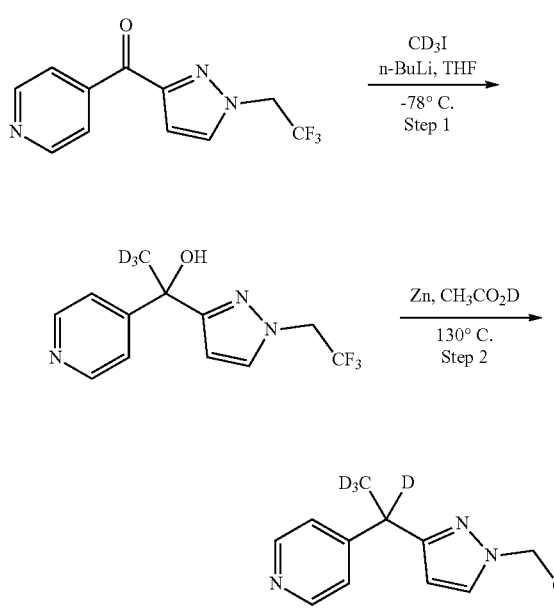

Step 1: 1-(Pyridin-4-yl)-1-(1-(2,2,2-trifluoroethyl)-1H-pyrazol-3-yl)ethan-2,2,2-$d_3$-1-ol. A solution of iodomethane-$d_3$ (dried over molecular sieves, 200 mg, 1.38 mmol, 4 equiv.) in anhydrous THF (6 mL, 0.23 M) under an atmosphere of argon was cooled to −78° C. To the solution was added n-butyllithium (1.6 M in hexanes, 1.47 mL, 2.35 mmol, 6.5 equiv.). The resulting mixture was stirred for 12 min at −78° C. The resulting solution was added slowly to a solution of pyridin-4-yl(1-(2,2,2-trifluoroethyl)-1H-pyrazol-3-yl)methanone (Intermediate 10, 88 mg, 0.345 mmol, 1.0 equiv.) in THF (3 mL) at −78° C. and stirred for 1 min. Then the reaction mixture was quenched with water (1 mL) and the resulting mixture was concentrated in vacuo. The residue was purified by silica gel column chromatography (0-10% MeOH/DCM) to 1-(pyridin-4-yl)-1-(1-(2,2,2-trifluoroethyl)-1H-pyrazol-3-yl)ethan-2,2,2-$d_3$-1-ol (11 mg, 12% yield) as a colorless film. LCMS: ESI-MS m/z: 275.2 [M+H]$^+$.

Step 2: 4-(1-(1-(2,2,2-Trifluoroethyl)-1H-pyrazol-3-yl)ethyl-1,2,2,2-$d_4$)pyridine. A solution of 1-(pyridin-4-yl)-1-(1-(2,2,2-trifluoroethyl)-1H-pyrazol-3-yl)ethan-2,2,2-$d_3$-1-ol (66 mg, 0.241 mmol, 1.0 equiv.) in acetic acid-d (30 mL, 0.33 M) was treated with zinc powder (157 mg, 2.41 mmol, 10 equiv.). The resulting mixture was stirred at 130° C. for 2 h. After filtration, the solution was treated with sodium bicarbonate until the pH measured 9-10. The mixture was concentrated in vacuo. The residue was purified by silica gel column chromatography (0-6% MeOH/DCM) to afford 4-(1-(1-(2,2,2-trifluoroethyl)-1H-pyrazol-3-yl)ethyl-1,2,2,2-$d_4$)pyridine (25 mg, 40% yield) as a colorless solid. $^1$H NMR (400 MHz, DMSO-$d_6$) δ 8.48-8.42 (m, 2H), 7.74 (d, J=2.3 Hz, 1H), 7.29-7.21 (m, 2H), 6.23 (d, J=2.4 Hz, 1H), 5.06 (q, J=9.2 Hz, 2H); LCMS: ESI-MS m/z: 260.2 [M+H]$^+$.

Example 81

(rac)-4-(Chloro(1-(2,2,2-trifluoroethyl)-1H-pyrazol-3-yl)methyl)pyridine

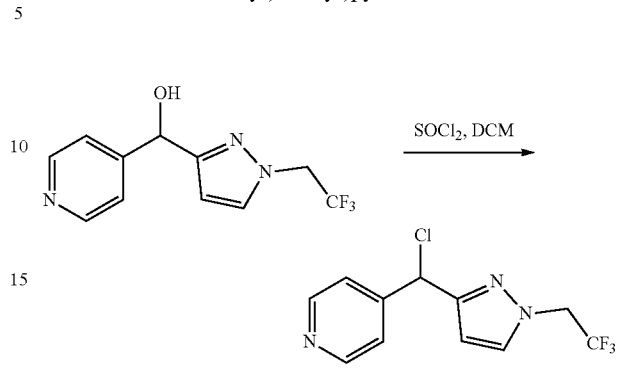

(rac)-4-(Chloro(1-(2,2,2-trifluoroethyl)-1H-pyrazol-3-yl)methyl)pyridine. To a solution of pyridin-4-yl(1-(2,2,2-trifluoroethyl)-1H-pyrazol-3-yl)methanol (Step 1, Intermediate 10, 28 mg, 0.11 mmol, 1.0 equiv.) in DCM (1 mL) at 0° C. was added SOCl$_2$ (246 mg, 2.07 mmol, 19 equiv.). The resulting mixture was stirred at room temperature for 2 h and then poured slowly into a cold Na$_2$CO$_3$ solution. The mixture was extracted with EtOAc (2×60 mL) and the combined organic layers were washed with brine, dried over anhydrous sodium sulfate, filtered and concentrated in vacuo. The residue was purified by RP-HPLC (Method D, 0-10% MeCN/0.1% TFA in H$_2$O) to afford to afford 4-(chloro(1-(2,2,2-trifluoroethyl)-1H-pyrazol-3-yl)methyl)pyridine (9 mg, 33% yield) as a colorless oil. $^1$H NMR (400 MHz, DMSO-$d_6$) δ 8.60 (s, 2H), 7.86 (d, J=2.4 Hz, 1H), 7.61-7.44 (m, 2H), 6.56-6.42 (m, 2H), 5.14 (q, J=9.2 Hz, 2H); LCMS: ESI-MS m/z: 276.1 [M+H]$^+$.

Example 82

(rac)-4-(1-(1-(2,2,2-Trifluoroethyl)-1H-pyrazol-3-yl)ethyl-1-d)pyridine

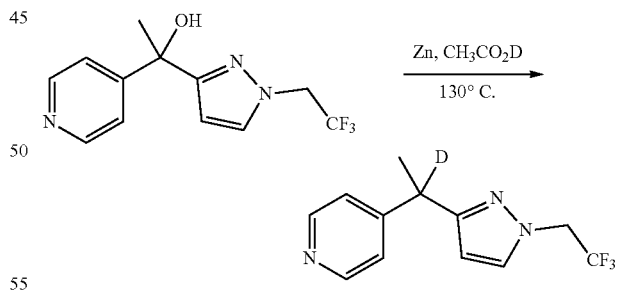

(rac)-4-(1-(1-(2,2,2-Trifluoroethyl)-1H-pyrazol-3-yl)ethyl-1-d)pyridine. A solution of 1-(pyridin-4-yl)-1-(1-(2,2,2-trifluoroethyl)-1H-pyrazol-3-yl)ethan-1-ol (Intermediate 7, 118 mg, 0.435 mmol, 1.0 equiv.) in acetic acid-d (3 mL, 0.145 M) was treated with zinc powder (24 mg, 4.35 mmol, 10 equiv.). The resulting mixture was stirred at 130° C. for 8 h. After filtration, the filtrate was treated with NaHCO$_3$ solution until the pH measured 9-10. The resulting mixture was concentrated in vacuo. The residue was purified by silica gel column chromatography (0-7% MeOH/DCM) to afford 4-(1-(1-(2,2,2-trifluoroethyl)-1H-pyrazol-3-yl)ethyl- 1-d)pyridine (91 mg, 81% yield) as a clear oil. $^1$H NMR (400 MHz, DMSO-d$_6$) δ 8.51-8.42 (m, 2H), 7.75 (d, J=2.4 Hz, 1H), 7.27 (ddd, J=9.8, 4.4, 1.8 Hz, 2H), 6.24 (d, J=2.3 Hz, 1H), 5.07 (q, J=9.2 Hz, 2H), 1.53 (s, 3H); LCMS: ESI-MS m/z: 257.1 [M+H]$^+$.

Example 83

4-((5-Methyl-1-(2,2,2-trifluoroethyl)-1H-pyrazol-3-yl)methyl)pyridine

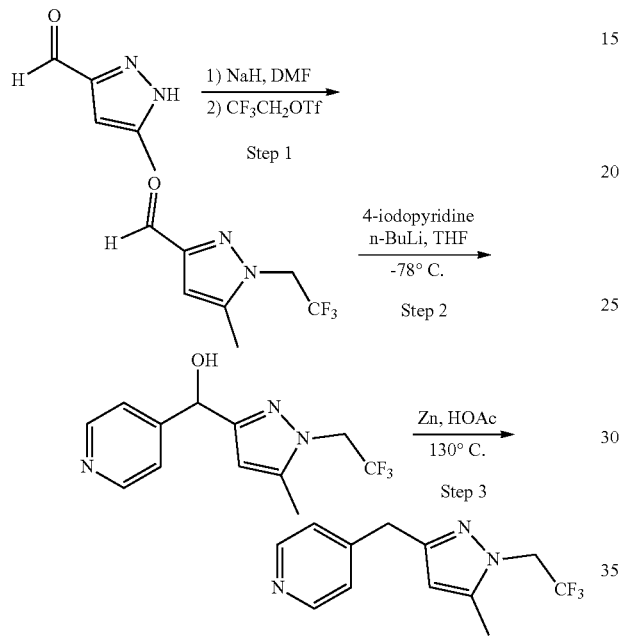

Step 1: 5-Methyl-1-(2,2,2-trifluoroethyl)-1H-pyrazole-3-carbaldehyde. Cs$_2$CO$_3$ (2.67 g, 8.18 mmol, 1.3 equiv.) was added slowly to a solution of 5-methyl-1H-pyrazole-3-carbaldehyde (0.693 g, 6.29 mmol, 1.0 equiv.) and 2,2,2-trifluoroethyl trifluoromethanesulfonate (1.75 g, 7.55 mmol, 1.2 equiv.) in DMF (32 mL) at 0° C. and the resulting mixture was stirred at room temperature for 5 h. The mixture was diluted with EtOAc (190 mL) and sequentially washed with water and brine. The organic layer was dried over anhydrous sodium sulfate, filtered, and concentrated in vacuo. The residue was purified by RP-HPLC (Method D, 0-20% MeCN/0.1% TFA in H$_2$O) to afford to afford 5-methyl-1-(2,2,2-trifluoroethyl)-1H-pyrazole-3-carbaldehyde (0.91 g, 75% yield) as a colorless oil. LCMS: ESI-MS m/z: 193.1 [M+H]$^+$.

Step 2: 5-Methyl-1-(2,2,2-trifluoroethyl)-1H-pyrazol-3-yl)(pyridin-4-yl)methanol. A solution of 4-iodopyridine (2.05 g, 9.99 mmol, 4 equiv.) in anhydrous THF (24 mL, 0.42 M) under an atmosphere of argon was cooled to −78° C. To the solution was added n-butyllithium (1.6 M in hexanes, 6.25 mL, 9.99 mmol, 4 equiv.). The resulting mixture was stirred for 8 min at −78° C. The resulting solution was added slowly to a solution of 5-methyl-1-(2,2,2-trifluoroethyl)-1H-pyrazole-3-carbaldehyde (480 mg, 2.5 mmol, 1.0 equiv.) in THF (4 mL) at −78° C. and stirred for 21 min at the same temperature. Then the reaction mixture was quenched with water and extracted with EtOAc. The combined organic layers were washed with brine, dried over anhydrous sodium sulfate, filtered and concentrated in vacuo. The residue was purified by silica gel column chromatography (0-10% MeOH/DCM) to afford 5-methyl-1-(2,2,2-trifluoroethyl)-1H-pyrazol-3-yl)(pyridin-4-yl)methanol (27 mg, 4% yield) as a clear oil. LCMS: ESI-MS m/z: 272.1 [M+H]$^+$.

Step 3: 4-((5-Methyl-1-(2,2,2-trifluoroethyl)-1H-pyrazol-3-yl)methyl)pyridine. A solution of 5-methyl-1-(2,2,2-trifluoroethyl)-1H-pyrazol-3-yl)(pyridin-4-yl)methanol (27 mg, 0.10 mmol, 1.0 equiv.) in acetic acid (6 mL, 0.167 M) was treated with zinc powder (65 mg, 1.0 mmol, 10 equiv.). The resulting mixture was stirred at 130° C. for 17 h. After filtration, the filtrate was treated with Na$_2$CO$_3$ solution to pH 9-10 and the resulting mixture was concentrated in vacuo. The residue was purified by silica gel column chromatography (0-7% MeOH/DCM) to afford 4-((5-methyl-1-(2,2,2-trifluoroethyl)-1H-pyrazol-3-yl)methyl)pyridine (4 mg, 16% yield) as a clear oil. $^1$H NMR (400 MHz, acetonitrile-d$_3$) δ 8.47-8.41 (m, 2H), 7.23-7.17 (m, 2H), 5.92 (s, 1H), 4.70 (q, J=8.8 Hz, 2H), 3.87 (s, 2H), 2.24 (s, 3H); LCMS: ESI-MS m/z: 256.1 [M+H]$^+$.

Example 84

1-((3-Methylpyridin-4-yl)methyl)-N-(2,2,2-trifluoroethyl)-1H-pyrazol-3-amine

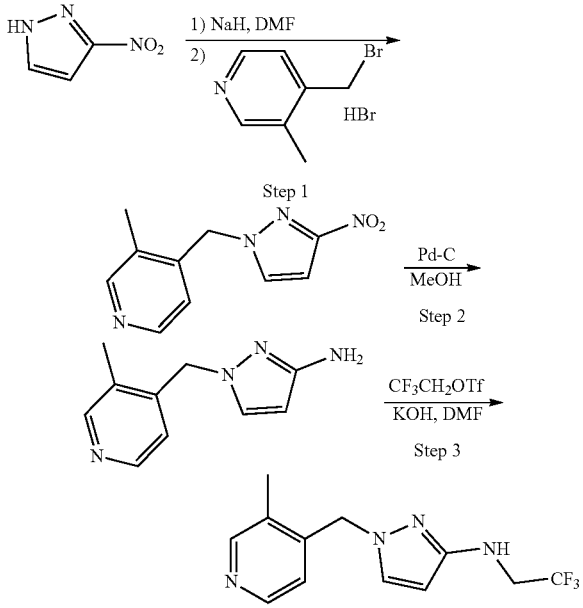

Step 1: 3-Methyl-4-((3-nitro-1H-pyrazol-1-yl)methyl)pyridine. NaH (60% in mineral oil, 82.7 mg, 1.57 mmol, 4.5 equiv.) was added to a solution of 3-nitro-1H-pyrazole (79 mg, 0.70 mmol, 2 equiv.) in DMF (4 mL) at 0° C. and stirred at 0° C. for 10 min. The resulting mixture was added to a solution of 4-(bromomethyl)-3-methylpyridine hydrogen bromide salt (93 mg, 0.345 mmol, 1.0 equiv.) in DMF (4 mL) at 0° C. The resulting mixture was stirred at room temperature for 2 h. The reaction mixture was quenched with water and concentrated in vacuo. The residue was purified by silica gel column chromatography (0-25% EtOAc (containing 1% Et$_3$N) in DCM) to afford 3-methyl- 4-((3-nitro-1H-pyrazol-1-yl)methyl)pyridine (32 mg, 42% yield) as a colorless film. LCMS: ESI-MS m/z: 219.1 [M+H]$^+$.

Step 2: 1-((3-Methylpyridin-4-yl)methyl)-1H-pyrazol-3-amine. A solution of 3-methyl-4-((3-nitro-1H-pyrazol-1-yl)methyl)pyridine (32 mg, 0.147 mmol, 1 equiv.) in MeOH (4 mL) was degassed with argon, then Pd—C (10%, wetted with water, 312 mg, 0.293 mmol, 2 equiv.) was added. After it was degassed with argon, H$_2$ balloon was installed, and the reaction stirred at room temperature under a hydrogen atmosphere for 2 h. The reaction mixture was filtered and filtrate was concentrated in vacuo to afford 1-((3-methylpyridin-4-yl)methyl)-1H-pyrazol-3-amine (27 mg, 98% yield) as a white solid. LCMS: ESI-MS m/z: 189.1 [M+H]$^+$.

Step 3: 1-((3-Methylpyridin-4-yl)methyl)-N-(2,2,2-trifluoroethyl)-1H-pyrazol-3-amine. 2,2,2-Trifluoroethyl trifluoromethanesulfonate (200 mg, 0.86 mmol, 6 equiv.) was added slowly to a mixture of 1-[(3-methylpyridin-4-yl)methyl]-1H-pyrazol-3-amine (27 mg, 0.143 mmol, 1.0 equiv.) and KOH (40 mg, 1.0 mmol, 5.8 equiv.) in DMF (1.3 mL) at 0° C. The resulting mixture was stirred at room temperature for 8 h. The reaction mixture was quenched with water and concentrated in vacuo. The residue was purified by RP-HPLC (Method D, 0-30% MeCN/0.1% TFA in H$_2$O) to afford 1-((3-methylpyridin-4-yl)methyl)-N-(2,2,2-trifluoroethyl)-1H-pyrazol-3-amine (8.0 mg, 20% yield), as a white solid. $^1$H NMR (400 MHz, acetonitrile-d$_3$) δ 12.8-13.4 (m, 1H), 8.50 (s, 1H), 8.45 (d, J=6.2 Hz, 1H), 7.60 (s, 1H), 7.17-7.19 (m, 1H), 5.89 (s, 1H), 5.43 (s, 2H), 3.87 (q, J=9.4 Hz, 2H), 2.48 (s, 3H); LCMS: ESI-MS m/z: 271.1 [M+H]$^+$.

Example 85

N-Ethyl-1-(pyridin-4-ylmethyl)-1H-pyrazol-3-amine

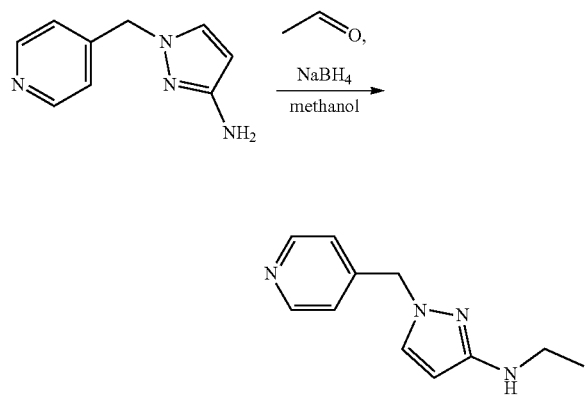

N-Ethyl-1-(pyridin-4-ylmethyl)-1H-pyrazol-3-amine. To a solution of 1-(pyridin-4-ylmethyl)-1H-pyrazol-3-amine (Intermediate 2, 60 mg, 0.345 mmol, 1.0 equiv.) in methanol (1 mL) was added acetaldehyde (0.2 mL, 99%, 3.45 mmol, 10 equiv.) at 0° C. via syringe. The resulting solution was allowed to warm to 20° C. over 2 h. Sodium borohydride (65.55 mg, 1.725 mmol, 5.0 equiv.) was added and the resulting mixture was stirred for 2 h. The reaction was concentrated in vacuo and the crude product was purified by silica gel column chromatography (0-5% methanol in DCM) to afford N-ethyl-1-(pyridin-4-ylmethyl)-1H-pyrazol-3-amine (15 mg, 0.074 mmol, 21% yield) as a white solid. $^1$H-NMR (DMSO-d$_6$, 400 MHz) δ 8.49 (d, J=6.0 Hz, 2H), 7.53 (d, J=2.4 Hz, 1H), 7.07 (d, J=5.6 Hz, 2H), 5.50 (d, J=2.4 Hz, 1H), 5.13 (s, 2H), 5.08 (br, 1H), 3.00-2.97 (m, 2H), 1.07 (t, J=6.8 Hz, 3H); LCMS: ESI-MS m/z: 203.1 [M+H]$^+$.

Example 86

N-Methyl-1-(pyridin-4-ylmethyl)-1H-pyrazol-3-amine

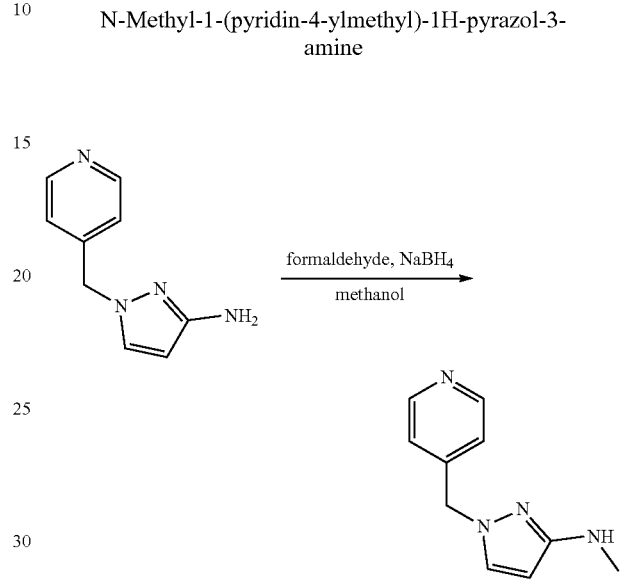

N-methyl-1-(pyridin-4-ylmethyl)-1H-pyrazol-3-amine. To a solution of 1-(pyridin-4-ylmethyl)-1H-pyrazol-3-amine (Intermediate 2, 50 mg, 0.287 mmol, 1.0 equiv.) in methanol (1 mL) was added polyformaldehyde (86 mg, 2.87 mmol, 10 equiv.). After the addition, the mixture was stirred at room temperature for 2 h. Then, sodium borohydride (54.5 mg, 1.43 mmol, 5.0 equiv.) was added. The mixture was stirred for another 2 h, concentrated in vacuo, and the crude product was purified by silica gel column chromatography (0-5% methanol in DCM) to afford N-methyl-1-(pyridin-4-ylmethyl)-1H-pyrazol-3-amine (32 mg, 59% yield) as a white solid. $^1$H-NMR (DMSO-d$_6$, 400 MHz) δ 8.50 (d, J=8.8 Hz, 2H), 7.53 (d, J=2.4 Hz, 1H), 7.07 (d, J=6.4 Hz, 2H), 5.49 (d, J=2.4 Hz, 1H), 5.11 (s, 2H), 5.08-5.11 (m, 1H), 2.61 (d, J=5.2 Hz, 3H); LCMS: ESI-MS m/z: 189.0 [M+H]$^+$.

Example 87

N-(1-(Pyridin-4-ylmethyl)-1H-pyrazol-3-yl)acetamide

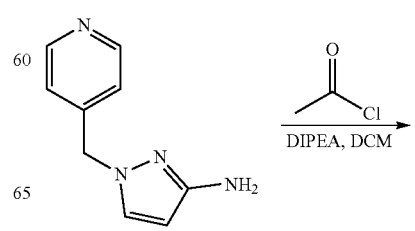

7.50 (d, J=6.4 Hz, 2H), 6.25 (d, J=2.4 Hz, 1H), 5.59 (s, 2H); LCMS: ESI-MS m/z: 307.0 [M+H]+.

Example 89

(R)-1-(1-(Pyridin-4-yl)ethyl)-N-(2,2,2-trifluoroethyl)-1H-pyrazol-3-amine

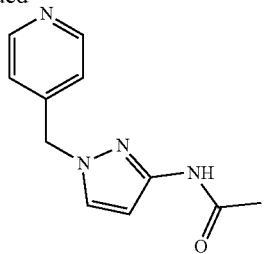

N-(1-(Pyridin-4-ylmethyl)-1H-pyrazol-3-yl)acetamide. To a mixture of 1-(pyridin-4-ylmethyl)-1H-pyrazol-3-amine (Intermediate 2, 50 mg, 0.287 mmol, 1.0 equiv.) and DIPEA (74 mg, 0.574 mmol, 2.0 equiv.) in dichloromethane (2 mL) was added acetyl chloride (34 mg, 0.431 mmol, 1.5 equiv.) at room temperature. After 2 h, the mixture was concentrated in vacuo, and the crude product was purified by silica gel column chromatography (0-5% methanol in DCM) to afford N-(1-(pyridin-4-ylmethyl)-1H-pyrazol-3-yl)acetamide (10 mg, 16% yield) as a white solid. $^{1}$H-NMR (DMSO-$d_6$, 400 MHz) δ 10.41 (s, 1H), 8.51 (dd, J=4.4, 1.6 Hz, 2H), 7.76 (d, J=2.0 Hz, 1H), 7.10 (dd, J=4.4, 1.6 Hz, 2H), 8.52 (d, J=2.4 Hz, 1H), 5.28 (s, 2H), 1.96 (s, 3H); LCMS: ESI-MS m/z: 217.1 [M+H]+.

Example 88

1,1,1-Trifluoro-N-(1-(pyridin-4-ylmethyl)-1H-pyrazol-3-yl)methanesulfonamide

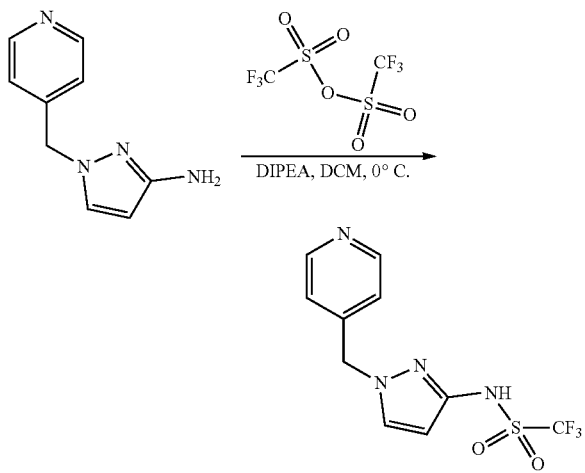

1,1,1-Trifluoro-N-(1-(pyridin-4-ylmethyl)-1H-pyrazol-3-yl)methanesulfonamide. To a mixture of 1-(pyridin-4-ylmethyl)-1H-pyrazol-3-amine (Intermediate 2, 50 mg, 0.287 mmol, 1.0 equiv.) and DIPEA (74 mg, 0.574 mmol, 2.0 equiv.) in DCM (2 mL) was added trifluoromethanesulfonic anhydride (121 mg, 0.431 mmol, 1.5 equiv.) at 0° C. After the addition, the mixture was stirred at room temperature for 2 h. The mixture was concentrated in vacuo, and the crude product was purified by silica gel column chromatography (0-5% methanol in DCM) to afford 1,1,1-trifluoro-N-(1-(pyridin-4-ylmethyl)-1H-pyrazol-3-yl)methanesulfonamide (10 mg, 11% yield) as a white solid. $^{1}$H-NMR (DMSO-$d_6$, 400 MHz) δ 8.79 (d, J=6.4 Hz, 2H), 7.96 (d, J=2.0 Hz, 1H),

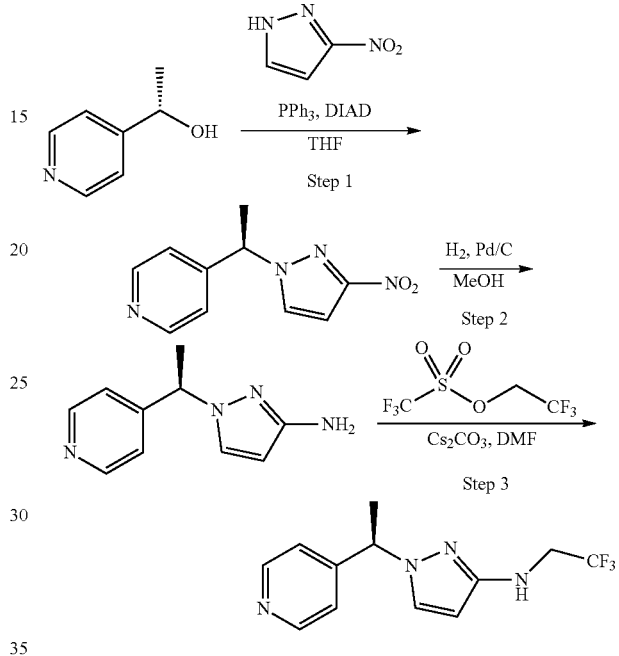

Step 1: (R)-4-(1-(3-Nitro-1H-pyrazol-1-yl)ethyl)pyridine. To a mixture of (S)-1-(pyridin-4-yl)ethan-1-ol (200 mg, 1.626 mmol, 1.0 equiv.), 3-nitro-1H-pyrazole (238 mg, 2.11 mmol, 1.3 equiv.) and triphenylphosphine (553 mg, 2.11 mmol, 1.3 equiv.) in anhydrous THF (10 mL) was added DIAD (426 mg, 2.11 mmol, 1.3 equiv.) dropwise at 0° C. under nitrogen. After the addition, the mixture was stirred at room temperature for 48 h. The mixture was concentrated in vacuo, and the crude product was purified by silica gel column chromatography (5%-15% ethyl acetate in petroleum ether) to afford (R)-4-(1-(3-nitro-1H-pyrazol-1-yl)ethyl)pyridine (180 mg, 51% yield) as a light yellow solid. LCMS: ESI-MS m/z: 219.0 [M+H]+.

Step 2: (R)-1-(1-(Pyridin-4-yl)ethyl)-1H-pyrazol-3-amine. To a stirred solution of (R)-4-(1-(3-nitro-1H-pyrazol-1-yl)ethyl)pyridine (180 mg, 0.825 mmol) in methanol (10 mL) was added Pd/C (10%, 20 mg). The mixture was stirred under a H$_2$ atmosphere at room temperature for 6 h. The mixture was filtered and the filtrate was concentrated in vacuo. The crude product was purified by silica gel column (0-10% methanol in DCM) to afford (R)-1-(1-(pyridin-4-yl)ethyl)-1H-pyrazol-3-amine (90 mg, 58% yield) as a light yellow solid. LCMS: ESI-MS m/z: 189.0 [M+H]+.

Step 3: (R)-1-(1-(Pyridin-4-yl)ethyl)-N-(2,2,2-trifluoroethyl)-1H-pyrazol-3-amine. To a mixture of (R)-1-(1-(pyridin-4-yl)ethyl)-1H-pyrazol-3-amine (90 mg, 0.478 mmol, 1.0 equiv.) and cesium carbonate (311 mg, 0.956 nmol, 2.0 equiv.) in DMF (3 mL) was added 2,2,2-trifluoroethyl trifluoromethanesulfonate (333 mg, 1.43 mmol, 1.5 equiv.). The mixture was stirred at room temperature for 8 h. The reaction was then filtered. The filtrate was concentrated in vacuo and the crude product was purified by silica gel column chromatography (0-10% methanol in DCM) to afford (R)-1-(1-(pyridin-4-yl)ethyl)-N-(2,2,2-trifluoroethyl)-1H-pyrazol-3-amine (31 mg, 0.114 mmol, 24% yield) as a white solid. $^1$H-NMR (CD$_3$OD, 400 MHz) δ 8.46 (d, J=6.0 Hz, 2H), 7.57 (d, J=2.4 Hz, 1H), 7.18-7.16 (m, 2H), 5.73 (d, J=2.8 Hz, 1H), 5.44-5.39 (m, 1H), 3.84-3.77 (m, 2H), 1.82 (d, J=7.2 Hz, 3H); LCMS: ESI-MS m/z: 271.0 [M+H]$^+$.

Chiral Analysis Conditions (ee %: 99%):
Injection Volume: 5 μL
Co-Solvent: MeOH (0.2% Methanol Ammonia)
Column: Amylose-2 4.6*150 mm 5 μm
Column Temperature: 40.1° C.
CO$_2$ Flow Rate: 3.6 mL/min
Co-Solvent Flow Rate: 0.4 mL/min
Co-Solvent %: 10
Total Flow: 4 mL/min
Front Pressure: 146 kPa
Back Pressure: 121 kPa
Pressure Drop: 25 kPa
PDA Start Wavelength: 214 nm
PDA Start Wavelength: 359 nm
Retention time: 1.28 min Example 90

N-Methyl-1-(pyridin-4-ylmethyl)-N-(2,2,2-trifluoroethyl)-1H-pyrazol-3-amine

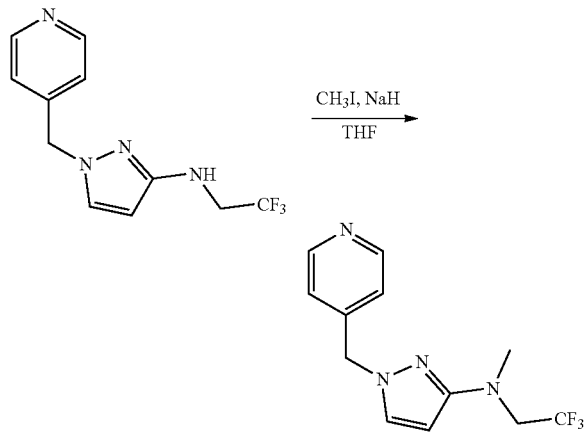

N-Methyl-1-(pyridin-4-ylmethyl)-N-(2,2,2-trifluoroethyl)-1H-pyrazol-3-amine. To a stirred solution of 1-(pyridin-4-ylmethyl)-N-(2,2,2-trifluoroethyl)-1H-pyrazol-3-amine (Example 26, 40 mg, 0.156 mmol, 1.0 equiv.) in anhydrous THF (2 mL) was added sodium hydride (12.5 mg, 60% in mineral oil, 0.312 mmol, 2.0 equiv.) under nitrogen. After 1 h, iodomethane (33.2 mg, 0.234 mmol, 1.5 equiv.) was added. The mixture was stirred at room temperature for another 2 h. The mixture was diluted with ethyl acetate (10 mL), washed with water (2×4 mL) and brine (4 mL), the organic layer was collected, dried over anhydrous sodium sulfate, filtered and concentrated in vacuo. The residue was purified by silica gel column chromatography (0-5% methanol in DCM) to afford N-methyl-1-(pyridin-4-ylmethyl)-N-(2,2,2-trifluoroethyl)-1H-pyrazol-3-amine (10 mg, 0.037 mmol, 23% yield) as a white solid. $^1$H-NMR (CDCl$_3$, 400 MHz) δ 8.54 (d, J=2.4 Hz, 2H), 7.25 (s, 1H), 7.02 (d, J=6.0 Hz, 2H), 5.67 (d, J=2.4 Hz, 1H), 5.15 (s, 2H), 3.86 (dd, J=6.0, 5.2 Hz, 2H), 3.02 (s, 2H); LCMS: ESI-MS m/z: 271.0 [M+H]$^+$.

Example 91

(rac)-N-Methyl-N-(1-(1-(pyridin-4-yl)ethyl)-1H-pyrazol-3-yl)thiazol-2-amine

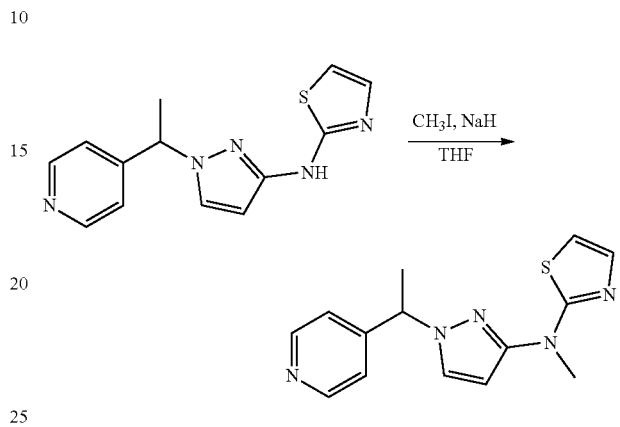

N-Methyl-N-(1-(1-(pyridin-4-yl)ethyl)-1H-pyrazol-3-yl)thiazol-2-amine. To a stirred solution of N-(1-(1-(pyridin-4-yl)ethyl)-1H-pyrazol-3-yl)thiazol-2-amine (Example 1, 10 mg, 0.037 mmol, 1.0 equiv.) in anhydrous DMF (0.4 mL) was added sodium hydride (3 mg, 60% in mineral oil, 0.074 mmol, 2.0 equiv.) at room temperature. The mixture was stirred for 30 min and then iodomethane (8 mg, 0.056 mmol, 1.5 equiv.) was added. The mixture was stirred at room temperature for another 2 h. The mixture was concentrated in vacuo and the crude product was purified by silica gel column chromatography (0%-10% methanol in DCM) to afford N-methyl-N-(1-(1-(pyridin-4-yl)ethyl)-1H-pyrazol-3-yl)thiazol-2-amine (5 mg, 47% yield) as a white solid. $^1$H-NMR (CD$_3$OD, 400 MHz) δ 8.48 (s, 2H), 7.75 (d, J=2.4 Hz, 1H), 7.32 (s, 2H), 7.26 (d, J=3.6 Hz, 1H), 6.80 (d, J=3.6 Hz, 1H), 6.25 (d, J=2.4 Hz, 1H), 5.55-5.60 (m, 1H), 3.59 (s, 3H), 1.91 (d, J=7.2 Hz, 3H); LCMS: ESI-MS m/z: 286.0 [M+H]$^+$.

Example 92

(rac)-4-(1-(1-Benzyl-1H-pyrazol-3-yl)ethyl)pyridine

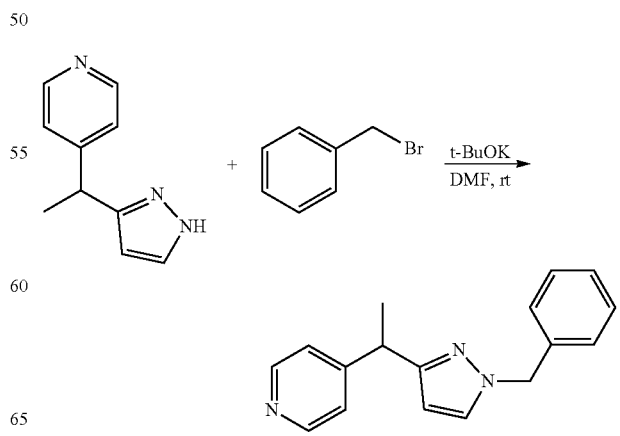

(rac)-4-(1-(1-Benzyl-1H-pyrazol-3-yl)ethyl)pyridine. To a solution of 4-(1-(1H-pyrazol-3-yl)ethyl)pyridine (50 mg, 0.29 mmol, 1.0 equiv.) in anhydrous DMF (3 mL) was added potassium tert-butoxide (65 mg, 0.58 mmol, 2.0 equiv.) and (bromomethyl)benzene (148 mg, 0.87 mmol, 3.0 equiv.) at 0° C. The resulting mixture was warmed and stirred room temperature for 16 h. The mixture was diluted with EtOAc (30 mL) and washed with water (2×10 mL) and brine (10 mL). The organic fraction was dried over anhydrous sodium sulfate, filtered, and concentrated in vacuo. The crude material was purified by silica gel column chromatography (5-50% EtOAc in hexanes) to afford (rac)-4-(1-(1-benzyl-1H-pyrazol-3-yl)ethyl)pyridine (7.7 mg, 10% yield) as a yellow oil. $^1$H NMR (400 MHz, CDCl$_3$) δ 8.43 (d, J=6.0 Hz, 2H), 7.27-7.23 (m, 3H), 7.20 (s, 1H), 7.13-7.10 (m, 4H), 5.98 (d, J=2 Hz, 1H), 5.21 (s, 2H), 4.14 (q, J=7.2 Hz, 1H), 1.58 (d, J=7.2 Hz, 3H); LCMS: ESI-MS m/z: 264.1 [M+H]$^+$.

Example 93

N-(Cyclopropylmethyl)-1-(pyridin-4-ylmethyl)-1H-pyrazol-3-amine

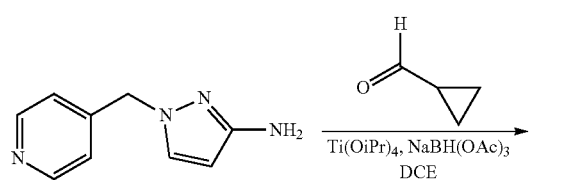

N-(cyclopropylmethyl)-1-(pyridin-4-ylmethyl)-1H-pyrazol-3-amine. To a mixture of 1-(pyridin-4-ylmethyl)-1H-pyrazol-3-amine (Intermediate 2, 50 mg, 0.287 mmol, 1.0 equiv.), cyclopropanecarbaldehyde (22 mg, 0.316 mmol, 1.1 equiv.) in 1,2-di chloroethane (2 mL) was added titanium (1V) isopropoxide (98 mg, 0.344 mmol, 1.2 equiv.) at room temperature. The mixture was stirred at room temperature for 3 h, and then sodium triacetoxyborohyride (182 mg, 0.861 mmol, 3.0 equiv.) was added. After the addition, the mixture was stirred at room temperature for another 3 h. The mixture was diluted with DCM (5 mL), quenched with the addition of water (5 mL) and stirred for 3 min. The precipitate was filtered off, the organic layer was separated, dried over anhydrous sodium sulfate, filtered and concentrated in vacuo. The crude product was purified by silica gel column (0%-10% methanol in DCM) to afford N-(cyclopropylmethyl)-1-(pyridin-4-ylmethyl)-1H-pyrazol-3-amine (25 mg, 38% yield) as a white solid. $^1$H-NMR (DMSO-d$_6$, 400 MHz) δ 8.35-8.34 (m, 2H), 7.37 (d, J=2.0 Hz, 1H), 6.92 (d, J=4.3 Hz, 2H), 5.37 (d, J=2.1 Hz, 1H), 5.04-5.01 (m, 1H), 4.97 (s, 2H), 2.71-2.68 (m, 2H), 0.85-0.82 (m, 1H), 0.24-0.22 (m, 2H), 0.01 (d, J=4.7 Hz, 2H); LCMS: ESI-MS m/z: 229.1 [M+H]$^+$.

Example 94

N-Propyl-1-(pyridin-4-ylmethyl)-1H-pyrazol-3-amine

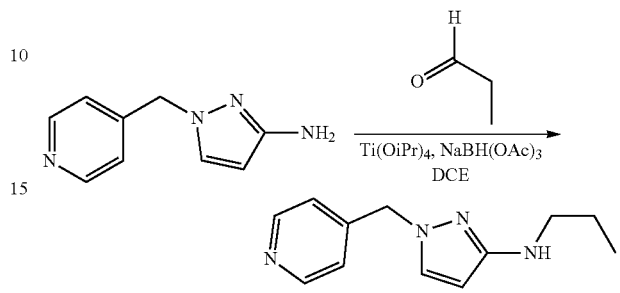

N-Propyl-1-(pyridin-4-ylmethyl)-1H-pyrazol-3-amine. The compound was prepared following the procedure for EXAMPLE 93. Purified by silica gel column (0%-10% methanol in DCM), 40% yield. $^1$H-NMR (CDCl$_3$, 400 MHz) δ 8.54 (d, J=6.4 Hz, 2H), 7.22 (d, J=2.4 Hz, 1H), 7.02 (d, J=6.4 Hz, 2H), 5.63 (d, J=2.4 Hz, 1H), 5.12 (s, 2H), 3.11 (t, J=7.2 Hz, 2H), 1.61 (d, J=7.6 Hz, 2H), 0.97 (t, J=7.2 Hz, 3H); LCMS: ESI-MS m/z: 217.2 [M+H]$^+$.

Example 95

N-(Cyclobutylmethyl)-1-(pyridin-4-ylmethyl)-1H-pyrazol-3-amine

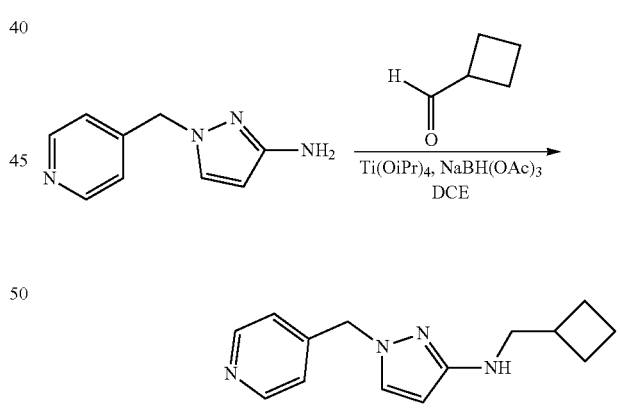

N-(Cyclobutylmethyl)-1-(pyridin-4-ylmethyl)-1H-pyrazol-3-amine. The compound was prepared following the procedure for EXAMPLE 93. Purified by silica gel column (0-10% methanol in DCM), 40% yield. $^1$H-NMR (DMSO-d$_6$, 400 MHz) δ 8.49 (dd, J=4.4, 1.6 Hz, 2H), 7.51 (d, J=2.3 Hz, 1H), 7.07 (d, J=6.0 Hz, 2H), 5.49 (d, J=2.3 Hz, 1H), 5.11 (s, 2H), 5.10-5.07 (m, 1H), 3.00-2.97 (m, 2H), 2.48-2.43 (m, 1H), 1.99-1.92 (m, 2H), 1.85-1.77 (m, 2H), 1.69-1.62 (m, 2H); LCMS: ESI-MS m/z: 243.0 [M+H]$^+$.

Example 96

N-(2-Fluoroethyl)-1-(pyridin-4-ylmethyl)-1H-pyrazol-3-amine

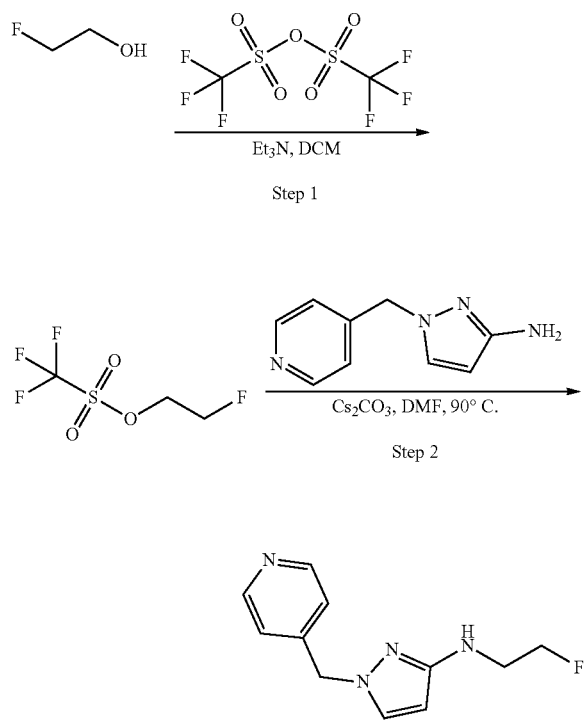

Step 1: 2-Fluoroethyl trifluoromethanesulfonate. To a stirred solution of 2-fluoroethan-1-ol (1.07 g, 0.0167 mol, 1.0 equiv.) and triethylamine (3.37 g, 0.0334 mol, 2.0 equiv.) in DCM (10 mL) was added trifluoromethanesulfonic anhydride (7.06 g, 0.025 mol, 1.50 equiv.) dropwise at 0° C. under nitrogen. After the addition, the mixture was stirred at room temperature for 2 h. The mixture was washed with water (5 mL), the organic fraction was dried over sodium sulfate, filtered and concentrated in vacuo to afford crude 2-fluoroethyl trifluoromethanesulfonate (1.27 g) as a light yellow liquid, which would be used without further purification. LCMS: ESI-MS m/z: 195.0[M−H]$^-$. No UV absorption.

Step 2: N-(2-Fluoroethyl)-1-(pyridin-4-ylmethyl)-1H-pyrazol-3-amine. A mixture of 2-fluoroethyl trifluoromethanesulfonate (81 mg, 0.415 mmol, 1.0 equiv.), 1-(pyridin-4-ylmethyl)-1H-pyrazol-3-amine (Intermediate 2, 54 mg, 0.311 mmol, 0.75 equiv.), and cesium carbonate (270 mg, 0.83 mmol, 2.0 equiv.) in DMF (2 mL) was stirred at 90° C. for 8 h. The mixture was cooled, filtered, the filtrate was concentrated in vacuo. The crude product was purified by silica gel column chromatography (0-10% methanol in DCM) to afford N-(2-fluoroethyl)-1-(pyridin-4-ylmethyl)-1H-pyrazol-3-amine (15 mg, 22% yield) as a white solid. $^1$H-NMR (CD$_3$OD, 400 MHz) δ 8.48 (d, J=3.6 Hz, 2H), 7.51 (d, J=2.4 Hz, 1H), 7.16 (d, J=6.0 Hz, 2H), 5.72 (d, J=2.4 Hz, 1H), 5.24 (s, 2H), 4.59 t, J=4.8 Hz, 1H), 4.47 (t, J=4.8 Hz, 1H), 3.46 (t, J=5.2 Hz, 1H), 3.38 (t, J=4.8 Hz, 1H); LCMS: ESI-MS m/z: 221.1 [M+H]$^+$.

Example 97

N-Cyclobutyl-1-(pyridin-4-ylmethyl)-1H-pyrazol-3-amine

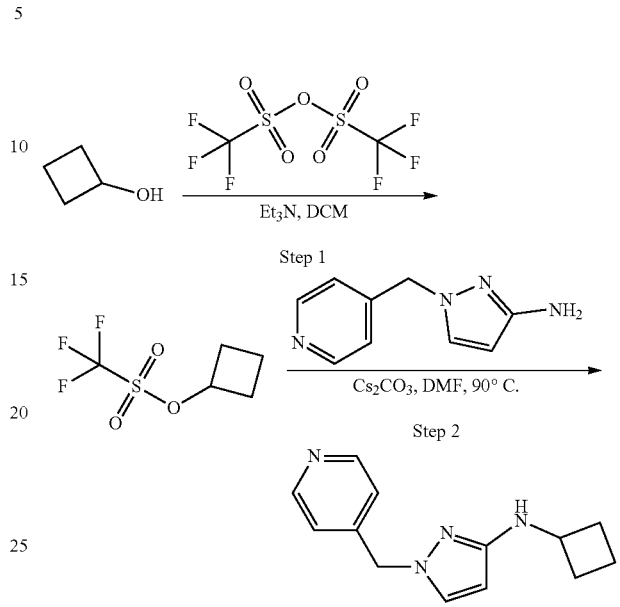

N-Cyclobutyl-1-(pyridin-4-ylmethyl)-1H-pyrazol-3-amine. The compound was prepared following the procedure for Step 1 and Step 2 EXAMPLE 96. Purified by silica gel column chromatography (0-10% methanol in DCM), 25% yield. $^1$H-NMR (CDCl$_3$, 400 MHz) δ 8.55 (dd, J=4.4, 1.6 Hz, 2H), 7.23 (d, J=2.0 Hz 1H), 7.02 (d, J=6.4 Hz, 2H), 5.85-5.77 (m, 1H), 5.65 (d, J=2.4 Hz 1H), 5.15-5.07 (m, 4H), 3.22 (t, J=6.6 Hz, 2H), 2.39-2.34 (m, 2H); LCMS: ESI-MS m/z: 229.0 [M+H]$^+$.

Example 98

N-Cyclopropyl-1-(pyridin-4-ylmethyl)-1H-pyrazol-3-amine

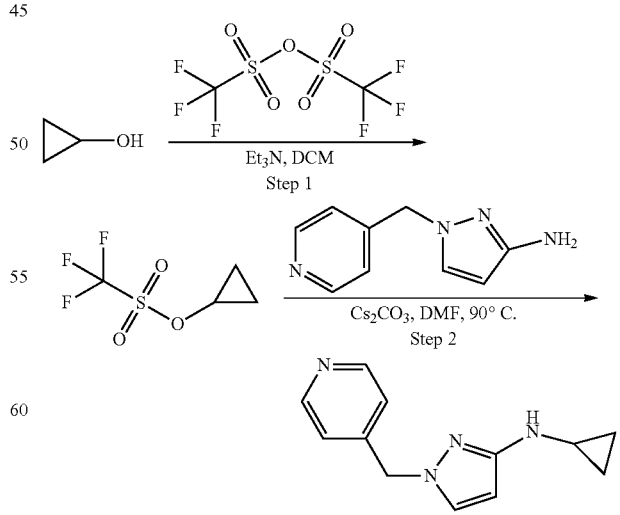

N-Cyclopropyl-1-(pyridin-4-ylmethyl)-1H-pyrazol-3-amine. The compound was prepared following the procedure for Step 1 and Step 2 EXAMPLE 96. Purified by silica gel column chromatography (0-10% methanol in DCM), 26% yield. ¹H-NMR (CD₃OD, 400 MHz) δ 8.45 (d, J=6.0 Hz, 2H), 7.48 (d, J=2.4 Hz, 1H), 7.13 (d, J=6.0 Hz, 2H), 5.59-5.99 (m, 1H), 5.68 (d, J=2.4 Hz, 1H), 5.20-5.24 (m, 3H), 5.07 (d, J=8.8 Hz, 1H), 3.72 (d, J=5.6 Hz, 2H); LCMS: ESI-MS m/z: 215.2 [M+H]⁺.

Example 99

(rac)-1-(1-(Pyridin-4-yl)propyl)-N-(2,2,2-trifluoroethyl)-1H-pyrazol-3-amine

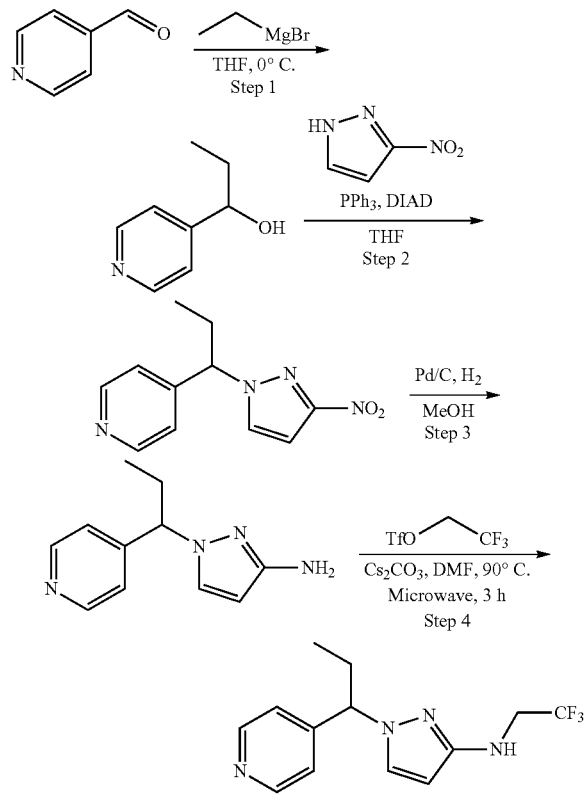

Step 1: (rac)-1-(Pyridin-4-yl)propan-1-ol. To a solution of isonicotinaldehyde (300 mg, 2.80 mmol, 1.0 equiv.) in anhydrous THF (5 mL) was added ethylmagnesium bromide (1 M in THF, 3.1 mL, 3.1 mmol, 1.1 equiv.) dropwise at 0° C. under nitrogen. After the addition, the mixture was stirred at room temperature for 2 h. The mixture was diluted with ethyl acetate (10 mL), washed with water (5 mL), brine (5 mL), the organic fraction was dried over sodium sulfate, filtered, and concentrated in vacuo. The crude product was purified by silica gel column (0-5% methanol in DCM) to afford 1-(pyridin-4-yl)propan-1-ol (140 mg, 36% yield) as a light yellow liquid. LCMS: ESI-MS m/z: 138.0 [M+H]⁺.

Step 2: (rac)-4-(1-(3-Nitro-1H-pyrazol-1-yl)propyl)pyridine. To a mixture of 1-(pyridin-4-yl)propan-1-ol (140 mg, 1.02 mmol, 1.0 equiv.), 3-nitro-1H-pyrazole (150 mg, 1.33 mmol, 1.3 equiv.) and triphenylphosphine (348 mg, 1.33 mmol, 1.3 equiv.) in anhydrous THF (10 mL) was added DIAD (269 mg, 1.33 mmol, 1.3 equiv.) dropwise at 0° C. under nitrogen. After the addition, the mixture was stirred at room temperature for 48 h. The mixture was concentrated in vacuo and the crude product was purified by silica gel column chromatography (5%-15% ethyl acetate in petroleum ether) to afford 4-(1-(3-nitro-1H-pyrazol-1-yl)propyl)pyridine (90 mg, 38% yield) as a light yellow solid. LCMS: ESI-MS m/z: 233.0 [M+H]⁺.

Step 3: 1-(1-(Pyridin-4-yl)propyl)-1H-pyrazol-3-amine. To a stirred solution of 4-(1-(3-nitro-1H-pyrazol-1-yl)propyl)pyridine (90 mg, 0.388 mmol) in methanol (10 mL) was added Pd/C (10%, 20 mg). The mixture was stirred under a H₂ atmosphere at room temperature for 8 h. The mixture was filtered and the filtrate was concentrated in vacuo. The crude product was purified by silica gel column chromatography (0%-10% methanol in DCM) to afford 1-(1-(pyridin-4-yl)propyl)-1H-pyrazol-3-amine (60 mg, 76% yield) as a light yellow solid. LCMS: ESI-MS m/z: 203.0 [M+H]⁺.

Step 4: 1-(1-(Pyridin-4-yl)propyl)-N-(2,2,2-trifluoroethyl)-1H-pyrazol-3-amine. A mixture of 1-(1-(pyridin-4-yl)propyl)-1H-pyrazol-3-amine (40 mg, 0.198 mmol, 1.0 equiv.), 2,2,2-trifluoroethyl trifluoromethanesulfonate (69 mg, 0.297 mmol, 1.5 equiv.), and cesium carbonate (129 mg, 0.396 mmol, 2.0 equiv.) in DMF (3 mL) was stirred at 90° C. with microwave irradiation for 3 h. The mixture was cooled to room temperature and filtered. The filtrate was concentrated in vacuo and the crude product was purified by silica gel column chromatography (0%-5% methanol in DCM) to afford 1-(1-(pyridin-4-yl)propyl)-N-(2,2,2-trifluoroethyl)-1H-pyrazol-3-amine (10 mg, 18% yield) as a white solid. ¹H-NMR (CD₃OD, 400 MHz) δ 8.49 (s, 2H), 7.55 (d, J=2.4 Hz, 1H), 7.34 (d, J=5.6 Hz, 2H), 5.71 (d, J=2.8 Hz, 1H), 5.15-5.11 (m, 1H), 3.86-3.79 (m, 2H), 2.38-2.28 (m, 1H), 2.20-2.11 (m, 1H), 0.96 (t, J=14.4 Hz, 3H); LCMS: ESI-MS m/z: 285.0 [M+H]⁺.

Example 100

(rac)-1-(1-(Pyridin-4-yl)ethyl)-N-(1,1,1-trifluoropropan-2-yl)-1H-pyrazol-3-amine

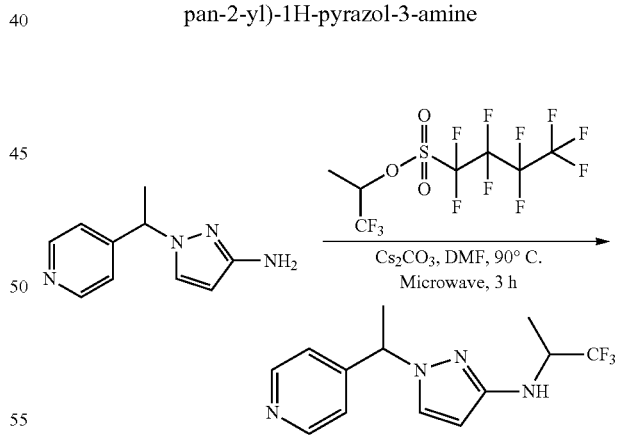

(rac)-1-(1-(Pyridin-4-yl)ethyl)-N-(1,1,1-trifluoropropan-2-yl)-1H-pyrazol-3-amine. The starting material was intermediate 1. The compound was prepared following the procedure for Step 4 of EXAMPLE 98. The final product was purified by silica gel column chromatography (0%-5% methanol in DCM), 25% yield. ¹H-NMR (CD₃OD, 400 MHz) δ 8.47 (s, 1H), 7.57 (s, 1H), 7.16 (s, 2H), 5.71 (s, 1H), 5.42 (d, J=6.8 Hz, 1H), 4.21-4.17 (m, 1H), 1.83 (d, J=6.8 Hz, 3H), 1.33 (s, 3H); LCMS: ESI-MS m/z: 285.0 [M+H]⁺.

Example 101

(rac)-N-(2,2-Difluoroethyl)-1-(1-(pyridin-4-yl)ethyl)-1H-pyrazol-3-amine

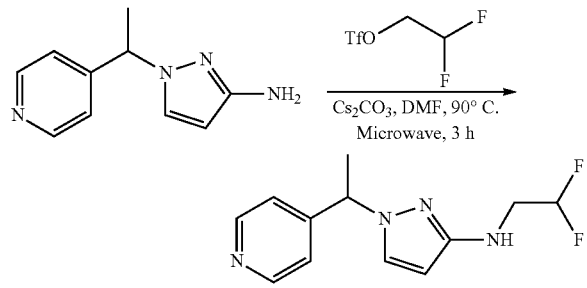

(rac)-N-(2,2-difluoroethyl)-1-(1-(pyridin-4-yl)ethyl)-1H-pyrazol-3-amine. The starting material was intermediate 1. The compound was prepared following the procedure for Step 4 of EXAMPLE 98. The final product was purified by silica gel column chromatography (0%-5% methanol in DCM), 20% yield. $^1$H-NMR (CD$_3$OD, 400 MHz) δ 8.45 (d, J=6.4 Hz, 2H), 7.55 (d, J=2.8 Hz, 1H), 7.15 (d, J=6.4 Hz, 2H), 5.89-6.06 (m, 1H), 5.68 (d, J=2.4 Hz, 2H), 5.39 (d, J=7.2 Hz, 1H), 3.41-3.49 (m, 2H), 1.80 (d, J=6.4 Hz, 3H); LCMS: ESI-MS m/z: 253.1 [M+H]$^+$.

Example 102

4-{[3-(2,2-Difluoroethyl)-1H-pyrazol-1-yl]methyl}pyridine

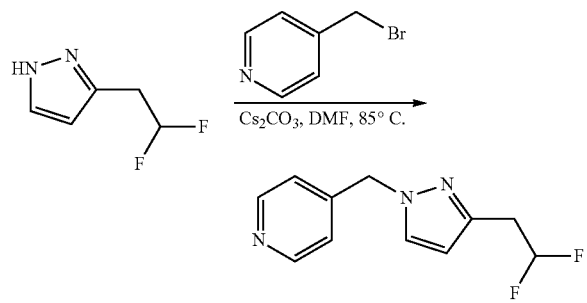

4-{[3-(2,2-Difluoroethyl)-1H-pyrazol-1-yl]methyl}pyridine. A solution of 4-(bromomethyl)pyridine hydrobromide (144 mg, 0.568 mmol, 3 equiv.), 3-(2,2-difluoroethyl)-1H-pyrazole (25 mg, 0.189 mmol, 1 equiv.) and cesium carbonate (370 mg, 1.14 mmol, 6 equiv.) in DMF (20 mL) was heated for 4 h at 85° C. The reaction was quenched by the addition of water (100 mL). The resulting solution was extracted with EtOAc (3×100 mL) and the organic layers were combined and washed with brine. The organic layer was separated, dried over Na$_2$SO$_4$, and concentrated in vacuo. The crude product was purified by RP-HPLC (10-40% MeCN/H$_2$+0.1% FA) to afford 4-{[3-(2,2-difluoroethyl)-1H-pyrazol-1-yl]methyl}pyridine (42 mg, 5%) as a white solid. $^1$H NMR (400 MHz, CDCl$_3$) δ 8.57 (d, J=4.0 Hz, 2H), 7.41 (m, 1H), 7.02 (d, J=4.0 Hz, 2H), 6.28 (m, 1H), 6.17 to 5.87 (m, 1H) 5.30 (s, 2H), 5.30 (s, 2H), 3.27 to 3.17 (m, 2H); LCMS: ESI-MS m/z: 224 [M+H]+.

Example 103

4-{[3-(1,1,2,2,2-Pentafluoroethyl)-1H-pyrazol-1-yl]methyl}pyridine

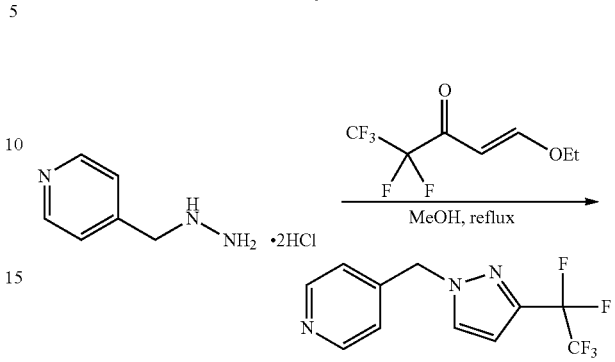

4-{[3-(1,1,2,2,2-Pentafluoroethyl)-1H-pyrazol-1-yl]methyl}pyridine. To a solution of (E)-1-ethoxy-4,4,5,5,5-pentafluoropent-1-en-3-one (236 mg, 0.812 mmol) and MeOH (2.5 mL) was added 4-(hydrazinylmethyl)pyridine-dihydrochloride (100 mg, 0.812 mmol). The reaction mixture was heated in a reaction vial to reflux. After 3 h, the reaction mixture was cooled to rt. The reaction mixture was concentrated in vacuo and purified by RP-HPLC (10-70% MeCN/H$_2$O, 0.1% FA) to afford 4-{[3-(1,1,2,2,2-pentafluoroethyl)-1H-pyrazol-1-yl]methyl}pyridine (3.1 mg, 1%) as a clear oil. $^1$H NMR (400 MHz, CDCl$_3$) δ 8.64 (d, J=4.0 Hz, 2H), 7.53 (m, 1H), 7.10 (d, J=4.0 Hz, 2H), 6.67 (d, J=4.0 Hz, 1H), 5.44 (s, 2H); LCMS: ESI-MS m/z: 278.1 [M+H]$^+$.

Example 104 and 105

4-{[4-Fluoro-3-(2,2,2-trifluoroethyl)-1H-pyrazol-1-yl]methyl}pyridine and (rac)-4-{Fluoro[3-(2,2,2-trifluoroethyl)-1H-pyrazol-1-yl]methyl}pyridine

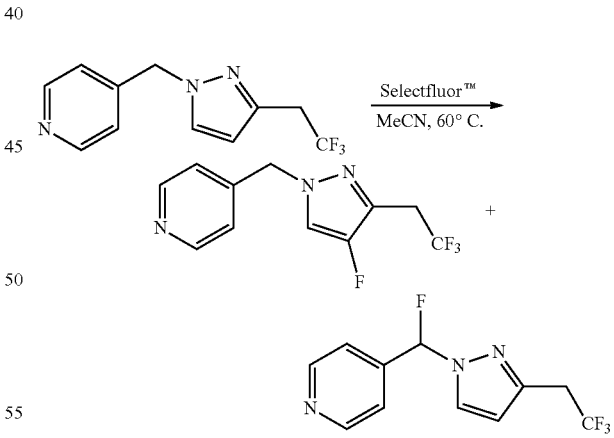

4-{[4-Fluoro-3-(2,2,2-trifluoroethyl)-1H-pyrazol-1-yl]methyl}pyridine and (rac)-4-{Fluoro[3-(2,2,2-trifluoroethyl)-1H-pyrazol-1-yl]methyl}pyridine. To a solution of 4-{[3-(2,2,2-trifluoroethyl)-1H-pyrazol-1-yl]methyl}pyridine (EXAMPLE 20, 25 mg, 0.167 mmol) and MeCN (2 mL) was added Selectfluor™ (118 mg, 0.333 mmol). The reaction mixture was heated to 60° C. After 1 h, the reaction mixture was purified directly by RP-HPLC (10-90% MeCN/H$_2$O, 0.1% FA) to afford 4-{[4-fluoro-3-(2,2,2-trifluoroethyl)-1H-pyrazol-1-yl]methyl}pyridine (1 mg, 2%) and 4-{fluoro[3-(2,2,2-trifluoroethyl)-1H-pyrazol-1-yl]methyl}pyridine (1.6 mg, 4%).

Example 104

4-{[4-Fluoro-3-(2,2,2-trifluoroethyl)-1H-pyrazol-1-yl]methyl}pyridine. $^1$H NMR (400 MHz, CDCl$_3$) δ 8.73 (d, J=4.0 Hz, 2H), 7.48-7.43 (m, 3H), 5.46 (s, 2H), 3.55-3.48 (m, 2H); LCMS: ESI-MS m/z: 259.7 [M+H]$^+$.

Example 105

(rac)-4-{Fluoro[3-(2,2,2-trifluoroethyl)-1H-pyrazol-1-yl]methyl}pyridine. $^1$H NMR (400 MHz, CDCl$_3$) δ 8.82 (d, J=4.0 Hz, 2H), 7.62 (m, 2H), 7.49 (m, 1H), 7.27 (d, J=48.0 Hz, 1H), 6.47 (m, 1H), 3.53-3.47 (m, 2H); LCMS: ESI-MS m/z: 259.7 [M+H]$^+$.

Example 106

3-(4-Chlorophenyl)-N-{1-[(pyridin-4-yl)methyl]-1H-pyrazol-3-yl}propanamide

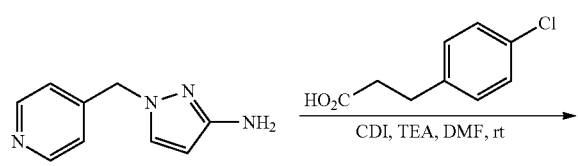

3-(4-Chlorophenyl)-N-{1-[(pyridin-4-yl)methyl]-1H-pyrazol-3-yl}propenamide. A solution of 3-(4-chlorophenyl)propanoic acid (31.8 mg, 0.172 mmol, 1.2 equiv.) and CDI (27.9 mg, 0.172 mmol, 1.2 equiv.) in DMF (0.3 mL) was stirred at room temperature overnight. A solution of 1-[(pyridin-4-yl)methyl]-1H-pyrazol-3-amine (Intermediate 2, 25.0 mg, 0.144 mmol) and triethylamine (80.0 μL, 0.574 mmol, 4 equiv.) in DMF (0.2 mL) was added. After 2 h, the reaction mixture was filtered through a 0.2 μm PTFE syringe tip filter and purified by RP-HPLC (10-40% MeCN in H$_2$O+0.1% FA). Fractions containing the desired mass were combined and concentrated in vacuo, then redissolved in MeOH and treated with tetraalkylammonium carbonate, polymer-bound beads and intermittently swirled for 30 min. The beads were filtered off and the filtrate was concentrated in vacuo to afford 3-(4-chlorophenyl)-N-{1-[(pyridin-4-yl)methyl]-1H-pyrazol-3-yl}propanamide (8.6 mg, 18%) as a pink-orange solid. $^1$H NMR (400 MHz, DMSO-d$_6$) δ 10.45 (s, 1H), 8.56-8.39 (m, 2H), 7.77 (d, J=2.3 Hz, 1H), 7.35-7.27 (m, 2H), 7.24 (d, J=8.3 Hz, 2H), 7.13-6.99 (m, 2H), 6.53 (d, J=2.3 Hz, 1H), 5.27 (s, 2H), 2.85 (t, J=7.6 Hz, 2H), 2.55 (t, J=7.7 Hz, 2H); LCMS: ESI-MS m/z: 340.7 [M+H]$^+$.

Example 107

(rac)-4-{1-[3-(2,2-Difluoroethyl)-1H-pyrazol-1-yl]ethyl}pyridine

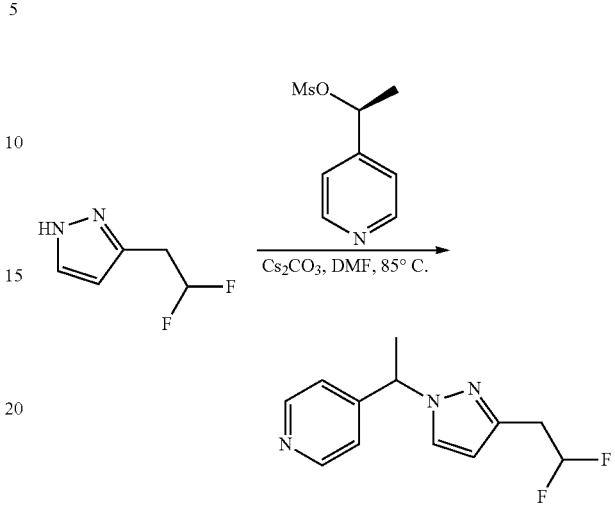

(rac)-4-{1-[3-(2,2-Difluoroethyl)-1H-pyrazol-1-yl]ethyl}pyridine. A solution of (1S)-1-(pyridin-4-yl)ethyl methanesulfonate (19.2 mg, 0.094 mmol, 3equiv.), 3-(2,2-difluoroethyl)-1H-pyrazole (4.2 mg, 0.032 mmol, 3equiv.) and Cs$_2$CO$_3$ (31 mg, 0.094 mmol, 3equiv.) in DMF (1 mL). The resulting solution was stirred for 4 h at 85° C. The reaction was then quenched by the addition of water (100 mL). The resulting solution was extracted with EtOAc and the organic layers combined. The resulting mixture was washed with brine, dried over anhydrous sodium sulfate, filtered, and concentrated in vacuo. The crude product was purified by RP-HPLC (10-90% MeCN/H$_2$O, 0.1% FA) to afford 4-{1-[3-(2,2-difluoroethyl)-1H-pyrazol-1-yl]ethyl}pyridine (0.7 mg, 8%) as a white solid. $^1$H NMR (400 MHz, CDCl$_3$) δ 8.47 (d, J=4.0 Hz, 2H), 7.76 (m, 1H), 7.15 (d, J=4.0 Hz, 2H), 6.31 (m, 1H), 6.19-6.02 (m, 1H), 5.64-5.59 (m, 1H), 3.21-3.12 (m, 2H), 1.89 (d, J=4.0 Hz, 3H); LCMS: ESI-MS m/z: 238.1 [M+H]$^+$.

Example 108

(rac)-1-[1-(Pyridin-4-yl)ethyl]-1H-pyrazole-3-carbaldehyde

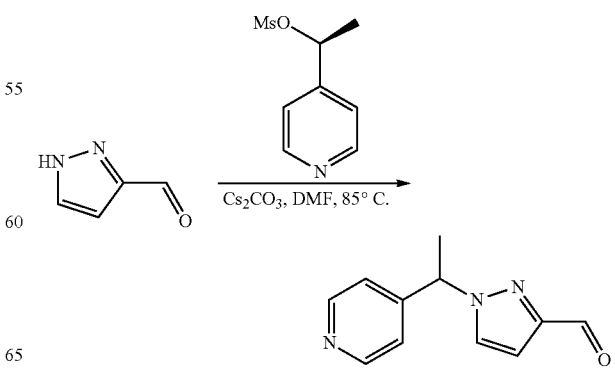

(rac)-1-[1-(Pyridin-4-yl)ethyl]-1H-pyrazole-3-carbaldehyde. A solution of (1S)-1-(pyridin-4-yl)ethyl methanesulfonate (0.3 g, 1.49 mmol, 1 equiv.), 1H-pyrazole-4-carbaldehyde (0.172 g, 1.79 mmol, 1.20 equiv.) and Cs$_2$CO$_3$ (1.21 g, 3.73 mmol, 2.5 equiv.) in DMF (4 mL). The resulting solution was stirred for 4 h at 85° C. The reaction was then quenched by the addition of water (100 mL). The resulting solution was extracted with of ethyl acetate (3×100 mL) and the organic layers combined. The resulting mixture was washed with of brine (100 mL), dried over anhydrous Na$_2$SO$_4$ and concentrated in vacuo. The crude product was purified by silica flash chromatography (0-100% EtOAc: hex) to afford 1-[1-(pyridin-4-yl)ethyl]-1H-pyrazole-3-carbaldehyde (130 mg, 43%). $^1$H NMR (400 MHz, CDCl$_3$) δ 10.01 (s, 1H), 8.60 (d, J=8.0 Hz, 2H), 7.51 (d, J=4.0 Hz, 1H), 7.07 (d, J=8.0 Hz, 2H), 6.88 (d, J=4.0 Hz, 1H), 5.62-5.56 (m, 1H), 1.97 (d, J=8.0 Hz, 3H); LCMS: ESI-MS m/z: 202.1 [M+H]$^+$.

Example 109

3-Methyl-4-{[3-(2,2,2-trifluoroethyl)-1H-pyrazol-1-yl]methyl}pyridine

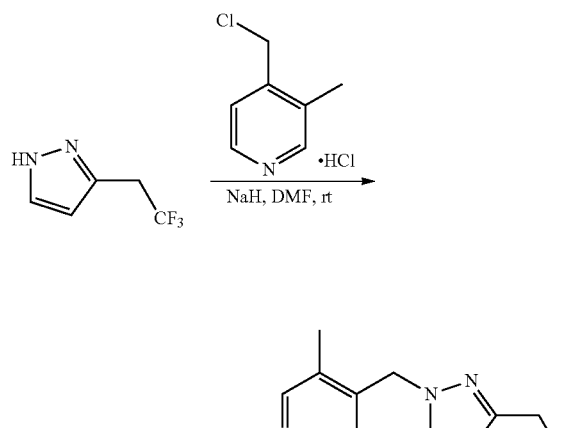

3-Methyl-4-{[3-(2,2,2-trifluoroethyl)-1H-pyrazol-1-yl]methyl}pyridine. To a solution of 3-(2,2,2-trifluoroethyl)-1H-pyrazole; 4-(chloromethyl)-3-methylpyridine (50 mg, 0.171 mmol, 1.0 equiv.), 4-(chloromethyl)-3-methylpyridine hydrochloride (91.6 mg, 0.514 mmol, 3.0 equiv.) and dry DMF (2 mL) was added 60% NaH (20.6 mg, 0.514 mmol, 3.0 equiv.) at rt under an atmosphere of N$_2$ and stirred at rt overnight. Purified by RP-HPLC (10-70% MeCN/H$_2$O, 0.1% FA) to afford 3-methyl-4-{[3-(2,2,2-trifluoroethyl)-1H-pyrazol-1-yl]methyl}pyridine (18.3 mg, 38%) as a red-orange oil. $^1$H NMR (400 MHz, CDCl$_3$) δ 8.46 (s, 1H), 8.42 (d, J=4.0 Hz, 1H), 7.41 (m, 1H), 6.69 (d, J=4.0 Hz, 1H), 6.38 (m, 1H), 5.34 (s, 2H), 3.55-3.47 (m, 2H), 2.34 (s, 3H); LCMS: ESI-MS m/z: 256.6 [M+H]$^+$.

Example 110 and Example 111

(R)-4-(1-(1-(2,2-Difluoroethyl)-1H-pyrazol-3-yl)ethyl)pyridine and (S)-4-(1-(1-(2,2-Difluoroethyl)-1H-pyrazol-3-yl)ethyl)pyridine

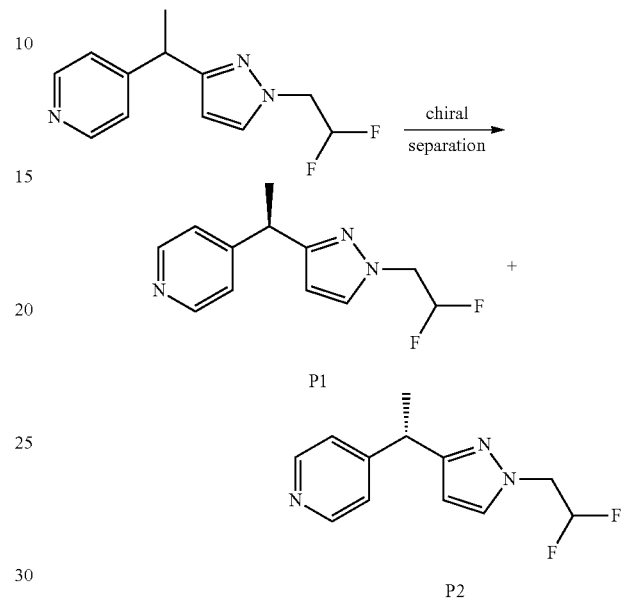

The racemic mixture Example 18 was separated into the corresponding enantiomers by chiral SFC separation to afford (R)-4-(1-(1-(2,2-Difluoroethyl)-1H-pyrazol-3-yl)ethyl)pyridine and (S)-4-(1-(1-(2,2-Difluoroethyl)-1H-pyrazol-3-yl)ethyl)pyridine. Absolute stereochemistry was not determined.

(R)-4-(1-(1-(2,2-Difluoroethyl)-1H-pyrazol-3-yl)ethyl)pyridine and (S)-4-(1-(1-(2,2-Difluoroethyl)-1H-pyrazol-3-yl)ethyl)pyridine $^1$H NMR (400 MHz, CDCl$_3$) δ 8.58 (d, J=8.0 Hz, 2H), 7.61 (d, J=8.0 Hz, 2H), 7.47 (m, 1H), 6.34-5.90 (m, 2H), 4.49-4.31 (m, 3H), 1.71 (d, J=8.0 Hz, 3H); LCMS: ESI-MS m/z: 238.1 [M+H]$^+$.
Chiral Separation Conditions:
Instrument: SFC-150 (Thar, Waters)
Column: OD 20×250 mm, 10 micron (Daicel)
Column temperature: 35° C.
Mobile phase: CO$_2$/IPA (0.5% MeOH·NH$_4$)=90/10
Flow rate: 100 g/min
Back pressure: 100 bar
Detection wavelength: 214 nm
Cycle time: 2 min
Sample solution: 1000 mg dissolved in 80 ml MeOH
Injection volume: 1.0 mL
Chiral Analysis Conditions:
Column: OD-H 100×4.6 mm, 5 micron
Column temperature: 40° C.
Co-solvent: Hexanes/MeOH/EtOH (100/15/15)
Detection wavelength: 254 nm
Injection volume: 5 µL
Retention times: P1=4.25 min; P2=4.78 min

Example 112

(rac)-3-Chloro-4-(1-(1-(2,2,2-trifluoroethyl)-1H-pyrazol-3-yl)ethyl)pyridine

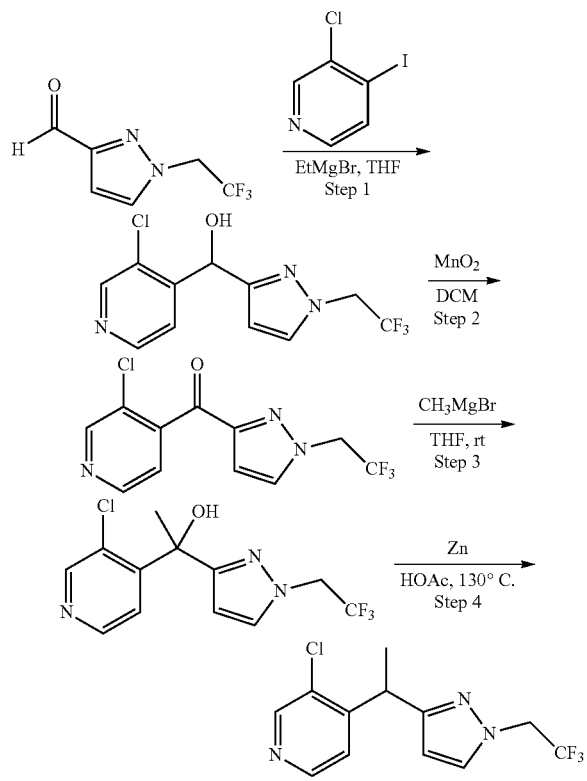

Step 1: (rac)-(3-Chloropyridin-4-yl)(1-(2,2,2-trifluoroethyl)-1H-pyrazol-3-yl)methanol. To a solution of 3-chloro-4-iodopyridine (240 mg, 1.0 mmol, 1.0 equiv.) in anhydrous THF (10 mL, 0.1M) under nitrogen atmosphere EtMgBr (3.0 M in diethyl ether, 0.4 mL, 1.2 mmol, 1.2 equiv.) was added. The resulting mixture was stirred at room temperature for 30 min, and 1-(2,2,2-trifluoroethyl)-1H-pyrazole-3-carbaldehyde (Intermediate 6, 178 mg, 1 mmol, 1.0 equiv.) was added as a solution in anhydrous THF (1 mL) and stirred at room temperature for 1 h. The reaction was quenched with water (5 mL) and extracted with EtOAc (3×10 mL). The combined organic layers were dried over anhydrous sodium sulfate, filtered, and concentrated in vacuo to afford (3-chloropyridin-4-yl)(1-(2,2,2-trifluoroethyl)-1H-pyrazol-3-yl)methanol (200 mg, 69% yield) as a brown oil. The material was carried forward to the next step without further purification. LCMS: ESI-MS m/z: 292.0 [M+H]+.

Step 2: (3-Chloropyridin-4-yl)(1-(2,2,2-trifluoroethyl)-1H-pyrazol-3-yl)methanone. A solution of (3-chloropyridin-4-yl)(1-(2,2,2-trifluoroethyl)-1H-pyrazol-3-yl)methanol (200 mg, 0.69 mmol, 1.0 equiv.) in DCM (20 mL, 0.034 M) was treated with MnO$_2$ (0.6 g, 6.9 mmol, 10 equiv.) and the resulting mixture was stirred at room temperature for 5 h. The reaction mixture was filtered, and the filtrate was concentrated in vacuo to afford (3-chloropyridin-4-yl) (1-(2,2,2-trifluoroethyl)-1H-pyrazol-3-yl)methanone (180 mg, 0.62 mmol, 90% yield) as a brown oil. The material was carried forward to the next step without further purification. LCMS: ESI-MS m/z: 290 [M+H]+.

Step 3: 1-(3-Chloropyridin-4-yl)-1-(1-(2,2,2-trifluoroethyl)-1H-pyrazol-3-yl)ethan-1-ol. To a solution of (3-chloropyridin-4-yl)(1-(2,2,2-trifluoroethyl)-1H-pyrazol-3-yl)methanone (180 mg, 0.62 mmol, 1.0 equiv.) in anhydrous THF (10 mL, 0.07 M), MeMgBr (3.0 M in diethyl ether, 0.6 mL, 1.80 mmol, 2.9 equiv.) was added under nitrogen atmosphere at room temperature. The resulting reaction mixture was stirred at room temperature for 2 h and quenched with water (5 mL) and extracted with EtOAc (3×10 mL). The combined organic layers were dried over anhydrous sodium sulfate, filtered, and concentrated in vacuo to afford 1-(3-chloropyridin-4-yl)-1-(1-(2,2,2-trifluoroethyl)-1H-pyrazol-3-yl)ethan-1-ol (110 mg, 58% yield) as a brown oil. The material was carried forward to the next step without further purification. LCMS: ESI-MS m/z: 306.0 [M+H]+.

Step 4: (rac)-3-Chloro-4-(1-(1-(2,2,2-trifluoroethyl)-1H-pyrazol-3-yl)ethyl)pyridine. A solution of 1-(3-chloropyridin-4-yl)-1-(1-(2,2,2-trifluoroethyl)-1H-pyrazol-3-yl)ethan-1-ol (110 mg, 0.36 mmol, 1.0 equiv.) in acetic acid (20 mL, 0.018 M) was treated with zinc powder (471 mg, 7.2 mmol, 20 equiv.). The resulting mixture was heated to reflux for 16 h. The mixture was filtered, and then the solution was treated with sodium carbonate until the pH was adjusted to 9-10. The mixture was further diluted with water (40 mL), extracted with EtOAc (4×20 mL). The combined organic layers were dried over sodium sulfate, filtered, and concentrated in vacuo to give a crude product which was purified by silica gel column chromatography (0-5% MeOH/DCM) to afford (rac)-3-chloro-4-(1-(1-(2,2,2-trifluoroethyl)-1H-pyrazol-3-yl)ethyl)pyridine (50 mg, 47% yield) as a white solid. LCMS: ESI-MS m/z: 290.0 [M+H]+.

Example 113 and 113a (R)-3-Chloro-4-(1-(1-(2,2,2-trifluoroethyl)-1H-pyrazol-3-yl)ethyl)pyridine and (S)-3-Chloro-4-(1-(1-(2,2,2-trifluoroethyl)-1H-pyrazol-3-yl)ethyl)pyridine

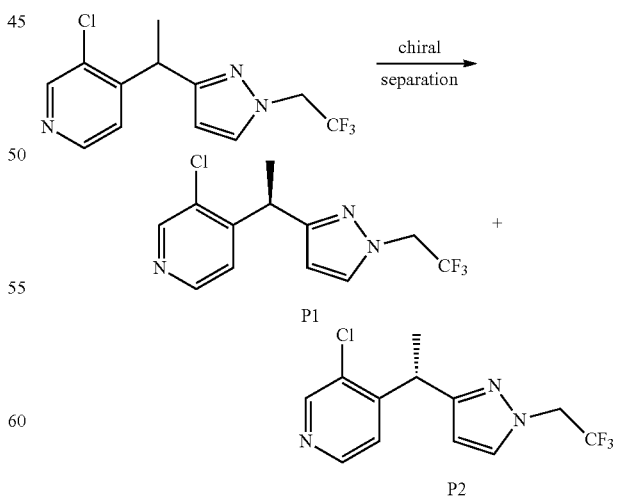

(R)-3-Chloro-4-(1-(1-(2,2,2-trifluoroethyl)-1H-pyrazol-3-yl)ethyl)pyridine and (S)-3-Chloro-4-(1-(1-(2,2,2-trifluoroethyl)-1H-pyrazol-3-yl)ethyl)pyridine. The racemic mixture Example 112 was separated into the corresponding enantiomers by chiral SFC separation to afford (R)-3-chloro-4-(1-(1-(2,2,2-trifluoroethyl)-1H-pyrazol-3-yl)ethyl)pyridine and (S)-3-chloro-4-(1-(1-(2,2,2-trifluoroethyl)-1H-pyrazol-3-yl)ethyl)pyridine. Absolute stereochemistry was not determined.

Example 113

Retention times: P1=8.761 min: $^1$H NMR (400 MHz, CDCl$_3$) δ 8.54 (s, 1H), 8.38 (d, J=5.2 Hz, 1H), 7.46 (d, J=2.4 Hz, 1H), 7.13 (d, J=5.2 Hz, 1H), 6.18 (d, J=2.4 Hz, 1H), 4.71 (m, 3H), 1.63 (d, J=7.2 Hz, 3H).

Example 113a

Retention time: P2=9.747 min: $^1$H NMR (400 MHz, CDCl$_3$) δ 8.54 (s, 1H), 8.38 (d, J=5.2 Hz, 1H), 7.46 (d, J=2.4 Hz, 1H), 7.13 (d, J=5.2 Hz, 1H), 6.18 (d, J=2.4 Hz, 1H), 4.71 (m, 3H), 1.63 (d, J=7.2, 3H).

Example 114 and 114a (R)-4-(1-(1-(2,2-Difluoroethyl)-1H-pyrazol-3-yl)ethyl-2,2,2-d$_3$)pyridine and (S)-4-(1-(1-(2,2-Difluoroethyl)-1H-pyrazol-3-yl)ethyl-2,2,2-d$_3$)pyridine

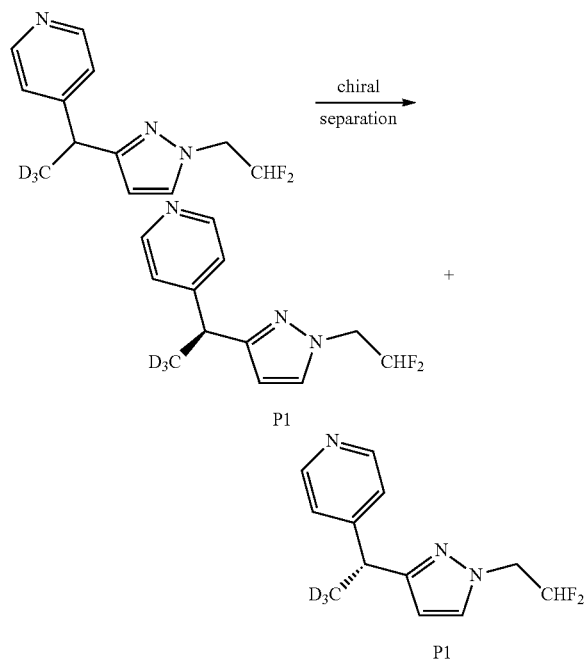

(R)-4-(1-(1-(2,2-Difluoroethyl)-1H-pyrazol-3-yl)ethyl-2,2,2-d$_3$)pyridine and (S)-4-(1-(1-(2,2-Difluoroethyl)-1H-pyrazol-3-yl)ethyl-2,2,2-d$_3$)pyridine. The racemic mixture Example 25 was separated into the corresponding enantiomers by chiral HPLC separation to afford (R)-4-(1-(1-(2,2-difluoroethyl)-1H-pyrazol-3-yl)ethyl-2,2,2-d$_3$)pyridine and (S)-4-(1-(1-(2,2-difluoroethyl)-1H-pyrazol-3-yl)ethyl-2,2,2-d$_3$)pyridine. Absolute stereochemistry was not determined.

Example 114

Retention times: P1=9.536 min.

Example 114a

Retention time: P2=11.167 min.
Chiral Separation Conditions:
Instrument: Gilson-281
Column: OJ 20*250 mm, 10 μm
Column temperature: 40° C.
Mobile phase: n-Hexane:EtOH=92:8 (with 0.1% DEA)
Flow rate: 40 mL/min
Back pressure: 1.20 bar
Detection wavelength: 214 nm
Cycle time: 28 min
Sample solution: 79 mg in 13 mL MeOH
Injection volume: 1 mL
Chiral Analysis Conditions:
Column: OJ-H 250×4.6 mm, 5 micron
Column temperature: 40° C.
Co-solvent: Hexanes/EtOAc (90:10) with 0.1% DEA
Detection wavelength: 254 nm and 214 nm
Injection volume: 8 μL
Retention times: P1=4.25 min; P2=4.78 min

Example A

Biological Assay

Each reaction was run at a volume of 20 μL containing 50 μM compound (dissolved in DMSO; final concentration of DMSO is 1% v/v), 40 nM human SARM1$_{(50-724)}$, 0.3 mM NMN, 20 μM NAD, 1 mM TCEP, 25 mM HEPES pH 7.4, 10 mM KCl and 10 mM MgCl$_2$. The reaction was incubated at room temperature for 60 minutes and quenched with 20 μL of 0.4% formic acid. The samples were run on Agilent HPLC 1260 Infinity II with Synergi 2.5 μM Fusion-RP 100 Å (100×3.0 mm) LC column from Phenomenex. Total run time for each sample was 4 minutes. The run was isocratic with 1.5% methanol in 40 mM ammonium acetate pH 6.0. Samples were run at a flow rate of 0.8 mL/min at 55° C. Peak areas of NAD and NAM were determined using OpenLAB CDS (Chem Station edition) software. For dose-response, the compound was diluted serially 1:3 in DMSO and added to the reaction starting at a final compound concentration of 100 μM in 1% DMSO.

IC$_{50}$ data according to the assay described above is provided in Table 1 below. IC$_{50}$<1 (+); 1≤IC$_{50}$<10 (++); 10≤IC$_{50}$≤100 (+++); and IC$_{50}$>100 (++++) for the exemplified compounds. Average NAD % inhibition at 50 μM and average NAM % inhibition at 50 μM are also provided in Table 1. % Inhibition 0-50% (*) and 51-100% (**).

TABLE 1

| Example# | SARM1 IC50 (μM) | Avg NAD % inhibition at 50 μM | Avg NAM % inhibition at 50 μM |
|---|---|---|---|
| 1 | + | | |
| 2 | + | | |
| 3 | ++ | | |
| 4 | ++ | | |
| 5 | ++ | | |
| 6 | ++ | | |
| 7 | ++ | | |
| 8a | | * | * |
| 8b | + | | |
| 9 | ++ | | |

TABLE 1-continued

| Example# | SARM1 IC50 (μM) | Avg NAD % inhibition at 50 μM | Avg NAM % inhibition at 50 μM |
|---|---|---|---|
| 10 | ++ | | |
| 11 | ++ | | |
| 12a | ++ | | |
| 12b | + | | |
| 13a | + | | |
| 13b | | ** | ** |
| 14 | ++ | | |
| 15 | ++ | | |
| 16 | ++ | | |
| 17 | ++ | | |
| 18 | ++ | | |
| 19 | ++ | | |
| 20 | ++ | | |
| 21 | ++ | | |
| 22 | ++ | | |
| 23 | ++ | | |
| 24 | + | | |
| 25 | ++ | | |
| 26 | +++ | * | * |
| 27 | ++ | | |
| 28 | ++ | | |
| 29 | + | | |
| 30 | ++ | | |
| 31 | ++ | | |
| 32 | | * | * |
| 33 | ++++ | ** | ** |
| 34 | | * | * |
| 35 | | * | * |
| 36 | | * | * |
| 37 | | * | * |
| 38 | ++ | | |
| 39 | | * | * |
| 40 | | * | * |
| 41 | | * | * |
| 42 | | * | * |
| 43 | | * | * |
| 44 | | * | * |
| 45 | | * | * |
| 46 | | * | * |
| 47 | | * | * |
| 48 | | * | * |
| 49 | | * | * |
| 50 | | * | * |
| 51 | | * | * |
| 52 | | * | * |
| 53 | | * | * |
| 54 | +++ | | |
| 55 | | ** | ** |
| 56 | | * | * |
| 57 | | * | * |
| 58 | | * | * |
| 59 | | * | * |
| 60 | +++ | | |
| 61 | | * | * |
| 62 | | * | * |
| 63 | ++ | | |
| 64 | | * | * |
| 65 | +++ | ** | ** |
| 66 | ++ | | |
| 67 | | ** | * |
| 68 | +++ | | |
| 69 | | ** | ** |
| 70 | | ** | ** |
| 71 | | * | * |
| 72 | | * | * |
| 73 | | ** | no data |
| 74 | ++ | | |
| 75 | | * | * |
| 76 | ++ | * | * |
| 77 | | * | * |
| 78 | ++ | | |
| 78a | ++ | | |
| 79 | +++ | | |
| 80 | + | | |
| 81 | +++ | | |
| 82 | + | | |
| 83 | +++ | | |
| 84 | +++ | | |
| 85 | | * | * |
| 86 | | * | * |
| 87 | | * | * |
| 88 | | * | * |
| 89 | +++ | | |
| 90 | +++ | | |
| 91 | | * | * |
| 92 | +++ | | |
| 93 | | * | * |
| 94 | | * | * |
| 95 | | * | * |
| 96 | | ** | ** |
| 97 | | * | * |
| 98 | | * | * |
| 99 | +++ | | |
| 100 | ++ | | |
| 101 | + | | |
| 102 | ++ | | |
| 103 | ++ | | |
| 104 | ++ | | |
| 105 | | * | * |
| 106 | | * | * |
| 107 | ++ | | |
| 108 | | * | * |
| 109 | ++ | | |
| 110 | +++ | | |
| 111 | ++ | | |
| 112 | ++ | | |
| 113 | ++ | | |
| 113a | ++ | | |
| 114 | | * | * |
| 114a | ++ | | |

Example B

Assessment of the Protective Effect of SARM1 Inhibitors in Multiple Sclerosis

To evaluate the ability of a SARM1 inhibitor to delay, prevent, or treat multiple sclerosis, a preclinical mouse model of experimental autoimmune encephalomyelitis (EAE) may be used (Lyons J A et al., Eur J of Immunology, 1999 29(11):3432-9). To induce EAE, female mice, 9-13 weeks old, may receive 0.1 ml subcutaneous injection (s.c.) of myelin oligo glycoprotein peptide (MOG35-55) suspension in complete Freund's adjuvant (CFA) in the upper and lower back, followed by intraperitoneal injection (i.p.) of pertussis toxin (100 ng) within 3 hours of MOG injection and again within 24 hours of MOG injection. Weight and clinical score of paralysis may be recorded daily starting at day 7 until day 28 post-MOG injection. A SARM1 inhibitor can be dosed orally (p.o.) daily or with the use of osmotic pumps implanted s.c. or i.p. as a stand-alone treatment, or in conjunction with current standard of care medication(s) either on the same day as MOG treatment or at the start of symptoms. Effective compounds will slow the development of disease and/or to decrease the severity of the symptoms.

Example C

Assessment of the Protective Effect of SARM1 Inhibitors in Chemotherapy-Induced Peripheral Neuropathy (CIPN)

To evaluate the ability of a SARM1 inhibitor to prevent CIPN, a mouse model of CIPN may be used. To induce peripheral neuropathy, mice may be treated with a specific chemotherapeutic known to cause peripheral neuropathy in humans (e.g., vincristine, paclitaxel, or oxaliplatin) (Geisler et al., *Brain* 2016, 139 (Pt 12):3092-3108; Wang M S et al., *Ann. Neurol.*, 2002, 52(4) 442-7; Sprowl et al., *Proc Natl Acad Sci* 2013, 110(27):11199). Peripheral neuropathy may be assessed with behavior tests of mechanical allodynia by measuring sensitivity in the footpad by increasing applied force of Von Frey filament, cold or heat sensitivity by measuring escape/pain behavior (e.g., jumping, paw licking or paw lifts) on a thermally controlled enclosed platform. Furthermore, behavior may be correlated with biomarkers of neuropathy (e.g., plasma neurofilament light) and by histologically examining intra-epidermal nerve fiber density in hind paw pad biopsies. SARM1 inhibitors may be dosed orally (p.o.) daily, or with the use of osmotic pumps implanted s.c. or i.p. at the start of the experiment. Effective compounds will prevent allodynia, prevent the increase of the neuropathy biomarker and/or prevent the decrease in IENF density relative to vehicle treated cohorts.

Example D

Assessment of the Protective Effect of SARM1 Inhibitors in Amyotrophic Lateral Sclerosis (ALS)

To evaluate the ability of a SARM1 inhibitor to delay, prevent, or treat ALS, a genetic mouse model of the disease may be used. Transgenic mice with the mutation TDP43Q331K have been shown to develop progressive motor deficits as measured by performance on the accelerating rotarod and by progressive hind limb weakness as measured by hind paw grip strength. Furthermore, plasma NfL levels may appear to be increased in the mutants. SARM1 inhibitors may be dosed with the use of osmotic pumps implanted s.c. or i.p. Effective compounds will protect from the neurodegeneration and show a decrease in plasma NfL, as well as delay and/or prevent progression of the motor deficits and hind limb weakness.

Example E

Assessment of the Protective Effect of SARM1 Inhibitors in Glaucoma

To evaluate the ability of SARM1 inhibitor to prevent glaucoma, several mouse models of the disease are utilized. The optic nerve crush (ONC) model of glaucoma is generated by applying transient pressure to the optic nerve with forceps to induce retrograde retinal ganglion cell death and replicate many of the changes observed in glaucomatous retinas, excluding increased ocular pressure. Other models of glaucoma mimic increased intraocular pressure and are generated by blockade of the trabecular network by injection of exogenous oil/microbeads or by laser-induced coagulation. At select time points in all of the aforementioned glaucoma models, eyes and optic nerves are harvested for histology to evaluate ocular damage. Retinal cross sections or flatmounts stained with markers of retinal ganglion cells, such as RBPMS or BRN2A, are used to determine the number of surviving cells. Optic nerve sections stained with neuronal specific markers such as SMI32 are used to determine surviving axon number and morphology. In both histological sample types, markers of neuroinflammation, such as GFAP or IBA1, are used to assess injury extent. SARM1 inhibitors will be dosed orally (p.o.) everyday with the use of osmotic pumps implanted s.c. or i.p. at the start of the experiment. Additionally, SARM1 inhibitors may be dosed via topical eye drops or by intravitreal, subconjunctival, subtenon, or retrobulbar injection. The compounds can prevent degeneration of retinal ganglion cells and their axons in the optic nerve, attenuate neuroinflammatory responses, and preserve visual function relative to vehicle treated cohorts.

Example F

Assessment of the Protective Effect of SARM1 Inhibitors in Traumatic Brain Injury (TBI)

To evaluate the ability of a SARM1 inhibitor to protect against TBI, a genetic mouse model of the disease may be used. Closed head TBI will be produced using a weight drop device as previously described in detail and as adapted for use in mice (Henninger et al., Brain 2016, 139 (Pt 4):1094). SARM1 inhibitors will be dosed orally (p.o.) everyday with the use of osmotic pumps implanted s.c. or i.p. at the start of the experiment. Effective compounds will be evaluated using multiple endpoints, primary endpoint being βAPP immunohistology after TBI. Secondary outcomes will include neurobehavioral deficits measured throughout the 4-week observation period using the NSS scale (Flierl et al., 2009, 4(9):1328), plasma phosphorylated neurofilament heavy chain (pNFH) and plasma neurofilament light chain (NfL) levels and cerebral neurochemical profiling.

Various modifications of the invention, in addition to those described herein, will be apparent to those skilled in the art from the foregoing description. Such modifications are also intended to fall within the scope of the appended claims. Each reference, including all patent, patent applications, and publications, cited in the present application is incorporated herein by reference in its entirety.

What is claimed is:
1. A compound of Formula Ib:

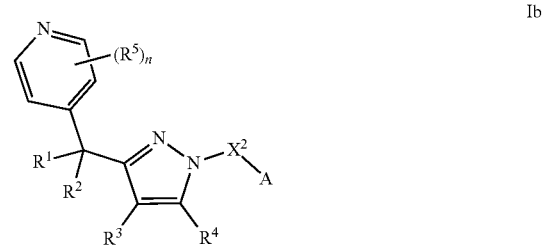

Ib or a pharmaceutically acceptable salt thereof, wherein:
$X^2$ is —$(CR^6R^7)_m$ or —$(CR^6R^7)_p$—C(=O)—$(CR^6R^7)_q$—;
A is halo, CN, Cy, or $C_{1-3}$ haloalkyl;
$R^1$, $R^2$, $R^3$, $R^4$, and $R^5$ are each independently selected from H, D, halo, $CH_3$, $CH_2CH_3$, $CD_3$, $CH_2CD_3$, and $CD_2CD_3$;
$R^6$ and $R^7$ are each independently selected from H, D, halo, methyl, ethyl, and $C_{1-3}$ haloalkyl;
Cy is selected from $C_{6-10}$ aryl, $C_{3-7}$ cycloalkyl, 5-6 membered heteroaryl, and 4-7 membered heterocycloalkyl, each optionally substituted by 1, 2, 3, 4, or 5 $R^{Cy}$ substituents independently selected from halo, $C_{1-4}$ alkyl, $C_{1-4}$ haloalkyl, CN, $NO_2$, $OR^a$, $SR^a$, $C(O)R^b$, $C(O)NR^cR^d$, $C(O)OR^a$, $OC(O)R^b$, $OC(O)NR^cR^d$, $NR^cR^d$, $NR^cC(O)R^b$, $NR^cC(O)OR^a$, $NR^cC(O)NR^cR^d$, $C(=NR^e)R^b$, $C(=NR^e)NR^cR^d$, $NR^cC(=NR^e)NR^cR^d$, $NRCS(O)R^b$, $NRCS(O)_2R^b$, $NRCS(O)_2NR^cR^d$, $S(O)R^b$, $S(O)NR^cR^d$, $S(O)_2R^b$, and $S(O)_2NR^cR^d$;
or two adjacent $R^{Cy}$ substituents together with the atoms to which they are attached form a fused phenyl, $C_{3-7}$ cycloalkyl, 5-6 membered heteroaryl, or 4-7 membered heterocycloalkyl ring, each optionally substituted by 1, 2, 3, 4, or 5 substituents independently selected from halo, $C_{1-4}$ alkyl, $C_{1-4}$ haloalkyl, CN, $NO_2$, $OR^a$, $SR^a$, $C(O)R^b$, $C(O)NR^cR^d$, $C(O)OR^a$, $OC(O)R^b$, $OC(O)NR^cR^d$, $NR^cR^d$, $NR^cC(O)R^b$, $NR^cC(O)OR^a$, $NR^cC(O)NR^cR^d$, $C(=NR^e)R^b$, $C(=NR^e)NR^cR^d$, $NR^cC(=NR^e)NR^cR^d$, $NRcS(O)R^b$, $NRcS(O)_2R^b$, $NRCS(O)_2NR^cR^d$, $S(O)R^b$, $S(O)NR^cR^d$, $S(O)_2R^b$, and $S(O)_2NR^cR^d$;

each $R^a$, $R^b$, $R^c$, and $R^d$ is independently selected from H, $C_{1-4}$ alkyl, and $C_{1-4}$ haloalkyl, wherein said $C_{1-4}$ alkyl is optionally substituted with 1, 2, or 3 substituents independently selected from OH, CN, amino, halo, $C_{1-4}$ alkyl, $C_{1-4}$ alkoxy, $C_{1-4}$ haloalkyl, and $C_{1-4}$ haloalkoxy;

each $R^e$ is independently selected from H, $C_{1-4}$ alkyl, and CN;

m is 1, 2, or 3;

n is 0, 1, or 2;

p is 0, 1, or 2; and q is 0, 1, or 2.

2. The compound of claim 1, or a pharmaceutically acceptable salt thereof, wherein $X^2$ is $-(CR^6R^7)_m-$.

3. The compound of claim 1, or a pharmaceutically acceptable salt thereof, wherein $X^2$ is $CH_2$.

4. The compound of claim 1, or a pharmaceutically acceptable salt thereof, wherein A is halo, CN, or $C_{1-3}$ haloalkyl.

5. The compound of claim 1, or a pharmaceutically acceptable salt thereof, wherein A is F, CN, $CHF_2$, or $CF_3$.

6. The compound of claim 1, or a pharmaceutically acceptable salt thereof, wherein one of $R^1$ and $R^2$ is H and the other of $R^1$ and $R^2$ is H, D, halo, $CH_3$, $CH_2CH_3$, or $CD_3$.

7. The compound of claim 1, or a pharmaceutically acceptable salt thereof, wherein one of $R^1$ and $R^2$ is H and the other of $R^1$ and $R^2$ is H, $CH_3$, $CH_2CH_3$, or $CD_3$.

8. The compound of claim 1, or a pharmaceutically acceptable salt thereof, wherein $R^3$ and $R^4$ are each independently selected from H, halo, and $CH_3$.

9. The compound of claim 1, or a pharmaceutically acceptable salt thereof, wherein $R^3$ and $R^4$ are each independently selected from H and halo.

10. The compound of claim 1, or a pharmaceutically acceptable salt thereof, wherein $R^3$ and $R^4$ are each independently selected from H and F.

11. The compound of claim 1, or a pharmaceutically acceptable salt thereof, wherein $R^3$ and $R^4$ are both H.

12. The compound of claim 1, or a pharmaceutically acceptable salt thereof, wherein each $R^5$ is independently selected from H, halo, and $CH_3$.

13. The compound of claim 1, or a pharmaceutically acceptable salt thereof, wherein each $R^5$ is independently selected from H and $CH_3$.

14. The compound of claim 1, or a pharmaceutically acceptable salt thereof, wherein $R^6$ and $R^7$ are each independently selected from H, halo, and methyl.

15. The compound of claim 1, or a pharmaceutically acceptable salt thereof, wherein $R^6$ and $R^7$ are each independently selected from H and methyl.

16. The compound of claim 1, or a pharmaceutically acceptable salt thereof, wherein $R^6$ and $R^7$ are both H.

17. The compound of claim 1, or a pharmaceutically acceptable salt thereof, wherein Cy is $C_{3-7}$ cycloalkyl.

18. The compound of claim 1, or a pharmaceutically acceptable salt thereof, wherein Cy is 4-7 membered heterocycloalkyl substituted by 2 $R^{Cy}$ substituents that together with the atoms to which they are attached form a fused phenyl.

19. The compound of claim 1, or a pharmaceutically acceptable salt thereof, wherein Cy is selected from $C_{6-10}$ aryl and 5-6 membered heteroaryl, each optionally substituted by 1, 2, 3, 4, or 5 $R^{Cy}$ substituents independently selected from halo, $C^{1-4}$ alkyl, $C^{1-4}$ haloalkyl, CN, NO2, $OR^a$, $SR^a$, $C(O)R^b$, $C(O)NR^cR^d$, $C(O)OR^a$, $OC(O)R^b$, $OC(O)NR^cR^d$, $NR^cR^d$, $NR^cC(O)R^b$, $NR^cC(O)OR^a$, $NR^cC(O)NR^cR^d$, $C(=NR^e)R^b$, $C(=NR^e)NR^cR^d$, $NR^cC(=NR^e)NR^cR^d$, $NRCS(O)R^b$, $NRCS(O)_2R^b$, $NRCS(O)_2NR^cR^d$, $S(O)R^b$, $S(O)NR^cR^d$, $S(O)_2R^b$, and $S(O)_2NR^cR^d$;

or two adjacent $R^{Cy}$ substituents together with the atoms to which they are attached form a fused phenyl, $C_{3-7}$ cycloalkyl, 5-6 membered heteroaryl, or 4-7 membered heterocycloalkyl ring, each optionally substituted by 1, 2, 3, 4, or 5 substituents independently selected from halo, $C_{1-4}$ alkyl, $C_{1-4}$ haloalkyl, CN, $NO_2$, $OR^a$, $SR^a$, $C(O)R^b$, $C(O)NR^cR^d$, $C(O)OR^a$, $OC(O)R^b$, $OC(O)NR^cR^d$, $NR^cR^d$, $NR^cC(O)R^b$, $NR^cC(O)OR^a$, $NR^cC(O)NR^cR^d$, $C(=NR^e)R^b$, $C(=NR^e)NR^cR^d$, $NR^cC(=NR^e)NR^cR^d$, $NR^cS(O)R^b$, $NR^cS(O)_2R^b$, $NRCS(O)_2NR^cR^d$, $S(O)R^b$, $S(O)NR^cR^d$, $S(O)_2R^b$, and $S(O)_2NR^cR^d$.

20. The compound of claim 1, or a pharmaceutically acceptable salt thereof, wherein Cy is selected from phenyl and 5-membered heteroaryl, each optionally substituted by 1, 2, 3, 4, or 5 $R^{Cy}$ substituents independently selected from halo, $C_{1-4}$ alkyl, $C_{1-4}$ haloalkyl, CN, $NO_2$, $OR^a$, $SR^a$, $C(O)R^b$, $C(O)NR^cR^d$, $C(O)OR^a$, $OC(O)R^b$, $OC(O)NR^cR^d$, $NR^cR^d$, $NRCC(O)R^b$, $NR^cC(O)OR^a$, $NR^cC(O)NR^cR^d$, $C(=NR^e)R^b$, $C(=NR^e)NR^cR^d$, $NR^cC(=NR^e)NR^cR^d$, $NRCS(O)R^b$, $NRCS(O)_2R^b$, $NRCS(O)_2NR^cR^d$, $S(O)R^b$, $S(O)NR^cR^d$, $S(O)_2R^b$, and $S(O)_2NR^cR^d$;

or two adjacent $R^{Cy}$ substituents together with the atoms to which they are attached form a fused phenyl, $C_{3-7}$ cycloalkyl, 5-6 membered heteroaryl, or 4-7 membered heterocycloalkyl ring, each optionally substituted by 1, 2, 3, 4, or 5 substituents independently selected from halo, $C_{1-4}$ alkyl, $C_{1-4}$ haloalkyl, CN, $NO_2$, $OR^a$, $SR^a$, $C(O)R^b$, $C(O)NR^cR^d$, $C(O)OR^a$, $OC(O)R^b$, $OC(O)NR^cR^d$, $NR^cR^d$, $NR^cC(O)R^b$, $NR^cC(O)OR^a$, $NR^cC(O)NR^cR^d$, $C(=NR^e)R^b$, $C(=NR^e)NR^cR^d$, $NR^cC(=NR^e)NR^cR^d$, $NR^cS(O)R^b$, $NR^cS(O)_2R^b$, $NR^cS(O)_2NR^cR^d$, $S(O)R^b$, $S(O)NR^cR^d$, $S(O)_2R^b$, and $S(O)_2NR^cR^d$.

21. The compound of claim 1, or a pharmaceutically acceptable salt thereof, wherein n is 0 or 1.

22. The compound of claim 1, or a pharmaceutically acceptable salt thereof, wherein n is 0.

23. The compound of claim 1, or a pharmaceutically acceptable salt thereof, wherein m is 1 or 2.

24. The compound of claim 1, or a pharmaceutically acceptable salt thereof, wherein m is 1.

25. The compound of claim 1, or a pharmaceutically acceptable salt thereof, wherein p is 0 or 1 and q is 0 or 1.

26. The compound of claim 1, or a pharmaceutically acceptable salt thereof, wherein one of p and q is 1 and the other is 0.

27. A compound of claim 1, which is selected from:
2-(3-(Pyridin-4-ylmethyl)-1H-pyrazol-1-yl)acetonitrile;
4-((1-(2,2-Difluoroethyl)-1H-pyrazol-3-yl)methyl)pyridine;
(rac)-2-(3-(1-(Pyridin-4-yl)ethyl)-1H-pyrazol-1-yl)acetonitrile;
(R)-2-(3-(1-(Pyridin-4-yl)ethyl)-1H-pyrazol-1-yl)acetonitrile;

(S)-2-(3-(1-(Pyridin-4-yl)ethyl)-1H-pyrazol-1-yl)acetonitrile;
(S)-4-(1-(1-(2,2,2-Trifluoroethyl)-1H-pyrazol-3-yl)ethyl)pyridine;
(R)-4-(1-(1-(2,2,2-Trifluoroethyl)-1H-pyrazol-3-yl)ethyl)pyridine;
(rac)-4-(1-(1-(2,2-Difluoroethyl)-1H-pyrazol-3-yl)ethyl)pyridine;
4-((1-(2,2,2-Trifluoroethyl)-1H-pyrazol-3-yl)methyl)pyridine;
(rac)-4-(1-(1-(2,2,2-Trifluoroethyl)-1H-pyrazol-3-yl)ethyl-2,2,2-d$_3$)pyridine;
(rac)-4-(1-(4-Fluoro-1-(2,2,2-trifluoroethyl)-1H-pyrazol-3-yl)ethyl)pyridine;
3-Methyl-4-((1-(2,2,2-trifluoroethyl)-1H-pyrazol-3-yl)methyl)pyridine;
(rac)-4-(1-(1-(2,2,2-Trifluoroethyl)-1H-pyrazol-3-yl)ethyl)pyridine;
(rac)-4-(1-(1-(2,2-Difluoroethyl)-1H-pyrazol-3-yl)ethyl-2,2,2-d$_3$)pyridine;
(rac)-4-(1-(1-(2,2,2-Trifluoroethyl)-1H-pyrazol-3-yl)propyl)pyridine;
(R)-3-Fluoro-4-(1-(1-(2,2,2-trifluoroethyl)-1H-pyrazol-3-yl)ethyl)pyridine;
(S)-3-Fluoro-4-(1-(1-(2,2,2-trifluoroethyl)-1H-pyrazol-3-yl)ethyl)pyridine;
(rac)-4-(Fluoro(1-(2,2,2-trifluoroethyl)-1H-pyrazol-3-yl)methyl)pyridine;
(rac)-4-(1-(1-(2,2,2-Trifluoroethyl)-1H-pyrazol-3-yl)ethyl-1,2,2,2-d$_4$)pyridine;
(rac)-4-(Chloro(1-(2,2,2-trifluoroethyl)-1H-pyrazol-3-yl)methyl)pyridine;
(rac)-4-(1-(1-(2,2,2-Trifluoroethyl)-1H-pyrazol-3-yl)ethyl-1-d)pyridine;
4-((5-Methyl-1-(2,2,2-trifluoroethyl)-1H-pyrazol-3-yl)methyl)pyridine;
(rac)-4-(1-(1-Benzyl-1H-pyrazol-3-yl)ethyl)pyridine;
(R)-4-(1-(1-(2,2-Difluoroethyl)-1H-pyrazol-3-yl)ethyl)pyridine;
(S)-4-(1-(1-(2,2-Difluoroethyl)-1H-pyrazol-3-yl)ethyl)pyridine;
(rac)-3-Chloro-4-(1-(1-(2,2,2-trifluoroethyl)-1H-pyrazol-3-yl)ethyl)pyridine;
(R)-3-Chloro-4-(1-(1-(2,2,2-trifluoroethyl)-1H-pyrazol-3-yl)ethyl)pyridine;
(S)-3-Chloro-4-(1-(1-(2,2,2-trifluoroethyl)-1H-pyrazol-3-yl)ethyl)pyridine;
(R)-4-(1-(1-(2,2-Difluoroethyl)-1H-pyrazol-3-yl)ethyl-2,2,2-d$_3$)pyridine; and
(S)-4-(1-(1-(2,2-Difluoroethyl)-1H-pyrazol-3-yl)ethyl-2,2,2-d$_3$)pyridine, or a pharmaceutically acceptable salt of any of the aforementioned.

28. A pharmaceutical composition comprising a compound of claim 1, or a pharmaceutically acceptable salt thereof, and at least one pharmaceutically acceptable carrier.

29. A method of inhibiting SARM1 comprising contacting the SARM1 with a compound of claim 1, or a pharmaceutically acceptable salt thereof.

30. The method of claim 29 wherein the contacting is carried out in vitro.

31. The method of claim 29 wherein the contacting is carried out in vivo.

32. A method of inhibiting axonal degeneration in a patient in need thereof comprising administering to the patient an inhibiting amount of a compound of claim 1, or a pharmaceutically acceptable salt thereof.

33. The method of claim 32 wherein the axonal degeneration is caused by abnormal reduction or depletion of NAD+ in the axons.

34. A method of treating a disease associated with abnormal expression or activity of SARM1 in a patient in need thereof comprising administering to the patient a therapeutically effective amount of a compound of claim 1, or a pharmaceutically acceptable salt thereof.

35. The compound of claim 1 that is

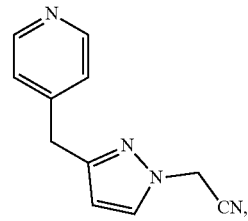 [SMILES: N#CCn1ccc(Cc2ccncc2)n1]

or a pharmaceutically acceptable salt thereof.

36. The compound of claim 1 that is

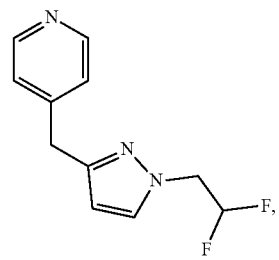 [SMILES: FC(F)Cn1ccc(Cc2ccncc2)n1]

or a pharmaceutically acceptable salt thereof.

37. The compound of claim 1 that is

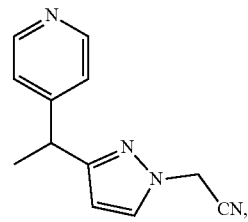 [SMILES: CC(c1ccncc1)c1ccn(CC#N)n1]

or a pharmaceutically acceptable salt thereof.

38. The compound of claim 1 that is

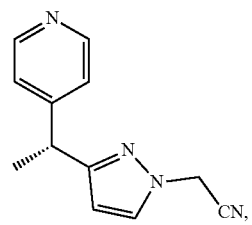 [SMILES: C[C@H](c1ccncc1)c1ccn(CC#N)n1]

or a pharmaceutically acceptable salt thereof.

39. The compound of claim 1 that is

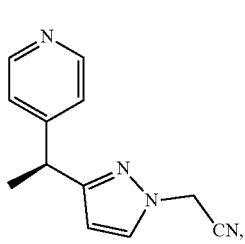 [SMILES: C[C@@H](c1ccncc1)c1ccn(CC#N)n1]

or a pharmaceutically acceptable salt thereof.

40. The compound of claim 1 that is

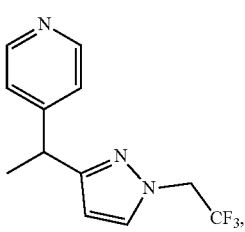 [SMILES: CC(c1ccncc1)c1ccn(CC(F)(F)F)n1]

or a pharmaceutically acceptable salt thereof.

41. The compound of claim 1 that is

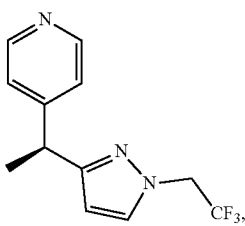 [SMILES: C[C@@H](c1ccncc1)c1ccn(CC(F)(F)F)n1]

or a pharmaceutically acceptable salt thereof.

42. The compound of claim 1 that is

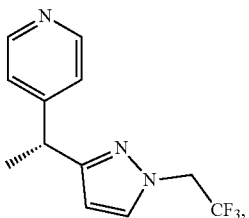

or a pharmaceutically acceptable salt thereof.

43. The compound of claim 1 that is

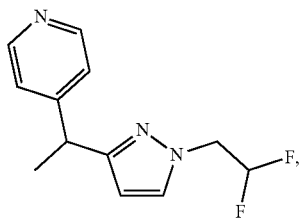 [SMILES: CC(c1ccncc1)c1ccn(CC(F)F)n1]

or a pharmaceutically acceptable salt thereof.

44. The compound of claim 1 that is

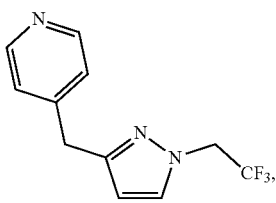 [SMILES: FC(F)(F)Cn1ccc(Cc2ccncc2)n1]

or a pharmaceutically acceptable salt thereof.

45. The compound of claim 1 that is

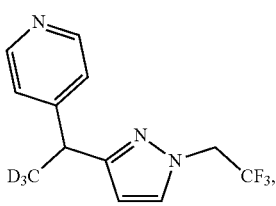 [SMILES: [2H]C([2H])([2H])C(c1ccncc1)c1ccn(CC(F)(F)F)n1]

or a pharmaceutically acceptable salt thereof.

46. The compound of claim 1 that is

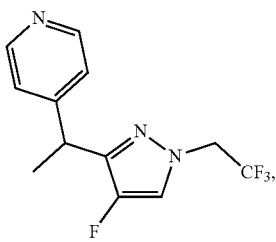 [SMILES: CC(c1ccncc1)c1nn(CC(F)(F)F)cc1F]

or a pharmaceutically acceptable salt thereof.

47. The compound of claim 1 that is

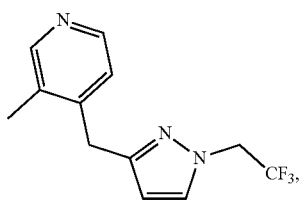 [SMILES: Cc1cnccc1Cc1ccn(CC(F)(F)F)n1]

or a pharmaceutically acceptable salt thereof.

48. The compound of claim 1 that is

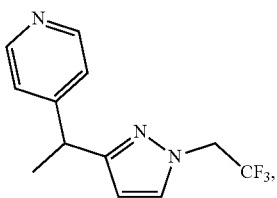 [SMILES: CC(c1ccncc1)c1ccn(CC(F)(F)F)n1]

or a pharmaceutically acceptable salt thereof.

49. The compound of claim 1 that is

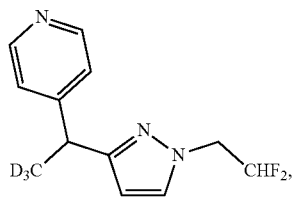

or a pharmaceutically acceptable salt thereof.

50. The compound of claim 1 that is

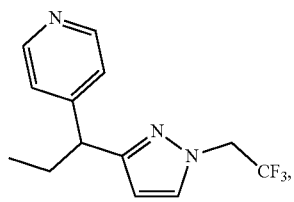 [SMILES: CCC(c1ccncc1)c1ccn(CC(F)(F)F)n1]

or a pharmaceutically acceptable salt thereof.

51. The compound of claim 1 that is

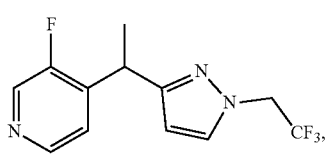 [SMILES: CC(c1ccn(CC(F)(F)F)n1)c1ccncc1F]

or a pharmaceutically acceptable salt thereof.

52. The compound of claim 1 that is

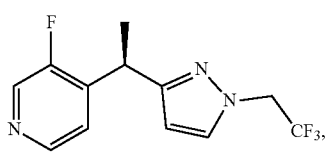

or a pharmaceutically acceptable salt thereof.

53. The compound of claim 1 that is

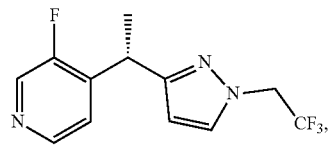

or a pharmaceutically acceptable salt thereof.

54. The compound of claim 1 that is

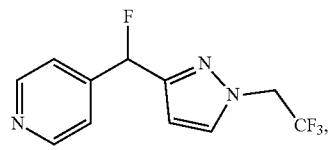

or a pharmaceutically acceptable salt thereof.

55. The compound of claim 1 that is

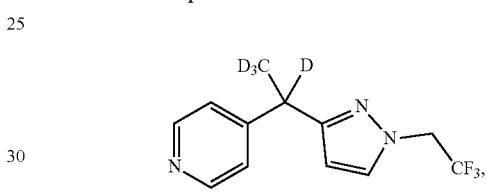

or a pharmaceutically acceptable salt thereof.

56. The compound of claim 1 that is

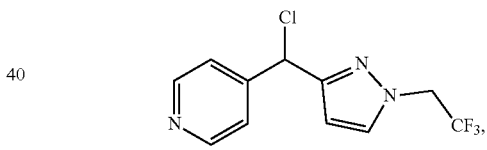

or a pharmaceutically acceptable salt thereof.

57. The compound of claim 1 that is

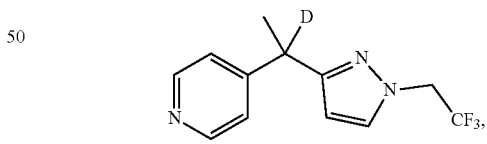

or a pharmaceutically acceptable salt thereof.

58. The compound of claim 1 that is

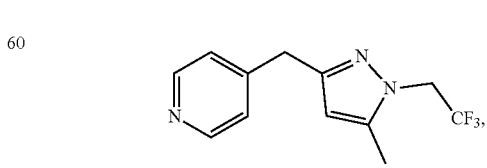

or a pharmaceutically acceptable salt thereof.

59. The compound of claim 1 that is

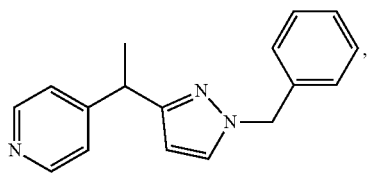 [SMILES: CC(c1ccncc1)c1ccn(Cc2ccccc2)n1]

or a pharmaceutically acceptable salt thereof.

60. The compound of claim 1 that is

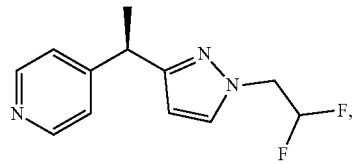 [SMILES: C[C@H](c1ccncc1)c1ccn(CC(F)F)n1]

or a pharmaceutically acceptable salt thereof.

61. The compound of claim 1 that is

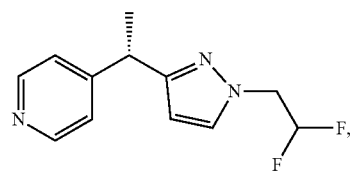 [SMILES: C[C@@H](c1ccncc1)c1ccn(CC(F)F)n1]

or a pharmaceutically acceptable salt thereof.

62. The compound of claim 1 that is

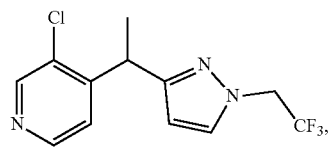

or a pharmaceutically acceptable salt thereof.

63. The compound of claim 1 that is

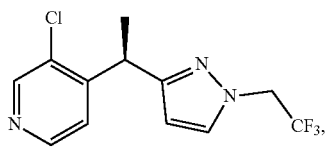

or a pharmaceutically acceptable salt thereof.

64. The compound of claim 1 that is

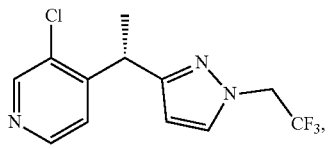

or a pharmaceutically acceptable salt thereof.

65. The compound of claim 1 that is

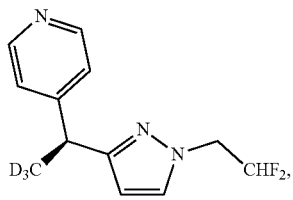 [SMILES: [2H]C([2H])([2H])[C@@H](c1ccncc1)c1ccn(CC(F)F)n1]

or a pharmaceutically acceptable salt thereof.

66. The compound of claim 1 that is

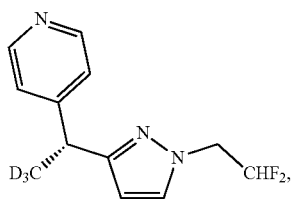 [SMILES: [2H]C([2H])([2H])[C@H](c1ccncc1)c1ccn(CC(F)F)n1]

or a pharmaceutically acceptable salt thereof.

* * * * *

UNITED STATES PATENT AND TRADEMARK OFFICE
CERTIFICATE OF CORRECTION

PATENT NO. : 11,945,796 B2  
APPLICATION NO. : 17/475896  
DATED : April 2, 2024  
INVENTOR(S) : Sean Pomeroy Brown et al.

Page 1 of 2

It is certified that error appears in the above-identified patent and that said Letters Patent is hereby corrected as shown below:

In the Claims

Column 120, Lines 63-64:  
In Claim 1, please replace:  
"NRCS(O)R$^b$, NRCS(O)$_2$R$^b$, NRCS(O)$_2$NR$^c$R$^d$" with --NR$^c$S(O)R$^b$, NR$^c$S(O)$_2$R$^b$, NR$^c$S(O)$_2$NR$^c$R$^d$--

Column 121, Lines 8-9:  
In Claim 1, please replace:  
"NRcS(O)R$^b$, NRcS(O)$_2$R$^b$, NRCS(O)$_2$NR$^c$R$^d$" with --NR$^c$S(O)R$^b$, NR$^c$S(O)$_2$R$^b$, NR$^c$S(O)$_2$NR$^c$R$^d$--

Column 122, Line 1:  
In Claim 18, please replace:  
"R$^C$y" with --R$^{Cy}$--

Column 122, Line 12:  
In Claim 19, please replace:  
"NRCS(O)R$^b$, NRCS(O)$_2$R$^b$, NRCS(O)$_2$NR$^c$R$^d$" with --NR$^c$S(O)R$^b$, NR$^c$S(O)$_2$R$^b$, NR$^c$S(O)$_2$NR$^c$R$^d$--

Column 122, Line 24:  
In Claim 19, please replace:  
"NRCS(O)$_2$NR$^c$R$^d$" with --NR$^c$S(O)$_2$NR$^c$R$^d$--

Column 122, Line 32:  
In Claim 20, please replace:  
"NRCC(O)R$^b$" with --NR$^c$C(O)R$^b$--

Column 122, Line 34:  
In Claim 20, please replace:  
"NRCS(O)R$^b$, NRCS(O)$_2$R$^b$, NRCS(O)$_2$NR$^c$R$^d$" with --NR$^c$S(O)R$^b$, NR$^c$S(O)$_2$R$^b$, NR$^c$S(O)$_2$NR$^c$R$^d$--

Signed and Sealed this  
Twelfth Day of November, 2024

*Katherine Kelly Vidal*

Katherine Kelly Vidal  
*Director of the United States Patent and Trademark Office*

CERTIFICATE OF CORRECTION (continued)
U.S. Pat. No. 11,945,796 B2

Column 122, Line 8:
In Claim 19, please replace:
"NO2" with --$NO_2$--